(12) United States Patent
Edwards et al.

(10) Patent No.: US 10,322,239 B2
(45) Date of Patent: *Jun. 18, 2019

(54) MEDICAMENT DELIVERY DEVICE FOR ADMINISTRATION OF OPIOID ANTAGONISTS INCLUDING FORMULATIONS FOR NALOXONE

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US); Frank E. Blondino, Henrico, VA (US)

(73) Assignee: kaleo, Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/797,844

(22) Filed: Oct. 30, 2017

(65) Prior Publication Data

US 2018/0126082 A1 May 10, 2018

Related U.S. Application Data

(63) Continuation of application No. 14/605,512, filed on Jan. 26, 2015, now Pat. No. 9,814,838, which is a
(Continued)

(51) Int. Cl.
*A61M 5/31* (2006.01)
*A61M 5/32* (2006.01)
(Continued)

(52) U.S. Cl.
CPC ........ *A61M 5/3129* (2013.01); *A61M 5/2033* (2013.01); *A61M 5/3204* (2013.01);
(Continued)

(58) Field of Classification Search
CPC .... A61M 11/00; A61M 11/007; A61M 15/08; A61M 2202/048; A61M 5/2033;
(Continued)

(56) References Cited

U.S. PATENT DOCUMENTS 2,409,656 A  10/1946 Austin
2,960,087 A  11/1960 Uytenbogaart
(Continued)

FOREIGN PATENT DOCUMENTS

CN  101057830  10/2007
DE  2019296  11/1971
(Continued)

OTHER PUBLICATIONS

"Solutions for Medical Devices," 3M Brochure, © 3M, (2006), 80-6201-3490-0, 8 pages.
(Continued)

*Primary Examiner* — Imani N Hayman

(57) ABSTRACT

Medicament delivery devices for administration of opioid antagonists are described herein. In some embodiments, an apparatus includes a housing, a medicament container disposed within the housing and an energy storage member disposed within the housing. The medicament container is filled with a naloxone composition that includes naloxone or salts thereof, a tonicity-adjusting agent, and a pH-adjusting agent, whereby the osmolality of the naloxone composition ranges from about 250-350 mOsm and the pH ranges from about 3-5. The energy storage member is configured to produce a force to deliver the naloxone composition.

26 Claims, 129 Drawing Sheets

Related U.S. Application Data continuation of application No. 14/062,516, filed on Oct. 24, 2013, now Pat. No. 8,939,943, which is a continuation-in-part of application No. 13/036,720, filed on Feb. 28, 2011, now Pat. No. 8,627,816, which is a continuation-in-part of application No. 13/357,935, filed on Jan. 25, 2012, now Pat. No. 9,084,849.

(60) Provisional application No. 61/436,301, filed on Jan. 26, 2011.

(51) Int. Cl.
    *A61M 5/20* (2006.01)
    *A61M 11/00* (2006.01)
    *A61M 15/08* (2006.01)

(52) U.S. Cl.
    CPC .......... *A61M 5/3232* (2013.01); *A61M 11/00* (2013.01); *A61M 11/007* (2014.02); *A61M 15/08* (2013.01); *A61M 5/2046* (2013.01); *A61M 2202/048* (2013.01)

(58) Field of Classification Search
    CPC .............. A61M 5/2046; A61M 5/3129; A61M 5/3204; A61M 5/3232
    See application file for complete search history.

(56) References Cited

U.S. PATENT DOCUMENTS

| | | |
|---|---|---|
| 3,055,362 A | 9/1962 | Uytenbogaart |
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,945,379 A | 3/1976 | Pritz et al. |
| 4,031,889 A | 6/1977 | Pike |
| 4,086,062 A | 4/1978 | Hach |
| 4,108,177 A | 8/1978 | Pistor |
| 4,186,741 A | 2/1980 | Cesaro |
| 4,226,235 A | 10/1980 | Sarnoff et al. |
| 4,227,528 A | 10/1980 | Wardlaw |
| 4,258,713 A | 3/1981 | Wardlaw |
| 4,284,077 A | 8/1981 | Wagner |
| 4,360,019 A | 11/1982 | Portner et al. |
| 4,378,015 A | 3/1983 | Wardlaw |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,172 A | 7/1988 | Baldwin |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,906,463 A | 3/1990 | Cleary |
| 4,915,695 A | 4/1990 | Koobs |
| 4,941,880 A | 7/1990 | Burns |
| 4,955,871 A | 9/1990 | Thomas |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,842 A | 3/1992 | Bechtold et al. |
| 5,092,843 A | 3/1992 | Monroe et al. |
| 5,096,715 A | 3/1992 | Sinclair |
| 5,104,380 A | 4/1992 | Holman et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,271,527 A | 12/1993 | Haber et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,318,544 A | 6/1994 | Drypen et al. |
| 5,343,519 A | 8/1994 | Feldman |
| 5,344,407 A | 9/1994 | Ryan |
| 5,354,284 A | 10/1994 | Haber et al. |
| 5,354,286 A | 10/1994 | Mesa et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,395,345 A | 3/1995 | Gross |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,514,135 A | 5/1996 | Earle |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,587,381 A | 12/1996 | Sinclair |
| 5,610,992 A | 3/1997 | Hickman |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,813,570 A | 9/1998 | Fuchs et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |

(56) References Cited

U.S. PATENT DOCUMENTS

| | | |
|---|---|---|
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,866,154 A | 2/1999 | Bahal |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,503 A | 8/2000 | Stradella |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,280,421 B1 | 8/2001 | Kirchhofer et al. |
| 6,284,765 B1 | 9/2001 | Caffrey |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,321,942 B1 | 11/2001 | Krampen et al. |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,382,465 B1 | 5/2002 | Greiner-Perth |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,499 B1 | 7/2002 | Guiffray |
| 6,425,897 B2 | 7/2002 | Overes et al. |
| 6,428,517 B1 | 8/2002 | Hochman et al. |
| 6,428,528 B2 | 8/2002 | Sadowski |
| 6,446,839 B1 | 9/2002 | Ritsche |
| 6,475,181 B1 | 11/2002 | Potter et al. |
| 6,478,769 B1 | 11/2002 | Parker |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,233 B1 | 4/2003 | Fukui et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,610,271 B2 | 8/2003 | Wermeling |
| 6,613,010 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,708,846 B1 | 3/2004 | Fuchs et al. |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |

(56) References Cited

U.S. PATENT DOCUMENTS

| | | |
|---|---|---|
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,948,492 B2 | 9/2005 | Wermeling et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,074,211 B1 | 7/2006 | Heiniger et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |
| 7,126,879 B2 | 10/2006 | Snyder |
| 7,158,011 B2 | 1/2007 | Brue |
| 7,158,040 B2 | 1/2007 | Morris |
| 7,190,988 B2 | 3/2007 | Say |
| 7,191,916 B2 | 3/2007 | Clifford et al. |
| 7,229,458 B2 | 6/2007 | Boecker et al. |
| 7,237,549 B2 | 7/2007 | Stradella |
| 7,299,981 B2 | 11/2007 | Hickle et al. |
| 7,329,241 B2 | 2/2008 | Horvath et al. |
| 7,343,914 B2 | 3/2008 | Abrams et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,611,495 B1 | 11/2009 | Gianturco |
| 7,648,482 B2 | 1/2010 | Edwards et al. |
| 7,648,483 B2 | 1/2010 | Edwards et al. |
| 7,670,328 B2 | 3/2010 | Miller et al. |
| 7,674,246 B2 | 3/2010 | Gillespie et al. |
| 7,708,719 B2 | 5/2010 | Wilmot et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,806,866 B2 | 10/2010 | Hommann et al. |
| 7,850,662 B2 | 12/2010 | Veasey et al. |
| 7,901,377 B1 | 3/2011 | Harrison et al. |
| 7,901,384 B2 | 3/2011 | Kleyman et al. |
| 7,910,599 B2 | 3/2011 | Sinclair |
| 7,918,823 B2 | 4/2011 | Edwards et al. |
| 7,918,832 B2 | 4/2011 | Veasey et al. |
| 7,938,802 B2 | 5/2011 | Bicknell et al. |
| 7,938,808 B2 | 5/2011 | Pessin |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,021,344 B2 | 9/2011 | Edwards et al. |
| 8,123,719 B2 | 2/2012 | Edwards et al. |
| 8,162,886 B2 | 4/2012 | Sadowski et al. |
| 8,198,291 B2 | 6/2012 | Wermeling |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,313,466 B2 | 11/2012 | Edwards et al. |
| 8,348,096 B2 | 1/2013 | Greiner-Perth |
| 8,361,029 B2 | 1/2013 | Edwards et al. |
| 8,361,035 B2 | 1/2013 | Thorley et al. |
| 8,419,706 B2 | 4/2013 | Heldt et al. |
| 8,425,462 B2 | 4/2013 | Edwards et al. |
| 8,544,645 B2 | 10/2013 | Edwards et al. |
| 8,567,390 B2 | 10/2013 | Stadelhofer |
| 8,627,816 B2 | 1/2014 | Edwards et al. |
| 8,647,306 B2 | 2/2014 | Schwirtz et al. |
| 8,690,827 B2 | 4/2014 | Edwards et al. |
| 8,734,392 B2 | 5/2014 | Stadelhofer |
| 8,734,394 B2 | 5/2014 | Adams et al. |
| 8,747,357 B2 | 6/2014 | Stamp et al. |
| 8,920,377 B2 | 12/2014 | Edwards et al. |
| 8,926,594 B2 | 1/2015 | Edwards et al. |
| 8,939,943 B2 | 1/2015 | Edwards et al. |
| 8,939,959 B2 | 1/2015 | Baney et al. |
| 9,022,022 B2 | 5/2015 | Edwards et al. |
| 9,022,980 B2 | 5/2015 | Edwards et al. |
| 9,044,549 B2 | 6/2015 | Niklasson |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 9,352,099 B2 | 5/2016 | Roberts et al. |
| 9,586,011 B2 | 3/2017 | Roberts et al. |
| 2001/0005781 A1 | 6/2001 | Bergens et al. |
| 2001/0037087 A1 | 11/2001 | Knauer |
| 2002/0042596 A1 | 4/2002 | Hartlaub et al. |
| 2002/0072784 A1 | 6/2002 | Sheppard, Jr. et al. |
| 2002/0076679 A1 | 6/2002 | Aman |
| 2002/0079326 A1 | 6/2002 | Fuchs |
| 2002/0095120 A1 | 7/2002 | Larsen et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0105430 A1 | 6/2003 | Lavi et al. |
| 2003/0106824 A1 | 6/2003 | Wilmot et al. |
| 2003/0120212 A1 | 6/2003 | Dedig et al. |
| 2003/0120222 A1 | 6/2003 | Vaillancourt |
| 2003/0132128 A1 | 7/2003 | Mazur |
| 2003/0233070 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0084047 A1 | 5/2004 | Hickle |
| 2004/0092874 A1 | 5/2004 | Mazidji |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0180916 A1 | 9/2004 | Levine |
| 2004/0210199 A1 | 10/2004 | Atterbury et al. |
| 2004/0220524 A1 | 11/2004 | Sadowski et al. |
| 2004/0235731 A1 | 11/2004 | Lundgren et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0038062 A1 | 2/2005 | Burns et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0090782 A1 | 4/2005 | Marshall et al. |
| 2005/0092679 A1 | 5/2005 | Warby |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |

(56) References Cited

U.S. PATENT DOCUMENTS

| | | |
|---|---|---|
| 2005/0171477 A1 | 8/2005 | Rubin et al. |
| 2005/0177111 A1 | 8/2005 | Ozeri et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0192534 A1 | 9/2005 | Wolbring et al. |
| 2005/0197654 A1 | 9/2005 | Edman et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0083691 A1 | 4/2006 | Wermeling |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0223027 A1 | 10/2006 | Smith et al. |
| 2006/0233778 A1 | 10/2006 | Lundgren et al. |
| 2006/0235354 A1 | 10/2006 | Kaal et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0148097 A1 | 6/2007 | Finn et al. |
| 2007/0166187 A1 | 7/2007 | Song et al. |
| 2007/0184847 A1 | 8/2007 | Hansen et al. |
| 2007/0185053 A1 | 8/2007 | Linn |
| 2007/0203247 A1 | 8/2007 | Phillips et al. |
| 2007/0210147 A1 | 9/2007 | Morrone et al. |
| 2007/0212307 A1 | 9/2007 | Wermeling et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0261695 A1 | 11/2007 | Kottayil et al. |
| 2007/0265568 A1 | 11/2007 | Tsals et al. |
| 2007/0293826 A1 | 12/2007 | Wall et al. |
| 2008/0111685 A1 | 5/2008 | Olson et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0228143 A1 | 9/2008 | Stamp |
| 2008/0230057 A1 | 9/2008 | Sutherland |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0143761 A1 | 6/2009 | Cantor et al. |
| 2009/0176834 A1 | 7/2009 | Kottayil et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0211005 A1 | 8/2010 | Edwards et al. |
| 2010/0212663 A1 | 8/2010 | Vedrine et al. |
| 2010/0286612 A1 | 11/2010 | Cirillo |
| 2010/0331354 A1 | 12/2010 | Wermeling et al. |
| 2011/0060274 A1 | 3/2011 | Kuhn |
| 2011/0077589 A1 | 3/2011 | Karlsson et al. |
| 2011/0092954 A1 | 4/2011 | Jennings |
| 2011/0098655 A1 | 4/2011 | Jennings et al. |
| 2011/0189259 A1 | 8/2011 | Vasisht et al. |
| 2011/0295215 A1 | 12/2011 | Nielsen et al. |
| 2012/0046613 A1 | 2/2012 | Plumptre |
| 2012/0070495 A1 | 3/2012 | Shah et al. |
| 2012/0091026 A1 | 4/2012 | Chacornac et al. |
| 2012/0107783 A1 | 5/2012 | Julian et al. |
| 2012/0116319 A1 | 5/2012 | Grunhut |
| 2012/0172818 A1 | 7/2012 | Harms et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0270895 A1 | 10/2012 | Wermeling |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0302966 A1 | 11/2012 | Vedrine et al. |
| 2012/0310168 A1 | 12/2012 | Plumptre et al. |
| 2012/0310206 A1 | 12/2012 | Kouyoumjian et al. |
| 2012/0325865 A1 | 12/2012 | Forstreuter et al. |
| 2012/0330244 A1 | 12/2012 | Helmer et al. |
| 2013/0030367 A1 | 1/2013 | Wotton et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang et al. |
| 2013/0081953 A1 | 4/2013 | Bruna et al. |
| 2013/0110050 A1 | 5/2013 | Boyd et al. |
| 2013/0236872 A1 | 9/2013 | Laurusonis et al. |
| 2013/0266919 A1 | 10/2013 | Baker et al. |
| 2013/0317477 A1 | 11/2013 | Edwards et al. |
| 2015/0018379 A1 | 1/2015 | Strang et al. |
| 2015/0041496 A1 | 2/2015 | Kim et al. |
| 2015/0231336 A1 | 8/2015 | Edwards et al. |
| 2015/0297840 A1 | 10/2015 | Edwards et al. |
| 2016/0015895 A1 | 1/2016 | Edwards et al. |
| 2017/0035957 A1 | 2/2017 | Edwards et al. |
| 2017/0232206 A1 | 8/2017 | Edwards et al. |
| 2017/0333422 A1 | 11/2017 | Silverman et al. |
| 2018/0304017 A1 | 10/2018 | Edwards et al. |
| 2018/0304018 A1 | 10/2018 | Blondino et al. |
| 2019/0060557 A1 | 2/2019 | Edwards |

FOREIGN PATENT DOCUMENTS

| | | |
|---|---|---|
| EP | 0429039 B1 | 3/1995 |
| EP | 0346830 B1 | 5/1995 |
| EP | 1084765 B1 | 3/2001 |
| EP | 1287840 A1 | 3/2003 |
| EP | 1462134 A1 | 9/2004 |
| EP | 1712178 A2 | 10/2006 |
| FR | 2509615 | 1/1983 |
| FR | 2700959 | 2/1993 |
| GB | 2195544 A1 | 4/1988 |
| WO | WO 91/04760 | 4/1991 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/011778 | 2/2002 |
| WO | WO 2002/024257 | 3/2002 |
| WO | WO 2002/051471 | 7/2002 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |

(56) References Cited

FOREIGN PATENT DOCUMENTS

| WO | WO 2003/057283 | 7/2003 |
|---|---|---|
| WO | WO 2003/070191 | 8/2003 |
| WO | WO 2003/095001 | 11/2003 |
| WO | WO 2003/097133 | 11/2003 |
| WO | WO 2004/041330 | 5/2004 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/020906 | 3/2005 |
| WO | WO 2005/050526 | 6/2005 |
| WO | WO 2005/070481 | 8/2005 |
| WO | WO 2005/077441 | 8/2005 |
| WO | WO 2006/045525 | 5/2006 |
| WO | WO 2006/085175 | 8/2006 |
| WO | WO 2006/085204 | 8/2006 |
| WO | WO 2006/109778 | 10/2006 |
| WO | WO 2006/125692 | 11/2006 |
| WO | WO 2007/032962 | 3/2007 |
| WO | WO 2007/083115 | 7/2007 |
| WO | WO 2007/088444 | 8/2007 |
| WO | WO 2008/005315 | 1/2008 |
| WO | WO 2008/034060 | 3/2008 |
| WO | WO 2008/148864 | 12/2008 |
| WO | WO 2009/040595 | 4/2009 |
| WO | WO 2013/044172 | 3/2013 |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html>, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1>, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Scholz, O., "Drug depot in a tooth," [online] [retrieved on Feb. 6, 2007] Retrieved from the Internet <URL: http://www.fraunhofer.de/fhg/En/press/pi/2007/02Mediendienst22007Thema2.jsp?print=true>, 1 page.

Heartsine Technology, samaritan™ Pad Accessories [online] [retrieved on Jun. 1, 2007] Retrieved from the Internet <URL: http://www.heartsine.com/aboutsam-accessories.htm>, 4 pages.

CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.

CliniSense Corporation, "LifeTrack Technology a new method to detect improper storage." Stability [online] [retrieved on Jun. 1, 2007] Retrieved from the Internet <URL: http://www.clinisense.com/tech.htm>, 2 pages.

AED Professionals™ Brochure [online] [retrieved on Jun. 1, 2007] Retrieved from the Internet <URL: http://www.aedprofessionals.com>, 4 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/DRUGDELIVERY/200702/TEMPLATES/PAGEVIEWER-PRINT?PG-44&PM-8.

O'Hagan, D. et al., "Novel approaches to pediatric vaccine delivery," Advanced Drug Delivery Reviews, 58:29-51 (2006).

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.

Boseley, S., "Families to receive antidote to help drug users who overdose," Guardian News and Media, Jun. 25, 2009. [retrieved on May 27, 2011] Retrieved from the Internet <URL: http://www.guardian.co.uk/society/2009/jun/25/drug-overdose-antidote-naloxone-families>.

McDougall, L., "Addicts to be given personal supply of anti-overdose drug," The Herald Scotland, May 28, 2006. Retrieved from the Internet <URL: http://www.heraldscotland.com/sport/spl/aberdeen/addicts-to-be-given-personal-supply-of-anti-overdose-drug-heroin-controversial-lifesaving-plan-projects-aim-to-cut-rising-death-toll-making-naloxone-treatment-more-readily-available-119181>.

BD Accuspray™ Nasal Spray System, 2004, Retrieved from the Internet <URL: http://www.bd.com/press/pdfs/flu/bd_accuspray.pdf>, 1 page.

Colliver, V., "Naloxone saves lives of overdosed opiate users," San Francisco Chronicle, Oct. 14, 2010 [retrieved Aug. 14, 2013] Retrieved from the Internet <URL: http://www.sfgate.com/health/article/Naloxone-saves-lives-of-overdosed-opiate-users-3249978.php>.

Terry, D., "A Shot That Saves the Lives of Addicts Is Now in Their Hands," The New York Times, Jul. 24, 2010 [retrieved Aug. 14, 2013] Retrieved from the Internet <URL: http://www.nytimes.com/2010/07/25/us/25cncnaloxone.html>.

Szalavitz, M., "Should an Overdose Antidote Be Made More Accessible?" TIME, Dec. 9, 2010 [retrieved on Aug. 14, 2013] Retrieved from the Internet <URL: http://healthland.time.com/2010/12/09/should-an-overdose-antidote-be-made-more-accessible/>.

Okie, S., "A Flood of Opioids, a Rising Tide of Deaths," The New England Journal of Medicine, Nov. 18, 2010, 363:1981-1985 [online], [retrieved on Aug. 14, 2013] Retrieved from the Internet <URL: http://www.nejm.org/doi/full/10.1056/NEJMp1011512>.

Wermeling, D. P., "A response to the opioid overdose epidemic: naloxone nasal spray," Drug Deliv. and Transl. Res., 3:63-74 (2013).

Wermeling, D. P., "Opioid Harm Reduction Strategies: Focus on Expanded Access to Intranasal Naloxone," Pharmacotherapy, 30(7):627-631 (2010).

Djupesland, P. G., "Nasal drug delivery devices: characteristics and performance in a clinical perpsective—a review," Drug Deliv. and Transl. Res., Published online: Oct. 18, 2012, 21 pages.

"Martindale Pharma Launches Prenoxad Injection in UK for Emergency Treatment of Opioid Overdose," Pharmabiz.com, May 6,

(56) References Cited

OTHER PUBLICATIONS

2013 [online], [retrieved on Nov. 26, 2014] Retrieved from the Internet <URL: http://www.pharmabiz.com/NewsDetails.aspx?aid=75187&sid=2>, 1 page.
"Therapeutic Intranasal Drug Delivery: Needleless Treatment Options for Medical Problems," Intranasal.net [online], [retrieved on Dec. 16, 2010] Retrieved from the Internet <URL: http://intranasal.net/OpiateOverdose/>, 10 pages.
Prenoxad Injection: Client's Guide to Prenoxad Injection, Martindale Pharma, Apr. 2013, 16 pages.
Prenoxad Injection: Pharmacists's Guide, Martindale Pharma, Apr. 2013, 6 pages.
Prenoxad Injection: Packaging Leaflet: Information for the User, Martindale Pharma, Nov. 2012, 2 pages.
Prenoxad Injection: Summary of Product Characteristics, Martindale Pharma, Apr. 2013, 4 pages.
Edwards, E. S., Dissertation: "Development of a novel approach to assess qualitative and quantitative dynamics associated with the subcutaneous or intramuscular administration of pharmaceuticals and associated parenteral delivery systems," B.S. Biology, Virginia Commonwealth University (Dec. 2011).
Bennett, J. et al., "Subcutaneous administration of midazolam: A comparison of the bioject jet injector with the conventional syringe and needle," J Oral Maxillofac Surg, 56(11):1249-1254 (1998).
Brearley, C. et al., "Pharmacokinetics of recombinant human growth hormone administered by cool.clickTM 2, a new needle-free device, compared with subcutaneous administration using a conventional syringe and needle," BMC Clin Pharmacol, 7:10 (2007), 7 pages.
Simons, F. E. R. et al., "Epinephrine absorption in adults: intramuscular versus subcutaneous injection," J Allergy Clin Immunol, 108(5), 871-873 (2001).
Kerum, G. et al., "Blood glucose and free insulin levels after the administration of insulin by conventional syringe or jet injector in insulin treated type 2 diabetics," Horm. Metabol. Res., 19:422-425 (1987).
Halle, J.-P. et al., "Twice daily mixed regular and NPH insulin injections with new jet injector versus conventional syringes: pharmacokinetics of insulin absorption," Diabetes Care, 9(3):279-282 (1986).
Taylor, R. et al., "Plasma free insulin profiles after administration of insulin by jet and conventional syringe injection," Diabetes Care, 4(3):377-379 (1981).
Biocryst Pharmaceuticals, Inc., Biocryst Press Release, "Biocryst reports preliminary results from a phase II clinical trial of peramivir in subjects with acute influenza," Retrieved from the Internet: <http://investor.shareholder.com/biocryst/releasedetail.cfm?ReleaseID=264815> (Sep. 19, 2007), 3 pages.
Marx, D. et al., "Multi-Dose Container for Nasal and Ophthalmic Drugs: A Preservative Free Future?," Chapter 20 of Drug Development—A Case Study Based Insight into Modern Strategies, isBN: 978-953-307-257-9 (Nov. 2011).

Harm Reduction Coalition, "How to Give Nasal Spray Naloxone," [online], [retrieved on May 27, 2015] Retrieved from the Internet: <http://http://harmreduction.org/wp-content/uploads/2014/10/OD-Response-administer-naloxone-intranasal-instructions.pdf> (undated).
Elsemiek, E.C. et al., "Improved Pharmacokinetic and Pharmacodynamic Profile of Rapid-Acting Insulin Using Needle-Free Jet Injection Technology," Emerging Treatments and Technologies, *Diabetes Care* 34:1804-1808 (Aug. 2011).
Lewis, J. et al., "Needle-Free Subcutaneous Sumatriptan (Sumavel™ DosePro™ Bioequivalence and Ease of Use," *Headache*, 2009;49:1435-1444 (Nov./Dec. 2009).
Schram, J. et al., "Transdermal Drug Delivery by Jet Injectors: Energetics of Jet Formation and Penetration," *Pharmaceutical Research*, vol. 19, No. 11 (Nov. 2002).
Verhagen, A. et al., A1032:C1038 "Pharmacokinetics and pharmacodynamics of a single dose of recombinant human growth hormone after subcutaneous administration by jet-injection: comparison with conventional needle-injection," Eur J Clin Pharmacol 49:69-72 (Feb. 10, 1995).
Dahan, Albert et al., "Incidence, Reversal, and Prevention of Opioid-induced Respiratory Depression," *Anesthesiology* vol. 112, No. 1: 226-238 (Jan. 2010).
Clarke, S. F. J. et al., "Naloxone in Opioid Poisoning: Walking the tightrope," *Emerg Med J* vol. 22: 612-616 (2005).
International Search Report and Written Opinion for International Patent Application No. PCT/US06/03415, dated Jul. 13, 2006, 10 pages.
International Search Report and Written Opinion for International Patent Application No. PCT/US07/007626, dated Sep. 29, 2008.
Examination Report for Australian Patent Application No. 2011218756, dated Nov. 1, 2011.
Examination Report for Australian Patent Application No. 2011218756, dated Feb. 1, 2013.
Notice of Acceptance for Australian Patent Application No. 2011218756, dated Apr. 12, 2013.
Non-Final Office Action for U.S. Appl. No. 13/036,720, dated May 17, 2013.
Final Office Action for U.S. Appl. No. 13/036,720, dated Nov. 5, 2013.
International Search Report and Written Opinion for International Application No. PCT/US2012/026708, dated Jun. 7, 2012.
Non-Final Office Action for U.S. Appl. No. 14/062,516, dated Apr. 22, 2014.
Final Office Action for U.S. Appl. No. 14/062,516, dated Sep. 23, 2014.
Office Action for U.S. Appl. No. 14/153,575, dated Jan. 30, 2015.
Office Action for U.S. Appl. No. 14/335,490, dated May 8, 2015.
Office Action for U.S. Appl. No. 14/694,725, dated Dec. 17, 2015.
Office Action for British Patent Application No. 1315737.5, dated Feb. 28, 2017.
Search Report for European Patent Application No. 12751771.2, dated Jun. 13, 2017.
Office Action for U.S. Appl. No. 15/631,076, dated Apr. 8, 2019.

MEDICAMENT DELIVERY DEVICE FOR ADMINISTRATION OF OPIOID ANTAGONISTS INCLUDING FORMULATIONS FOR NALOXONE

CROSS REFERENCE TO RELATED APPLICATIONS

This application is a continuation of U.S. patent application Ser. No. 14/605,512, entitled "Medicament Delivery Device for Administration of Opioid Antagonists Including Formulations for Naloxone," filed Jan. 26, 2015, which is a continuation of U.S. patent application Ser. No. 14/062,516, now U.S. Pat. No. 8,939,943, entitled "Medicament Delivery Device for Administration of Opioid Antagonists Including Formulations for Naloxone," filed Oct. 24, 2013, which is a continuation-in-part of U.S. patent application Ser. No. 13/357,935, now U.S. Pat. No. 9,084,849, entitled "Medicament Delivery Devices for Administration of a Medicament within a Prefilled Syringe," filed Jan. 25, 2012, which claims priority to U.S. Provisional Patent Application No. 61/436,301, entitled "Devices and Methods for Delivering Lyophilized Medicaments," filed Jan. 26, 2011, the disclosure of each of which is hereby incorporated by reference in its entirety. U.S. patent application Ser. No. 14/062,516 is also a continuation-in-part of U.S. patent application Ser. No. 13/036,720, now U.S. Pat. No. 8,627,816, entitled "Medicament Delivery Device for Administration of Opioid Antagonists Including Formulations for Naloxone," filed Feb. 28, 2011, the disclosure of which is hereby incorporated by reference in its entirety.

BACKGROUND

The embodiments described herein relate generally to medical device and pharmaceutical compositions, and more particularly to a medicament delivery device for administration of opioid antagonists, including formulations for naloxone.

Naloxone is a medicament that prevents and/or reverses the effects of opioids. Known formulations of naloxone can be used, for example, to treat respiratory depression and other indications that result from opioid toxicity. For example, known formulations for naloxone can be used to reverse and/or mitigate the effects of an overdose of a drug containing opioids, such as, for example, heroin. In such situations, it is desirable to deliver the naloxone formulation quickly and in a manner that will produce a rapid onset of action. Accordingly, known formulations of naloxone are often delivered either intranasally or via injection.

The delivery of naloxone intranasally or via injection, however, often involves completing a series of operations that, if not done properly, can limit the effectiveness of the naloxone formulation. For example, prior to delivering the naloxone, the user must first determine whether the patient's symptoms warrant the delivery of naloxone, and then couple a needle (or an atomizer) to a syringe containing the naloxone formulation. After the device is prepared for delivery, the user then selects the region of the body in which the naloxone is to be delivered, and manually produces a force to deliver the naloxone. In some situations, such as, for example, when the patient is in an ambulance or a hospital setting, the user then inserts an intravenous catheter to administer the naloxone. Additionally, after the delivery of the naloxone formulation, the user must dispose of the device properly (e.g., to prevent needle sticks in instances where the naloxone is injected) and seek further medical attention for the patient. Accordingly, known formulations of naloxone are often delivered by a healthcare provider in a controlled environment (e.g. a hospital, physician's office, clinic or the like). Access to emergency medical facilities and/or trained health care providers, however, is not always available when an individual is suffering from an overdose. Moreover, because naloxone is often administered during an emergency situation, even experienced and/or trained users may be subject to confusion and/or panic, thereby compromising the delivery of the naloxone formulation.

Known devices for delivering naloxone also require that the user manually generate the force and/or pressure required to convey the naloxone from the device into the body. For example, to deliver naloxone using known syringes, the user manually depresses a plunger into the syringe body. The force generated by manually depressing a plunger, however, can be sporadic, thus resulting in undesirable fluctuations in the flow of the naloxone and/or incomplete delivery of the full dose. Such fluctuations and variability can be particularly undesirable when the naloxone is being atomized for intranasal delivery. Moreover, in certain situations, the user may be unable to generate sufficient force to provide the desired flow rate and/or flow characteristics (e.g., for an atomizer) of the naloxone.

Additionally, because naloxone is often delivered by a healthcare provider in a controlled environment, known formulations of naloxone are generally stored under controlled conditions, and for limited periods of time. For example, known naloxone formulations are often formulated to be stored between 20 and 25 degrees Celsius. Accordingly, known naloxone formulations are not compatible for being carried by a patient or a third party (e.g., a relative of friend of the patient) for long periods of time.

Thus, a need exists for improved methods and devices for delivering opioid antagonists, such as, for example, devices that provide for the delivery of naloxone by untrained users. Additionally, a need exists for naloxone formulations that can be exposed to a wide range of environmental conditions for long periods of time.

SUMMARY

Medicament delivery devices for administration of opioid antagonists and chemical compositions used within such devices are described herein. In some embodiments, a naloxone composition can be formulated for use in a delivery device of the types shown and described herein. The naloxone composition includes an effective amount of naloxone i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. In some embodiments, the naloxone composition can include a pH-adjusting agent, such as, for example, at least one of hydrochloric acid, citric acid, acetic acid, phosphoric acid, or combinations thereof. In some embodiments, the naloxone composition can include one or more tonicity-adjusting agents, such as, for example, at least one of dextrose, glycerin, mannitol, potassium chloride, sodium chloride, or combinations thereof. Because the naloxone composition may be stored in the medicament container of a delivery device for extended periods of time under varying storage conditions, in some embodiments the naloxone composition can include stabilizers to prevent or inhibit decomposition of the naloxone during storage.

In some embodiments, an apparatus includes a housing, a medicament container disposed within the housing and an energy storage member disposed within the housing. The medicament container is filled with a naloxone composition that includes naloxone or salts thereof, a tonicity-adjusting agent, and a pH-adjusting agent, whereby the osmolality of the naloxone composition ranges from about 250-350 mOsm and the pH ranges from about 3-5. The energy storage member is configured to produce a force to deliver the naloxone composition.

In some embodiments, the medicament delivery device can further include an elastomeric member disposed within the medicament container that is configured to be compatible with the naloxone composition. Said another way, in some embodiments, an elastomeric member disposed within the medicament container can be formulated to prevent undesired leaching and/or reaction with the naloxone composition. In some embodiments, the elastomeric member is formulated to include a polymer and a curing agent. The polymer includes at least one of bromobutyl or chlorobutyl, and the curing agent includes at least one of sulfur or metal compounds, e.g., metal oxides such as zinc oxide or magnesium oxide, etc.

In some embodiments, the medicament delivery device can include an electronic circuit system coupled to the housing. The electronic circuit system is configured to produce an output when the electronic circuit system is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

In some embodiments, an apparatus includes a housing, a medicament container and a movable member. The medicament container is configured to move within the housing between a first position and a second position in response to a force produced by an energy storage member. A proximal end portion of the medicament container includes a flange and has a plunger disposed therein. The movable member is configured to move within the housing. A first shoulder of the movable member is configured to exert the force on the flange to move the medicament container from the first position to the second position. A portion of the first shoulder is configured to deform when the medicament container is in the second position such that at least a portion of the force is exerted upon the plunger. A second shoulder of the movable member is configured to exert a retraction force on the flange to move the medicament container from the second position towards the first position.

BRIEF DESCRIPTION OF THE DRAWINGS

FIG. 137 is a cross-sectional perspective view of a portion of the electronic circuit system illustrated in FIG. 133, taken along line X-X in FIG. 136.

FIG. 138 is a schematic illustration of a medicament delivery device according to an embodiment.

FIG. 139 is a schematic illustration of a kit including a medicament container according to an embodiment.

DETAILED DESCRIPTION

Figure 1:
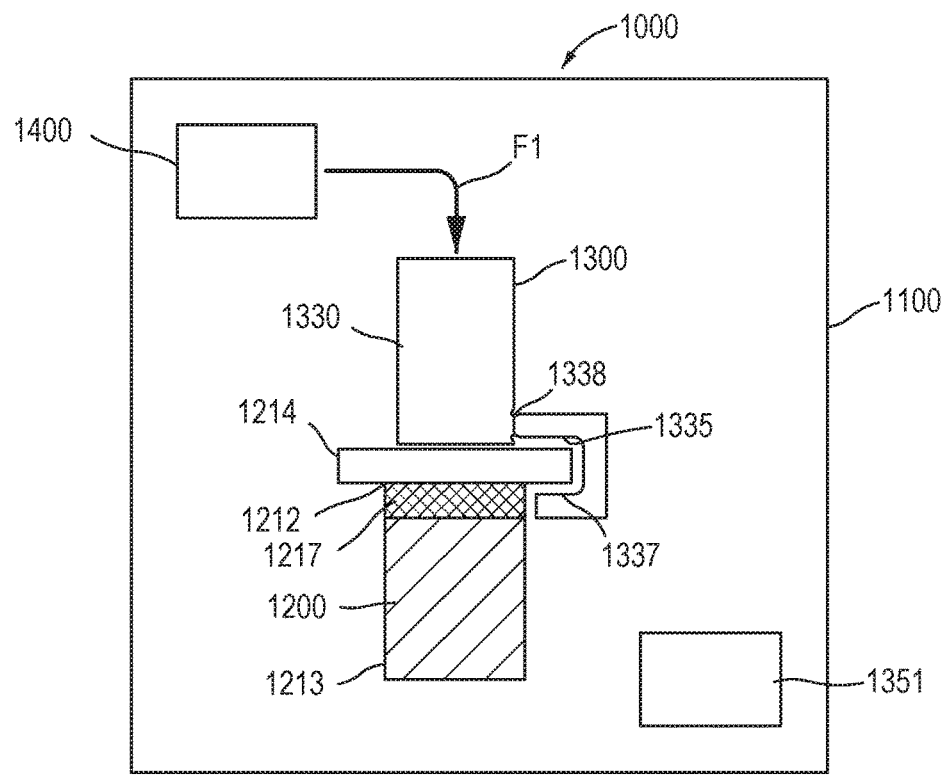
FIGS. 1-4 are schematic illustrations of a medicament delivery device according to an embodiment, in a first, second, third and fourth configuration, respectively.

Medicament delivery devices for administration of opioid antagonists and chemical compositions used within such devices are described herein. In some embodiments, a naloxone composition can be formulated for use in a delivery device of the types shown and described herein. The naloxone composition includes an effective amount of naloxone i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. In some embodiments, the naloxone composition can include a pH-adjusting agent, such as, for example, at least one of hydrochloric acid, citric acid, acetic acid, phosphoric acid, or combinations thereof. In some embodiments, the naloxone composition can include one or more tonicity-adjusting agents, such as, for example, at least one of dextrose, glycerin, mannitol, potassium chloride, sodium chloride, or combinations thereof. Because the naloxone composition may be stored in the medicament container of a delivery device for extended periods of time under varying storage conditions, in some embodiments the naloxone composition can include stabilizers to prevent or inhibit decomposition of the naloxone during storage.

In some embodiments, a medicament delivery device includes a housing, a medicament container disposed within the housing and an energy storage member disposed within the housing. The medicament container is filled with a naloxone composition that includes naloxone or salts thereof, a tonicity-adjusting agent, and a pH-adjusting agent, whereby the osmolality of the naloxone composition ranges from about 250-350 mOsm and the pH ranges from about 3-5. The energy storage member is configured to produce a force to deliver the naloxone composition.

In some embodiments, the medicament delivery device can further include an elastomeric member disposed within the medicament container that is configured to be compatible with the naloxone composition. Said another way, in some embodiments, an elastomeric member disposed within the medicament container can be formulated to prevent undesired leaching and/or reaction with the naloxone composition. In some embodiments, the elastomeric member is formulated to include a polymer and a curing agent. The polymer includes at least one of bromobutyl or chlorobutyl, and the curing agent includes at least one of sulfur, zinc or magnesium.

In some embodiments, the medicament delivery device can include an electronic circuit system coupled to the housing. The electronic circuit system is configured to produce an output when the electronic circuit system is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

In some embodiments, a medicament delivery device includes a housing, a medicament container disposed within the housing, a delivery member coupled to the medicament container, and an energy storage member. The medicament container is filled with a naloxone composition. The energy storage member is disposed within the housing, and is configured to produce a force to deliver the naloxone composition from the medicament container via the delivery member such that the delivery member atomizes the naloxone composition.

In some embodiments, a kit includes a case and a medicament container movably disposed within the case. The medicament container filled with a naloxone composition. The medicament container includes a delivery member coupled thereto. The delivery member can be, for example, a needle, an atomizer or any other mechanism through which the naloxone composition can be conveyed from the medicament container into a body.

Medicament delivery devices for administration of medicaments contained within a prefilled syringe are described herein. In some embodiments, an apparatus includes a housing, a medicament container and a movable member. The medicament container, which can be, for example, a prefilled syringe, is configured to move within the housing between a first position and a second position in response to a force produced by an energy storage member. The energy storage member can be, for example, a spring, a compressed gas container, an electrical energy storage member or the like. A proximal end portion of the medicament container includes a flange and has a plunger disposed therein. The movable member is configured to move within the housing. A first shoulder of the movable member is configured to exert the force on the flange to move the medicament container from the first position to the second position. A portion of the first shoulder is configured to deform when the medicament container is in the second position such that at least a portion of the force is exerted upon the plunger. A second shoulder of the movable member is configured to exert a retraction force on the flange to move the medicament container from the second position towards the first position.

In some embodiments, a medicament delivery device includes a housing, a medicament container, a movable member and an energy storage member. The medicament container is configured to move within the housing between a first position and a second position in response to a force produced by the energy storage member. A proximal end portion of the medicament container includes a flange and has a plunger disposed therein. The movable member is configured to exert the force on the medicament container to move the medicament container from the first position to the second position. An engagement portion of the movable member is configured to limit movement of a piston surface relative to the plunger when the medicament container moves from the first position to the second position such that the piston surface is spaced apart from the plunger. The engagement portion is configured to deform when the medicament container is in the second position such that the piston surface is in contact with the plunger.

In some embodiments, a medicament delivery device includes a housing, a medicament container, a first movable member and a second movable member. The medicament container is configured to move within the housing between a first position and a second position in response to a force produced by an energy storage member. A proximal end portion of the medicament container includes a flange and has a plunger disposed therein. The first movable member is configured to move within the housing, and is operably coupled to the energy storage member such that a first portion of the first movable member is configured to exert at least a portion of the force on the flange to move the medicament container from the first position to the second position. A second portion of the first movable member is configured to deform when the medicament container is in the second position such that at least a portion of the force is exerted upon the plunger. The second movable member is configured to move with the medicament container when the medicament container moves from the first position to the second position. The second movable member is configured to move relative to the medicament container to move the plunger within the medicament container after the second portion of the first movable member is deformed.

In some embodiments, a medical device includes a carrier configured to be disposed within a housing of the medical device. The carrier is configured to contain at least a proximal portion of a medicament container, such as, for example a prefilled syringe having a flange. A first shoulder of the carrier is in contact with a proximal surface of the flange and a second shoulder of the carrier is in contact with a distal surface of the flange. The carrier has a first engagement portion configured to engage a movable member such that when a first force is exerted by the movable member on the first engagement portion, the first shoulder transfers at least a portion of the first force to the proximal surface of the flange. The carrier has a second engagement portion configured to engage a retraction spring such that when a second force is exerted by the retraction spring on the second engagement portion, the second shoulder transfers at least a portion of the second force to the distal surface of the flange.

In some embodiments, the medical device further includes a damping member disposed between the first shoulder of the carrier and the proximal surface of the flange of the medicament container, or between the second shoulder of the carrier and the proximal surface of the flange of the medicament container. The damping member can be disposed such that a portion of the first force or a portion of the second force is received and/or absorbed by the damping member to reduce the possibility of damage to the medicament container and/or flange.

In some embodiments, a medical device includes a housing, a movable member and a medicament container. The movable member is disposed within the housing and has a first engagement portion, a second engagement portion and a retraction portion. The first engagement portion is configured to be coupled to an energy storage member. The second engagement portion is configured to be coupled to the medicament container such that a shoulder of the second engagement portion exerts a first force produced by the energy storage member on the medicament container to move the medicament container within the housing in a first direction. The retraction portion is configured to produce a second force to move the medicament container within the housing in a second direction. In some embodiments, the retraction portion includes a spring that is monolithically constructed with at least the second engagement portion.

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

Throughout the present specification, the words "a" or "an" are understood to mean "one or more" unless explicitly stated otherwise. Further, the words "a" or "an" and the phrase "one or more" may be used interchangeably.

FIGS. 1-4 are schematic illustrations of a medicament delivery device 1000 according to an embodiment in a first, second, third and fourth configuration, respectively. The medicament delivery device 1000 includes a housing 1100, a medicament container 1200, a movable member 1300, an energy storage member 1400 and a retraction member 1351. The housing 1100 can be any suitable size, shape, or configuration and can be made of any suitable material. For example, in some embodiments, the housing 1100 is an assembly of multiple parts formed from a plastic material and defines a substantially rectangular shape when assembled.

The medicament container 1200 is disposed within the housing 1100, and contains (i.e., is filled or partially filled with) a medicament. The medicament container 1200 includes a proximal end portion 1212 that has a flange 1214 and a distal end portion 1213 that is coupled to a needle (not shown in FIGS. 1-4). The medicament container 1200 includes an elastomeric member 1217 (also referred to herein as a "plunger"). The elastomeric member 1217 is formulated to be compatible with the medicament housed within the medicament container 1200. Similarly stated, the elastomeric member 1217 is formulated to minimize any reduction in the efficacy of the medicament that may result from contact (either direct or indirect) between the elastomeric member 1217 and the medicament. For example, in some embodiments, the elastomeric member 1217 can be formulated to minimize any leaching or out-gassing of compositions that may have an undesired effect on the medicament. The elastomeric member 1217 is disposed within the medicament container 1200 to seal the proximal end portion 1212 of the medicament container 1200. In some embodiments, the elastomeric member 1217 can be formulated to maintain its chemical stability, flexibility and/or sealing properties when in contact (either direct or indirect) with a medicament over a long period of time (e.g., for up to six months, one year, two years, five years or longer). The medicament container 1200 can be any container suitable for storing the medicament. In some embodiments, the medicament container 1200 can be, for example, a prefilled syringe having a staked needle at the distal end thereof. In those embodiments in which the medicament container 1200 is a prefilled syringe, the elastomeric member 1217 can be disposed within the medicament container 1200 during the fill process (e.g., before being placed in the housing 1100).

The energy storage member 1400 can be any suitable device or mechanism that, when actuated, produces a force F1 to deliver the medicament contained within the medicament container 1200. Similarly stated, the energy storage member 1400 can be any suitable device or mechanism that produces the force F1 such that the medicament is conveyed from the medicament container 1200 into a body of a patient. More specifically, the energy storage member 1400 produces the force F1 that moves the medicament container 1200 from a first position to a second position in a first direction indicated by the arrow AA in FIG. 2 and/or that moves the plunger 1217 from a first plunger position to a second plunger position as shown by the arrow BB in FIG. 3. The medicament can be conveyed into a body via any suitable mechanism, such as, for example, by injection. By employing the energy storage member 1400 to produce the force F1 rather than relying on a user to manually produce the delivery force, the medicament can be delivered into the body at the desired pressure and/or flow rate, and with the desired delivery characteristics. Moreover, this arrangement reduces the likelihood of partial delivery (e.g., that may result if the user is interrupted or otherwise rendered unable to manually produce the force to complete the delivery).

In some embodiments, the energy storage member 1400 can be a mechanical energy storage member, such as a spring, a device containing compressed gas, a device containing a vapor pressure-based propellant or the like. In other embodiments, the energy storage member 1400 can be an electrical energy storage member, such as a battery, a capacitor, a magnetic energy storage member or the like. In yet other embodiments, the energy storage member 1400 can be a chemical energy storage member, such as a container containing two substances that, when mixed, react to produce energy.

The energy storage member 1400 can be disposed within the housing in any position and/or orientation relative to the medicament container 1200. In some embodiments, for example, the energy storage member 1400 can be positioned within the housing 1100 spaced apart from the medicament container 1200. Moreover, in some embodiments, the energy storage member 1400 can be positioned such that a longitudinal axis of the energy storage member 1400 is offset from the medicament container 1200. In other embodiments, the energy storage member 1400 can substantially surround the medicament container 1200.

As shown in FIG. 1, the energy storage member 1400 is operably coupled to the movable member 1300, the medicament container 1200 and/or the medicament therein such that the force F1 delivers the medicament. In some embodiments, for example, the force F1 can be transmitted to the medicament container 1200 and/or the medicament therein via the movable member 1300. The movable member 1300 can be any suitable member, device, assembly or mechanism configured to move within the housing 1100. As shown in FIGS. 1-4, the movable member 1300 includes a piston portion 1330 configured to transmit the force F1 to the plunger 1217 disposed within the medicament container 1200.

The movable member 1300 includes a first shoulder 1335 and a second shoulder 1337. The first shoulder 1335 of the movable member 1300 is configured to exert the force F1, produced by the energy storage member 1400, on the flange 1214 of the medicament container 1200. In this manner, when the medicament delivery device 1000 is actuated to produce the force F1, movable member 1300 moves the medicament container 1200 from the first position (see FIG. 1, which corresponds to the first configuration of the medicament delivery device 1000) to the second position (see FIG. 2, which corresponds to the second configuration of the medicament delivery device 1000). In some embodiments, the movement of the medicament container 1200 within the housing 1100 results in a needle insertion operation. Although the first shoulder 1335 is shown as directly contacting the flange 1214 when the medicament delivery device 1000 is in the second configuration (FIG. 2), in other embodiments, there can be intervening structure (e.g., an o-ring, a damping member, or the like) disposed between the first shoulder 1335 and the flange 1214.

In some embodiments, the first shoulder 1335 of the movable member 1300 can be configured to maintain a distance between the piston portion 1330 of the movable member 1300 and the plunger 1217 when the medicament delivery device 1000 is in the first configuration (FIG. 1). Similarly stated, in some embodiments, the movable member 1300 and the medicament container 1200 are collectively configured such that the piston portion 1330 is spaced apart from the plunger 1217 when the medicament delivery device 1000 is in its storage configuration and/or when the medicament container 1200 is moving between its first position and its second position. In this manner, any preload or residual force produced by the energy storage member 1400 on the movable member 1300 is not transferred to the plunger 1217. Said another way, the plunger 1217 is isolated from the energy storage member 1400 during the storage configuration. Accordingly, this arrangement reduces and/or eliminates medicament leakage from the medicament container 1200.

Figure 3:
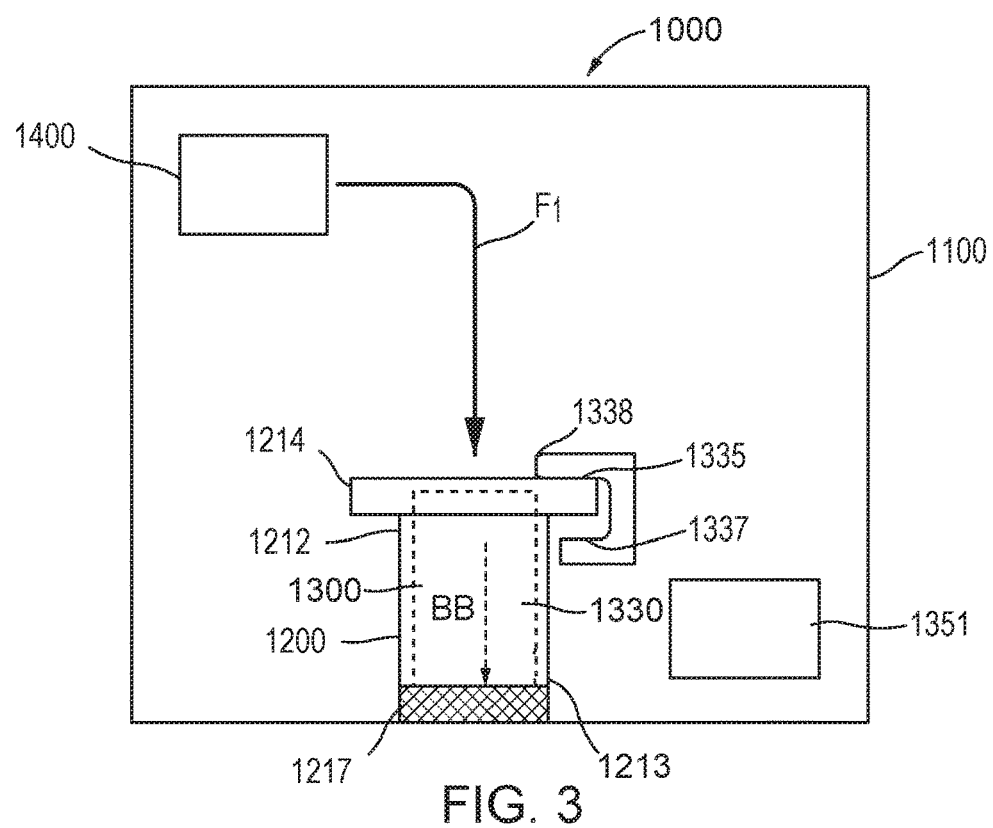

As shown in FIG. 3, the first shoulder 1335 includes a deformable portion 1338 configured to deform when the medicament container 1200 is in the second position such that at least a portion of the force F1 is exerted upon the plunger 1217. In some embodiments, the deformable portion 1338 can be separated from the piston portion 1330 of the movable member 1300. In other embodiments, the deformable portion 1338 is configured to bend, deform, rotate and/or otherwise move relative to the piston portion 1300 such that the piston portion 1330 is placed into contact (directly or indirectly via intervening structure) with the plunger 1217. Similarly stated, in some embodiments, the deformable portion 1338 is configured to bend, deform, rotate and/or otherwise move relative to the piston portion 1300 such that the first shoulder 1335 no longer maintains the distance between the piston portion 1300 and the plunger 1217. In this manner, the piston portion 1330 transmits at least a portion of the force F1 to the plunger 1217, thereby placing the medicament container 1200 into the third configuration (FIG. 3). More specifically, when the deformable portion 1338 deforms, the piston portion 1330 moves within the medicament container 1200 in the direction of the arrow BB (FIG. 3) and moves the plunger 1217 from the proximal end portion 1212 of the medicament container 1200 towards the distal end portion 1213 of the medicament container 1200. This arrangement allows for the delivery of the medicament contained within the medicament container 1200 into a body of a patient.

Figure 2:
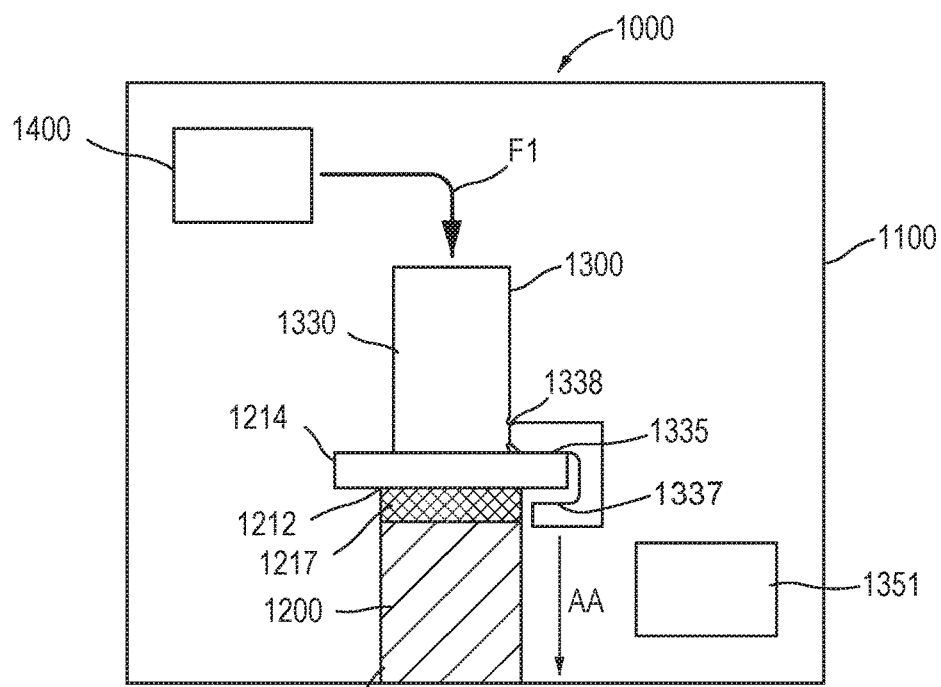

When the medicament is delivered, the retraction member 1351 exerts a retraction force F2 on at least the second shoulder 1337 of the movable member 1300 in a second direction, opposite the first direction. When the retraction force F2 is exerted, the second shoulder 1337 engages a distal surface of the flange 1214 of the medicament container 1200, thereby exerting at least a portion of the retraction force F2 on the flange 1214. Although the second shoulder 1337 is shown as directly contacting the flange 1214 when the medicament delivery device 1000 is in the fourth configuration (FIG. 4), in other embodiments, there can be intervening structure (e.g., an o-ring, a damping member, or the like) disposed between the second shoulder 1337 and the flange 1214. The exertion of the retraction force F2 on the flange 1214 moves the medicament container 1200 from the second position (e.g., the second and third configuration, as shown in FIGS. 2 and 3) in the direction of the arrow CC toward the first position. In this manner, the retraction member 1351 produces the retraction force F2 and moves the distal end portion 1213 of the medicament container 1200 (which can include, for example, a needle) away from the body of the patient and into the housing 1100 of the medicament delivery device 1000.

Figure 4:
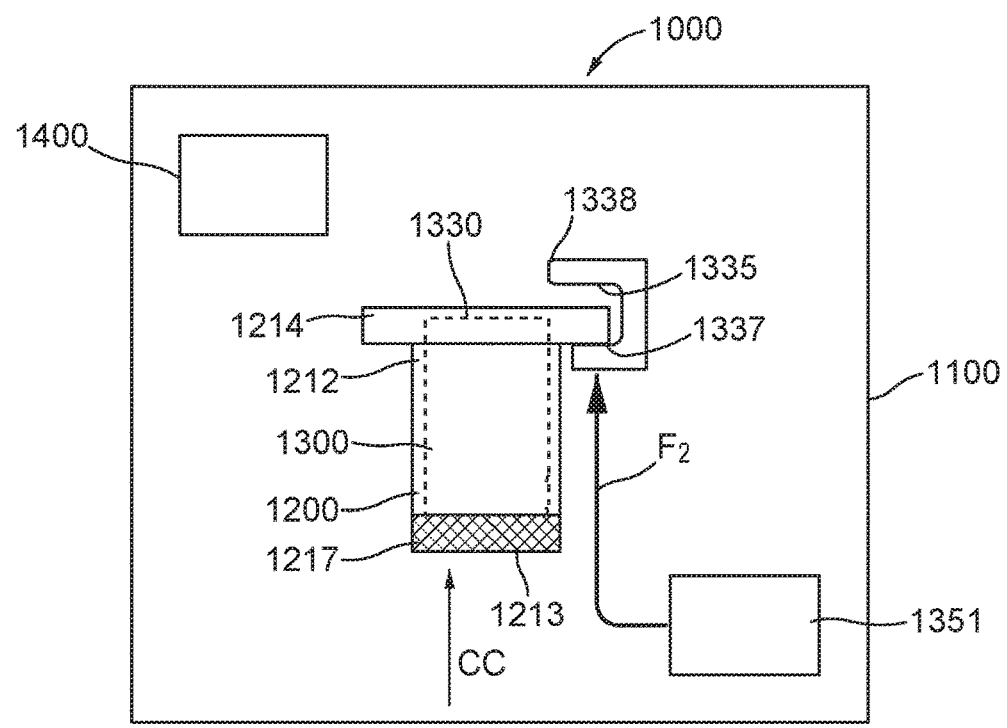

The retraction member 1351 can be any suitable device or mechanism that, when actuated, produces a force F2 to move the medicament container 1200 in the second direction as indicated by the arrow CC in FIG. 4. In some embodiments, the retraction member 1351 can be a mechanical energy storage member, such as a spring, a device containing compressed gas, a device containing a vapor pressure-based propellant or the like. In other embodiments, the retraction member 1351 can be an electrical energy storage member, such as a battery, a capacitor, a magnetic energy storage member or the like. In yet other embodiments, the retraction member 1351 can be a chemical energy storage member, such as a container containing two substances that, when mixed, react to produce energy. Although the retraction member 1351 is shown as being separate and distinct from the energy storage member 1400, in some embodiments, the energy storage member 1400 can be configured to produce the retraction force F2.

The retraction member 1351 can be in any position and/or orientation relative to the medicament container 1200. In some embodiments, for example, the retraction member 1351 can be positioned within the housing 1100 spaced apart from the medicament container 1200. Moreover, in some embodiments, the retraction member 1351 can be positioned such that a longitudinal axis of the retraction member 1351 is offset from the medicament container 1200. In other embodiments, the retraction member 1351 can substantially surround the medicament container 1200. In some embodiments, the retraction member 1351 is coupled to the second shoulder 1337 of the movable member 1300. In other embodiments, the retraction member 1351 is monolithically formed with the movable member 1300.

FIGS. 5-8 are schematic illustrations of a medicament delivery device 2000 according to an embodiment in a first, second, third and fourth configuration, respectively. The medicament delivery device 2000 includes a housing 2100, a medicament container 2200, a first movable member 2300, a second movable member 2345 and an energy storage member 2400. The housing 2100 can be any suitable size, shape, or configuration and can be made of any suitable material. For example, in some embodiments, the housing 2100 is an assembly of multiple parts formed from a plastic material and defines a substantially rectangular shape when assembled.

The medicament container 2200 is disposed within the housing 2100, and contains (i.e., is filled or partially filled with) a medicament. The medicament container 2200 includes a proximal end portion 2212 that has a flange 2214 and a distal end portion 2213 that is coupled to a delivery member, such as a needle, nozzle or the like (not shown in FIGS. 5-8). The medicament container 2200 includes an elastomeric member 2217. The elastomeric member 2217 is formulated to be compatible with the medicament housed within the medicament container 2200. Similarly stated, the elastomeric member 2217 is formulated to minimize any reduction in the efficacy of the medicament that may result from contact (either direct or indirect) between the elastomeric member 2217 and the medicament. For example, in some embodiments, the elastomeric member 2217 can be formulated to minimize any leaching or out-gassing of compositions that may have an undesired effect on the medicament. The elastomeric member 2217 is disposed within the medicament container 2200 to seal the proximal end portion 2212 of the medicament container 2200. In some embodiments, the elastomeric member 2217 can be formulated to maintain its chemical stability, flexibility and/or sealing properties when in contact (either direct or indirect) with a medicament over a long period of time (e.g., for up to six months, one year, two years, five years or longer). The medicament container 2200 can be any container suitable for storing the medicament. In some embodiments, the medicament container 2200 can be, for example, a prefilled syringe having a staked needle at the distal end thereof. In those embodiments in which the medicament container 1200 is a prefilled syringe, the elastomeric member 2217 is disposed within the medicament container 2200 during the fill process (e.g., before the prefilled syringe is placed in the housing 2100).

The energy storage member 2400 can be any suitable device or mechanism that, when actuated, produces a force F3 to deliver the medicament contained within the medicament container 2200. Similarly stated, the energy storage member 2400 can be any suitable device or mechanism that produces the force F3 such that the medicament is conveyed from the medicament container 2200 into a body of a patient. More specifically, the energy storage member 2400 produces the force F3 that moves the medicament container 2200 from a first position to a second position in a first direction indicated by the arrow DD in FIG. 6 and/or that moves the plunger 2217 from a first plunger position to a second plunger position, as shown by the arrow EE in FIG. 7. The medicament can be conveyed into a body via any suitable mechanism, such as, for example, by injection via a needle, nozzle or the like.

In some embodiments, the energy storage member 2400 can be a mechanical energy storage member, such as a spring, a device containing compressed gas, a device containing a vapor pressure-based propellant or the like. In other embodiments, the energy storage member 2400 can be an electrical energy storage member, such as a battery, a capacitor, a magnetic energy storage member or the like. In yet other embodiments, the energy storage member 2400 can be a chemical energy storage member, such as a container containing two substances that, when mixed, react to produce energy.

The energy storage member 2400 can be in any position and/or orientation relative to the medicament container 2200. In some embodiments, for example, the energy storage member 2400 can be positioned within the housing 2100 spaced apart from the medicament container 2200. Moreover, in some embodiments, the energy storage member 2400 can be positioned such that a longitudinal axis of the energy storage member 2400 is offset from the medicament container 2200. In other embodiments, the energy storage member 2400 can substantially surround the medicament container 2200.

Figure 5:
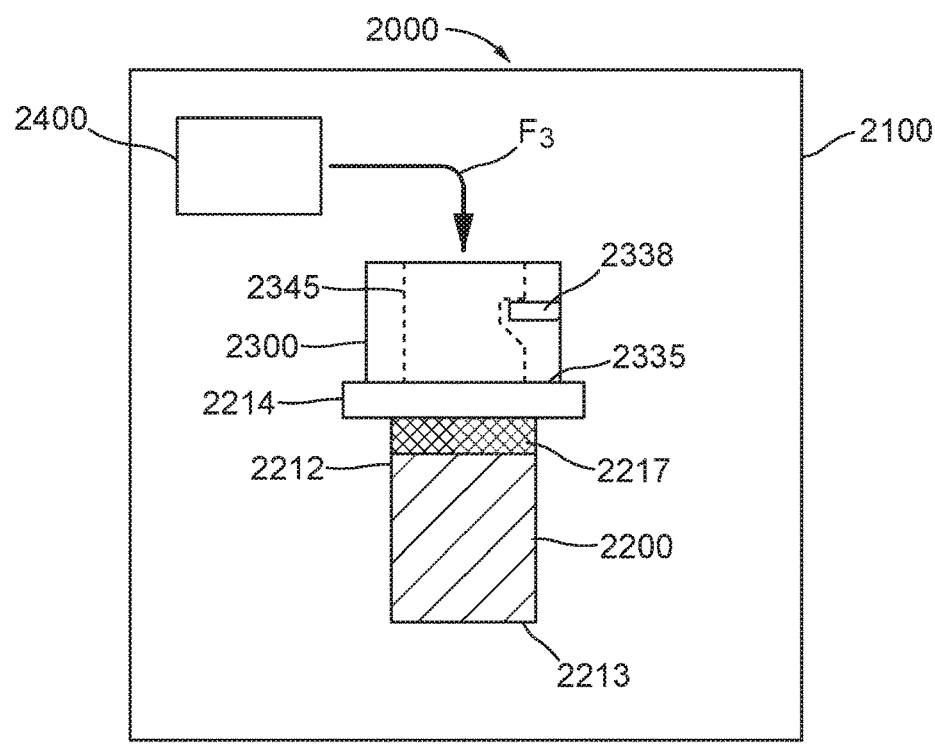
FIGS. 5-8 are schematic illustrations of a medicament delivery device according to an embodiment, in a first, second, third and fourth configuration, respectively.

As shown in FIG. 5, the energy storage member 2400 is operably coupled to the first movable member 2300, the second movable member 2345, the medicament container 2200 and/or the medicament therein such that the force F3 delivers the medicament. In some embodiments, for example, the force F3 can be transmitted to the medicament and/or the medicament container 2200 via the first movable member 2300 and/or the second movable member 2345. As described in more detail herein, the first movable member 2300 and the second movable member 2345 are collectively configured to transmit the force F3 to the plunger 2217 disposed within the medicament container 2200.

The first movable member 2300 includes a first portion 2335 and a second portion 2338. The first portion 2335 of the movable member 2300 is configured to transmit and/or exert at least a portion of the force F3 produced by the energy storage member 2400 on the flange 2214 of the medicament container 2200 to move the medicament container 2200 from the first position (see FIG. 5, which corresponds to the first configuration of the medicament delivery device 2000) to the second position (see FIG. 6, which corresponds to the second configuration of the medicament delivery device 2000). Although the medicament container 2200 is shown as being within the housing 2100 when the medicament container 2200 is in the second position, in some embodiments, the movement of the medicament container 2200 can result in a needle insertion operation in which a needle (not shown in FIGS. 5-8) is extended outside of the housing 2100. The first portion 2335 of the movable member 2300 can be, for example, a first shoulder, protrusion, sleeve or the like. Although the first portion 2335 is shown as directly contacting the flange 2214 when the medicament delivery device 2000 is in the second configuration (FIG. 6), in other embodiments, there can be intervening structure (e.g., an o-ring, a damping member, or the like) disposed between the first portion 2335 and the flange 2214.

Figure 6:
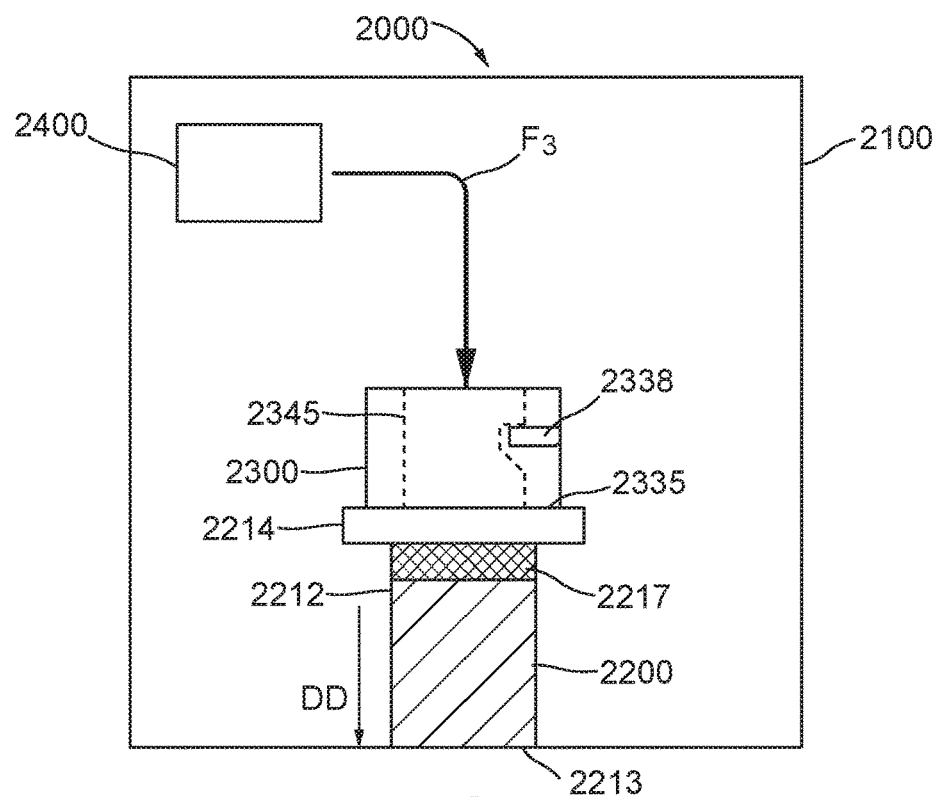

The second portion 2338 of the first movable member 2300 maintains the second movable member 2345 in a first position (FIGS. 5 and 6), relative to the medicament container 2200 and/or the first movable member 2300 when the medicament delivery device 2000 is in the first (i.e., storage) configuration (FIG. 5). In this manner, as shown in FIG. 6, at least a portion of the force F3 can be transferred from the energy storage member 2400 to the first movable member 2300 (and to the flange 2214) via the second movable member 2345. Thus, when the medicament container 2200 is moved from its first position to its second position, the second movable member 2345 moves with the medicament container 2200 and/or the first movable member 2300.

In some embodiments, the second portion 2338 can engage the second movable member 2345 to maintain a distance (e.g., an air gap, space, or void) between the second movable member 2345 and the plunger 2217, when the medicament container 2200 is in the first configuration (FIG. 1) and/or when the medicament container 2200 is moving between its first position and its second position. In this manner, any preload or residual force produced by the energy storage member 1400 on the second movable member 2345 is not transferred to the plunger 2217. Said another way, the plunger 2217 is substantially isolated from the energy storage member 2400 during the storage configuration and/or when the medicament container 2200 is moving.

Accordingly, this arrangement reduces and/or eliminates medicament leakage from the medicament container 2200.

Figure 7:
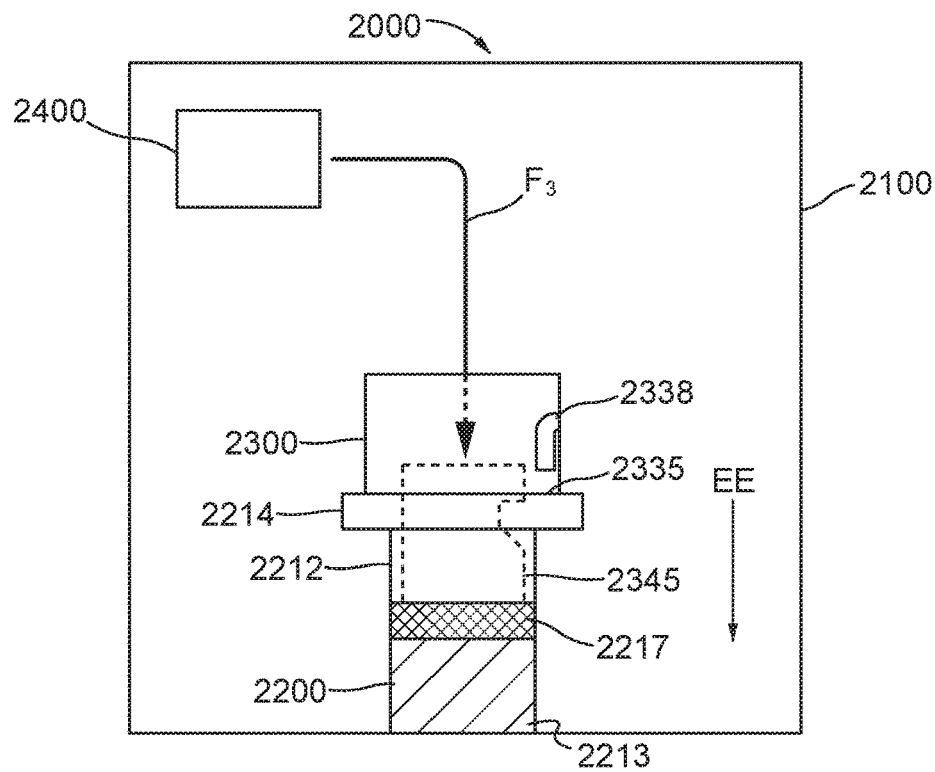
Figure 8:
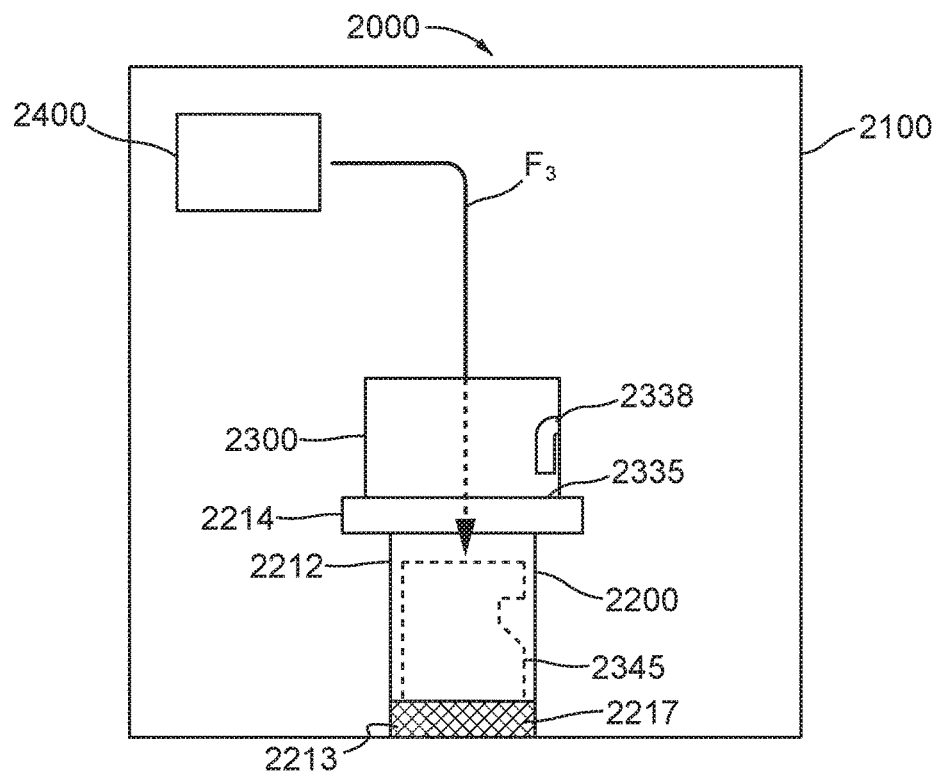

When the medicament container 2200 in the second position (FIGS. 6 and 7), the second portion 2338 of the first movable member 2300 is configured to deform (e.g., by a portion of the force F3), thereby allowing movement of the second movable member 2345 relative to the first movable member 2300 and/or the medicament container 2200. Thus, when the second portion 2338 of the first movable member 2300 deforms, at least a portion of the force F3 is exerted upon the plunger 2217. Similarly stated, when the medicament delivery device 2000 is in the second configuration (FIG. 6), a portion of the force F3 can deform the second portion 2338 of the movable member 2300 (FIG. 7). After the second portion 2338 is deformed, at least a portion of the force F3 is transmitted from the second movable member 2345 to the plunger 2217 to place the medicament container 2200 in the third configuration (FIG. 7). More specifically, when the second portion 2338 deforms, the second movable member 2345 moves in the direction of the arrow EE (FIG. 7) and moves the plunger 2217 from the proximal end portion 2212 of the medicament container 2200 toward the distal end portion 2213 of the medicament container 2200. Similarly stated, when the second portion 2338 deforms, the second movable member 2345 moves relative to the medicament container 2200 to move the plunger 2217 within the medicament container 2200. This arrangement allows for the delivery of the medicament contained within the medicament container 2200 into a body of a patient, as shown in FIG. 8.

In some embodiments, the medicament delivery device 2000 can include a retraction member (not shown in FIGS. 5-8). The retraction member can be any suitable device and/or mechanism configured to move the medicament container 2200 from the second position (e.g., the fourth configuration shown in FIG. 8) toward the first position (e.g. the first configuration shown in FIG. 5). In some embodiments, the retraction member can be substantially similar to the retraction member 1351 described with respect to FIGS. 1-4. In such embodiments, the retraction member can be configured to transmit a force to the flange 2214 of the medicament container 2200 and move the medicament container 2200 in a second direction opposite the first direction indicated by the arrow DD in FIG. 6.

Figure 9:
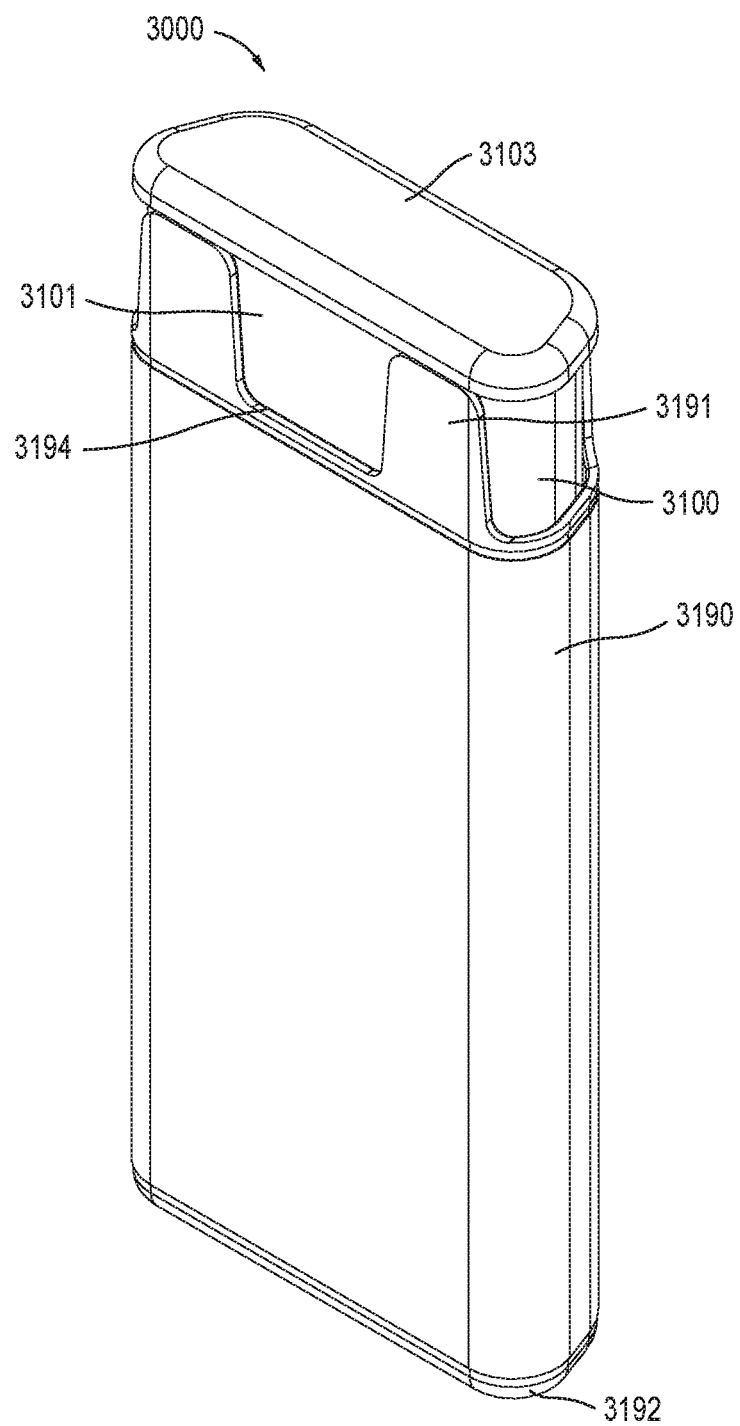
FIGS. 9 and 10 are perspective views of a medical injector according to an embodiment, in a first configuration.
Figure 10:
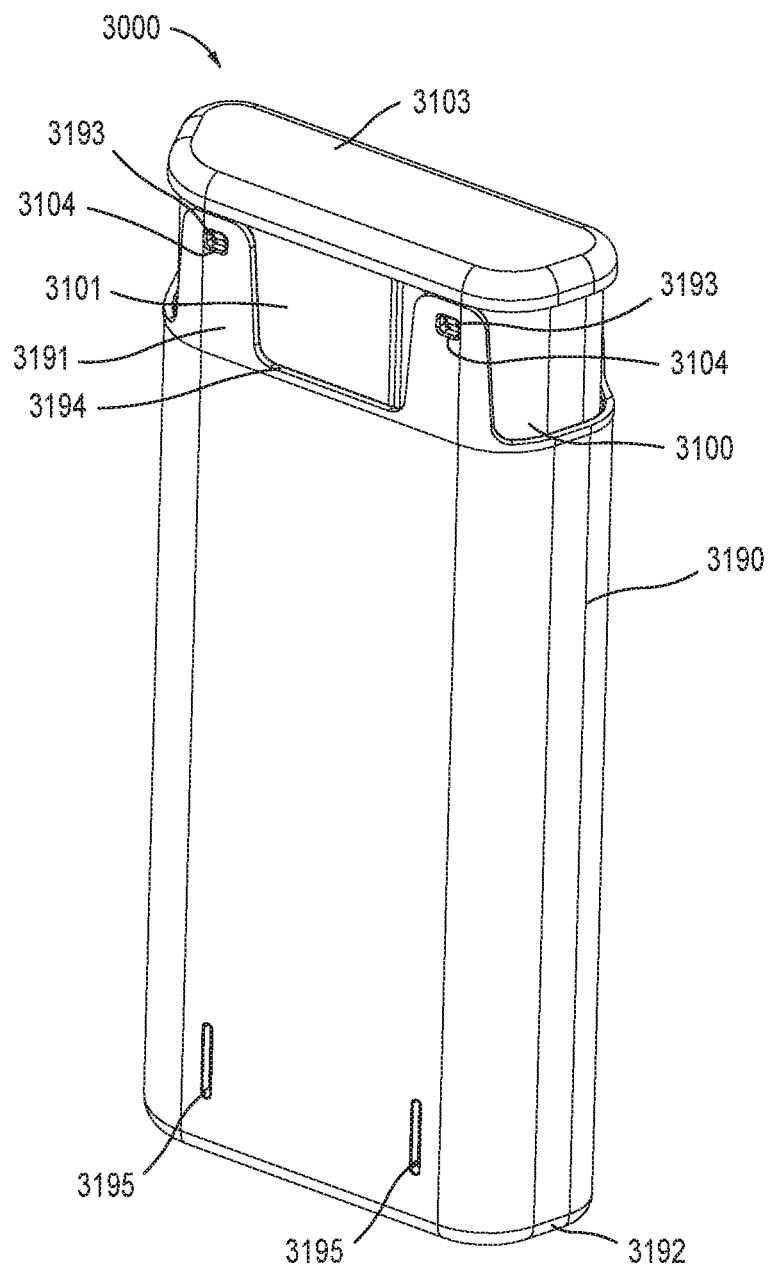
Figure 11:
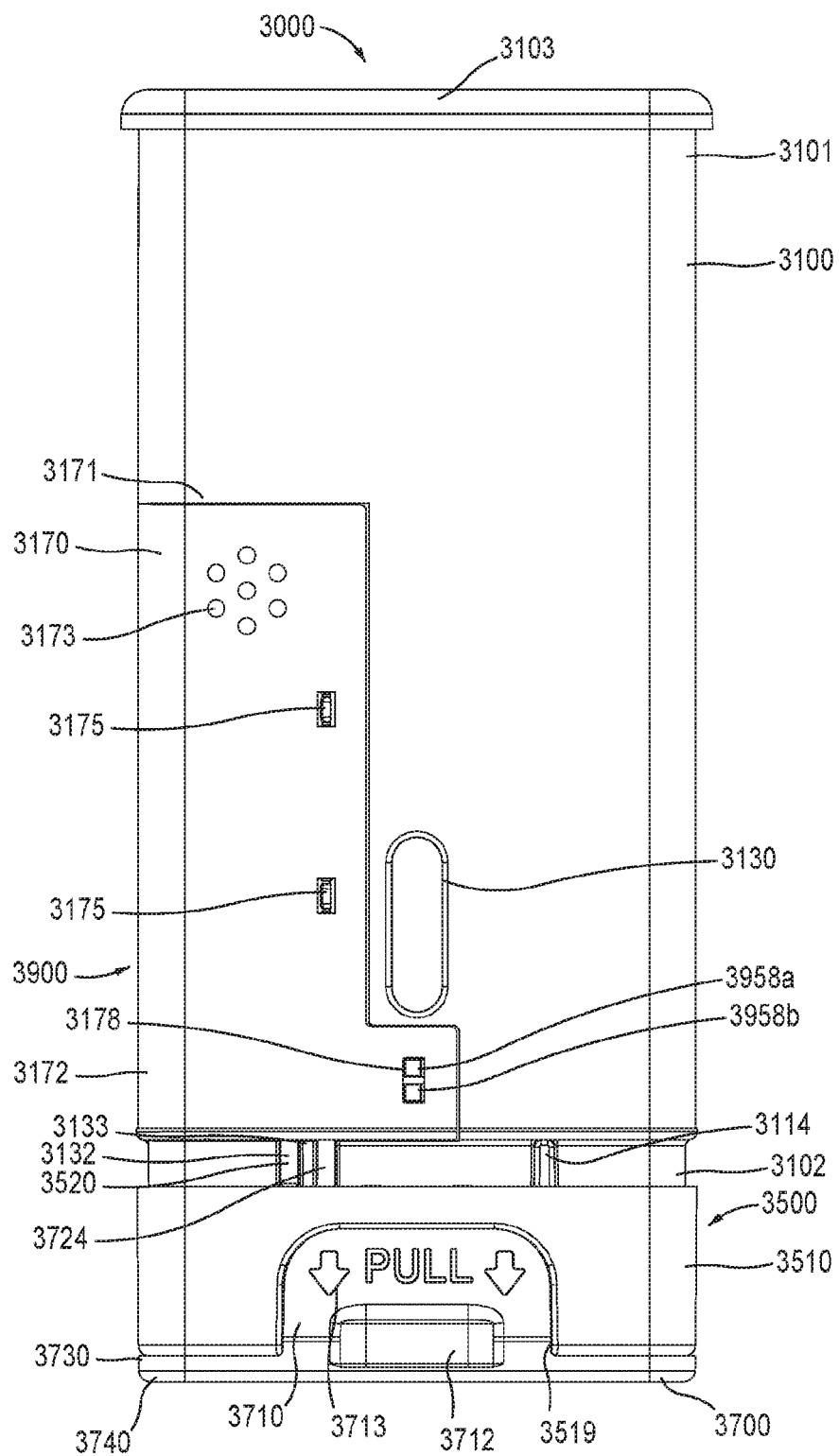
FIG. 11 is a front view of the medical injector illustrated in FIG. 9 with a cover removed.

In some embodiments, the medicament delivery device can be a medical injector configured to automatically deliver a medicament contained within a medicament container, such as, for example a prefilled syringe. For example, FIGS. 9-55 show a medical injector 3000, according to an embodiment. FIGS. 9-10 are perspective views of the medical injector 3000 in a first configuration (i.e., prior to use). The medical injector 3000 includes a housing 3100 (see e.g., FIGS. 11-17), a system actuation assembly 3500 (see e.g., FIGS. 18-21), a medicament container 3200 containing a medicament 3220 (see e.g., FIG. 22), a medicament delivery mechanism 3300 (see e.g., FIG. 26-28), an electronic circuit system 3900 (see e.g., FIGS. 29-39), a cover 3190 (see e.g., FIGS. 40-41), and a safety lock 3700 (see e.g., FIGS. 42-46). A discussion of the components of the medical injector 3000 will be followed by a discussion of the operation of the medical injector 3000.

As shown in FIGS. 11-17, the housing 3100 has a proximal end portion 3101 and a distal end portion 3102. The housing 3100 defines a first status indicator aperture 3130 and a second status indicator aperture 3160. The first status indicator aperture 3130 defined by the housing 3100 is located on a first side of the housing 3100, and the second status indicator aperture 3160 of the housing 3100 is located on a second side of the housing 3100. The status indicator apertures 3130, 3160 can allow a patient to monitor the status and/or contents of the medicament container 3200 contained within the housing 3100. For example, by visually inspecting the status indicator apertures 3130, 3160, a patient can determine whether the medicament container 3200 contains a medicament 3220 and/or whether the medicament 3220 has been dispensed.

Figure 15:
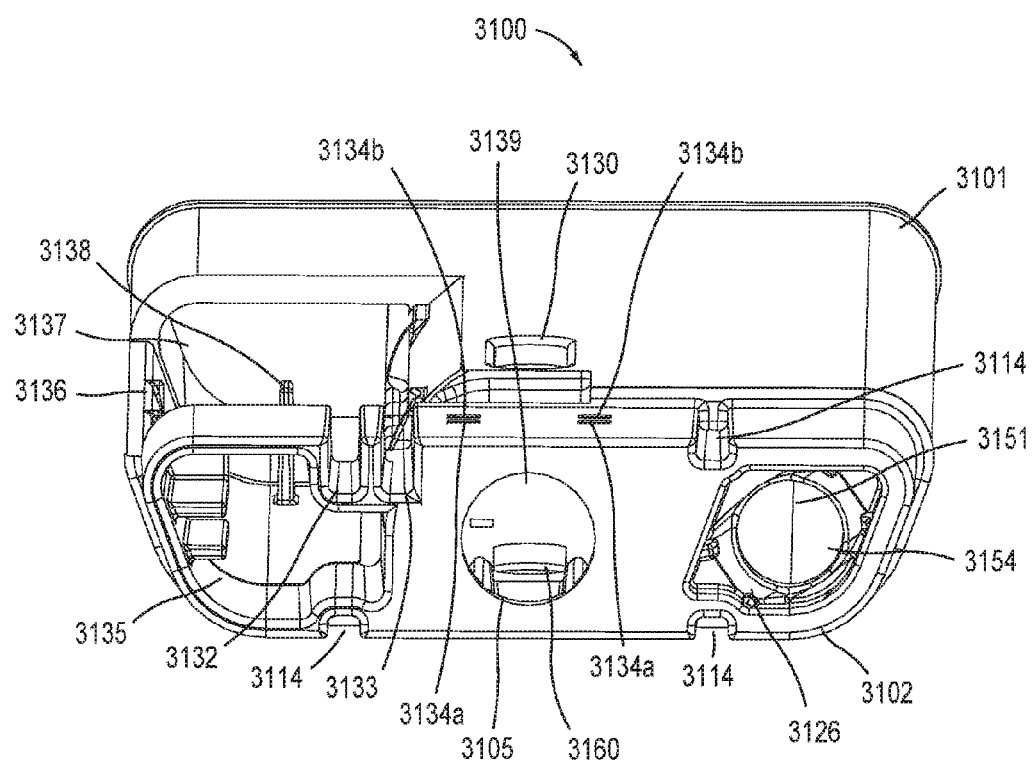
FIG. 15 is a bottom perspective view of a housing of the medical injector illustrated in FIG. 9.
Figure 16:
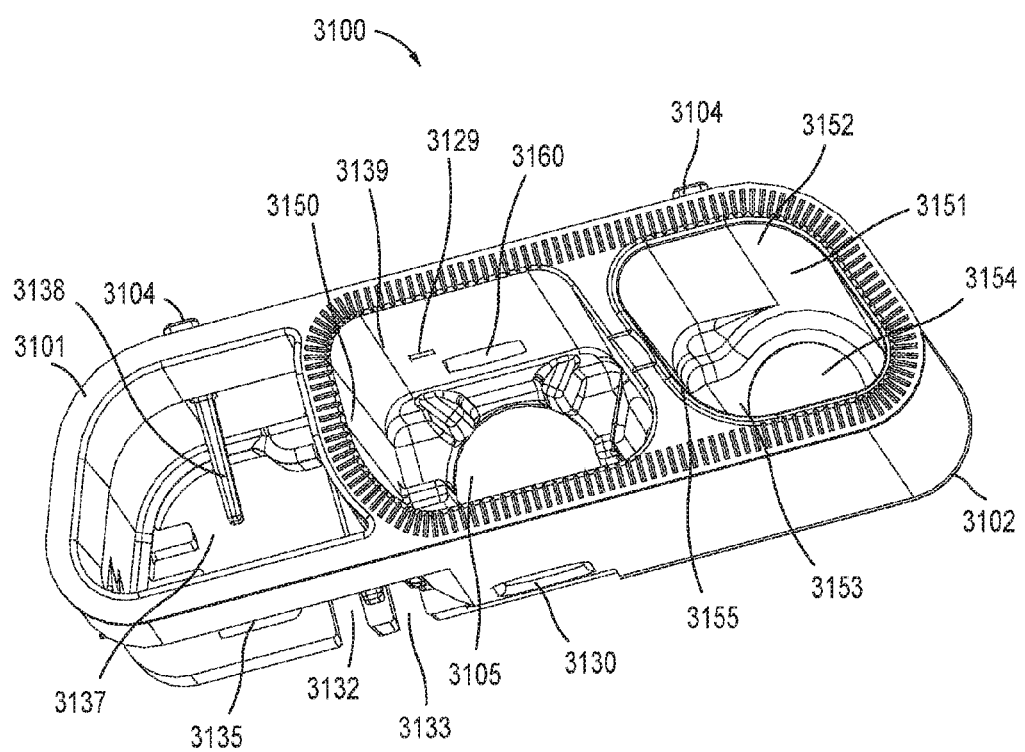
FIG. 16 is a top perspective view of a housing of the medical injector illustrated in FIG. 9.
Figure 18:
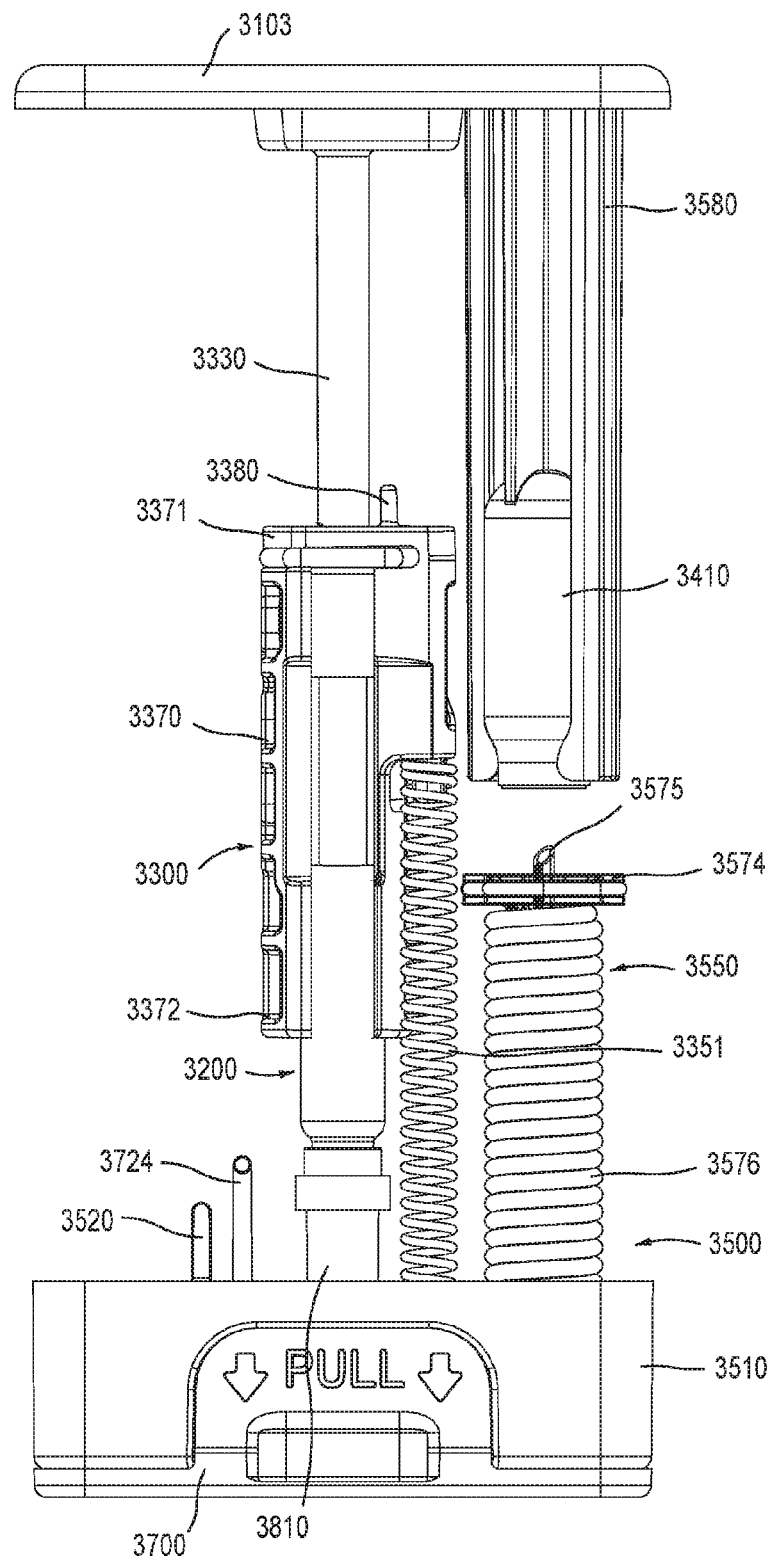
FIGS. 18 and 19 are front views of a medicament delivery mechanism of the medical injector illustrated in FIG. 9.
Figure 19:
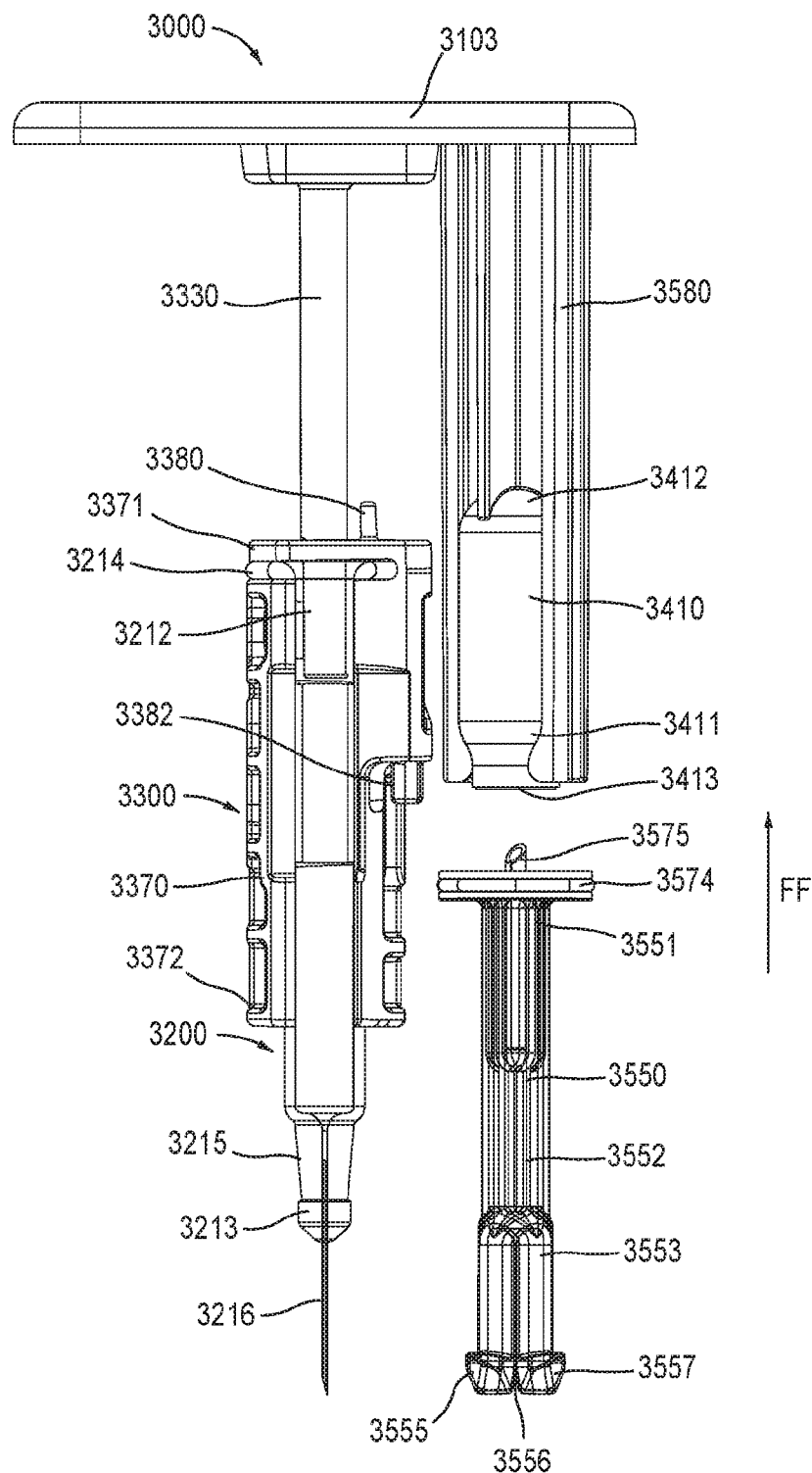
Figure 20:
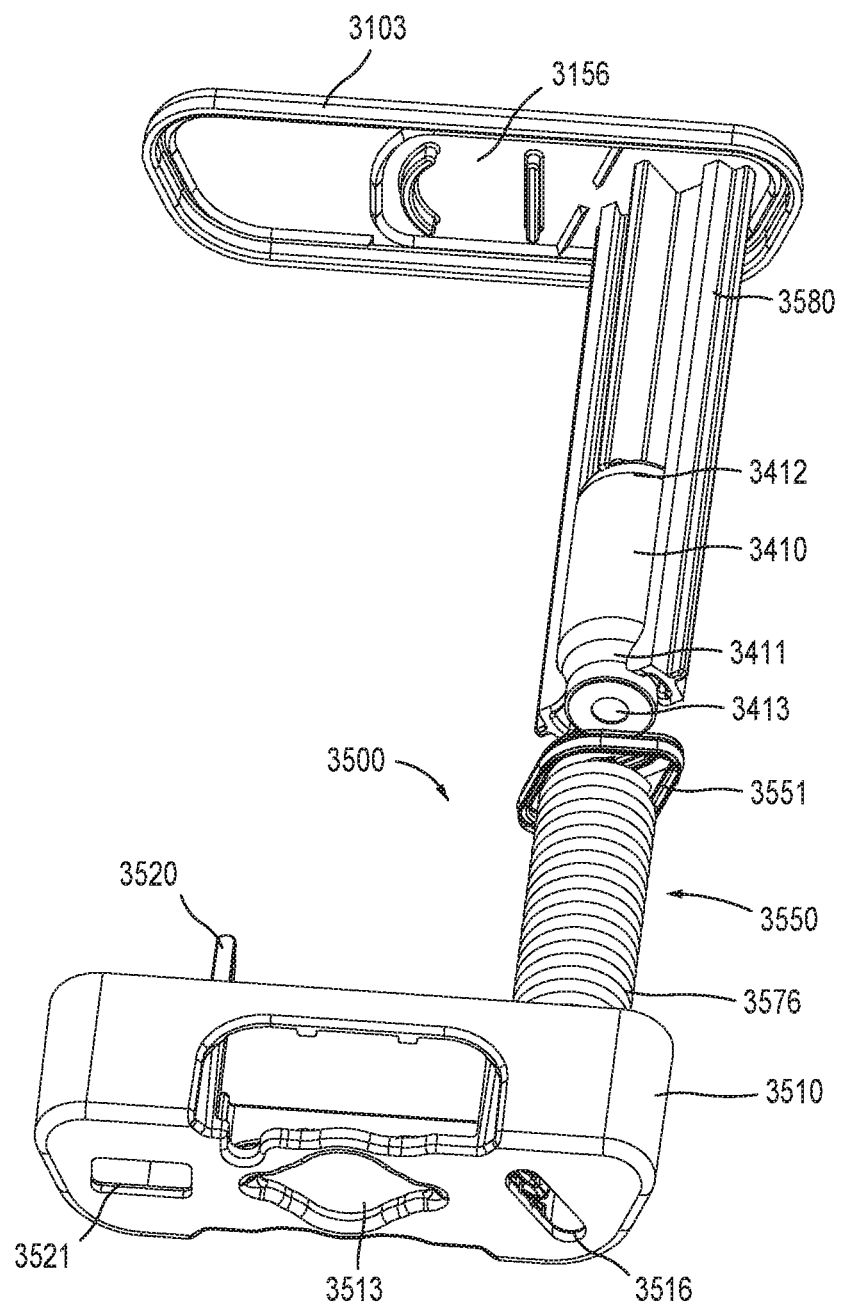
FIG. 20 is a perspective view of a portion of the medical injector illustrated in FIG. 9.

As shown in FIGS. 15 and 16, the housing 3100 defines a gas cavity 3151, a medicament cavity 3139 and an electronic circuit system cavity 3137. The gas cavity 3151 has a proximal end portion 3152 and a distal end portion 3153. The gas cavity 3151 is configured to receive the gas container 3410 and a portion of the system actuator assembly 3500 (e.g., a release member 3550 and the spring 3576, as shown in FIGS. 18 and 19) as described in further detail herein. The proximal end portion 3152 of the gas cavity 3151 is configured to receive the gas container retention member 3580 of a proximal cap 3103 of the housing 3100, as described in further detail herein. The gas cavity 3151 is in fluid communication with the medicament cavity 3139 via a gas passageway 3156 (see e.g., FIG. 17), as described in further detail herein, and the gas cavity 3151 is in fluid communication with a region outside the housing 3100 via a release member aperture 3154 (see e.g., FIGS. 15 and 16).

The medicament cavity 3139 is configured to receive the medicament container 3200 and at least a portion of the medicament delivery mechanism 3300. In particular, as described below, the medicament delivery mechanism 3300 includes a carrier 3370 and piston member 3330 movably disposed in the medicament cavity 3139. The medicament cavity 3139 is in fluid communication with a region outside the housing 3100 via a needle aperture 3105 (see e.g., FIGS. 15 and 16).

The electronic circuit system cavity 3137 is configured to receive the electronic circuit system 3900. The housing 3100 has protrusions 3136 (see e.g., FIG. 14) configured to stabilize the electronic circuit system 3900 when the electronic circuit system 3900 is disposed within the electronic circuit system cavity 3137. The outer surface of the housing 3100 is configured to receive a set of connection protrusions 3174A and connection protrusion 3174B of the electronic circuit system 3900 (see e.g., FIG. 32). In this manner, the electronic circuit system 3900 can be coupled to the housing 3100 within the electronic circuit system cavity 3137. In other embodiments, the electronic circuit system 3900 can be coupled within the electronic circuit system cavity 3137 by other suitable means such as an adhesive, a clip, a label and/or the like.

The electronic circuit system cavity 3137 is fluidically and/or physically isolated from the gas cavity 3151 and/or the medicament cavity 3139 by a sidewall 3150. The sidewall 3150 can be any suitable structure to isolate the electronic circuit system cavity 3137 within the housing 3100 from the gas cavity 3151 and/or the medicament cavity 3139 within the housing 3100. Similarly, the gas cavity 3151 and the medicament cavity 3139 are separated by a sidewall 3155 (see FIG. 16). In some embodiments, sidewall 3155 can be similar to the sidewall 3150, which isolates the gas cavity 3151 and the medicament cavity 3139 from the electronic circuit system cavity 3137. In other embodiments, the gas cavity 3151 can be fluidically and/or physically isolated from the medicament cavity 3139 by any suitable means. In yet other embodiments, the medicament cavity 3139 need not be fluidically and/or physically isolated from the electronic circuit system cavity 3137 and/or the gas cavity 3151.

Figure 12:
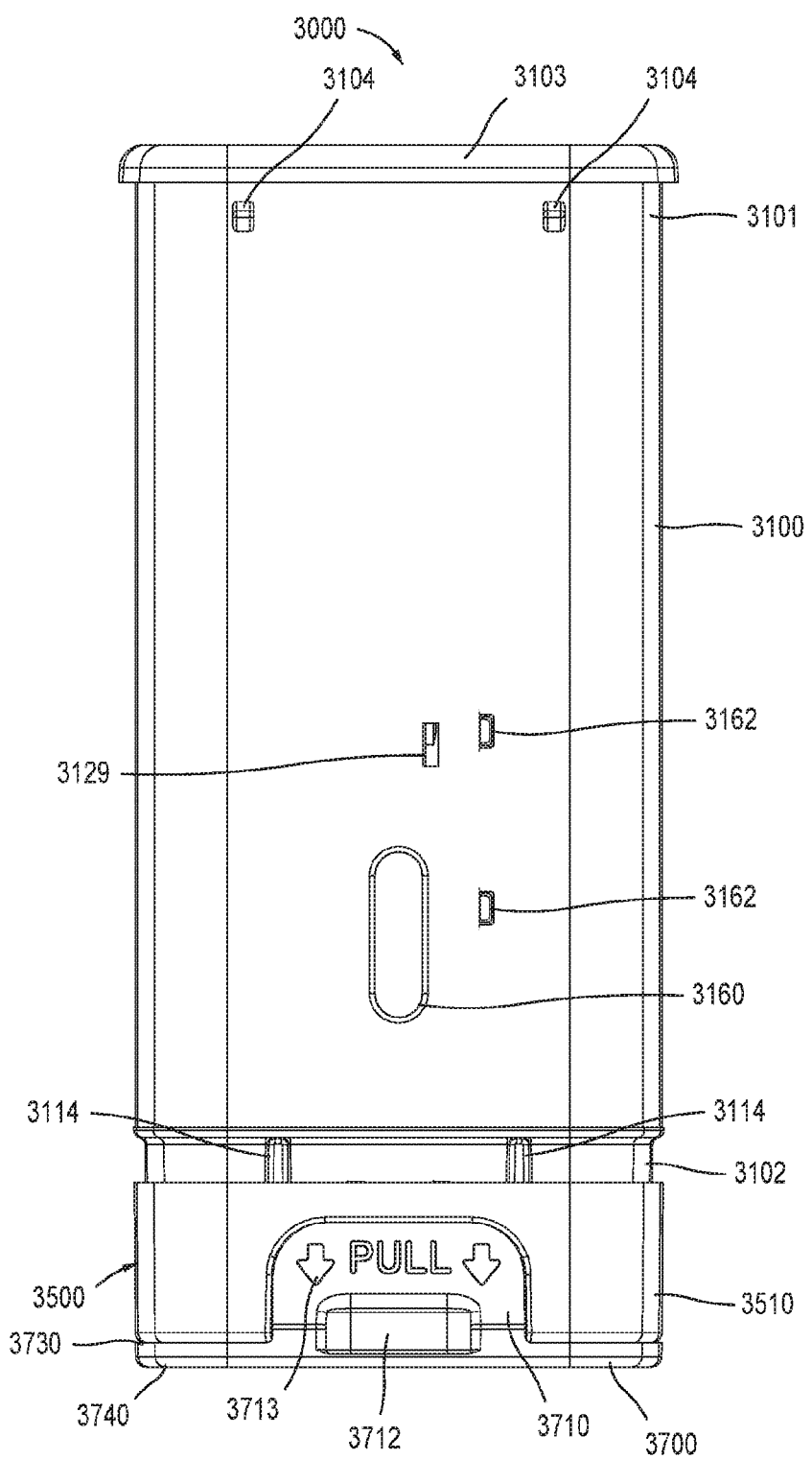
FIG. 12 is a back view of the medical injector illustrated in FIG. 9 with the cover removed.

The proximal end portion 3101 of the housing 3100 includes a proximal cap 3103 (see e.g., FIG. 17), a speaker protrusion 3138 (see e.g., FIGS. 14-16), and cover retention protrusions 3104 (see e.g., FIGS. 10 and 12). The speaker protrusion 3138 is configured to maintain a position of an audio output device 3956 of the electronic circuit system 3900 relative to the housing 3100 when the electronic circuit system 3900 is attached to the housing 3100, as described herein. The cover retention protrusions 3104 are configured to be received within corresponding openings 3193 defined by the cover 3190 (see e.g., FIG. 10) to retain the cover 3190 about the housing 3100. In this manner, as described in more detail herein, the cover 3190 is removably coupled to and disposed about at least a portion of the housing 3100.

Figure 17:
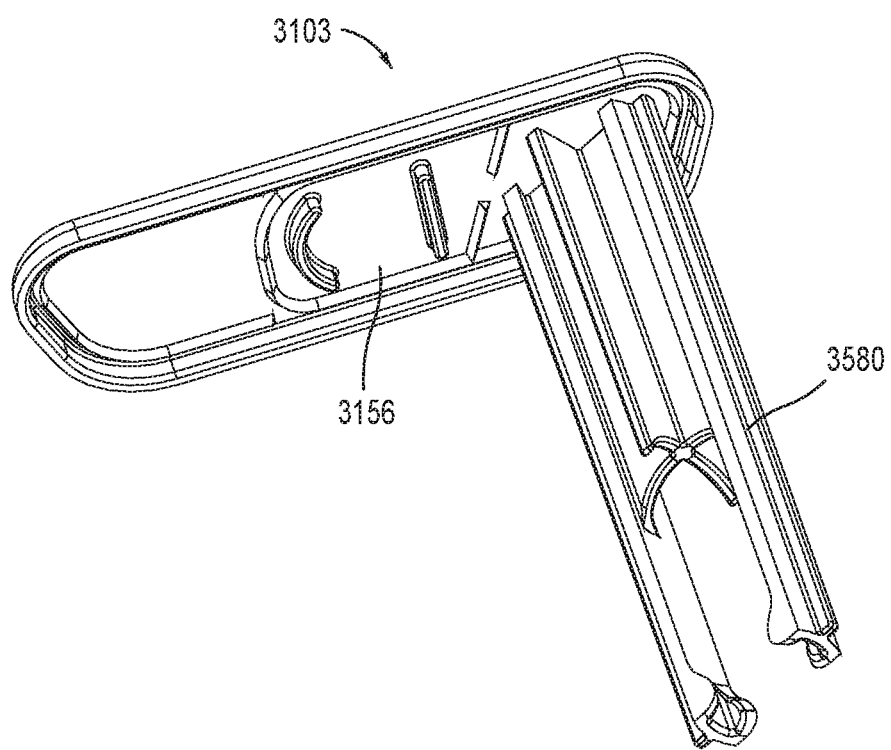
FIG. 17 is a perspective view of a proximal cap of the medical injector illustrated in FIG. 9.

As shown in FIG. 17, the proximal cap 3103 includes a gas container retention member 3580 and defines a gas passageway 3156. The gas container retention member 3580 is configured to receive and/or retain a gas container 3410 that contains a pressurized gas, as shown in FIG. 18. When the medical injector 3000 is actuated, pressurized gas from the gas container 3140 is conveyed from the gas cavity 3151 to the medicament cavity 3139 via the gas passageway 3156, as further described herein. Said another way, the gas passageway 3156 places the gas cavity 3151 in fluid communication with the medicament cavity 3139.

Figure 13:
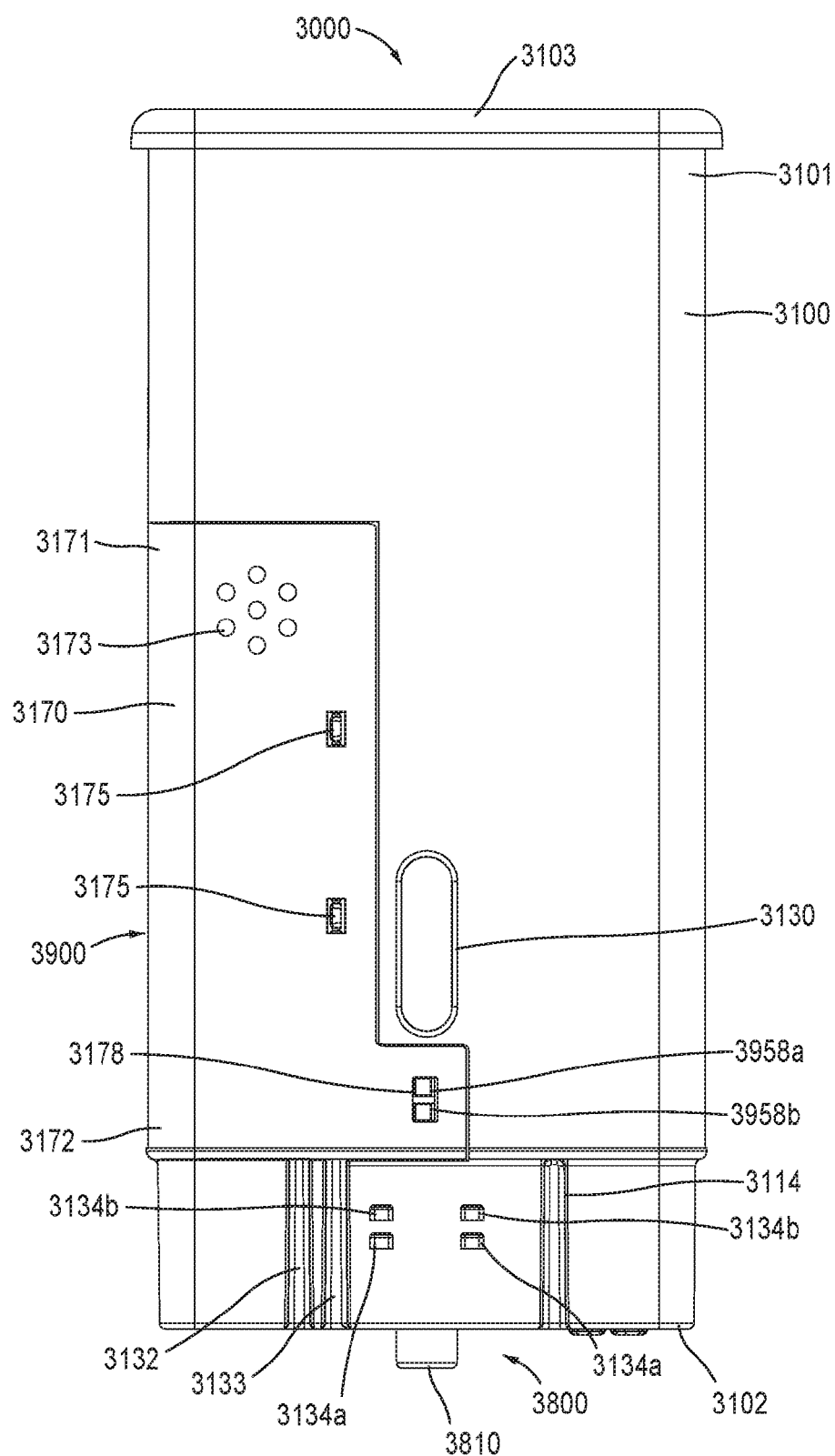
FIG. 13 is a front view of a portion of the medical injector illustrated in FIG. 9.
Figure 14:
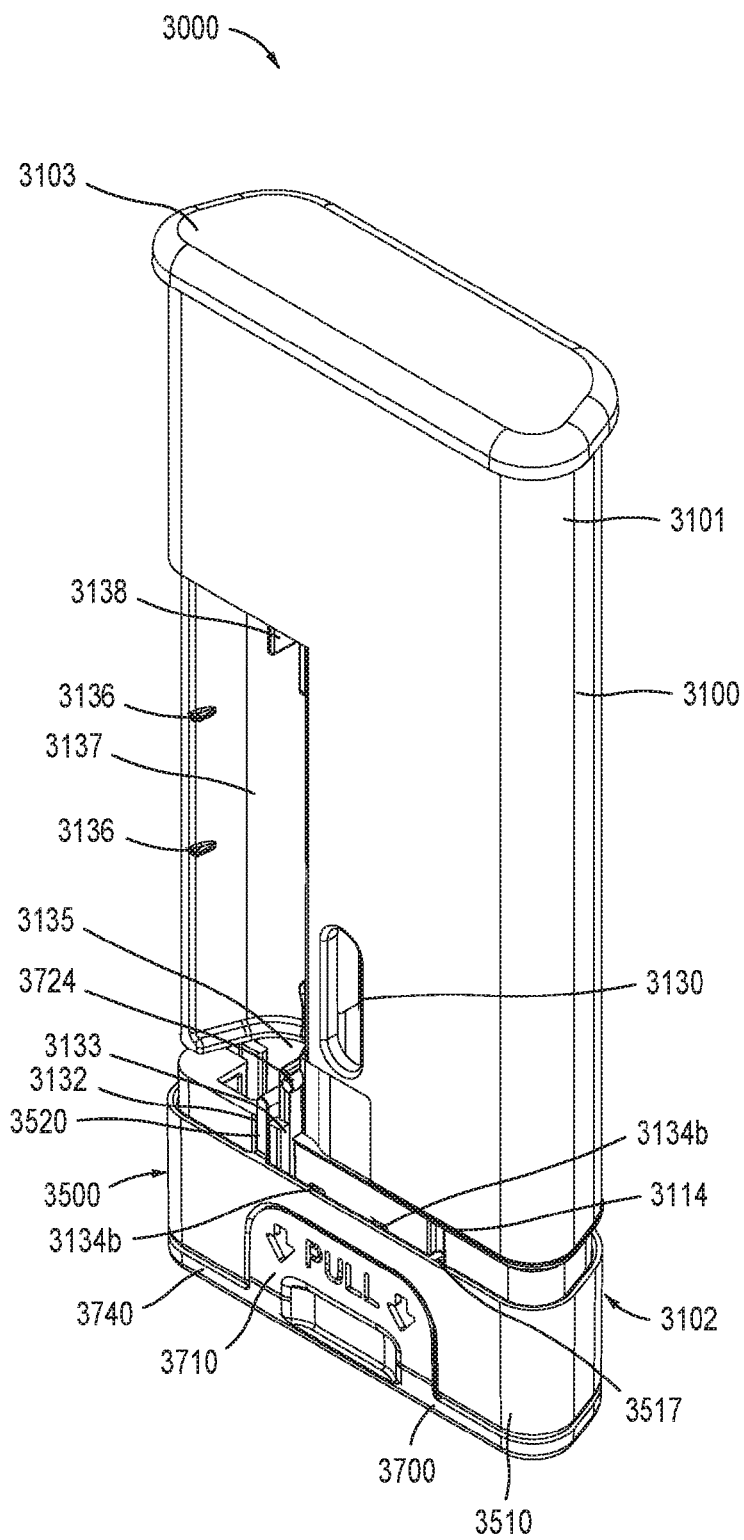
FIG. 14 is a perspective view of a portion of the medical injector illustrated in FIG. 9.

As shown in FIGS. 13 and 15, the distal end portion 3102 of the housing 3100 defines a battery isolation protrusion aperture 3135, a needle aperture 3105, a safety lock actuator groove 3133, a release member contact surface 3126, a release member aperture 3154, a base protrusion groove 3132, base retention recesses 3134A, 3134B, and base rail grooves 3114. The battery isolation protrusion aperture 3135 receives the battery isolation protrusion 3197 of the cover 3190 (see e.g., FIG. 41) when the cover 3190 is disposed about at least a portion of the housing 3100. The needle aperture 3105 is the opening through which the needle 3216 is disposed (see e.g., FIGS. 19, 51 and 52) when the medical injector 3000 is actuated, as described in further detail herein.

Figure 21:
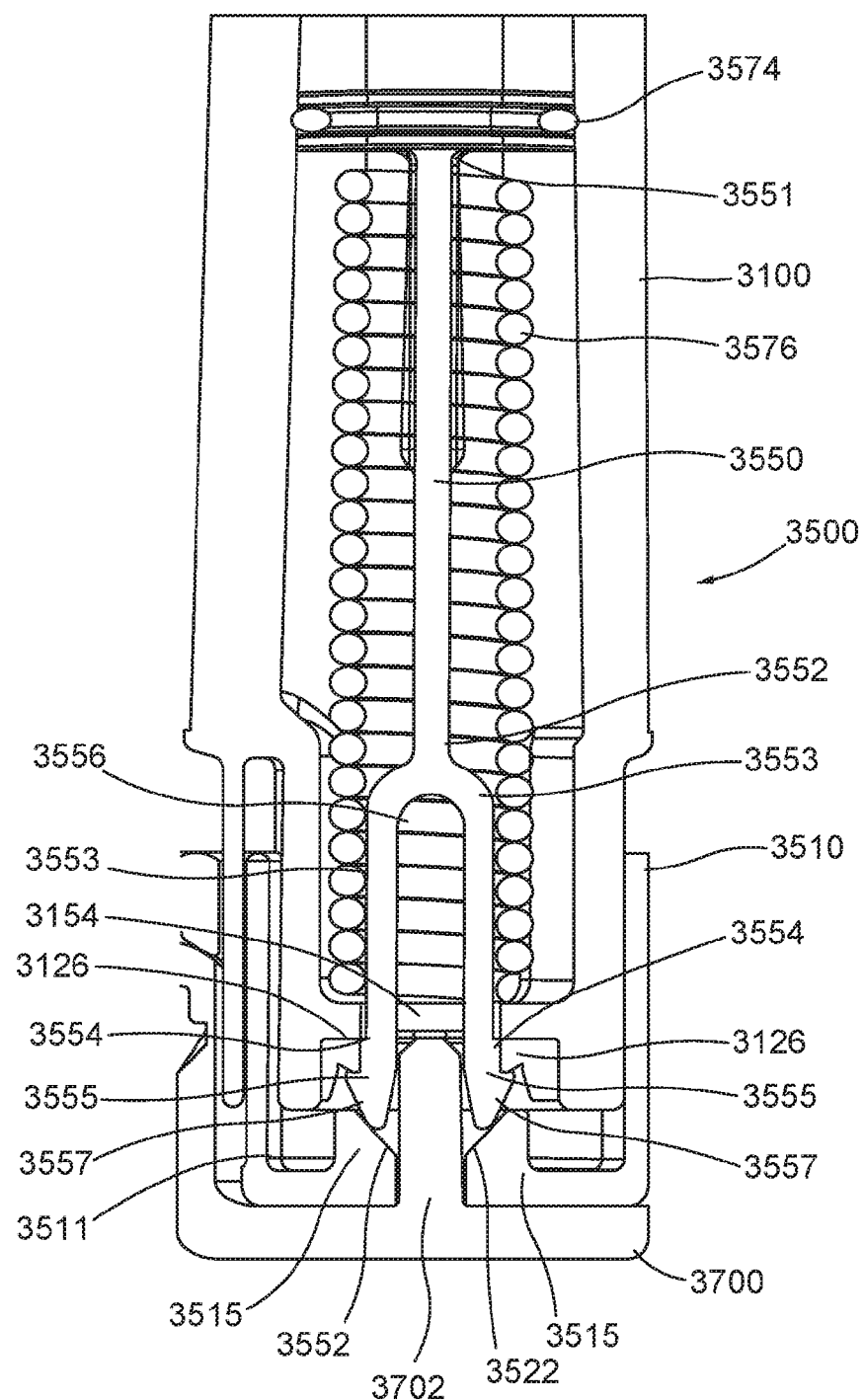
FIG. 21 is an enlarged cross-sectional view of a portion of the medical injector illustrated in FIG. 9.
Figure 43:
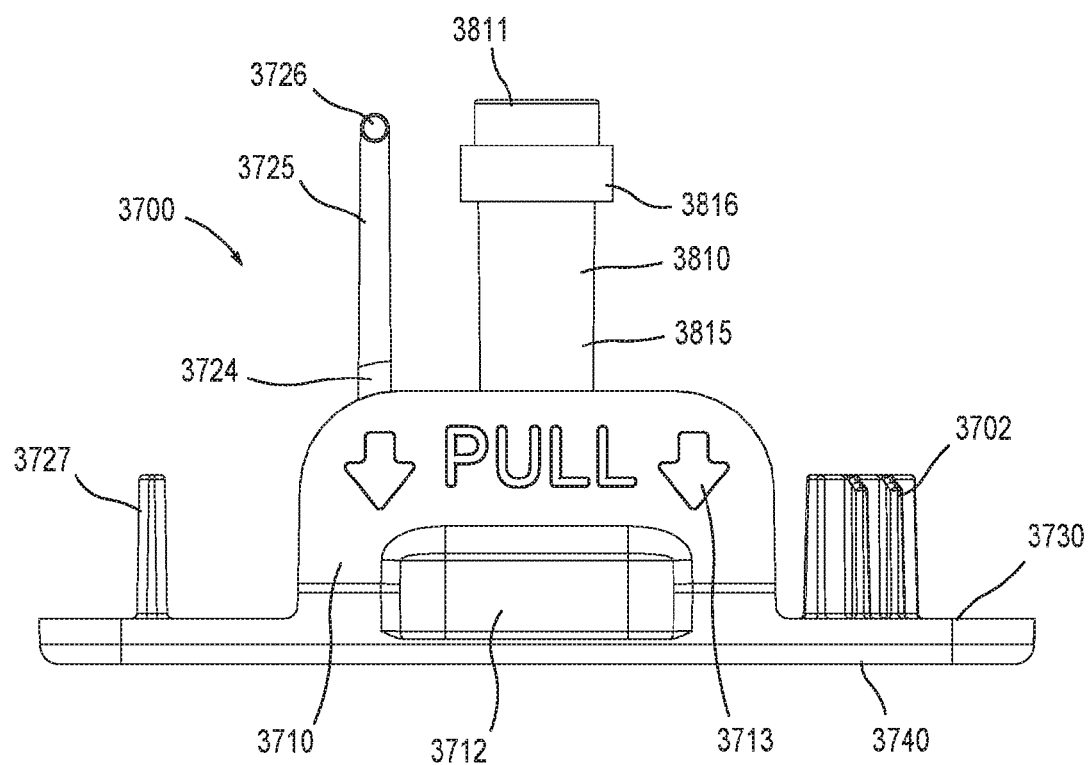
FIG. 43 is a front view of the safety lock of the medical injector illustrated in FIG. 42.
Figure 44:
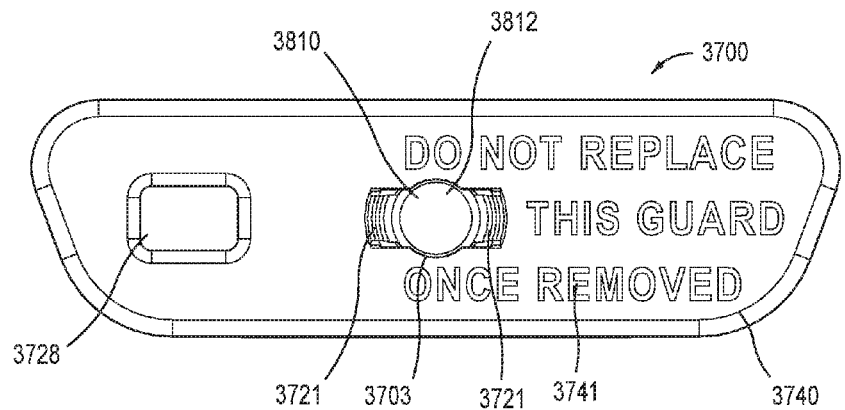
FIG. 44 is a bottom view of the safety lock of the medical injector illustrated in FIG. 42.

The safety lock actuator groove 3133 receives an actuator 3724 of the safety lock 3700 (see e.g., FIG. 43). As described in more detail herein, the actuator 3724 is configured to engage and/or activate the electronic circuit system 3900 when the safety lock 3700 is moved with respect to the housing 3100. The release member contact surface 3126 defines the release member aperture 3154. As shown in FIG. 21 and described in more detail below, the release member aperture 3154 receives a distal end portion 3552 of a release member 3550. As described in more detail below, a safety lock protrusion 3702 (see e.g., FIG. 42) is disposed within an opening 3556 between extensions 3553 of the release member 3550 (see e.g., FIGS. 19 and 21) such that an engagement surface 3554 of the extensions 3553 is engaged with the release member contact surface 3126 to prevent activation of the medical injector 3000. The safety lock 3700, its components and functions are described in more detail below.

The distal base retention recesses 3134A are configured to receive the base connection knobs 3518 of the actuator 3510 (also referred to herein as "base 3510," see e.g., FIG. 47) when the base 3510 is in a first position relative to the housing 3100. The proximal base retention recesses 3134B are configured to receive the base connection knobs 3518 of the base 3510 when the base 3510 is in a second position relative to the housing 3100. The base retention recesses 3134A, 3134B have a tapered proximal sidewall and a non-tapered distal sidewall. This allows the base retention recesses 3134A, 3134B to receive the base connection knobs 3518 such that the base 3510 can move proximally relative to the housing 3100, but cannot move distally relative to the housing 3100. Said another way, the distal base retention recesses 3134A are configured to prevent the base 3510 from moving distally when the base 3510 is in a first position and the proximal base retention recesses 3134B are configured to prevent the base 3510 from moving distally when the base 3510 is in a second position. Similarly stated, the proximal base retention recesses 3134B and the base connection knobs 3518 cooperatively to limit movement of the base to prevent undesirable movement of the base 3510 after the medical injector 3000 is actuated. The proximal base retention recesses 3134B and the base connection knobs 3518 also provide a visual cue to the user that the medical injector 3000 has been used.

The base actuator groove 3132 receives a protrusion 3520 of the base 3510. As described in more detail herein, the protrusion 3520 of the base 3510 is configured to engage the electronic circuit system 3900 when the base 3510 is moved with respect to the housing 3100. The base rail grooves 3114 receive the guide members 3517 of the base 3510 (see FIG. 47). The guide members 3517 of the base 3510 and the base rail grooves 3114 of the housing 3100 engage each other in a way that allows the guide members 3517 of the base 3510 to slide in a proximal and/or distal direction within the base rail grooves 3114 while limiting lateral movement of the guide members 3517. This arrangement allows the base 3510 to move in a proximal and/or distal direction with respect to the housing 3100 but prevents the base 3510 from moving in a lateral direction with respect to the housing 3100.

Figure 25:
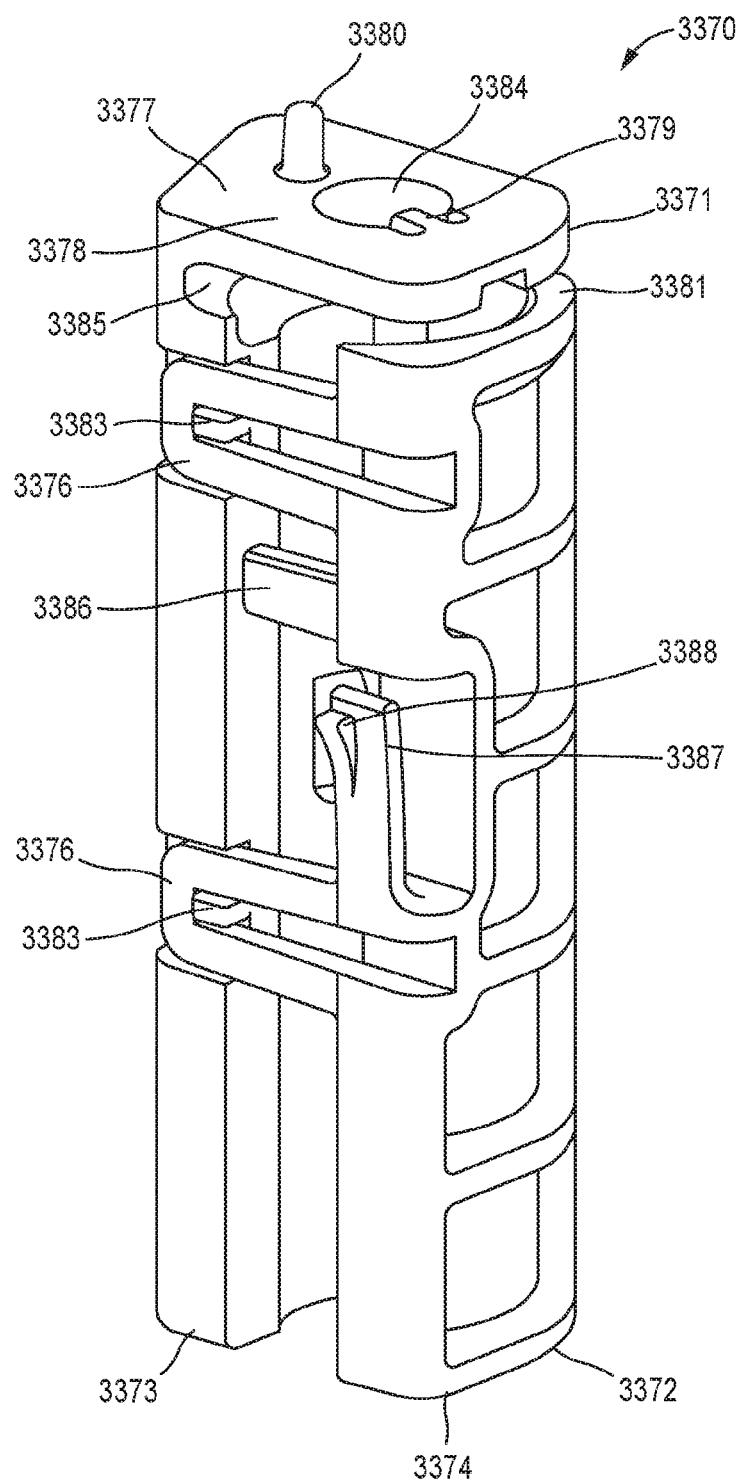
FIG. 25 is a perspective view of the carrier included in the medical injector illustrated in FIG. 9 in a second configuration.
Figure 26:
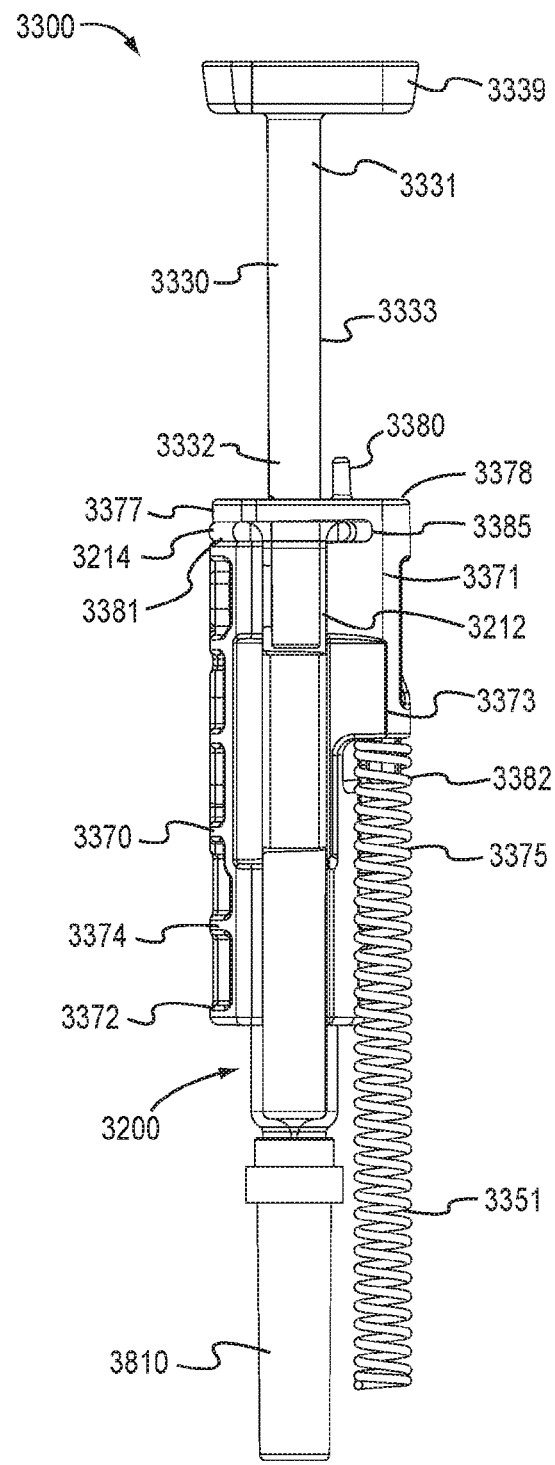
FIG. 26 is a perspective view of a portion of the medical injector illustrated in FIG. 9.
Figure 27:
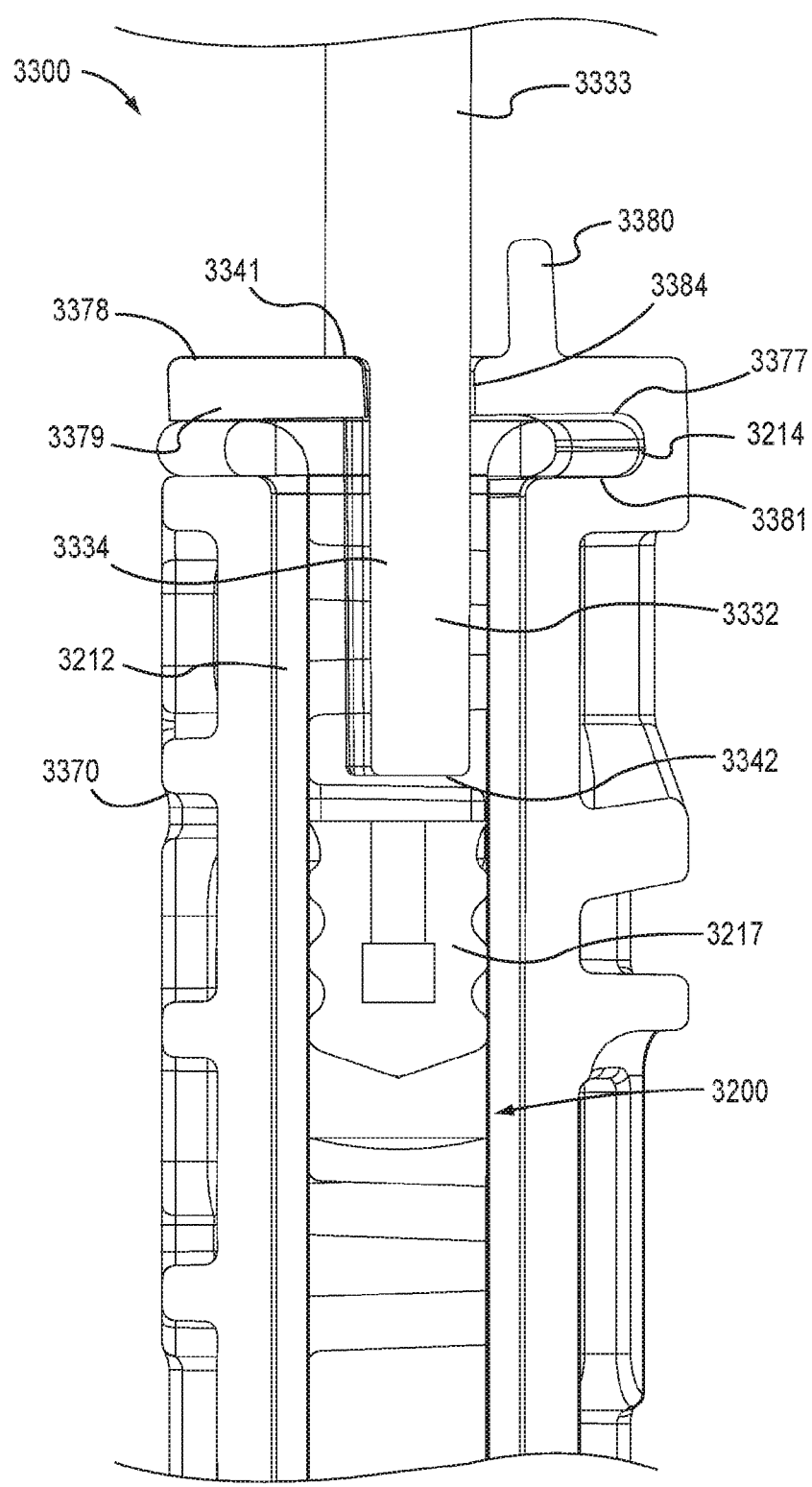
FIG. 27 is an enlarged front cross-sectional view of the portion of the medical injector illustrated in FIG. 26.
Figure 28:
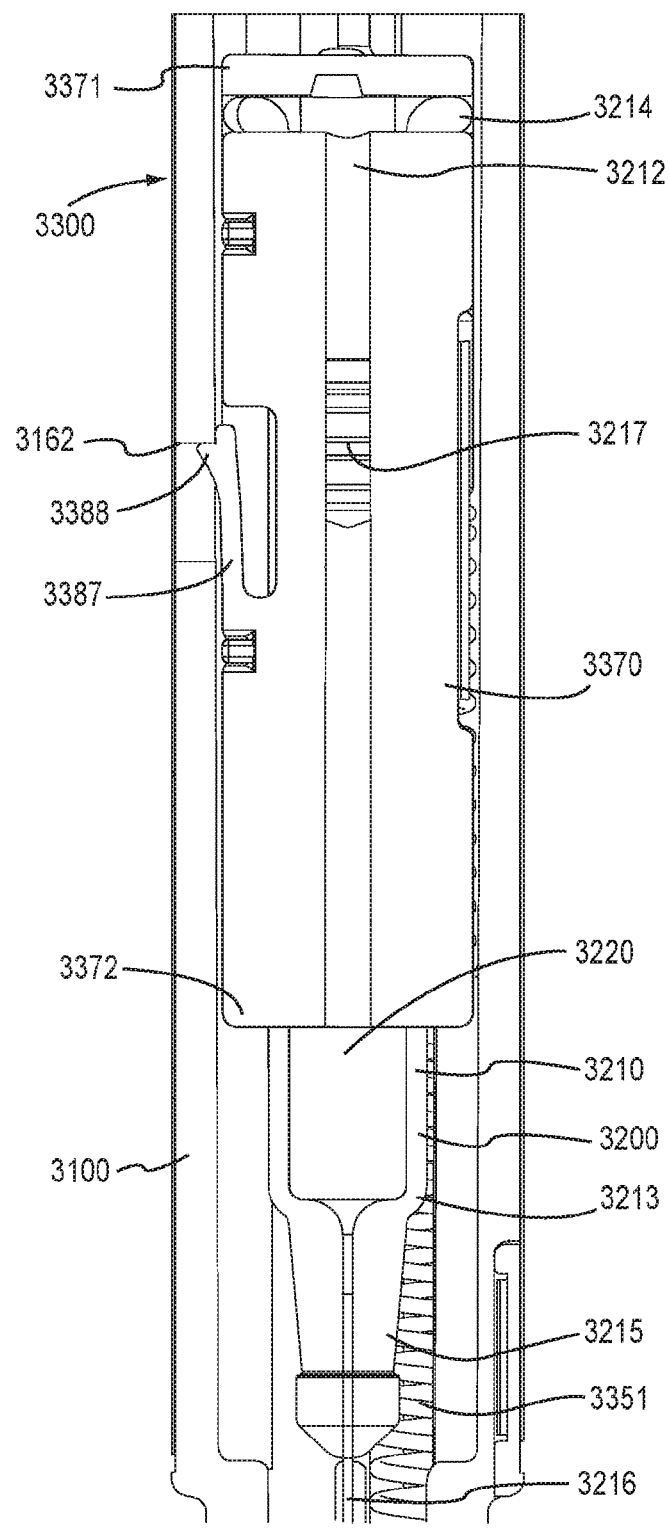
FIG. 28 is an enlarged side cross-sectional view of the portion of the medical injector illustrated in FIG. 26.
Figure 29:
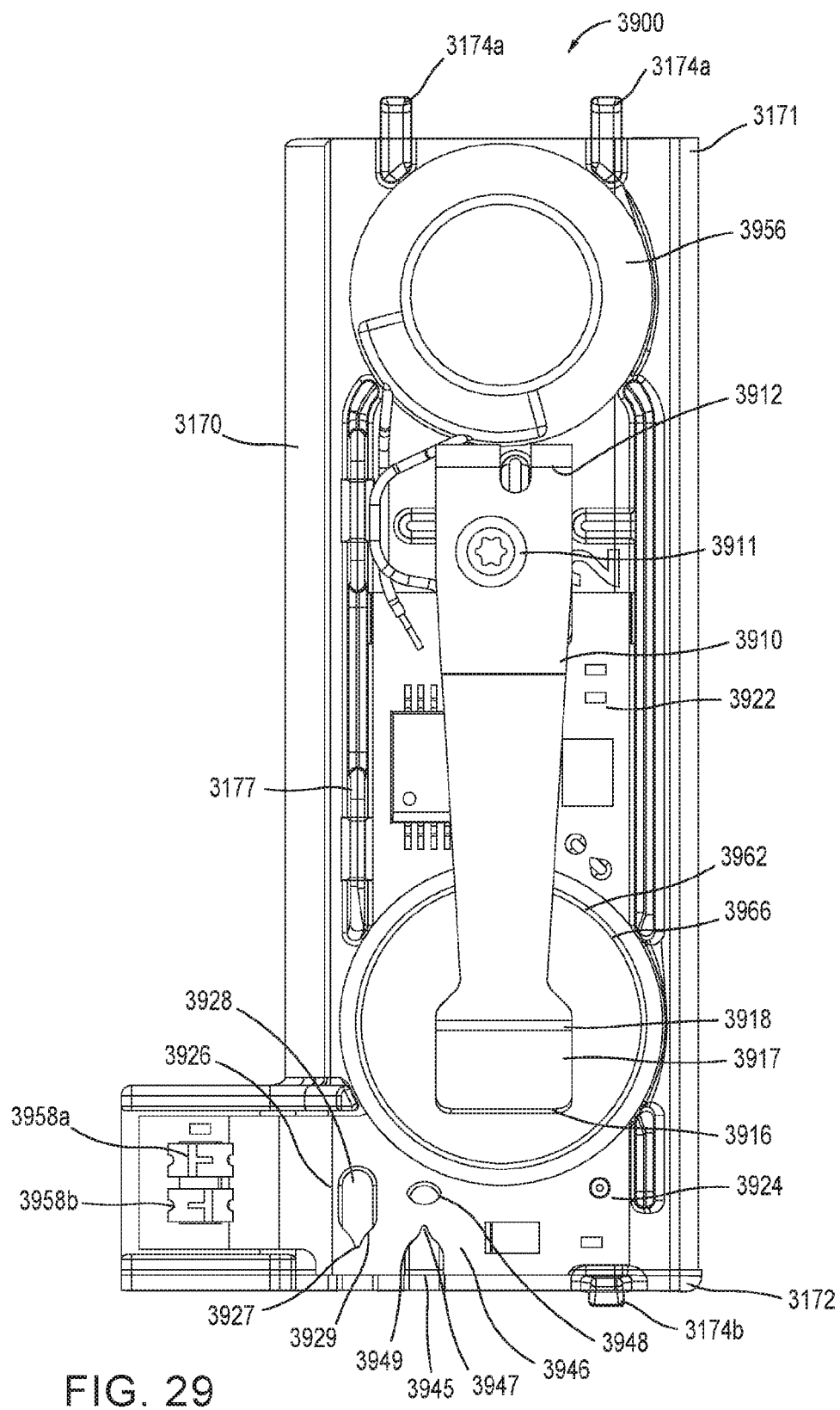
FIG. 29 is a back view of an electronic circuit system of the medical injector illustrated in FIG. 9.
Figure 30:
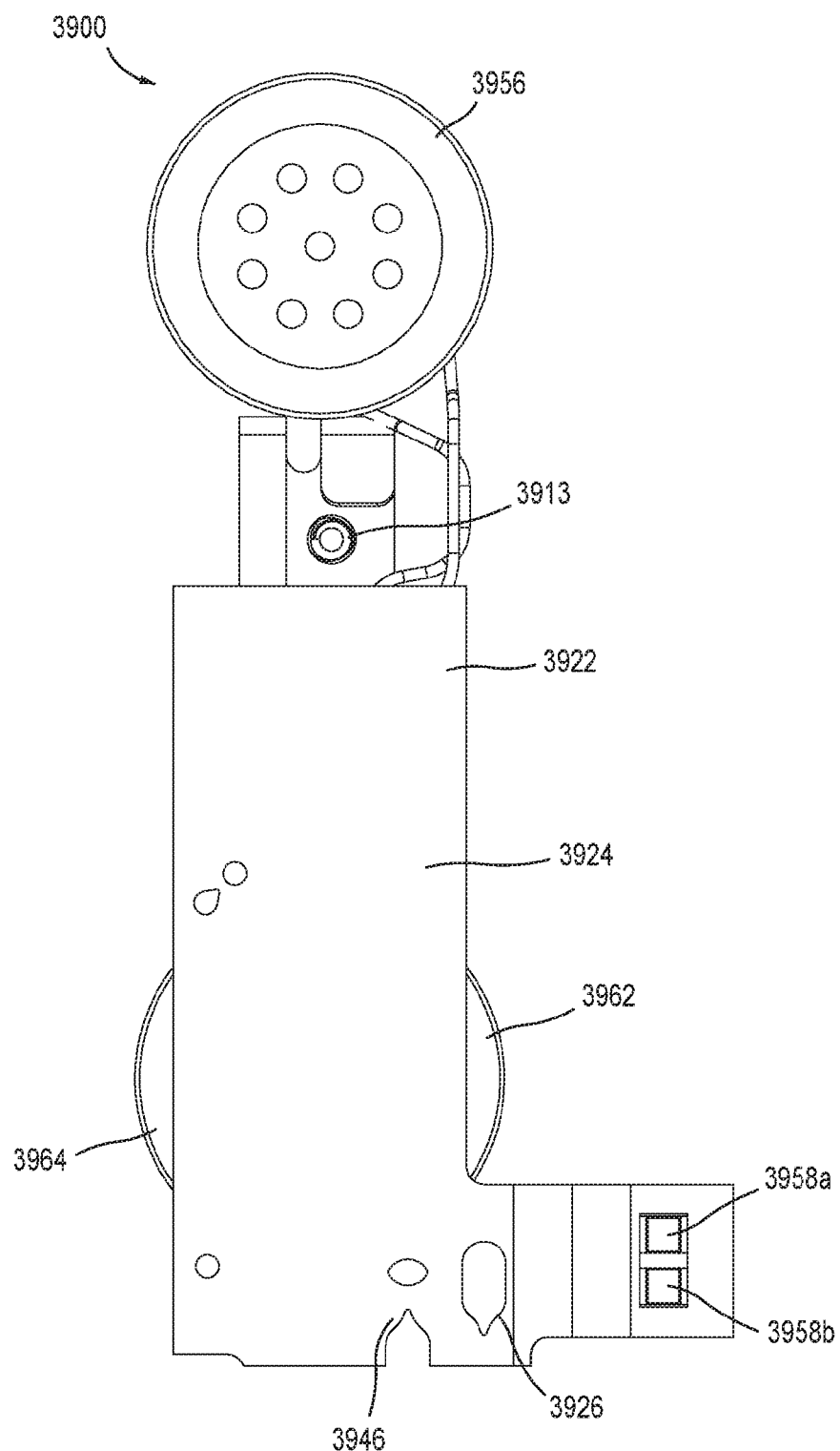
FIG. 30 is a front view of a portion of the electronic circuit system of the medical injector illustrated in FIG. 29.
Figure 31:
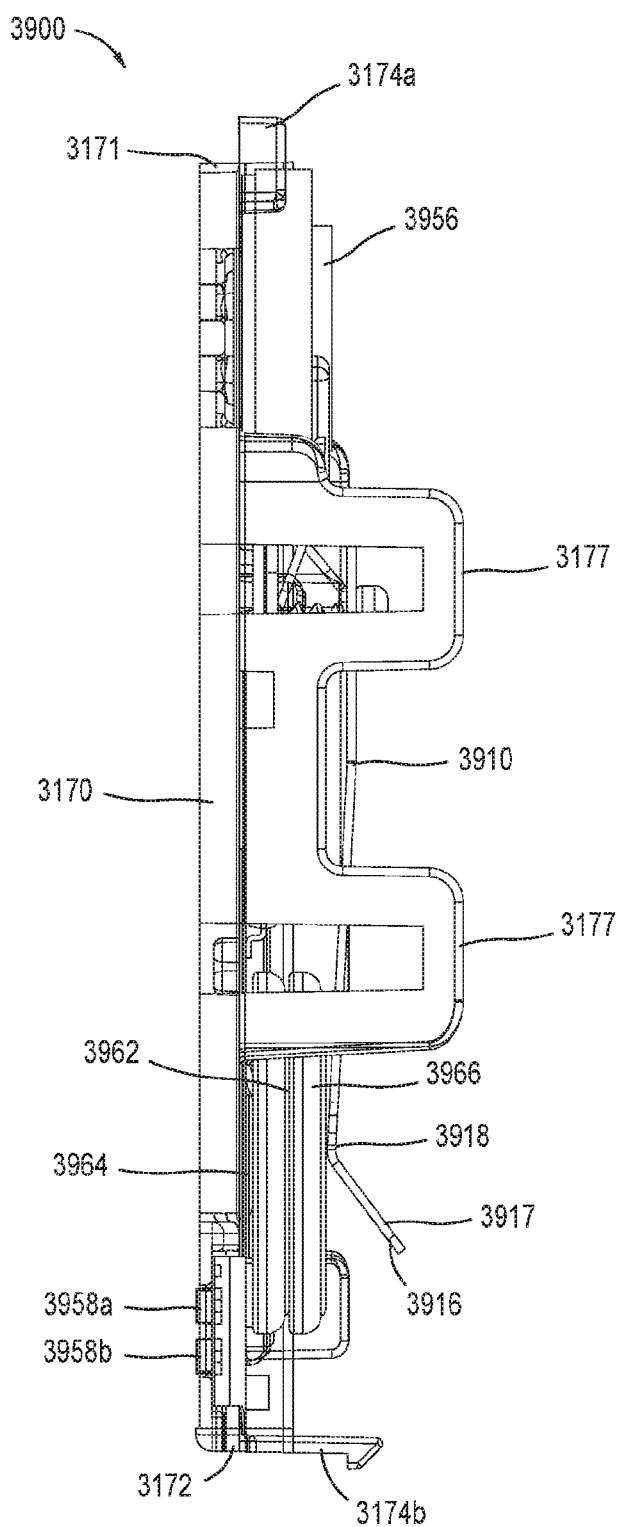
FIG. 31 is a side view of the electronic circuit system of the medical injector illustrated in FIG. 29.

FIGS. 18-28 show the medicament container 3200, the system actuator assembly 3500 and the medicament delivery mechanism 3300 of the medical injector 3000. The medicament container 3200 has a body 3210 with a distal end portion 3213 and a proximal end portion 3212. The body 3210 defines a volume that contains (i.e., is filled with or partially filled with) a medicament 3220 (see, e.g., FIGS. 22 and 28). The distal end portion 3213 of the medicament container 3200 includes a neck 3215 that is coupled to the needle 3216, as described below. The proximal end portion 3212 of the medicament container 3200 includes an elastomeric member 3217 (i.e., a plunger) that seals the medicament 3220 within the body 3210. The elastomeric member 3217 is configured to move within the body to inject the medicament 3220 from the medicament container 3200. More particularly, as shown in FIG. 27, the elastomeric member 3217 is configured to receive and/or contact a piston rod 3333 of a piston member 3330 (also referred to herein as "second movable member 3330") of the medicament delivery mechanism 3300.

The elastomeric member 3217 can be of any design or formulation suitable for contact with the medicament 3220. For example, the elastomeric member 3217 can be formulated to minimize any reduction in the efficacy of the medicament 3220 that may result from contact (either direct or indirect) between the elastomeric member 3217 and the medicament 3220. For example, in some embodiments, the elastomeric member 3217 can be formulated to minimize any leaching or out-gassing of compositions that may have an undesired effect on the medicament 3220. In other embodiments, the elastomeric member 3217 can be formulated to maintain its chemical stability, flexibility and/or sealing properties when in contact (either direct or indirect) with the medicament 3220 over a long period of time (e.g., for up to six months, one year, two years, five years or longer).

In some embodiments, the elastomeric member 3217 can be constructed from multiple different materials. For example, in some embodiments, at least a portion of the elastomeric member 3217 can be coated. Such coatings can include, for example, polydimethylsiloxane. In some embodiments, at least a portion of the elastomeric member 3217 can be coated with polydimethylsiloxane in an amount of between approximately 0.02 mg/cm$^2$ and approximately 0.80 mg/cm$^2$.

The proximal end portion 3212 of the body 3210 includes a flange 3214 configured to be disposed within a portion of the carrier 3370 (also referred to as a first movable member 3370), as described in further detail herein. The flange 3214 can be of any suitable size and/or shape. Although shown as substantially circumscribing the body 3210, in other embodiments, the flange 3214 can only partially circumscribe the body 3210.

Figure 22:
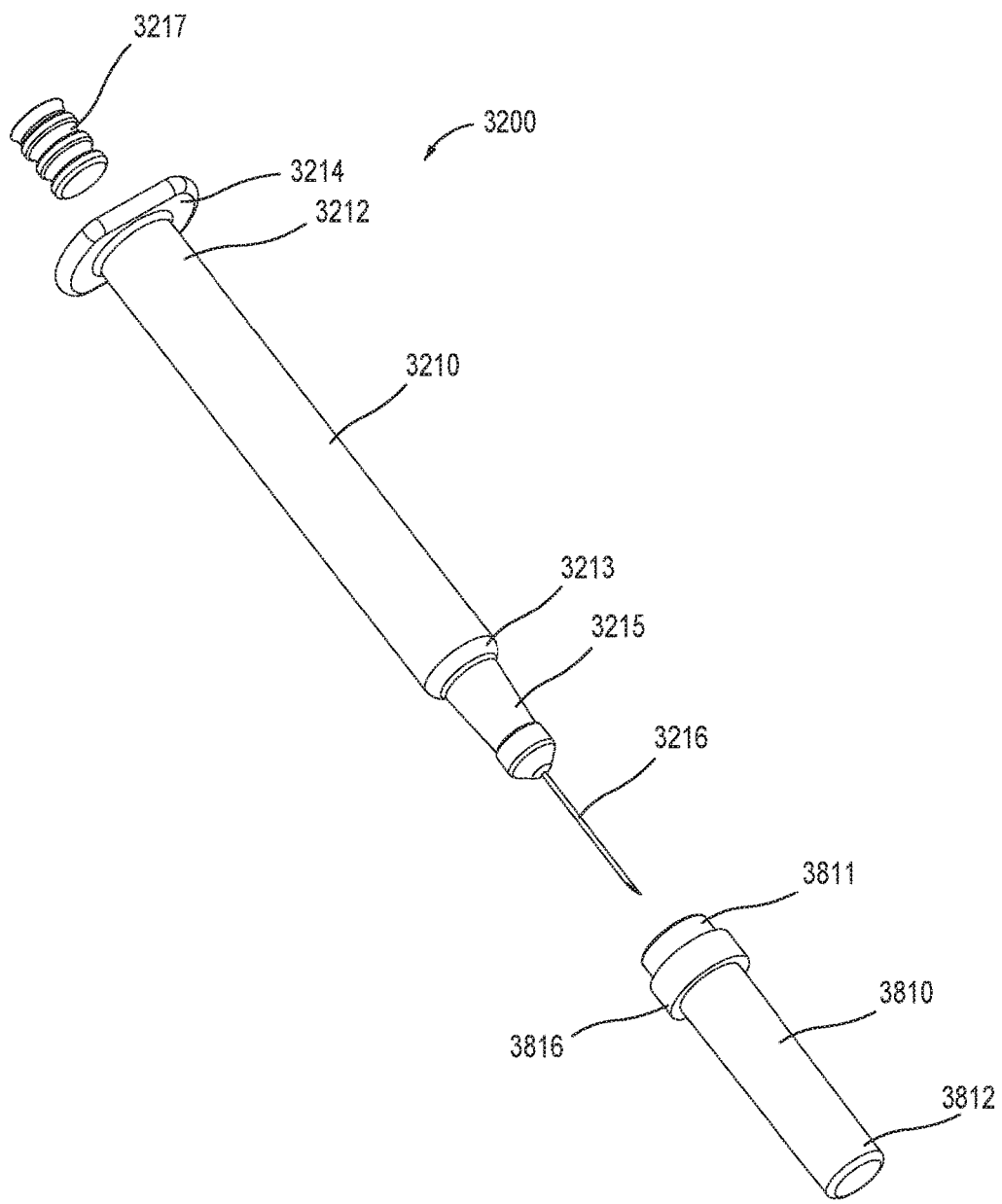
FIG. 22 is an exploded view of a medicament container of the medical injector illustrated in FIG. 9.
Figure 23:
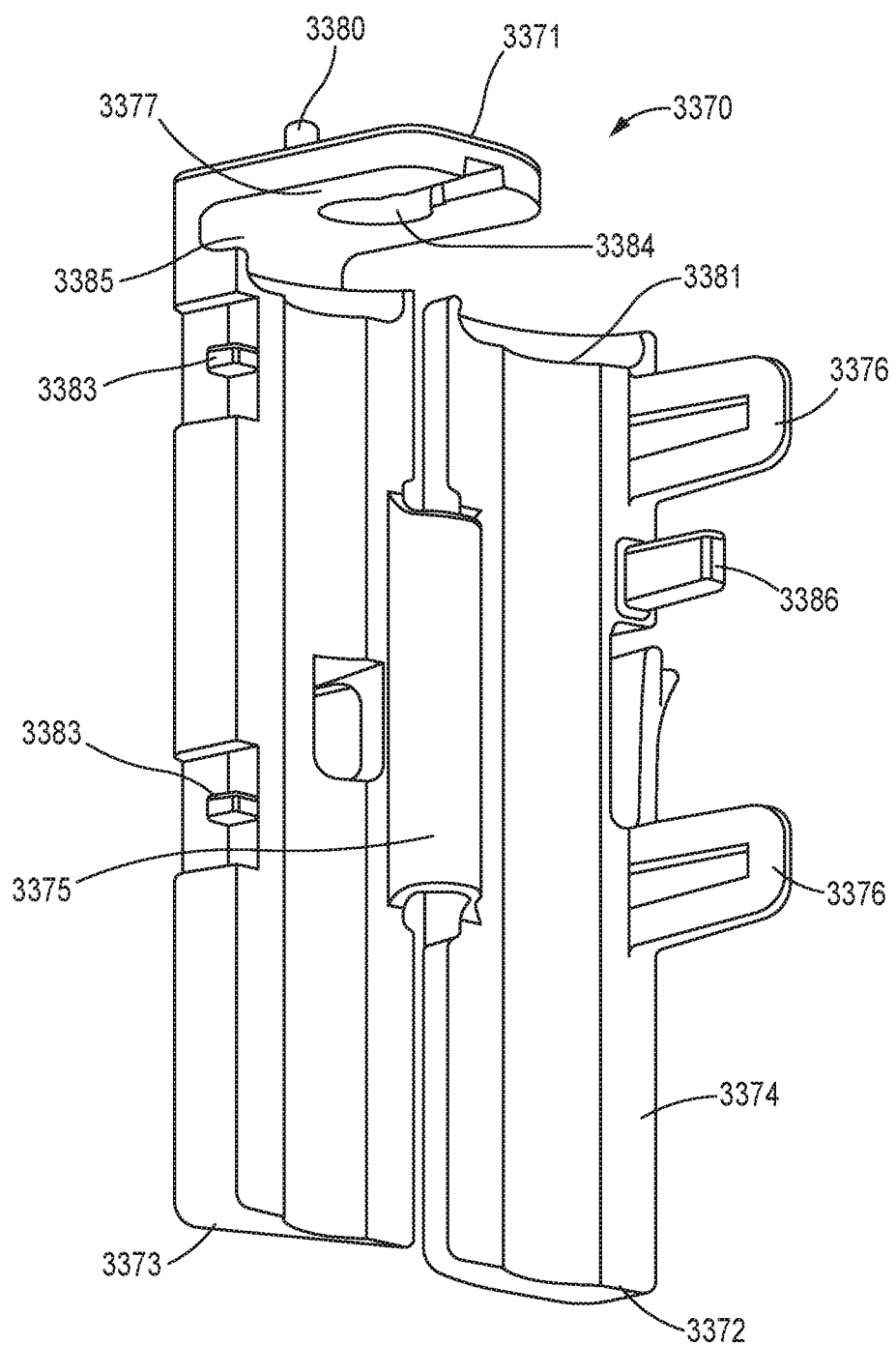
FIGS. 23 and 24 are perspective views of a carrier included in the medical injector illustrated in FIG. 9 in a first configuration.
Figure 24:
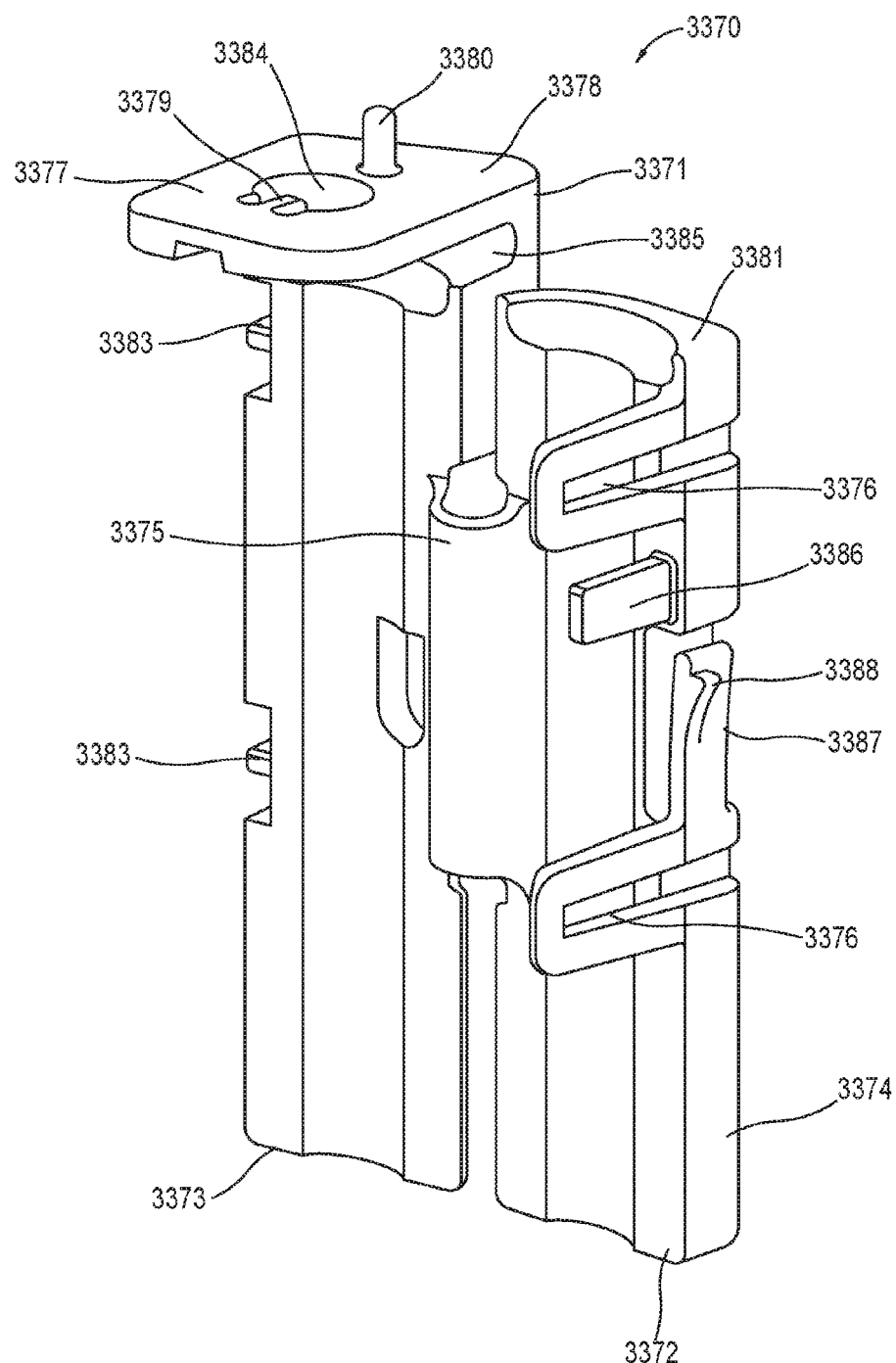

The medicament container 3200 can have any suitable size (e.g., length and/or diameter) and can contain any suitable volume of the medicament 3220. Moreover, the medicament container 3200 and the second movable member 3330 can be collectively configured such that the second movable member 3330 travels a desired distance within the medicament container 3200 (i.e., the "stroke") during an injection event. In this manner, the medicament container 3200, the volume of the medicament 3220 within the medicament container 3200 and the second movable member 3330 can be collectively configured to provide a desired fill volume and delivery volume. For example, the medicament container 3200, as shown in FIG. 22, is a prefilled syringe having a predetermined fill volume. Based on the predetermined fill volume, the second movable member 3330 can be configured to provide a desired delivery volume.

Moreover, the length of the medicament container 3200 and the length of the second movable member 3330 can be configured such that the medicament delivery mechanism 3300 can fit within the same housing 3100 regardless of the fill volume, the delivery volume and/or the ratio of the fill volume to the delivery volume. In this manner, the same housing and production tooling can be used to produce devices having various dosages of the medicament 3220. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

As shown in FIGS. 18-21, the system actuator assembly 3500 includes the base 3510, a release member 3550 and a spring 3576. FIG. 19 shows certain internal components of the medical injector 3000 without the base 3510 and the spring 3576 so that the release member 3550 can be more clearly shown.

The release member 3550 has a proximal end portion 3551 and a distal end portion 3552, and is movably disposed within the distal end portion 3153 of the gas cavity 3151. The proximal end portion 3551 of the release member 3550 includes a sealing member 3574 and a puncturer 3575. The sealing member 3574 is configured to engage the sidewall of the housing 3100 defining the gas cavity 3151 such that the proximal end portion 3152 of the gas cavity 3151 is fluidically isolated from the distal end portion 3153 of the gas cavity 3151. In this manner, when gas is released from the gas container 3410, the gas contained in the proximal end portion 3152 of the gas cavity 3151 is unable to enter the distal end portion 3153 of the gas cavity 3151. The puncturer 3575 of the proximal end portion 3551 of the release member 3550 is configured to contact and puncture a frangible seal 3413 on the gas container 3410 when the release member 3550 moves proximally within the gas cavity 3151, as shown by the arrow FF in FIG. 19.

The distal end portion 3552 of the release member 3550 includes extensions 3553. The extensions 3553 have projections 3555 that include tapered surfaces 3557 and engagement surfaces 3554. Further, the extensions 3553 define an opening 3556 between the extensions 3553. The engagement surfaces 3554 of the projections 3555 are configured to extend through the release member aperture 3154 of the housing 3100 and contact the release member contact surface 3126 of the housing 3100, as shown in FIG. 21. In this manner, the engagement surfaces 3554 of the projections 3555 limit proximal movement of the release member 3550 when the engagement surfaces 3554 are in contact with the release member contact surface 3126 of the housing 3100.

The opening 3556 defined by the extensions 3553 is configured to receive the safety lock protrusion 3702 of the safety lock 3700 (see e.g., FIGS. 21 and 42) when the safety lock 3700 is coupled to the housing 3100 and/or the base 3510. The safety lock protrusion 3702 is configured to prevent the extensions 3553 from moving closer to each other. Said another way, the safety lock protrusion 3702 is configured to ensure that the extensions 3553 remain spaced apart and the engagement surfaces 3554 of the projections 3555 remain in contact with the release member contact surface 3126 of the housing 3100. In some embodiments, for example, the release member 3550 and/or the extensions 3553 can be constructed from any suitable material configured to withstand deformation that may occur when exposed to a load over an extended period of time. In some embodiments, for example, the release member 3550 and/or the extensions 3553 can be constructed from brass.

The tapered surfaces 3557 of the projections 3555 are configured to contact tapered surfaces 3522 of contact protrusions 3515 on a proximal surface 3511 of the base 3510 (see e.g., FIGS. 21 and 47) when the base 3510 is moved proximally relative to the housing 3100. Accordingly, when the base 3510 is moved proximally relative to the housing 3100, the extensions 3553 are moved together by the tapered surfaces 3522 of the contact protrusions 3515. The inward movement of the extensions 3553 causes the release member 3550 to disengage the release member contact surface 3126 of the housing 3100, thereby allowing the release member 3550 to be moved proximally along its longitudinal axis as the spring 3576 expands.

The medicament delivery mechanism 3300 includes a gas container 3410, the carrier 3370 (also referred to herein as the first movable member 3370), the piston member 3330 (also referred to herein as the second movable member 3330), and a retraction spring 3351. As described above, the carrier 3370 and the piston member 3330 are each movably disposed within the medicament cavity 3139 of the housing 3100. The gas container 3410 is disposed within the gas cavity 3151 of the housing 3100.

The gas container 3410 includes a distal end portion 3411 and a proximal end portion 3412, and is configured to contain a pressurized gas. The distal end portion 3411 of the gas container 3410 contains a frangible seal 3413 configured to break when the puncturer 3575 of the proximal end portion 3551 of the release member 3550 contacts the frangible seal 3413. The gas container retention member 3580 of the proximal cap 3103 of the housing 3100 is configured to receive and/or retain the proximal end portion 3412 of the gas container 3410. Said another way, the position of the gas container 3410 within the gas cavity 3151 is maintained by the gas container retention member 3580. As shown in FIGS. 18 and 19, the length of the gas container retention member 3580 and the length of the release member 3550 collectively determine the distance between the puncturer 3575 and the frangible seal 3413 when the medical injector 3000 is in the storage configuration. Accordingly, this distance, which is the distance through which the puncturer 3575 travels when the medical injector 3000 is actuated, can be adjusted by changing the length of the gas container retention member 3580 and/or the length of the release member 3550. In some embodiments, the actuation time and/or the force exerted by the puncturer 3575 on the frangible seal 3413 can be adjusted by changing the distance between the puncturer 3575 and the frangible seal 3413.

Figure 52:
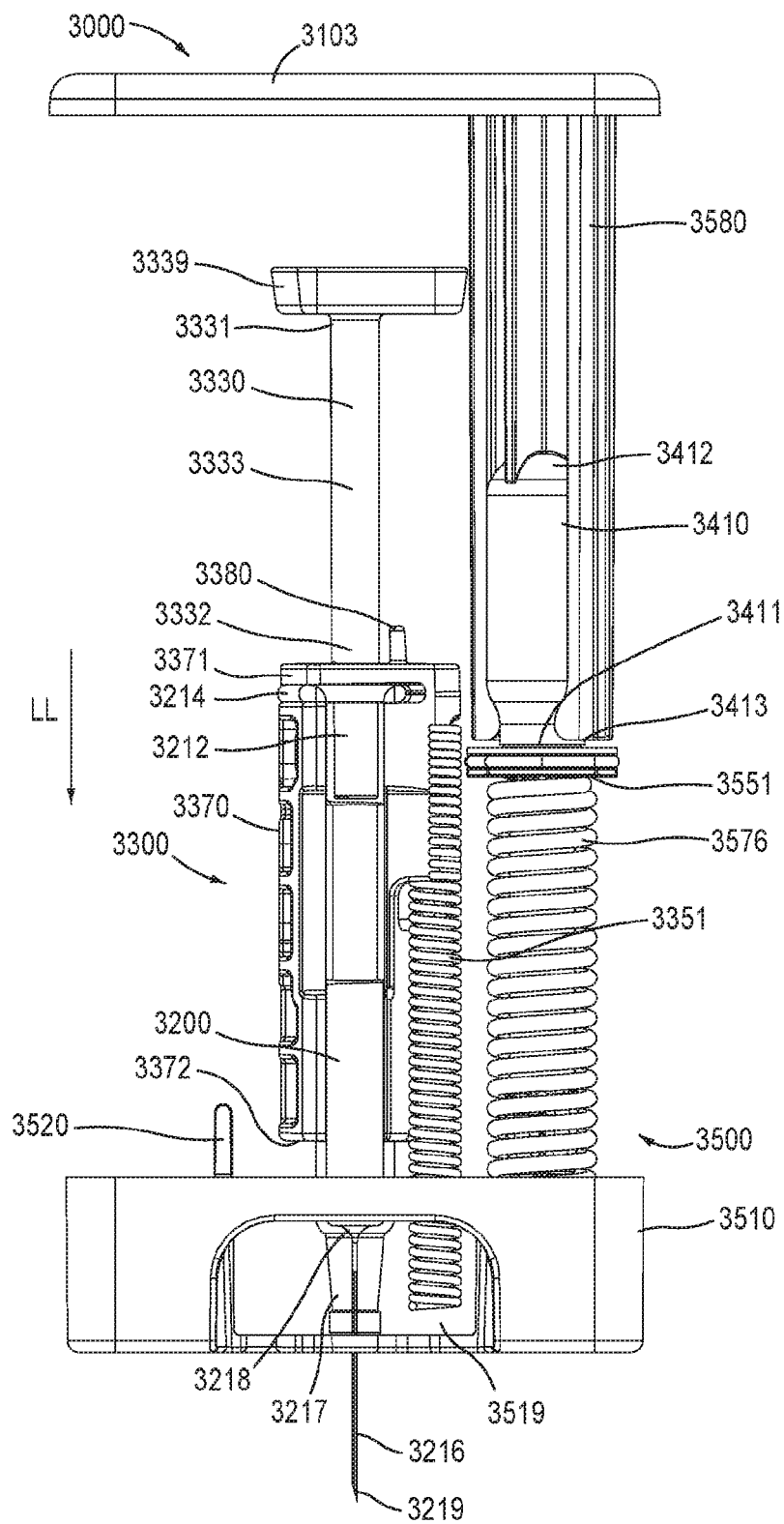
FIG. 52 is a front view of a portion of the medical injector illustrated in FIG. 9 in the fourth configuration (i.e., the needle insertion configuration).
Figure 53:
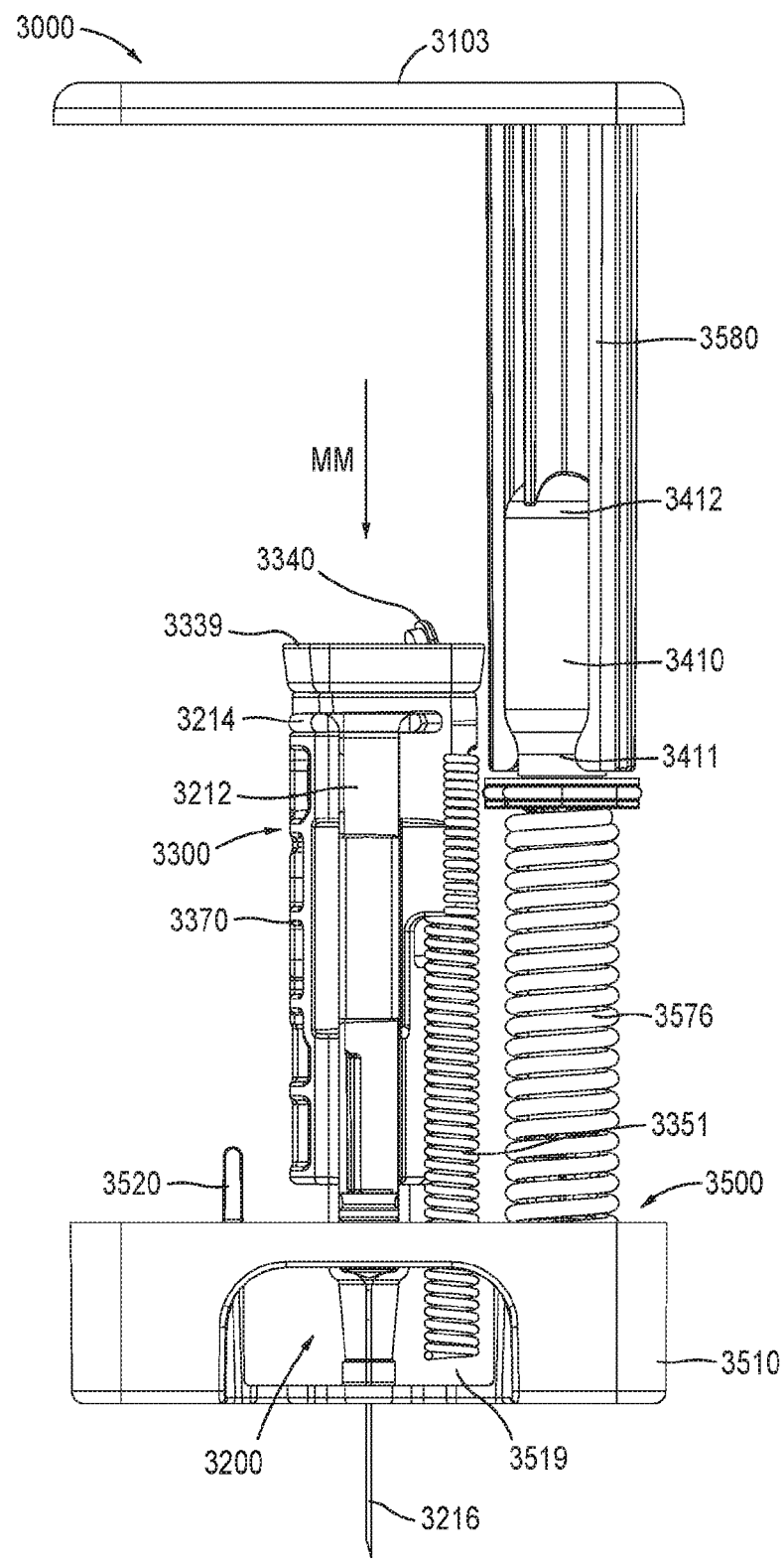
FIG. 53 is a front view of a portion of the medical injector illustrated in FIG. 9 in a fifth configuration (i.e., the injection configuration).

As shown in FIGS. 26 and 52, the piston member 3330 includes a piston rod 3333, and has a proximal end portion 3331 and a distal end portion 3332. The proximal end portion 3331 includes a sealing member 3339. The sealing member 3339 engages the sidewall of the housing 3100 to define a gas chamber (i.e., a volume within the medicament cavity 3139 between the proximal end of the housing 3100 and the proximal end of the piston member 3330) that receives the pressurized gas from the gas container 3410. The sealing member 3339 can be any suitable structure and or component to produce a substantially fluid-tight seal between the sidewall of the housing 3100 and the piston member 3330. The proximal end portion 3331 also includes a gas relief valve 3340 (see e.g., FIGS. 26 and 53-55) configured to be selectively actuated to allow fluid communication between the gas chamber and a volume outside of the gas chamber (e.g., the distal end portion of the medicament cavity 3139). As described in more detail below, the gas relief valve 3340 allows the gas pressure within the gas chamber to be reduced upon completion of the injection event.

Referring to FIG. 27, the distal end portion 3332 includes a first surface 3341 and a second surface 3342. The second surface 3342 is disposed through a piston rod opening 3384 of the carrier 3370 and within the proximal end portion 3212 of the medicament container 3200. The first surface 3341 is configured to contact a proximal surface 3378 of an engagement portion 3379 of the carrier 3370 when the medicament injector 3000 is in a first configuration (i.e., when the medicament container 3200 is in its first position). The distance between the first surface 3341 and the second surface 3342 is such that when the first surface 3341 is in contact with the engagement portion 3379 of the carrier 3370, the second surface 3342 is spaced apart from the elastomeric member 3217 within the medicament container 3200 (see e.g., FIG. 27). This arrangement limits any preload and/or residual force applied to the piston member 3330 (e.g., via the retraction spring 3351 and/or the pressurized gas) from being transferred to the plunger 3217. Said another way, the plunger 3217 is isolated from the piston member 3330 during the storage configuration and/or when the medicament container 3200 is moving distally within the housing 3100. Accordingly, this arrangement reduces and/or eliminates leakage of the medicament 3220 from the medicament container 3200.

As described in more detail herein, the piston member 3330 is configured to move within the medicament container 3200. Because the first surface 3341 is configured to contact the engagement portion 3379, the piston member 3330 applies a force to the proximal surface 3378 of the first shoulder 3377 such that the carrier 3370 and the piston member 3330 move together within the medicament cavity 3139. Moreover, when the medicament container 3200 is in its second position, the piston member 3330 can move relative to the carrier 3370 and/or the medicament container 3200 such that the second surface 3342 engages and/or contacts the elastomeric member 3217 to convey the medicament 3220 contained in the medicament container 3200. The piston member 3330 can be constructed of a resilient, durable and/or sealing material or combination of materials, such as a rubber.

The carrier 3370 of the medicament delivery mechanism 3300 includes a distal end portion 3372, a proximal end portion 3371, a first side portion 3373, a second side portion 3374 and a hinge portion 3375 (see e.g., FIGS. 23-28). The first side portion 3373 includes latch protrusions 3383 configured to be coupled to the corresponding latches 3376 of the second side portion 3374. The second side portion 3374 is configured to move relative to the first side portion 3373 via the hinge portion 3375 between an opened configuration (FIGS. 23 and 24) and a closed configuration (FIG. 25). This arrangement allows at least the proximal end portion 3212 of the medicament container 3200 to be disposed within (and/or removed from) the carrier 3370 when the carrier 3370 is in the opened configuration (see e.g., FIGS. 23 and 24). When the carrier 3370 is in the closed configuration (see e.g., FIGS. 25-28), the latches 3376 of the second side portion 3374 engage the latch protrusions 3383 of the first side portion 3373 to maintain the medicament container 3200 within the carrier 3370.

The proximal end portion 3371 of the carrier 3370 includes a first shoulder 3377 and a second shoulder 3381 that collectively define a flange groove 3385. The flange groove 3385 is configured to receive the flange 3214 of the proximal end portion 3212 of the medicament container 3200 (see e.g., FIG. 26). More particularly, the first shoulder 3377 is defined by the first side portion 3373, and the second shoulder 3381 is defined by portions of both the first side portion 3373 and the second side portion 3374. In this manner, the first shoulder 3377 is configured to contact a proximal surface of the flange 3214, either directly or via intervening structure (e.g., an o-ring, a damping member, or the like). Similarly, the second shoulder 3381 is configured to contact a distal surface of the flange 3214, either directly or via intervening structure (e.g., an o-ring, a damping member, or the like). In this manner, as described in more detail below, the first shoulder 3377 can transfer at least a portion of a distal force (i.e., an insertion force) to the flange 3214 to produce distal movement of the carrier 3370 and/or the medicament container 3200 within the housing 3100. The second shoulder 3381 can transfer at least a portion of a proximal force (i.e., a retraction force) to the flange 3214 to produce proximal movement of the carrier 3370 and/or the medicament container 3200 within the housing 3100.

The second side portion 3374 includes a protrusion 3386 configured to contact a surface of the first side portion 3373 when the carrier 3370 is in the closed configuration (FIG. 25). In this manner, the protrusion 3386 and the corresponding portion of the first side portion 3373 limits the movement of the second side portion 3374 relative to the first side portion 3373 when the carrier 3370 is in the closed configuration. Similarly stated, the protrusion 3386 of the second side portion 3374 contacts the first side portion 3373 to prevent the carrier 3370 from squeezing the medicament container 3200, when the carrier 3370 is in the closed configuration.

The second side portion 3374 includes a latch 3387 having a protrusion 3388. The protrusion 3388 of the latch 3387 is configured to engage a retraction lock protrusion 3162 defined by the sidewall of the housing 3100 defining the medicament cavity 3139 (see e.g., FIG. 28) when the carrier 3370 and the medicament container 3200 are in the first (i.e., storage) position. This arrangement allows the medicament delivery mechanism 3300 (e.g., the carrier 3370, the piston member 3330) and the medicament container 3200 to move in the distal direction within the housing 3100 but limits the movement of the carrier 3370 and the medicament container 3200 in the proximal direction. In this manner, the preload of the retraction spring 3351 is not transferred to the piston member 3330 and/or the engagement portion 3379 of the carrier 3370. Similarly stated, this arrangement prevents the medicament delivery mechanism 3300 from moving in the proximal direction when the medical injector 3000 is in the first configuration. This arrangement also limits proximal motion of the medicament delivery mechanism 3300 during assembly (e.g., when the needle sheath is being pressed about the needle).

As described above, the carrier 3370 includes the engagement portion 3379 configured to engage the first surface 3341 of the piston member 3330. The first shoulder 3377 is in contact with the proximal surface of the flange 3214 and therefore transmits a force from the piston member 3330 to move the medicament container 3200 from a first position to a second position when the medicament injector 3000 is actuated.

As shown in FIG. 26, the carrier 3370 also includes an engagement portion 3382 configured to engage the retraction spring 3351. Although the engagement portion 3382 is shown as including a protrusion about which a portion of the retraction spring 3351 is disposed, in other embodiments, the engagement portion 3382 can include any suitable features for engaging and/or retaining the retraction spring 3351 (e.g., a recess). The second shoulder 3381 is configured to engage the distal end of the flange 3214 and therefore transmits a retraction force produced by the retraction spring 3351 to move the medicament container 3200 from the second position toward the first position.

A proximal surface 3378 of the first shoulder 3377 of the carrier 3370 includes a gas valve actuator 3380. The gas valve actuator 3380 is configured to engage the gas relief valve 3340 (see e.g., FIG. 26) of the piston member 3330 to allow the pressurized gas contained within the gas chamber (i.e., the volume within the medicament cavity 3139 between the proximal end of the housing 3100 and the proximal end of the piston member 3330) to escape when the injection event is complete. Thus, after the gas pressure within the medicament cavity 3139 decreases below a certain level, the force exerted by the retraction spring 3351 on the carrier 3370 is sufficient to cause the carrier 3370 to move proximally within the housing 3100 (i.e., to retract). In addition, this arrangement results in there being substantially no residual force (from the pressurized gas) within the housing, which decreases stress on the components after the injection event.

Figure 36:
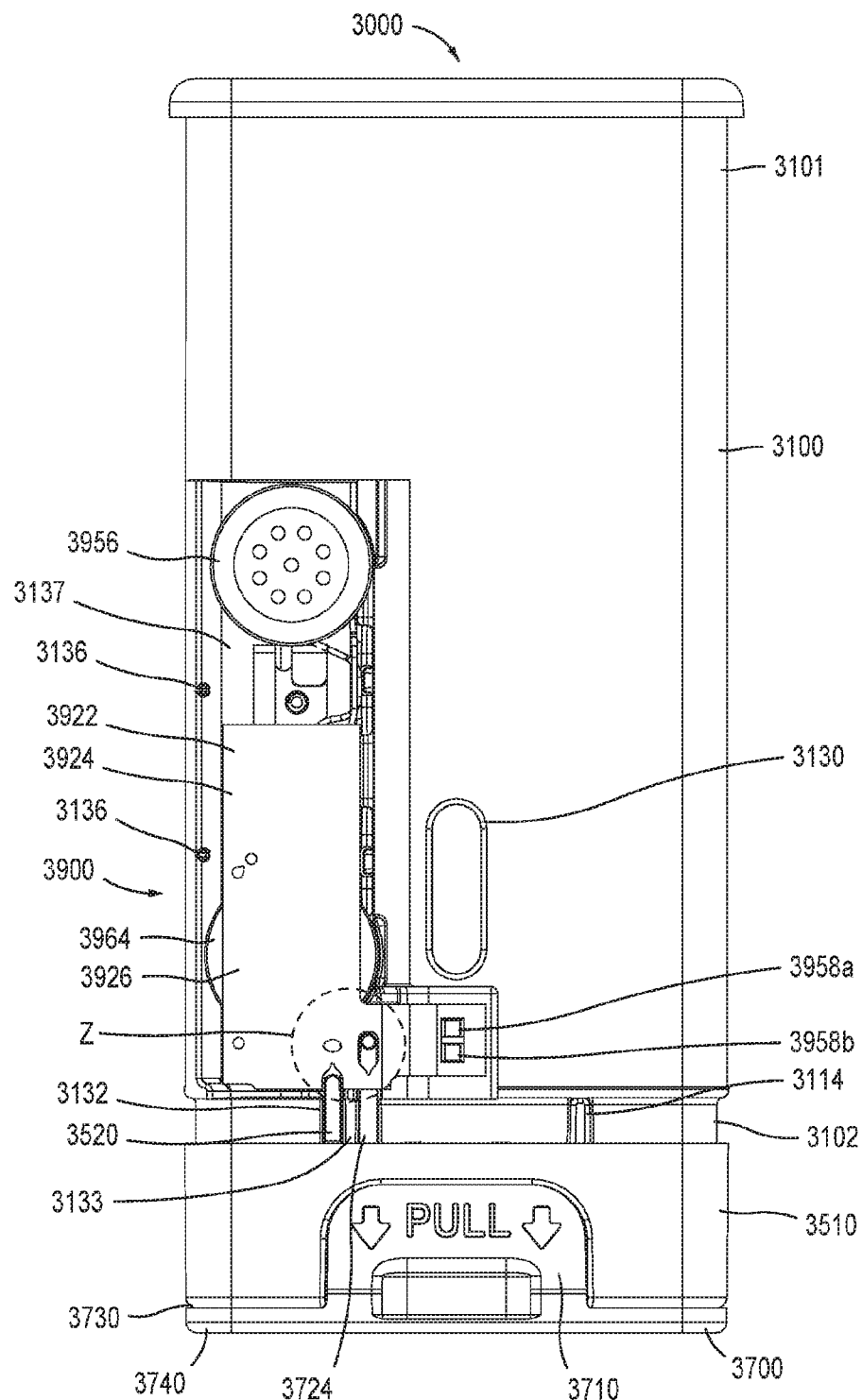
FIG. 36 is a front view of the medical injector illustrated in FIG. 9 in a first configuration showing the electronic circuit system.

FIGS. 29-39 show the electronic circuit system 3900. The electronic circuit system 3900 of the medical injector 3000 includes an electronic circuit system housing 3170, a printed circuit board 3922, a battery assembly 3962, an audio output device 3956, two light emitting diodes (LEDs) 3958A, 3958B and a battery clip 3910. As shown in FIG. 36, the electronic circuit system 3900 is disposed within the electronic circuit system cavity 3137 of the housing 3100. As described herein, the electronic circuit system 3900 is configured to output an electronic output associated with the use of the medical injector 3000.

The electronic circuit system housing 3170 of the electronic circuit system 3900 includes a distal end portion 3172 and a proximal end portion 3171. The proximal end portion 3171 includes connection protrusions 3174A and a battery clip protrusion 3176 (see e.g., FIG. 33). The connection protrusions 3174A are configured to matingly engage a surface of the sidewalls of the housing 3100 that define the electronic cavity 3137, as described above. In this manner, the electronic circuit system 3900 can be coupled to the housing 3100 within the electronic circuit system cavity 3137. In other embodiments, the electronic circuit system 3900 can be coupled to the housing 3100 by other suitable means such as an adhesive, a clip, a label and/or the like. As described in more detail herein, the battery clip protrusion 3176 is configured to hold the battery clip 3910 in place.

The proximal end portion 3171 of the electronic circuit system housing 3170 defines multiple sound apertures 3173. The audible output device 3956 is disposed against the proximal end portion 3171 of the electronic circuit system housing 3170 such that the front face of the audible output device 3956 is disposed adjacent the sound apertures 3173. In this manner, the sound apertures 3173 are configured to allow sound produced by the audio output device 3956 to pass from the audio output device 3956 to a region outside of the housing 3100.

Figure 32:
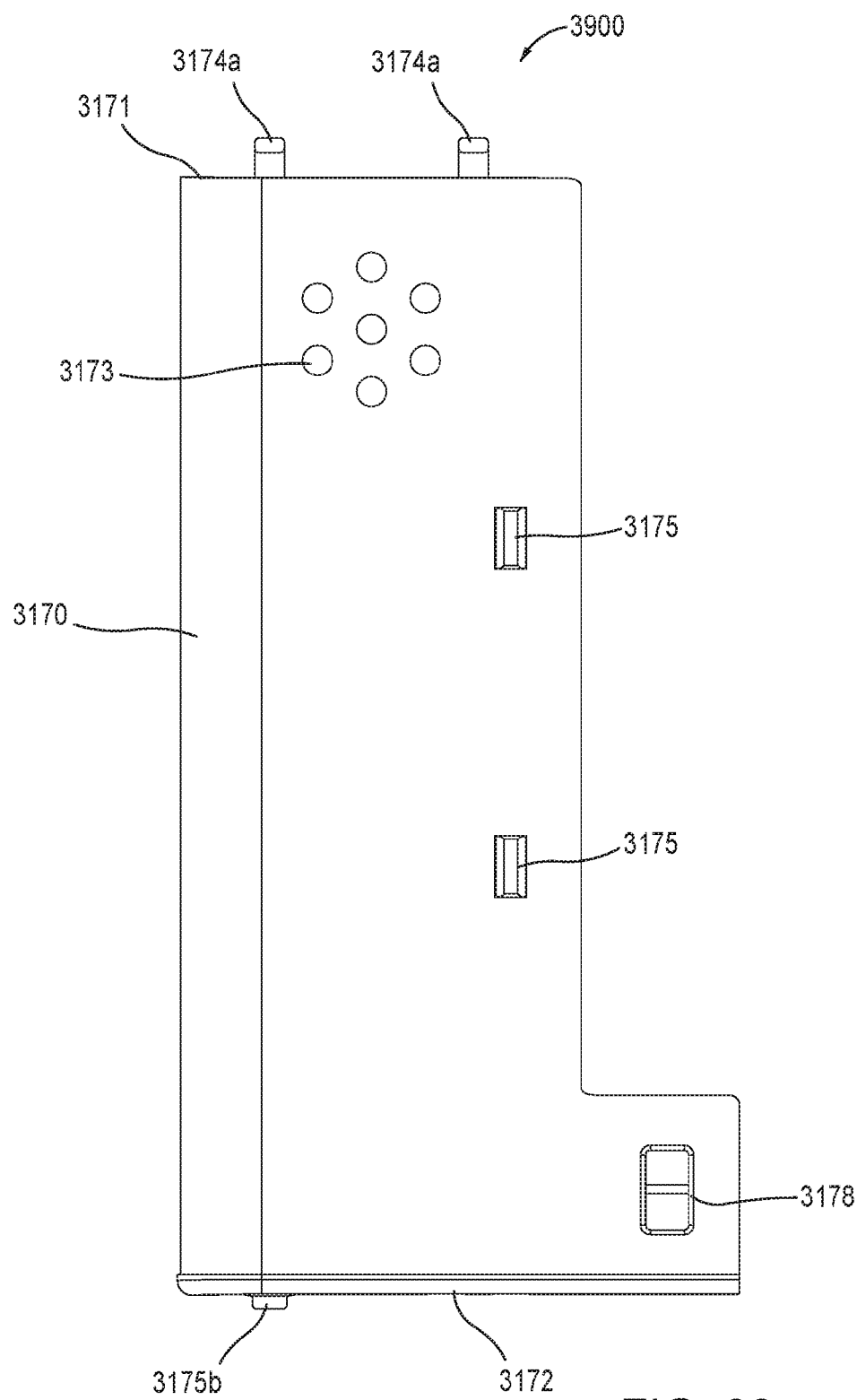
FIG. 32 is a front view of an electronic circuit system housing of the electronic circuit system illustrated in FIG. 29.
Figure 33:
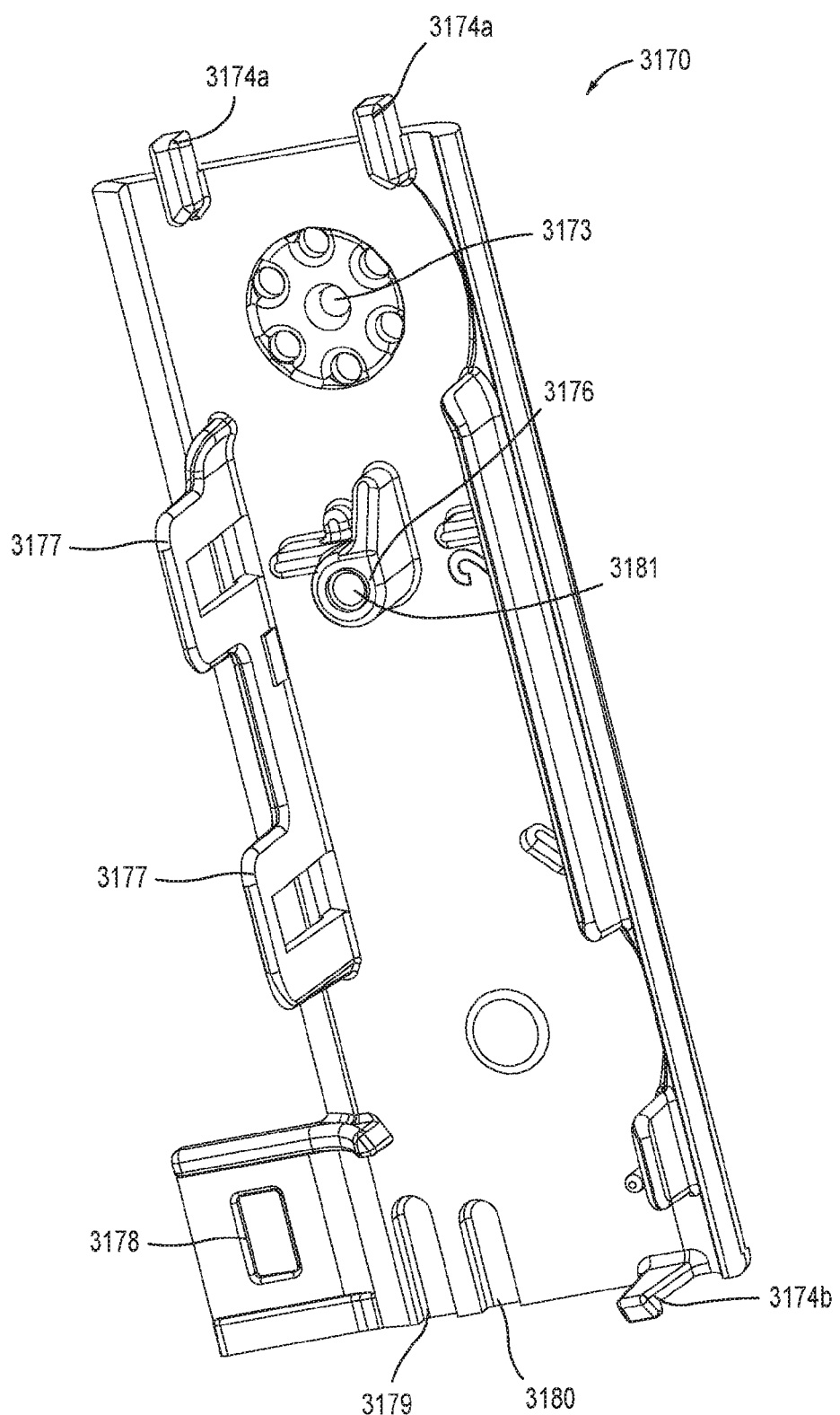
FIG. 33 is a perspective view of the electronic circuit system housing of the electronic circuit system illustrated in FIG. 32.
Figure 34:
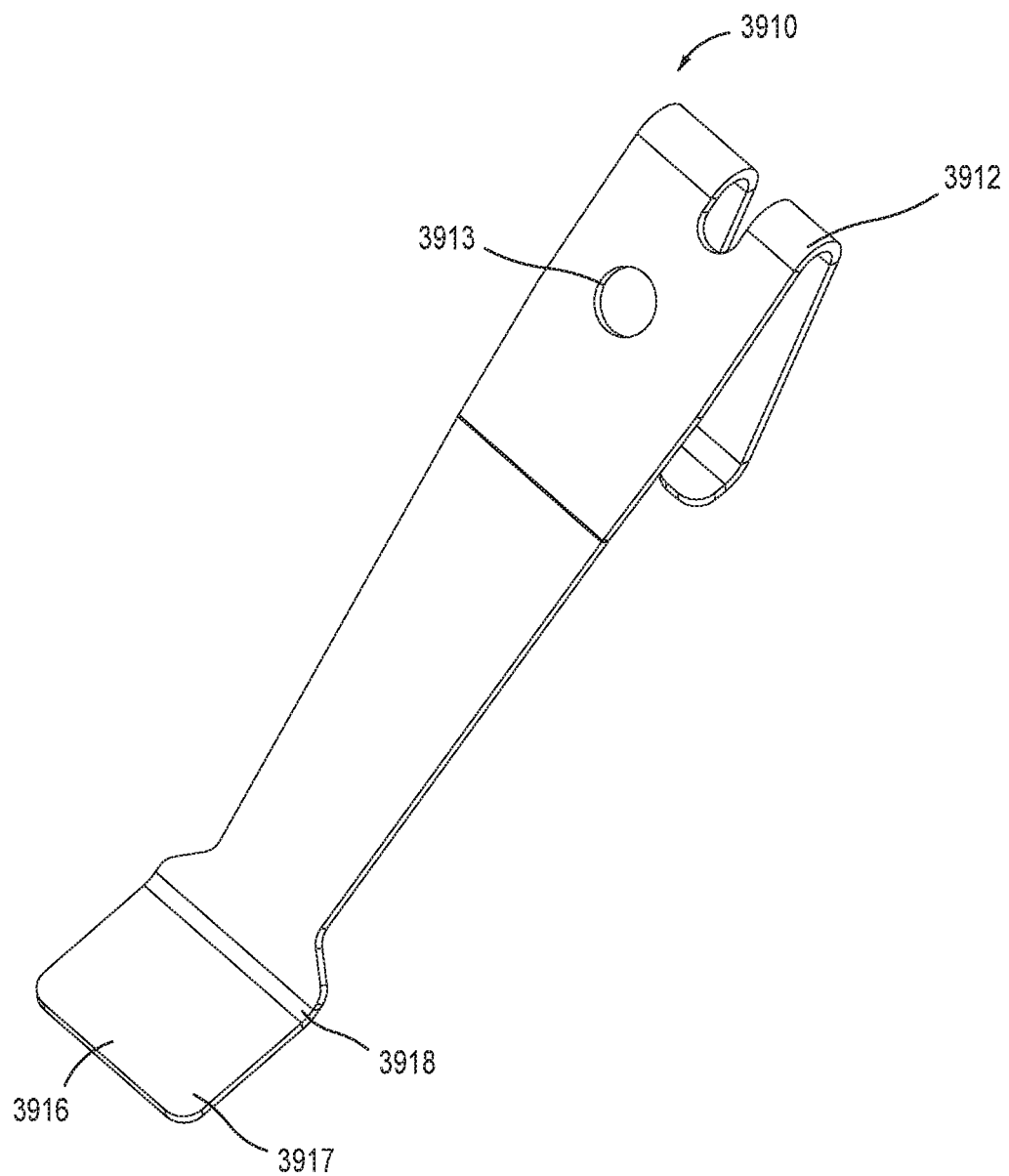
FIG. 34 is a perspective view of a battery clip of the electronic circuit system illustrated in FIG. 29.
Figure 35:
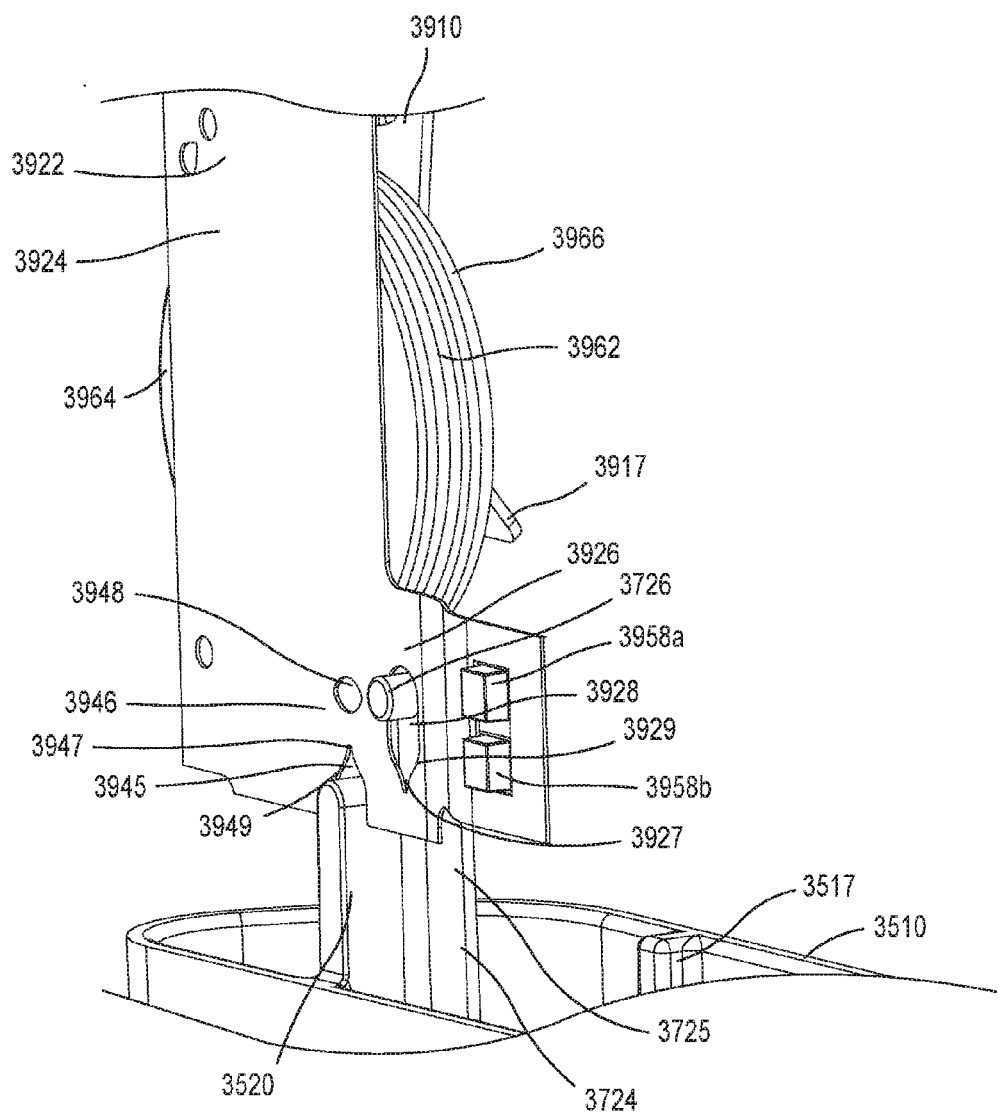
FIG. 35 is a perspective view of a portion of an electronic circuit system of the medical injector illustrated in FIG. 9, in a first configuration.

As shown in FIGS. 32 and 33, the distal end portion 3172 of the electronic circuit system housing 3170 includes the connection protrusion 3174B, a stiffening protrusion 3177 and defines an LED aperture 3178, apertures 3175, a safety lock actuator groove 3179 and a base actuator groove 3180. The LED aperture 3178 is configured to receive the LEDs 3958A, 3958B such that a user can view the LEDs 3958A, 3958B, which are described in more detail herein.

The connection protrusion 3174B extends from the distal end portion 3172 of the electronic circuit system housing 3170, and is configured to attach the electronic circuit system 3900 to the housing 3100, as described above. The stiffening protrusion 3177 is configured to have at least a portion received within and/or accessible via the apertures 3175 defined by the housing 3100 (see e.g., FIG. 11). The stiffening protrusion 3177 is configured to limit the bending (e.g., buckling) of the electronic circuit system housing 3170 when the electronic circuit system housing 3170 is coupled to the housing 3100. Moreover, a user can access the stiffening protrusion 3177 via the apertures 3175. In this manner, for example, the user can disengage the stiffening protrusion 3177 from the apertures 3175.

The safety lock actuator groove 3179 of the electronic circuit system housing 3170 is configured to be disposed adjacent the safety lock actuator groove 3133 of the distal end portion 3102 of the housing 3100. In this manner, the safety lock actuator groove 3179 of the electronic circuit system housing 3170 and the safety lock actuator groove 3133 of the distal end portion 3102 of the housing 3100 collectively receive the actuator 3724 of the safety lock 3700, which is described in more detail herein. Similarly, the base actuator groove 3180 of the electronic circuit system housing 3170 is configured to be disposed adjacent the base actuator groove 3132 of the distal end portion 3102 of the housing 3100. The base actuator groove 3180 of the electronic circuit system housing 3170 and the base actuator groove 3132 of the distal end portion 3102 of the housing 3100 collectively receive the protrusion 3520 of the base 3510, which is described in more detail herein.

The printed circuit board 3922 of the electronic circuit system 3900 includes a substrate 3924, a first actuation portion 3926 and a second actuation portion 3946. The substrate 3924 of the printed circuit board 3922 includes the electrical components for the electronic circuit system 3900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board).

Figure 37:
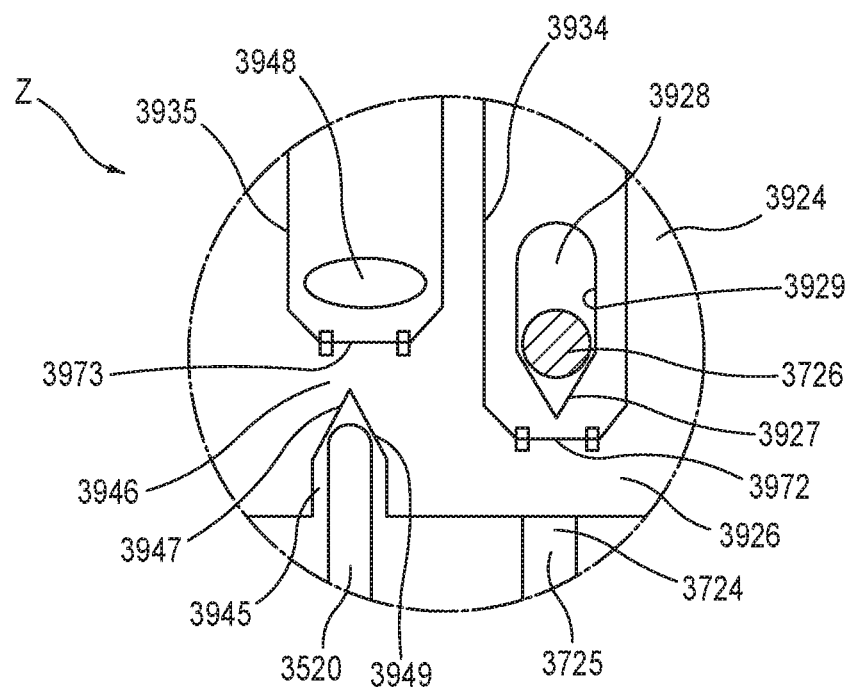
FIGS. 37-39 are front views of a portion of the electronic circuit system of the medical injector labeled as Region Z in FIG. 36 in a first configuration, a second configuration and a third configuration, respectively.
Figure 38:
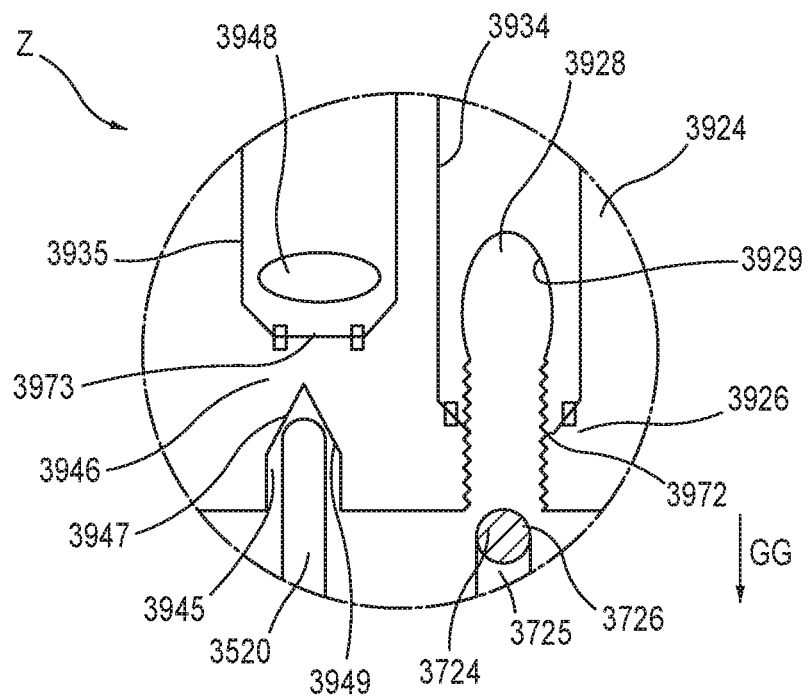
Figure 39:
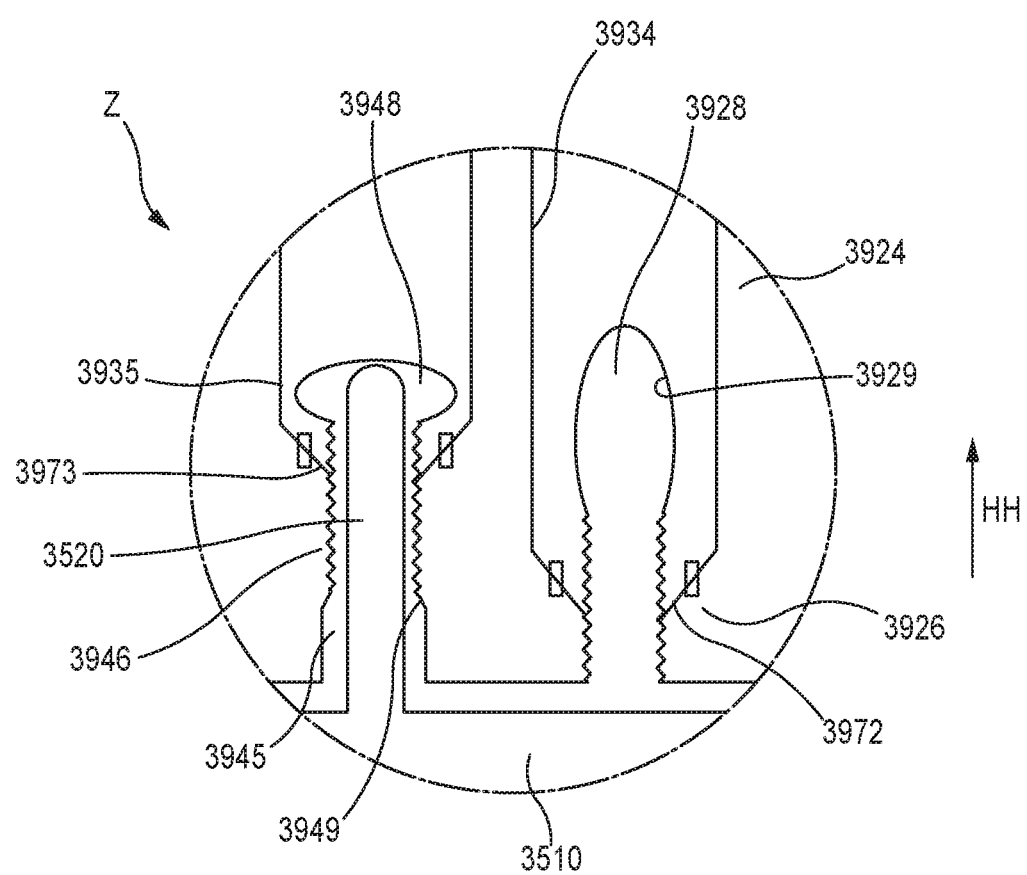

As shown in FIGS. 37-39, the first actuation portion 3926 includes a first electrical conductor 3934 and defines an opening 3928 having a boundary 3929. The opening 3928 of the first actuation portion 3926 is configured to receive a protrusion 3726 of the actuator 3724 of the safety lock 3700. The boundary 3929 of the first opening 3928 has a discontinuous shape, such as, for example, a teardrop shape, that includes a stress concentration riser 3927. The discontinuity and/or the stress concentration riser 3927 of the boundary 3929 can be of any suitable shape to cause the substrate 3924 to deform in a predetermined direction when the protrusion 3726 of the actuator 3724 of the safety lock 3700 is moved relative to the opening 3928, as shown by the arrow GG in FIG. 38.

The opening 3928 is defined adjacent the first electrical conductor 3934 that electronically couples the components included in the electronic circuit system 3900. The first electrical conductor 3934 includes a first switch 3972, which can be, for example a frangible portion of the first electrical conductor 3934. In use, when the safety lock 3700 is moved from a first position (see e.g., FIG. 37) to a second position (see e.g., FIG. 38), the actuator 3724 moves in a direction substantially parallel to a plane defined by a surface of the first actuation portion 3926 of the substrate 3924. The movement of the actuator 3724 causes the protrusion 3726 to move within the first opening 3928, as indicated by the arrow GG in FIG. 38. The movement of the protrusion 3726 tears the first actuation portion 3926 of the substrate 3924, thereby separating the portion of the first electrical conductor 3934 including the first switch 3972. Said another way, when the safety lock 3700 is moved from its first position to its second position (see e.g., FIG. 50), the actuator 3724 moves irreversibly the first switch 3972 from a first state (e.g., a state of electrical continuity) to a second state (e.g., a state of electrical discontinuity). Said yet another way, when the safety lock 3700 is moved from its first position to its second position, the actuator 3724 disrupts the first electrical conductor 3934.

The second actuation portion 3946 includes a second electrical conductor 3935 and defines an opening 3945, having a boundary 3949 and a tear propagation limit aperture 3948. As shown in FIGS. 36-39, the opening 3945 of the second actuation portion 3946 is configured to receive a portion of an actuator 3520 of the base 3510. The boundary 3949 of the opening 3945 has a discontinuous shape that includes a stress concentration riser 3947. The discontinuity and/or the stress concentration riser 3947 of the boundary 3949 can be of any suitable shape to cause the substrate 3924 to deform in a predetermined direction when the actuator 3520 of the base 3510 is moved in a proximal direction relative to the opening 3945, as shown by the arrow HH in FIG. 39.

The second electrical conductor 3935 includes a second switch 3973 disposed between the opening 3945 and the tear propagation limit aperture 3948, which can be, for example, a frangible portion of the second electrical conductor 3935. In use, when the base 3510 is moved from its first position to its second position (see e.g., FIG. 51), the actuator 3520 moves in a proximal direction, substantially parallel to a plane defined by a surface of the second actuation portion 3946 of the substrate 3924. The proximal movement of the actuator 3520 tears the second actuation portion 3946 of the substrate 3924, thereby separating the portion of the second electrical conductor 3935 including the second switch 3973. Said another way, when the base 3510 is moved from its first position to its second position, the actuator 3520 moves irreversibly the second switch 3973 from a first state (e.g., a state of electrical continuity) to a second state (e.g., a state of electrical discontinuity). The tear propagation limit aperture 3948 is configured to limit the propagation of the tear in the substrate 3924 in the proximal direction. Said another way, the tear propagation limit aperture 3948 is configured to ensure that the tear in the substrate 3924 does not extend beyond the tear propagation limit aperture 3948. The tear propagation limit aperture 3948 can be any shape configured to stop the propagation of a tear and/or disruption of the substrate 3924. For example, the tear propagation limit aperture 3948 can be oval shaped. In other embodiments, the proximal boundary of the tear propagation limit aperture 3948 can be reinforced to ensure that the tear in the substrate 3924 does not extend beyond the tear propagation limit aperture 3948.

In some embodiments, the safety lock 3700 and base 3510 can be configured to interact with mechanical and/or optical switches to produce an electronic output in a reversible manner.

The battery assembly 3962 of the electronic circuit system 3900 includes two batteries stacked on top of one another. In other embodiments, the electronic circuit system can include any number of batteries and/or any suitable type of power source. In some embodiments, for example, the battery assembly can include Lithium batteries such as, for example, CR1616, CR2016s, type AAA or the like. The battery assembly 3962 has a first surface 3964 and a second surface 3966. The first surface 3964 of the battery assembly 3962 can contact an electrical contact (not shown) disposed on the substrate 3924. The second surface 3966 of the battery assembly 3962 is configured to contact a contact portion 3918 of a distal end portion 3916 of a battery clip 3910. When both the electrical contact of the substrate 3924 and the contact portion 3918 of the distal end portion 3916 of the battery clip 3910 contact the battery assembly 3962, the batteries of the battery assembly 3962 are placed in electrical communication with the electronic circuit system 3900. Said another way, when the electrical contact of the substrate 3924 and the contact portion 3918 of the distal end portion 3916 of the battery clip 3910 contact the battery assembly 3962, the battery assembly 3962 is configured to supply power to the electronic circuit system 3900.

The battery clip 3910 (shown in FIG. 34) includes a proximal end portion 3912 and a distal end portion 3916. The proximal end portion 3912 defines a retention aperture

3913. The retention aperture 3913 is configured to receive a screw 3911 to couple the battery clip 3910 to the battery clip protrusion 3176 of the electronic circuit system housing 3170. In this manner, the battery clip protrusion 3176 maintains the position of the battery clip 3910 with respect to the electronic circuit system housing 3170 and/or the battery assembly 3962.

The distal end portion 3916 of the battery clip 3910 includes a contact portion 3918 and an angled portion 3917. As described above, the contact portion 3918 is configured to contact the second surface 3966 of the battery assembly 3962 to place the battery assembly 3962 in electrical communication with the electronic circuit system 3900. The angled portion 3917 of the distal end portion 3916 of the battery clip 3910 is configured to allow a proximal end portion 3236 of a battery isolation protrusion 3197 (see e.g., FIG. 41) to be disposed between the second surface 3966 of the battery assembly 3962 and the contact portion 3918 of the distal end portion 3916 of the battery clip 3910. When the battery isolation protrusion 3197 is disposed between the second surface 3966 of the battery assembly 3962 and the contact portion 3918 of the distal end portion 3916 of the battery clip 3910, the electrical path between the battery assembly 3962 and the remainder of the electrical circuit system 3900 is disrupted, thereby removing power from the electronic circuit system 3900. The contact portion 3918 of the distal end portion 3916 of the battery clip 3910 is biased such that when the battery isolation protrusion 3197 is removed, the contact portion 3918 will move into contact the second surface 3966 of the battery assembly 3962, thereby restoring electrical communication between the battery assembly 3962 and the electronic circuit system 3900. In some embodiments, the battery isolation protrusion 3197 can be repeatedly removed from between the second surface 3966 of the battery assembly 3962 and the contact portion 3918 of the distal end portion 3916 of the battery clip 3910 and reinserted. Said another way, the battery isolation protrusion 3197 and the battery clip 3910 collectively form a reversible on/off switch.

The audio output device 3956 of the electronic circuit system 3900 is configured to output audible sound to a user in response to use of the medical injector 3000. In some embodiments, the audible output device 3956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 3000 can have a network interface device (not shown) configured to operatively connect the electronic circuit system 3900 to a remote device (not shown) and/or a communications network (not shown). In this manner, the electronic circuit system 3900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 3900. In some embodiments, for example, the electronic circuit system 3900 can download information associated with a medical injector 3000, such as an expiration date, a recall notice, updated use instructions or the like. Similarly, in some embodiments, the electronic circuit system 3900 can upload information associated with the use of the medical injector 3000 via the network interface device (e.g., compliance information or the like).

Figure 40:
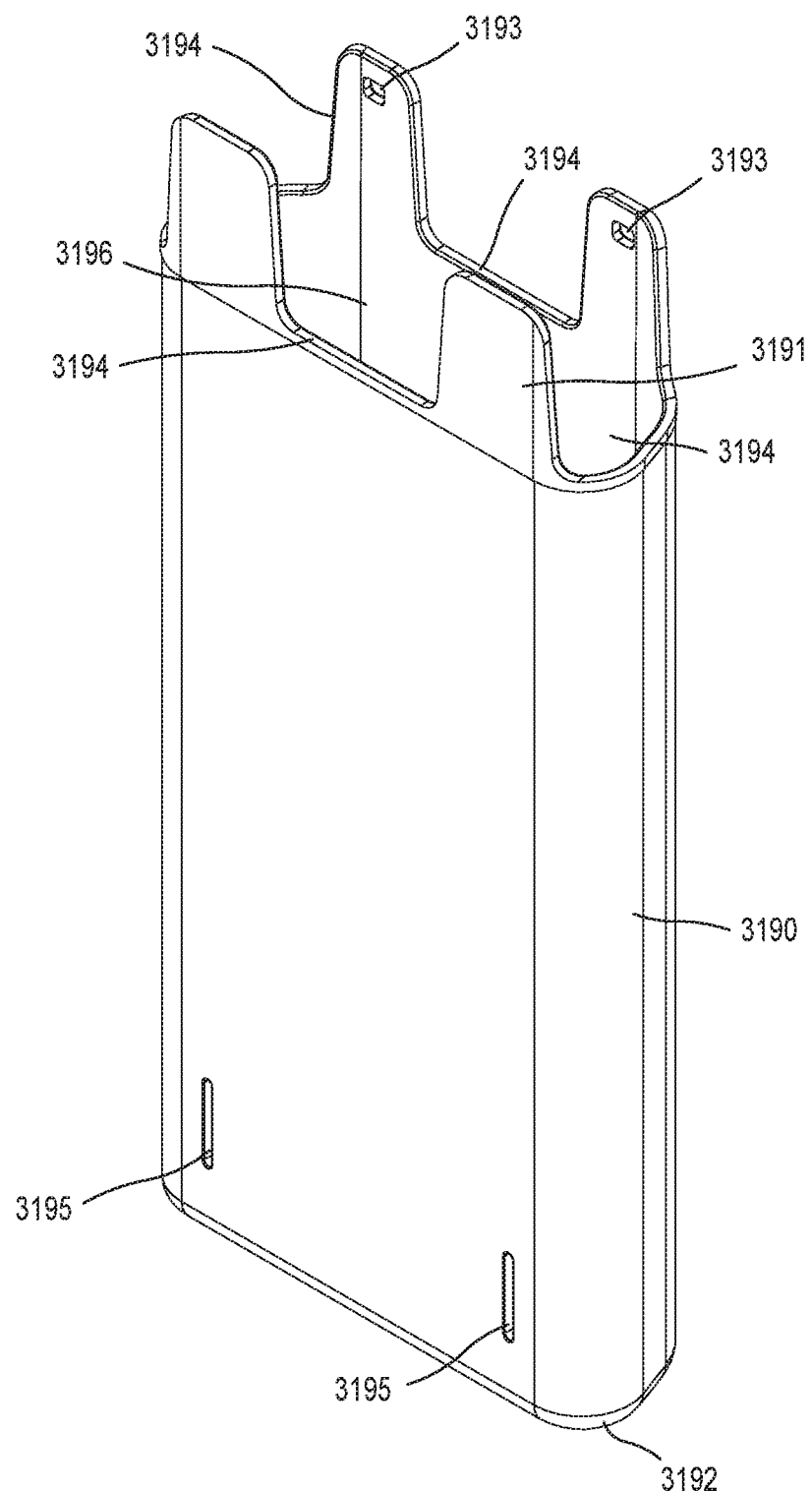
FIGS. 40 and 41 are perspective views of a cover of the medical injector illustrated in FIG. 9.
Figure 41:
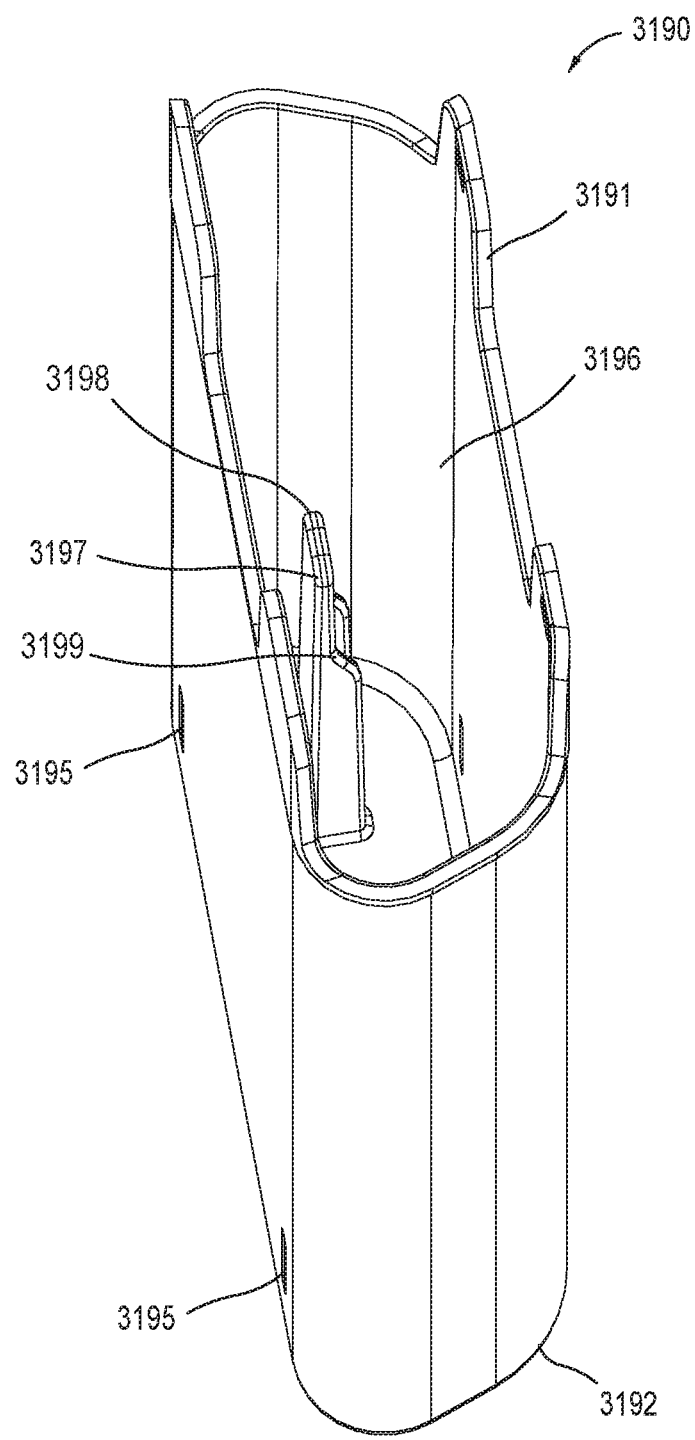
Figure 42:
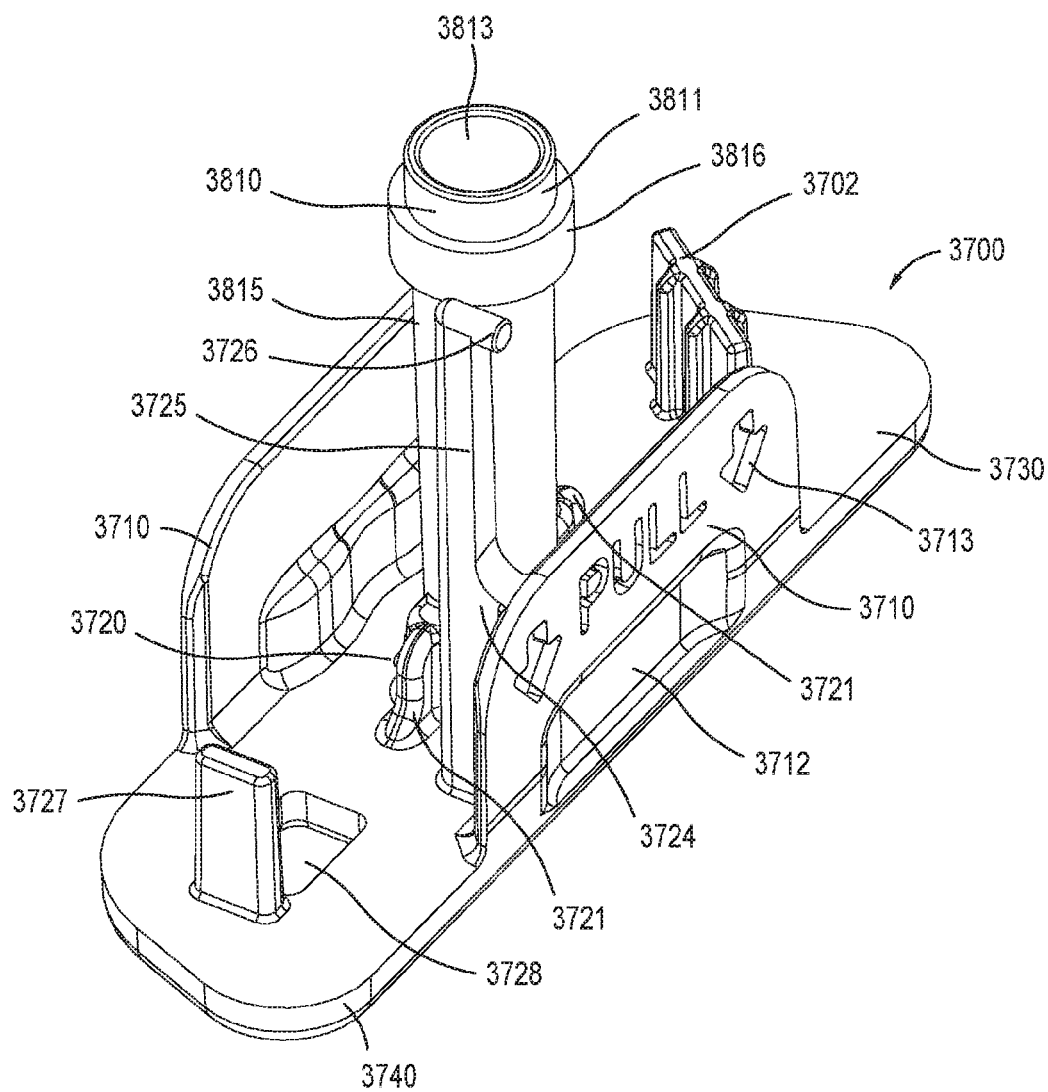
FIG. 42 is a perspective view of a safety lock of the medical injector illustrated in FIG. 9.

FIGS. 40 and 41 show the cover 3190 of the medical injector 3000. The cover 3190 includes a proximal end portion 3191 and a distal end portion 3192, and defines a cavity 3196. The cavity 3196 of the cover 3190 is configured to receive at least a portion of the housing 3100. Thus, when the portion of the housing 3100 is disposed within the cover 3190, the cover 3190 blocks an optical pathway between the medicament container 3200 and a region outside of the housing 3100. Similarly stated, when the portion of the housing 3100 is disposed within the cover 3190, the cover 3190 obstructs the first status indicator aperture 3130 and/or the second status indicator aperture 3160 of the housing 3100 to reduce the amount of light transmitted to the medicament 3220 within the medicament container 3200. In this manner, the life of the medicament 3220 can be extended by the prevention and/or reduction of degradation to the medicament 3220 that may be caused by ultra-violet radiation. In other embodiments, however, such those containing a medicament that is not sensitive to ultraviolet (UV) radiation, the cover 3190 can include viewing windows and/or openings that substantially correspond to the aperture 3130 and/or the aperture 3160.

The proximal end portion 3191 of the cover 3190 defines apertures 3193 configured to receive the cover retention protrusions 3104 of the housing 3100 (shown in FIGS. 10 and 12). In this manner, the apertures 3193 and the cover retention protrusions 3104 of the housing 3100 removably retain the cover 3190 about at least a portion of the housing 3100. Said another way, the apertures 3193 and the cover retention protrusions 3104 of the housing 3100 are configured such that the cover 3190 can be removed from a portion of the housing 3100 and then replaced about the portion of the housing 3100.

As described above, the electronic circuit system 3900 can be actuated when the housing 3100 is at least partially removed from the cover 3190. More particularly, the distal end portion 3192 of the cover 3190 includes the battery isolation protrusion 3197. The battery isolation protrusion 3197 includes a proximal end portion 3236 and a tapered portion 3237. The proximal end portion 3236 of the battery isolation protrusion 3197 is configured to be removably disposed between the second surface 3966 of the battery assembly 3962 and the contact portion 3918 of the distal end portion 3916 of the battery clip 3910, as described above.

The cover 3190 can be any suitable configuration and can include any suitable feature. For example, the cover 3190 includes openings 3195 and notches 3194. In some embodiments, the openings 3195 can receive inserts (not shown). The inserts can be flexible inserts and can increase friction between the cover 3190 and a surface. For example, the inserts can increase the friction between the cover 3190 and a surface on which the medical injector 3000 is placed, to prevent sliding. The notches 3194 are disposed at the proximal end of the cover 3190. In some embodiments, the notches 3194 can be used to reduce the material needed to manufacture the cover 3190.

FIGS. 42-46 show the safety lock 3700 of the medical injector 3000. The safety lock 3700 of the medical injector 3000 includes a proximal surface 3730, a distal surface 3740 opposite the proximal surface 3730 and a needle sheath 3810. The safety lock 3700 defines a needle sheath aperture 3703 and a battery isolation protrusion aperture 3728. The battery isolation protrusion aperture 3728 is configured to receive the battery isolation protrusion 3197 of the cover 3190 such that the battery isolation protrusion 3197 can be disposed within the electronic circuit system cavity 3137 and/or in engagement with the electronic circuit system 3900, as described above. Similarly stated, the battery isolation protrusion aperture 3728 of the safety lock 3700 is aligned with the battery isolation protrusion aperture 3135 of the housing 3100, such that the battery isolation protrusion 3197 can be disposed within the electronic circuit system cavity 3137 when the cover 3190 is disposed about a portion of the housing 3100.

The proximal surface 3730 of the safety lock 3700 includes a safety lock protrusion 3702, a stopper 3727, an actuator 3724, two opposing pull-tabs 3710 and an engagement portion 3720. As described above, when the safety lock 3700 is in a first (locked) position, the safety lock protrusion 3702 is configured to be disposed in the opening 3556 defined by the extensions 3553 of the distal end portion 3552 of the release member 3550 (see e.g., FIG. 21). Accordingly, the safety lock protrusion 3702 is configured to prevent the extensions 3553 from moving closer to each other, thereby preventing proximal movement of the release member 3550 and/or delivery of the medicament 3220. The stopper 3727 of the safety lock 3700 is a protrusion extending from the proximal surface 3730 of the safety lock 3700. The stopper 3727 is configured to contact a portion of the housing 3100 to limit the proximal movement of the safety lock 3700 relative to the housing 3100. In other embodiments, the stopper 3727 can be any structure configured to limit the proximal movement of the safety lock 3700.

The actuator 3724 of the safety lock 3700 has an elongated portion 3725 and a protrusion 3726. The elongated portion 3725 extends in a proximal direction from the proximal surface 3730. In this manner, the elongated portion 3725 can extend through a safety lock actuator opening 3524 of the base 3510 (see e.g., FIG. 47) and within the safety lock actuator groove 3133 of the housing 3100 and the safety lock actuator groove 3179 of the electronic circuit system housing 3170. The protrusion 3726 extends in a direction substantially transverse to the elongated portion 3725 and/or substantially parallel to the proximal surface 3730 of the safety lock 3700. As described above, the opening 3928 of the first actuation portion 3926 of the printed circuit board 3922 is configured to receive the protrusion 3726 of the actuator 3724 of the safety lock 3700.

The pull-tabs 3710 of the safety lock 3700 include a grip portion 3712 and indicia 3713. The grip portion 3712 of the pull-tabs 3710 provides an area for the user to grip and/or remove the safety lock 3700 from the rest of the medicament delivery system 3700. The indicia 3713 provide instruction on how to remove the safety lock 3700. The distal end surface 3740 also includes indicia 3741 (see e.g., FIG. 44). In some embodiments, for example, indicia can indicate the direction the user should pull the safety lock 3700 to remove the safety lock 3700.

The engagement portion 3720 of the safety lock 3700 includes engagement members 3721. The engagement members 3721 extend in a proximal direction from the proximal surface 3730. The engagement members 3721 have tabs 3722 that extend from a surface of the engagement members 3721. The tabs 3722 are configured to engage an outer surface 3815 of a distal end portion 3812 of the needle sheath 3810.

Figure 45:
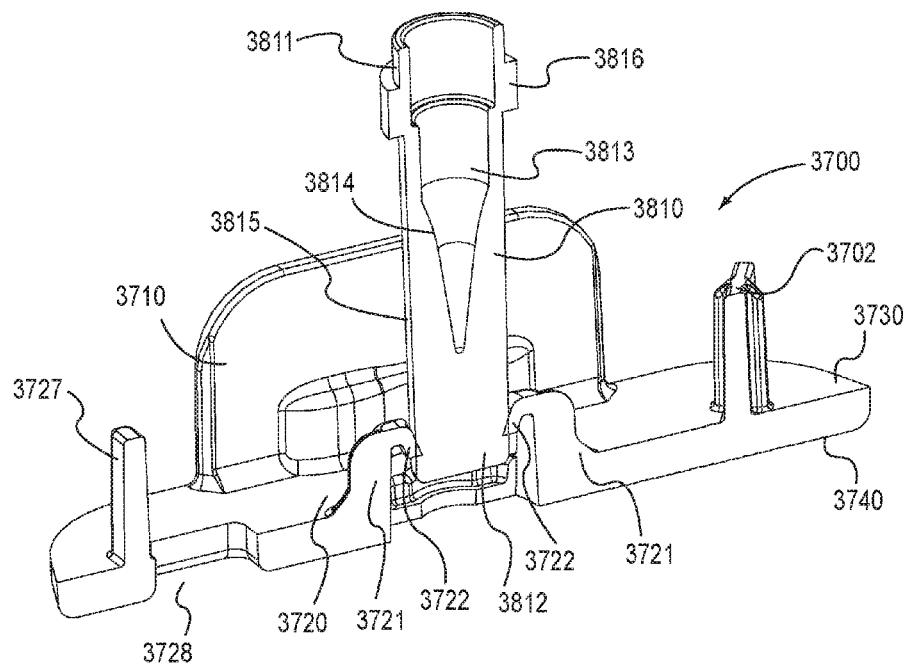
FIG. 45 is a cross-sectional view of the safety lock of the medical injector illustrated in FIG. 42.
Figure 46:
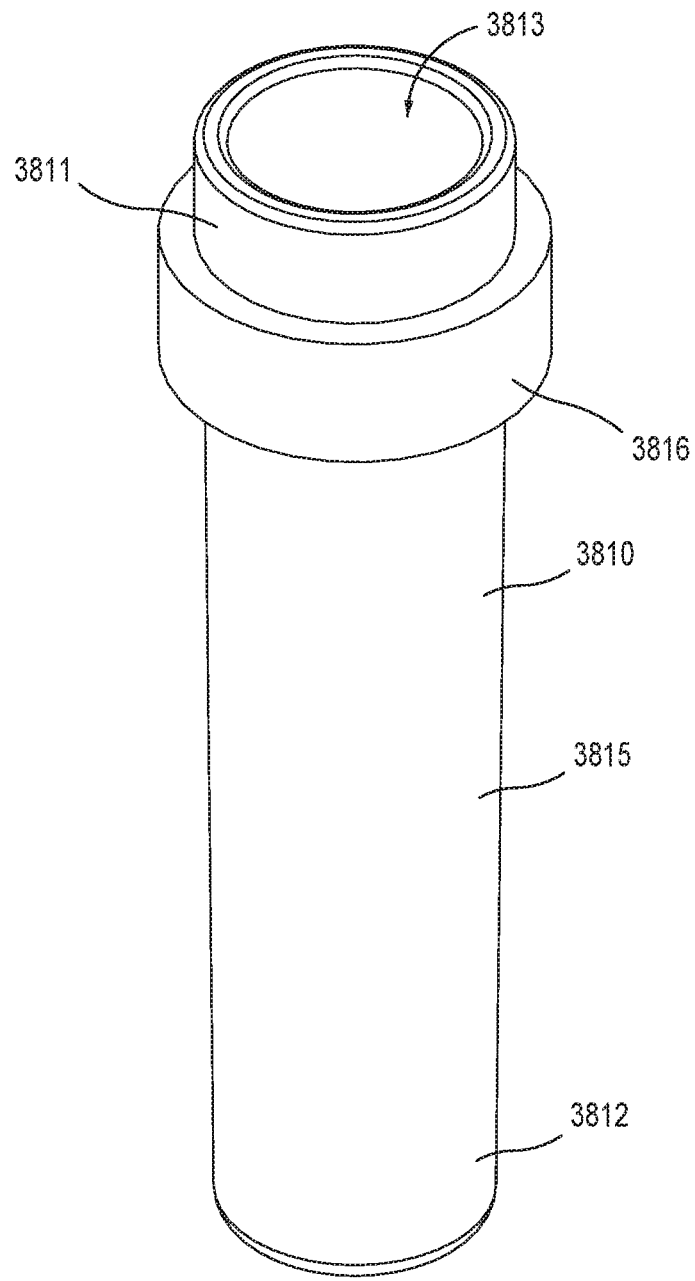
FIG. 46 is a perspective view of a needle sheath of the safety lock of the medical injector illustrated in FIG. 42.

As shown in FIGS. 45 and 46, the needle sheath 3810 includes the distal end portion 3812, a proximal end portion 3811 and a rib 3816. The needle sheath 3810 also defines a bore 3813. The bore 3813 is defined by a contoured portion 3814 of the needle sheath 3810, and is configured to receive the needle 3216 and/or a distal end portion of the 3213 of the medicament container 3200. The inner portion of the needle sheath 3810 defines a friction fit with the distal end portion 3213 of the medicament container 3200. In this manner, the needle sheath 3810 can protect the user from the needle 3216 and/or can keep the needle 3216 sterile before the user actuates the medical injector 3000. The proximal end portion 3811 of the needle sheath is configured to contact the body 3210 of the medicament container 3200.

The distal end portion 3812 of the needle sheath 3810 is configured to be inserted into a space defined between the tabs 3722 of the engagement members 3721 of the safety lock 3700. The tabs 3722 are angled and/or bent towards the distal direction to allow the distal end portion 3812 of the needle sheath 3810 to move between the engagement members 3721 in a distal direction, but not in a proximal direction. Similarly stated, the tabs 3722 include an edge that contacts the outer surface 3815 of the needle sheath 3810 to prevent the safety lock 3700 from moving in a distal direction relative to the needle sheath 3810. In this manner, the needle sheath 3810 is removed from the needle 3216 when the safety lock 3700 is moved in a distal direction with respect to the housing 3100 (see e.g., FIG. 50).

Figure 47:
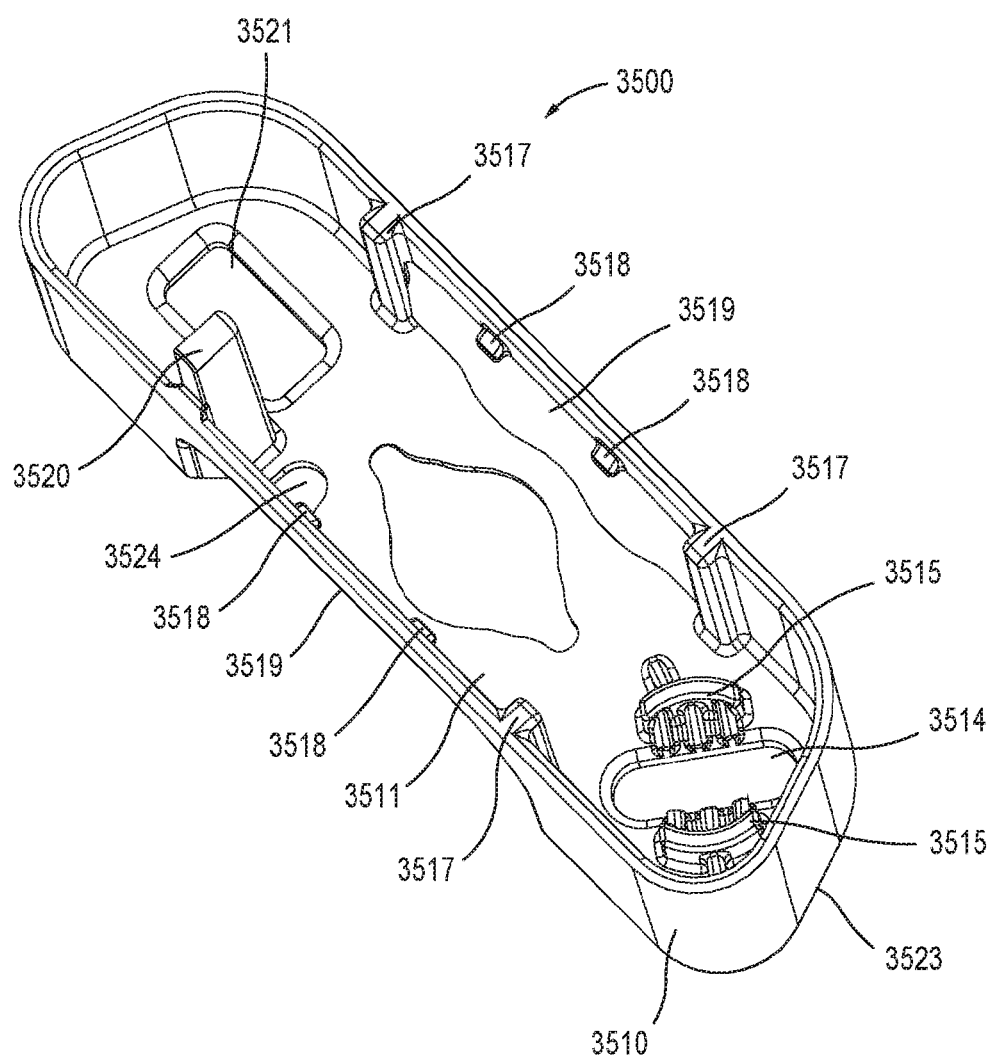
FIG. 47 is a perspective view of a base of the medical injector illustrated in FIG. 9.
Figure 48:
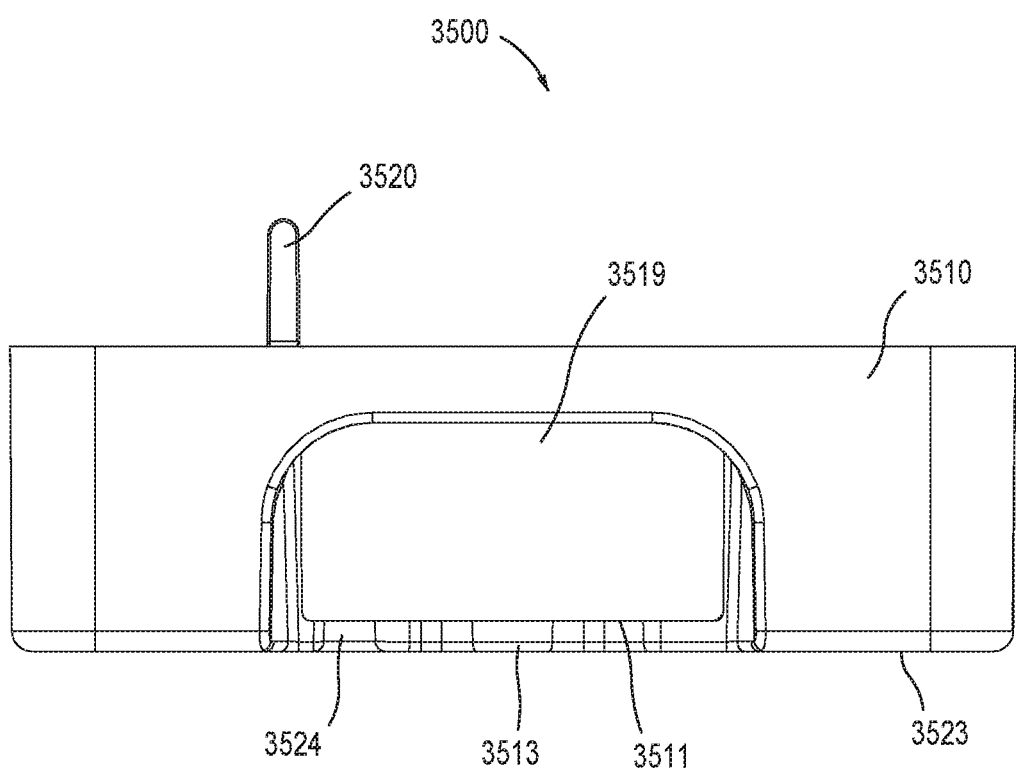
FIG. 48 is a front view of the base of the medical injector illustrated in FIG. 47.

FIGS. 47 and 48 show the base (or actuator) 3510 of the medical injector 3000. The base 3510 includes a proximal surface 3511, a distal surface 3523 and base connection knobs 3518. The base 3510 defines a needle aperture 3513, a safety lock protrusion aperture 3514, a battery isolation protrusion aperture 3521, a safety lock actuator opening 3524 and pull-tab openings 3519. The needle aperture 3513 is configured to receive the needle 3216 when the medical injector 3000 is actuated. The safety lock protrusion aperture 3514 of the base 3510 receives the safety lock protrusion 3702 of the safety lock 3700 when the safety lock 3700 is coupled to the housing 3100 and/or the base 3510. The battery isolation protrusion aperture 3521 of the base 3510 receives the battery isolation protrusion 3197 of the cover 3190 and the stopper 3727 of the safety lock 3700. The safety lock actuator opening 3524 receives the safety lock actuator 3724 of the safety lock 3700. The pull-tab openings 3519 are configured to receive the pull-tabs 3710 of the safety lock 3700.

The proximal surface 3511 of the base 3510 includes a protrusion 3520, guide members 3517 and protrusions 3515. The protrusion 3520 is configured to engage the substrate 3924 of the electronic circuit system 3900. As described above, the opening 3945 of the second actuation portion 3946 of the printed circuit board 3922 is configured to receive the actuator 3520 of the base 3510. The guide members 3517 of the base 3510 engage and/or slide within the base rail grooves 3114 of the housing 3100, as described above. The protrusions 3515 of the base 3510 engage the tapered surfaces 3557 of the extensions 3553 of the release member 3550. As described in further detail herein, when the safety lock 3700 is removed and the base 3510 is moved in a proximal direction with respect to the housing 3100, the protrusions 3515 of the base 3510 are configured to move the extensions 3553 of the release member 3550 closer to each other, actuating the medicament delivery mechanism 3300. As described above, the base connection knobs 3518 engage the base retention recesses 3134A, 3134B in a way that allows proximal movement of the base 3510 but limits distal movement of the base 3510.

Figure 49:
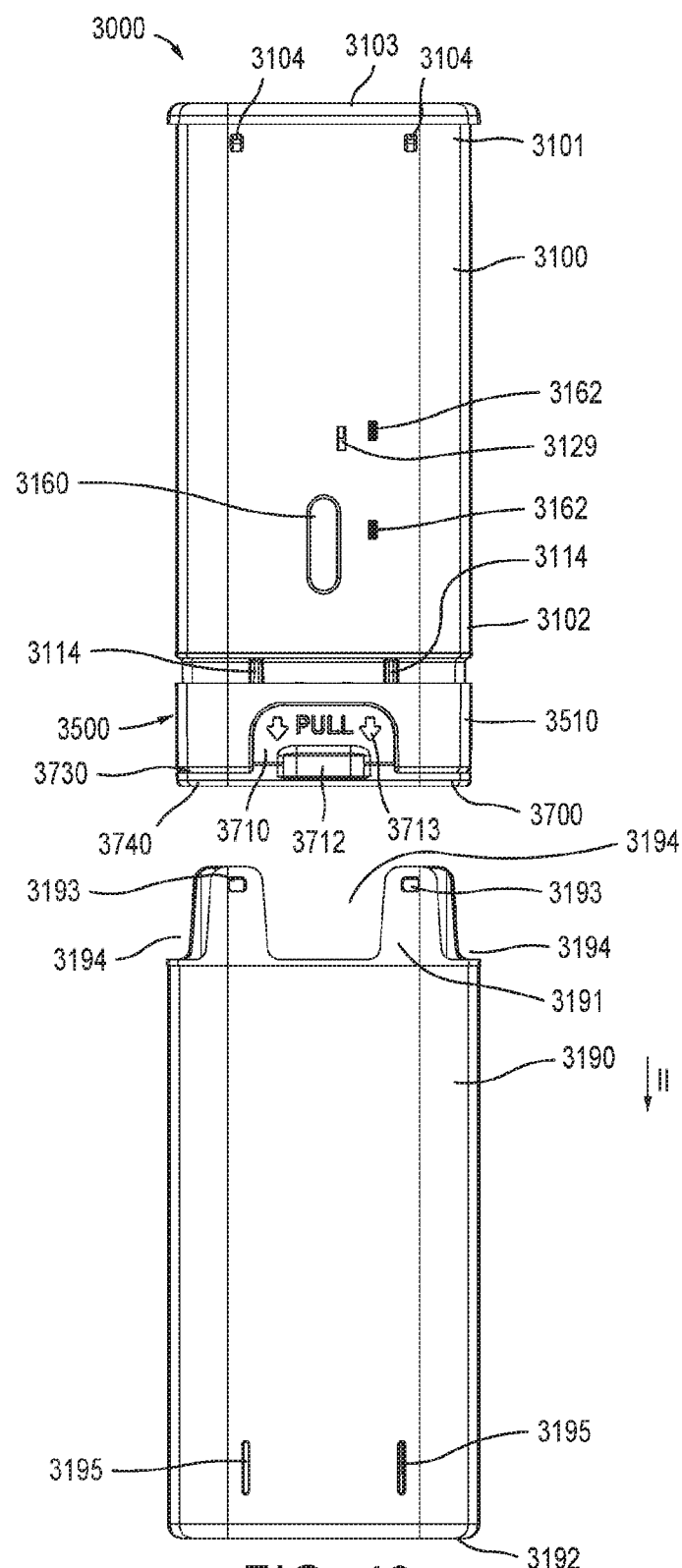
FIG. 49 is a back view of the medical injector illustrated in FIG. 9 in a second configuration.
Figure 50:
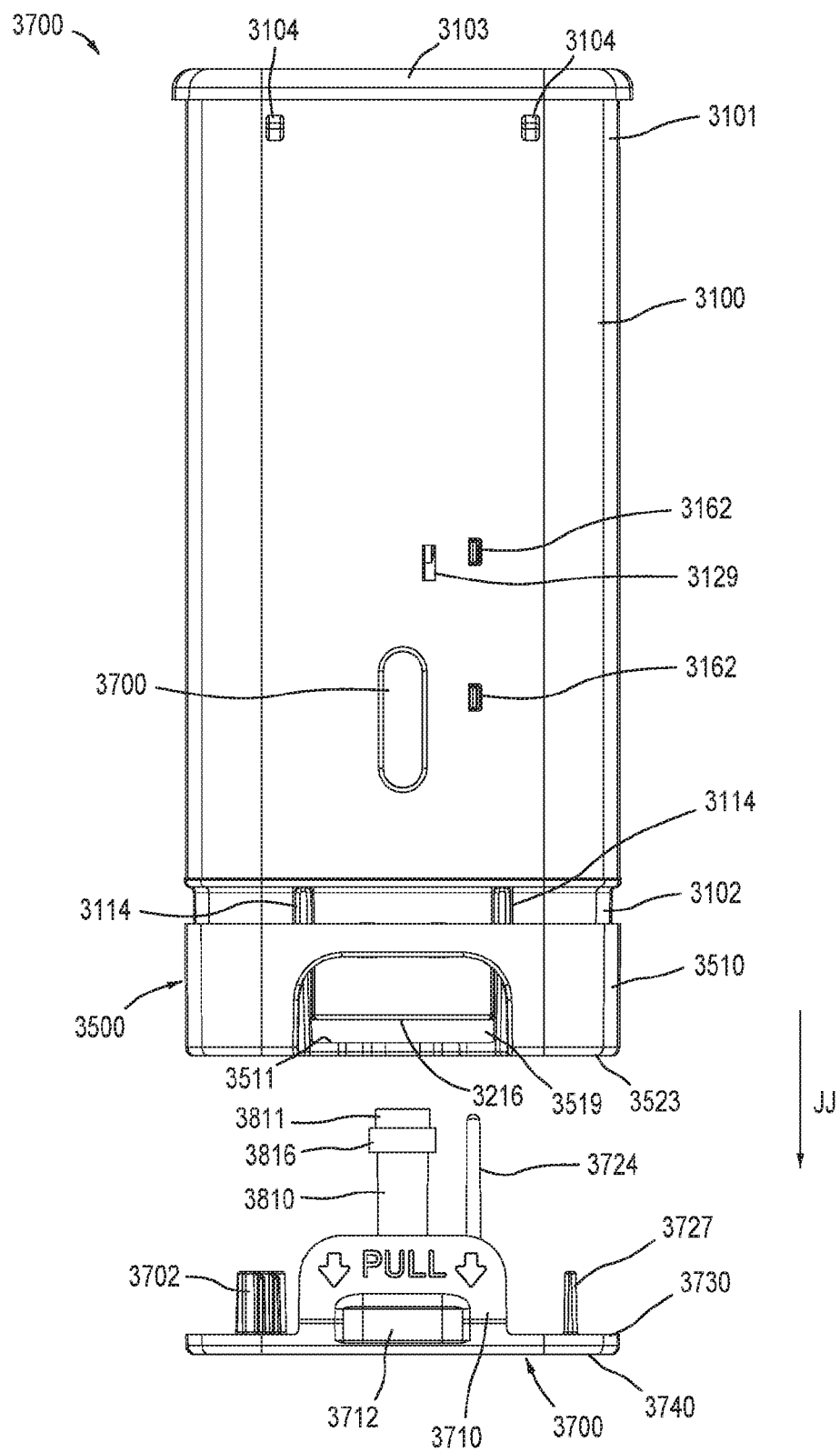
FIG. 50 is a back view of the medical injector illustrated in FIG. 9 in a third configuration.

As shown in FIG. 49, the medical injector 3000 is first enabled by moving the medicament delivery device 3000 from a first configuration to a second configuration by moving the cover 3190 from a first position to a second position. The cover 3190 is moved from the first position to the second position by moving it with respect to the housing 3100 in the direction shown by the arrow II in FIG. 49. When the cover 3190 is moved with respect to the housing 3100 in the direction II, the battery isolation protrusion 3197 is removed from the area between the battery clip 3910 and the second surface 3966 of the battery assembly 3962. In this manner, the battery assembly 3962 is operatively coupled to the electronic circuit system 3900 when the cover 3190 is removed, thereby providing power to the electronic circuit system 3900. Similarly stated, this arrangement allows the electronic circuit system 3900 to be actuated when the cover 3190 is removed.

When power is provided, as described above, the electronic circuit system 3900 can output one or more predetermined electronic outputs. For example, in some embodiments, the electronic circuit system 3900 can output an electronic signal associated with recorded speech to the audible output device 3956. Such an electronic signal can be, for example, associated with a .WAV file that contains a recorded instruction, instructing the user in the operation of the medical injector 3000. Such an instruction can state, for example, "Remove the safety tab near the base of the auto-injector." The electronic circuit system 3900 can simultaneously output an electronic signal to one and/or both of the LEDs 3958A, 3958B thereby causing one and/or both of the LEDs 3958A, 3958B to flash a particular color. In this manner, the electronic circuit system 3900 can provide both audible and visual instructions to assist the user in the initial operation of the medical injector 3000.

In other embodiments, the electronic circuit system 3900 can output an electronic output associated with a description and/or status of the medical injector 3000 and/or the medicament 3220 contained therein. For example, in some embodiments, the electronic circuit system 3900 can output an audible message indicating the symptoms for which the medicament 3220 should be administered, the expiration date of the medicament 3220, the dosage of the medicament 3220 or the like.

As described above, the medical injector 3000 can be repeatedly moved between the first configuration and the second configuration when the cover 3190 is moved repeatedly between the first position and the second position respectively. Said another way, the cover 3190 can be removed and replaced about the housing 3100 any number of times. When the cover 3190 is moved from the second position to the first position, the battery isolation protrusion 3197 is inserted between the battery clip 3910 and the second surface 3966 of the battery assembly 3962, deactivating the electronic circuit system 3900. When the cover is moved from the first position to the second position a second time, the electronic circuit system 3900 is once again activated. In this manner, the cover 3190 can be removed and the electronic circuit system 3900 can output an electronic output without compromising the sterility of the needle 3216.

After the cover 3190 is removed from the housing 3100, the medical injector 3000 can be moved from the second configuration (FIG. 49) to a third configuration (FIG. 50) by moving the safety lock 3700 from a first position to a second position. The safety lock 3700 is moved from a first position to a second position by moving the safety lock 3700 with respect to the housing 3100 in the direction shown by the arrow JJ in FIG. 50. When the safety lock 3700 is moved from the first position to the second position, the safety lock protrusion 3702 is removed from between the extensions 3553 of the release member 3550, thereby enabling the medicament delivery mechanism 3300. Moreover, as shown in FIGS. 37 and 38, when the safety lock 3700 is moved from the housing 3100, the actuator 3724 of the safety lock 3700 moves in the direction GG as shown in FIG. 38, irreversibly moving the first switch 3972 from a first state (e.g., a state of electrical continuity) to a second state (e.g., a state of electrical discontinuity). When the actuator 3724 of the safety lock 3700 moves irreversibly the first switch 3972 of the electronic circuit system 3900 to the second state, the electronic circuit system 3900 can output one or more predetermined electronic outputs. For example, in some embodiments, a processor (not shown) can output an electronic signal associated with recorded speech to the audible output device 3956. Such an electronic signal can be, for example, associated with a recorded message notifying the user of the status of the medical injector 3000. Such a status message can state, for example, "If ready to use the medical injector, pull off the red safety guard." The electronic circuit system 3900 can also simultaneously output an electronic signal to one and/or both of the LEDs 3958A, 3958B, thereby causing one and/or both of the LEDs 3958A, 3958B to stop flashing, change color or the like.

In some embodiments, the first actuation portion 3926 and the actuator 3724 can be configured such that the actuator 3724 must move a predetermined distance before the actuator 3724 engages the boundary 3929 of the opening 3928. For example, in some embodiments, the actuator 3724 must move approximately 0.200 inches before the actuator 3724 engages the boundary 3929 of the opening 3928. In this manner, the safety lock 3700 can be moved slightly without irreversibly moving the first switch 3972 of the electronic circuit system 3900 to the second state. Accordingly, this arrangement will permit the user to inadvertently and/or accidentally move the safety lock 3700 without actuating the electronic circuit system 3900.

In some embodiments, the electronic circuit system 3900 can be configured to output the status message for a predetermined time period, such as, for example, five seconds. After the predetermined time period has elapsed, the electronic circuit system 3900 can output an audible message further instructing the user in the operation of the medical injector 3000. Such an instruction can state, for example, "Place the base of the auto-injector against the patient's thigh. To complete the injection, press the base firmly against the patient's thigh." In some embodiments, the electronic circuit system 3900 can simultaneously output an electronic signal to one and/or both of the LEDs 3958A, 3958B, thereby causing one and/or both of the LEDs 3958A, 3958B to flash a particular color. In this manner, the electronic circuit system 3900 can provide both audible and/or visual instructions to assist the user in the placement and actuation of the medical injector 3000. In some embodiments, the electronic circuit system 3900 can be configured to repeat the instructions after a predetermined time period has elapsed.

As described above, in other embodiments, the medical injector 3000 can have a network interface device (not shown) configured to operatively connect the electronic circuit system 3900 to a remote device (not shown) and/or a communications network (not shown). In this manner, the electronic circuit system 3900 can send a wireless signal notifying a remote device that the safety lock 3700 of the medical injector 3000 has been removed and that the medical injector 3000 has been armed. In other embodiments, the electronic circuit system 3900 can send a wireless signal (e.g., a wireless 911 call) notifying an emergency responder that the medical injector 3000 has been armed, for example, via removal of the safety lock 3700.

After the safety lock 3700 is moved from the first position to the second position, the medical injector 3000 can be moved from the third configuration (FIG. 50) to a fourth configuration (FIG. 51) by moving the base 3510 from a first position to a second position. Similarly stated, the medical injector 3000 can be actuated by the system actuator assembly 3500 by moving the base 3510 proximally relative to the housing 3100. The base 3510 is moved from its first position to its second position by placing the medical injector 3000 against the body of the patient and moving the base 3510 with respect to the housing 3100 in the direction shown by the arrow KK in FIG. 51. Moving the base 3510 from the first position to the second position causes the protrusions 3515 on the proximal surface 3511 of the base 3510 to engage the tapered surfaces 3557 of the extensions 3553 of the release member 3550, thereby moving the extensions 3313 together. The inward movement of the extensions 3553 causes engagement surface 3554 of the release member 3550 to become disengaged from the base release surface 3126 of the housing 3100, thereby allowing the release member 3550 to be moved proximally along its longitudinal axis as the spring 3576 expands.

Figure 51:
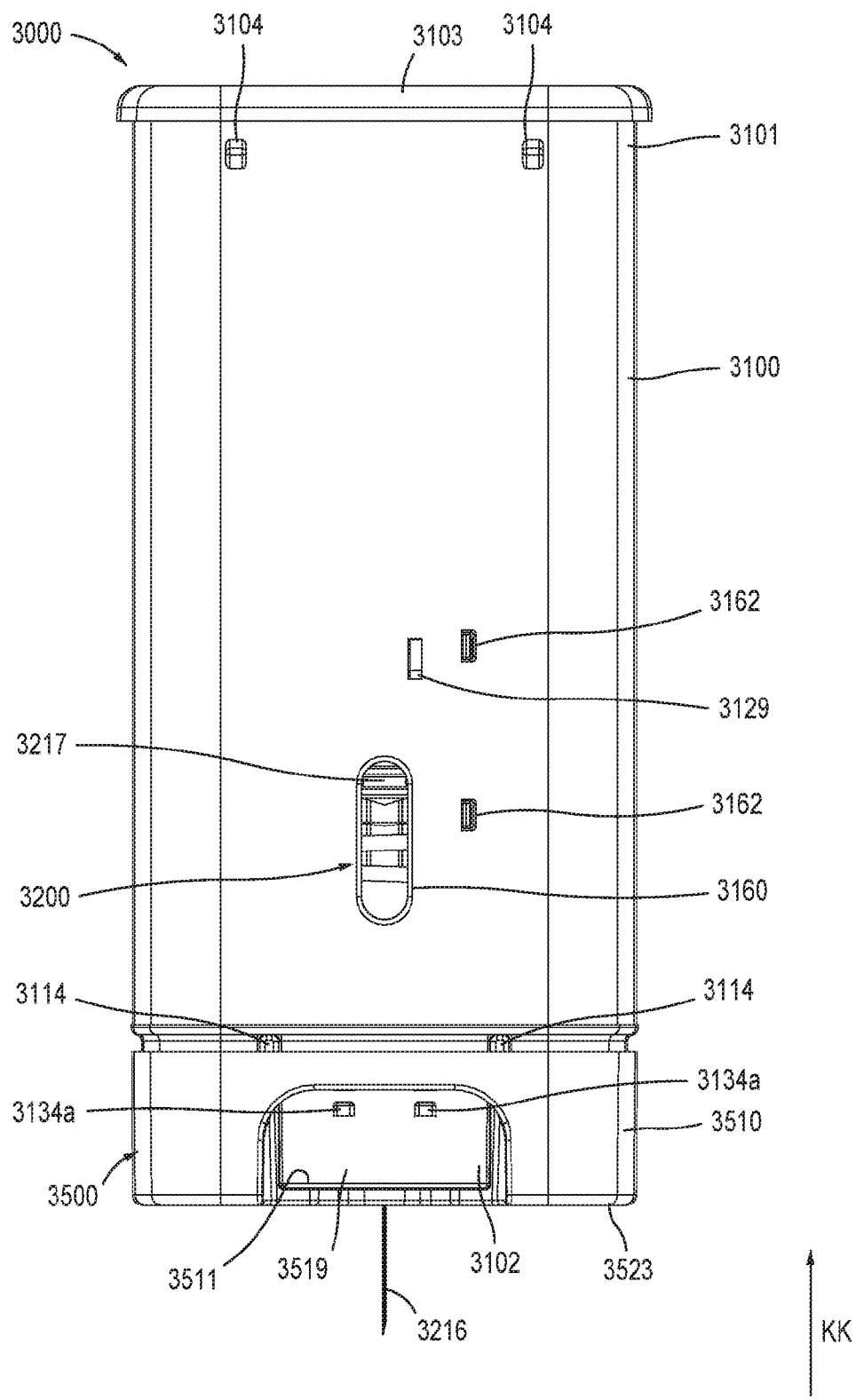
FIG. 51 is a back view of the medical injector illustrated in FIG. 9 in a fourth configuration (i.e., the needle insertion configuration).

When the base 3510 is moved from the first position to the second position, the system actuator assembly 3500 actuates the medicament delivery mechanism 3300, thereby placing the medical injector 3000 in its fourth configuration (i.e., the needle insertion configuration), as shown in FIGS. 51 and 52. More particularly, when the medical injector 3000 is in its fourth configuration, the puncturer 3575 of the release member 3550 is in contact with and/or disposed through the frangible seal 3413 of the gas container 3410.

After the frangible seal 3413 has been punctured, an actuating portion of a compressed gas flows from the gas container 3410, via the gas passageway 3156 and into the medicament cavity 3139. The gas applies gas pressure to the piston member 3330 causing the piston member 3330 and the carrier 3370 to move in a distal direction within the medicament cavity 3139, as shown by the arrow LL in FIG. 52. When the carrier 3370 moves distally within the medicament cavity 3139, the carrier 3370 and the medicament container 3200 are in a first configuration and collectively move toward a second position. In this manner, the medicament container 3200 and the needle 3216 contemporaneously move with piston member 3330 and/or the carrier 3370 in a distal direction. The movement of the needle 3216 in a distal direction causes the distal end portion of the needle 3216 to exit the housing 3100 and enter the body of a patient prior to administering the medicament 3220.

As described above, at least a portion of the force exerted by the compressed gas within the gas chamber upon the piston member 3330 is transferred to the first shoulder 3377 of the carrier 3370 by the contact between the first surface 3341 of the piston member 3330 and the engagement portion 3379 of the carrier 3370. This arrangement further allows at least a portion of the force to be transferred to the flange 3214 of the medicament container 3200. In this manner, the application of the force on the piston member 3330 results in the distal movement of the carrier 3370 and the medicament container 3200. Moreover, because the distal end portion 3332 of the piston member 3330 is configured such that the second surface 3342 is spaced apart from the elastomeric member 3217 within the medicament container 3200 (see e.g., FIG. 27), the force is not transferred to the elastomeric member 3217. In this manner, the elastomeric member 3217 is isolated from the piston member 3330 when the medicament container 3200 is moving distally within the housing 3100, which reduces and/or eliminates injection or leakage of the medicament 3220 from the medicament container 3200 during the needle insertion operation.

After the carrier 3370 and/or the needle 3216 have moved within the medicament cavity 3139 a predetermined distance, the carrier 3370 and the medicament container 3200 are moved from the first configuration to a second configuration. For example, in some embodiments, the retraction spring 3351 can be fully compressed and prevent the carrier 3370 from moving further in the distal direction. In other embodiments, a portion of the medicament container 3200 and/or a portion of the carrier 3370 can contact the housing 3100 when the needle insertion operation is completed, thereby limiting further distal movement of the carrier 3370, medicament container 3200 and/or the needle 3216. When the distal movement of the carrier 3370 is prevented, the gas within the gas chamber continues to apply gas pressure to the piston member 3330 causing the first surface 3341 of the piston member 3330 to deform a portion of the engagement portion 3379. Similarly stated, when the distal movement of the carrier 3370 is complete, the force applied by the pressurized gas exceeds a threshold value, thereby causing the piston member 3330 to deform the engagement portion 3379. In this manner, the engagement portion 3379 deforms (see e.g., FIG. 55) to place the carrier 3370 in its second configuration, in which the first surface 3341 of the piston member 3330 is no longer in contact with the engagement portion 3379 and/or the first shoulder 3377.

When the carrier 3370 is in the second configuration, the piston member 3330 continues to move in the distal direction relative to the carrier 3370 and/or the medicament container 3200. Similarly stated, the piston member 3330 moves with the carrier 3370 during the insertion operation (i.e., when the carrier 3370 is in its first configuration) and the piston member 3330 moves relative to the carrier 3370 (and the medicament container 3200) during the injection operation (i.e., when the carrier 3370 is in its second configuration). More particularly, after the engagement portion 3379 deforms, the piston rod 3333 of the piston member 3330 moves within the piston rod opening 3384 of the carrier 3370 and within the medicament container 3200, as shown by the arrow MM in FIG. 53. As the piston rod 3333 of the piston member 3330 moves within the carrier 3370 and medicament container 3200, the second surface 3342 of the piston rod 3333 contacts the elastomeric member 3217 and generates a pressure upon the medicament 3220 contained within the medicament container 3200, thereby allowing at least a portion of the medicament 3220 to flow out of the medicament container 3200 via the needle 3216. The medicament 3220 is delivered to a body of a user via the medicament delivery path defined by the medicament container 3200 and the needle 3216.

Figure 54:
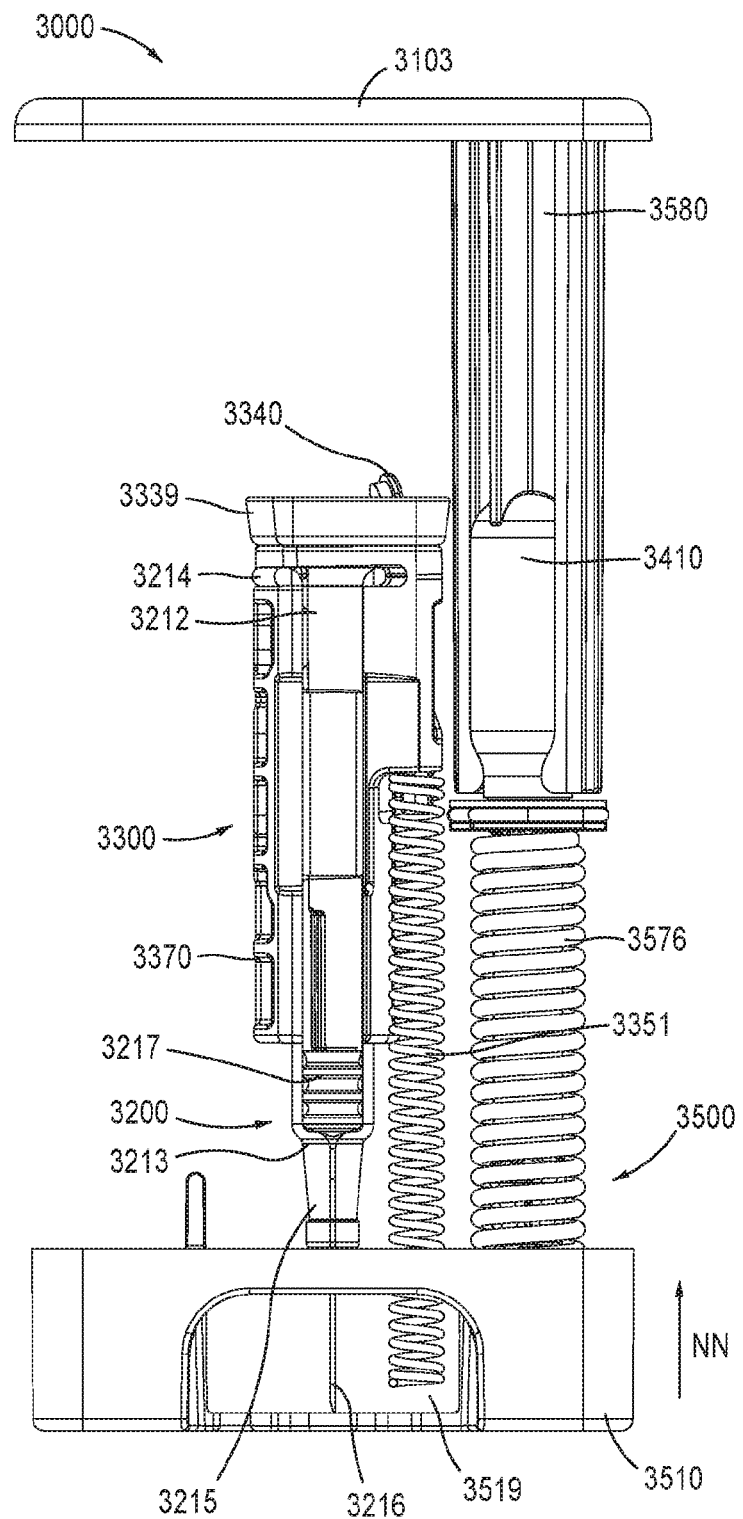
FIG. 54 is a front view of the medical injector illustrated in FIG. 9 in a sixth configuration (i.e., the retraction configuration).
Figure 55:
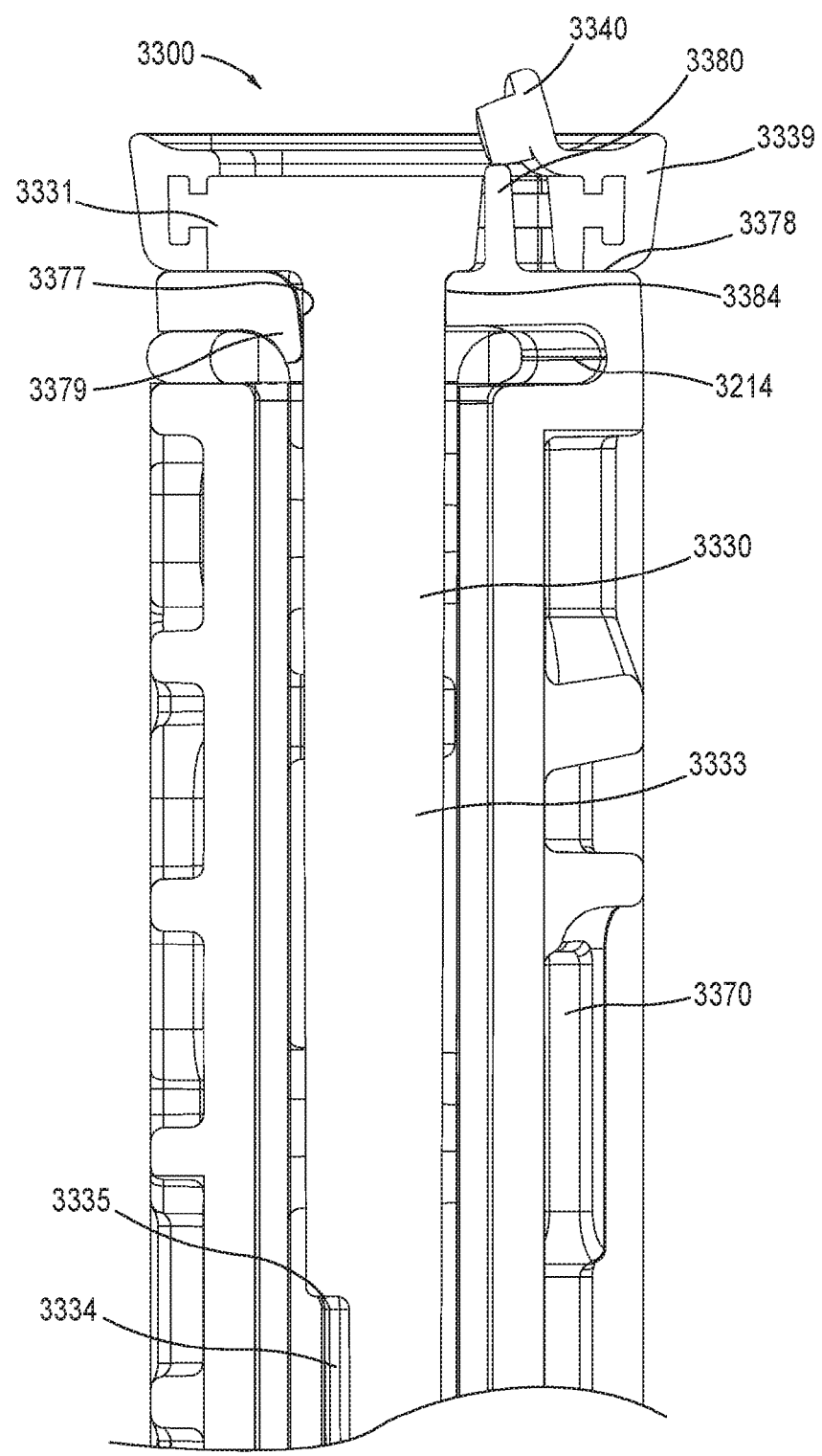
FIG. 55 is an enlarged front cross-sectional view of a portion the medical injector illustrated in FIG. 9 in the sixth configuration (i.e., the retraction configuration).

As shown in FIGS. 54 and 55, after the piston member 3330 moves a predetermined distance within the medicament container 3200, the gas valve actuator 3380 of the carrier 3370 engages the gas relief valve 3340 (see e.g., FIG. 55) of the piston member 3330 thereby allowing the pressurized gas contained within the gas chamber (i.e., the volume within the medicament cavity 3139 between the proximal end of the housing 3100 and the proximal end of the piston member 3330) to escape. Similarly stated, as the gas valve actuator 3380 of the carrier 3370 engages the gas relief valve 3340 of the piston member 3330, the pressure within the housing 3100 is reduced, thereby ending the injection event. In this manner, the pre-injection distance between the proximal end portion 3331 of the piston member 3330 and the gas valve actuator 3380 of the carrier 3370 can be adjusted to control the amount of the medicament 3220 to be injected. After the gas pressure within the medicament cavity 3139 decreases below a certain level, the force exerted by the retraction spring 3351 on the engagement portion 3382 of the carrier 3370 is sufficient to cause the carrier 3370 to move proximally within the housing 3100 (i.e., to retract). Additionally, the second shoulder 3381 engages the distal surface of the flange 3214 of the medicament container 3200 to move the medicament container 3200 proximally within the housing 3100, as shown by the arrow NN in FIG. 54.

As described above, the protrusion 3520 of the base 3510 actuates the electronic circuit 3900 to trigger a predetermined output or sequence of outputs when the base 3510 is moved from its first position to its second position (see, e.g., FIGS. 35-39). When the protrusion 3520 is moved in a proximal direction relative to the opening 3945, as shown by the arrow HH in FIG. 39, the electronic circuit system 3900 is actuated to output one or more predetermined electronic outputs. For example, in some embodiments, the electronic circuit system 3900 can output an electronic signal associated with recorded speech to the audible output device 3956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 3000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 3900 can also simultaneously output an electronic signal to one and/or both LEDs 3958A, 3958B, thereby causing one and/or both LEDs 3958A, 3958B to stop flashing, change color or the like, to provide a visual indication that the injection is complete. In other embodiments, the electronic circuit system 3900 can send a wireless signal notifying a remote device that the injection is complete. In this manner, a patient's compliance and/or adherence with the use of the system can be monitored.

In some embodiments, the second actuation portion 3946 and the protrusion 3520 of the base 3510 can be configured such that the base 3510 and/or the actuator 3520 must move a predetermined distance before the protrusion 3520 engages the boundary 3949 of the opening 3945. For example, in some embodiments, the protrusion 3520 must move approximately 0.200 inches before the actuator 3520 engages the boundary 3949 of the opening 3945. In this manner, the base 3510 can be moved slightly without irreversibly moving the second switch 3973 of the electronic circuit system 3900 to the second state. Accordingly, this arrangement will permit the user to inadvertently and/or accidentally move the base 3510 without actuating the electronic circuit system 3900.

While specific components are discussed with respect to the medical injector 3000, in other embodiments, some components can be modified and/or removed without substantially changing the medicament injection event. For example, FIGS. 56-59 show a portion of a medical injector 4000. That does not include an electronic circuit system (e.g., an electronic circuit system substantially similar to the electronic circuit system 3900 included in the medical injector 3000). In some embodiments, the electronic circuit system can be removed to limit the cost of the medical injector 4000. In those embodiments devoid of an electronic circuit system, for example the medical injector 4000 shown in FIGS. 56 and 57, the medical injector 4000 can still include components and/or portions configured to engage and/or interact with an electronic circuit system. For example, the medical injector 4000 includes a battery isolation protrusion 4197 of a cover 4190. In this manner, the cost of production and tooling can be reduced by reducing the number of component variations. Additionally, an electronic circuit system (e.g., similar to the electronic circuit system 3900 included in the medical injector 3000) can be easily added to the medical injector 4000 and disposed within an electronic circuit system cavity 4137 defined by the housing 4100.

Figure 56:
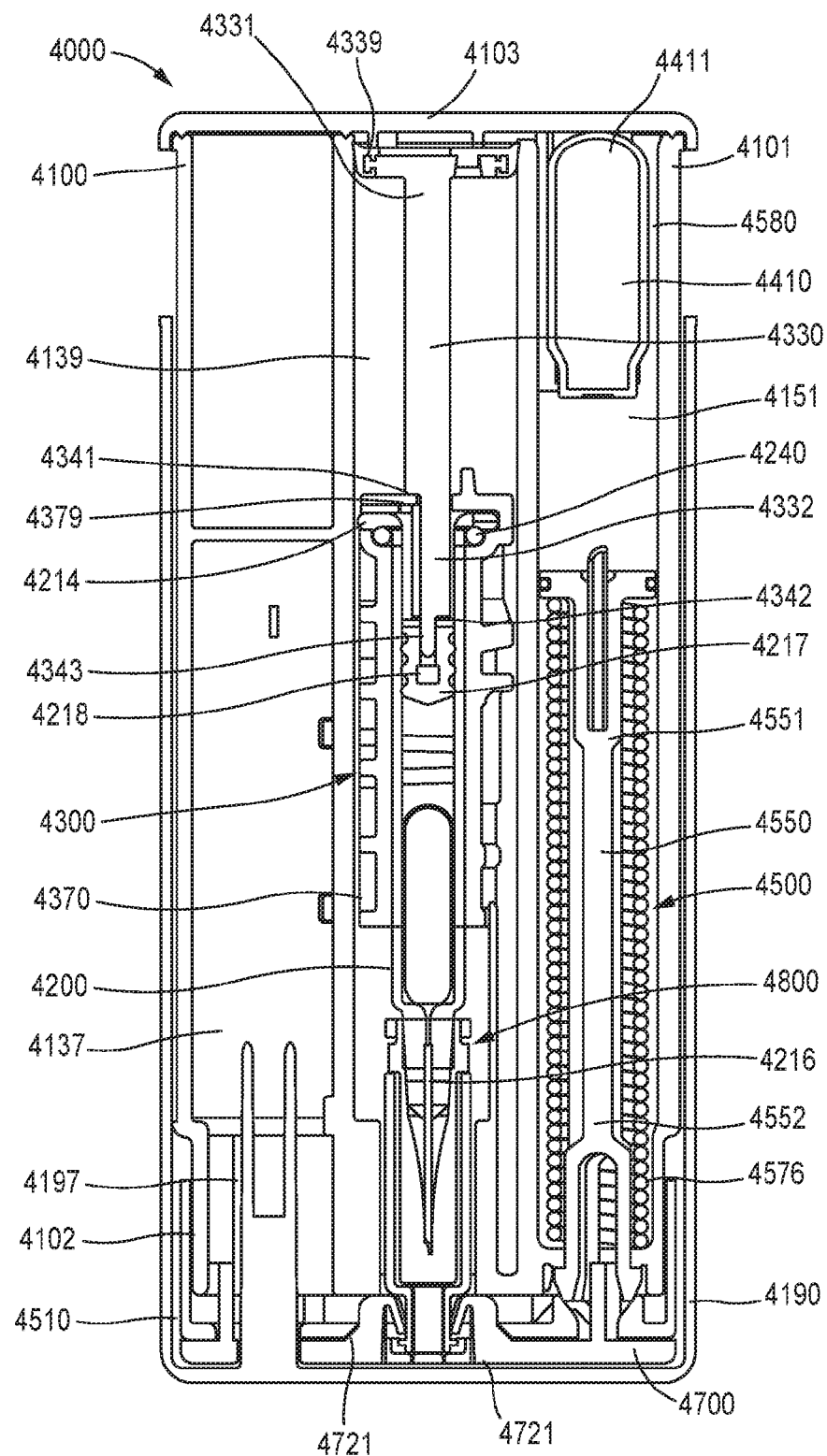
FIG. 56 is a cross-sectional front view of a medical injector according to an embodiment, in a first configuration.
Figure 57:
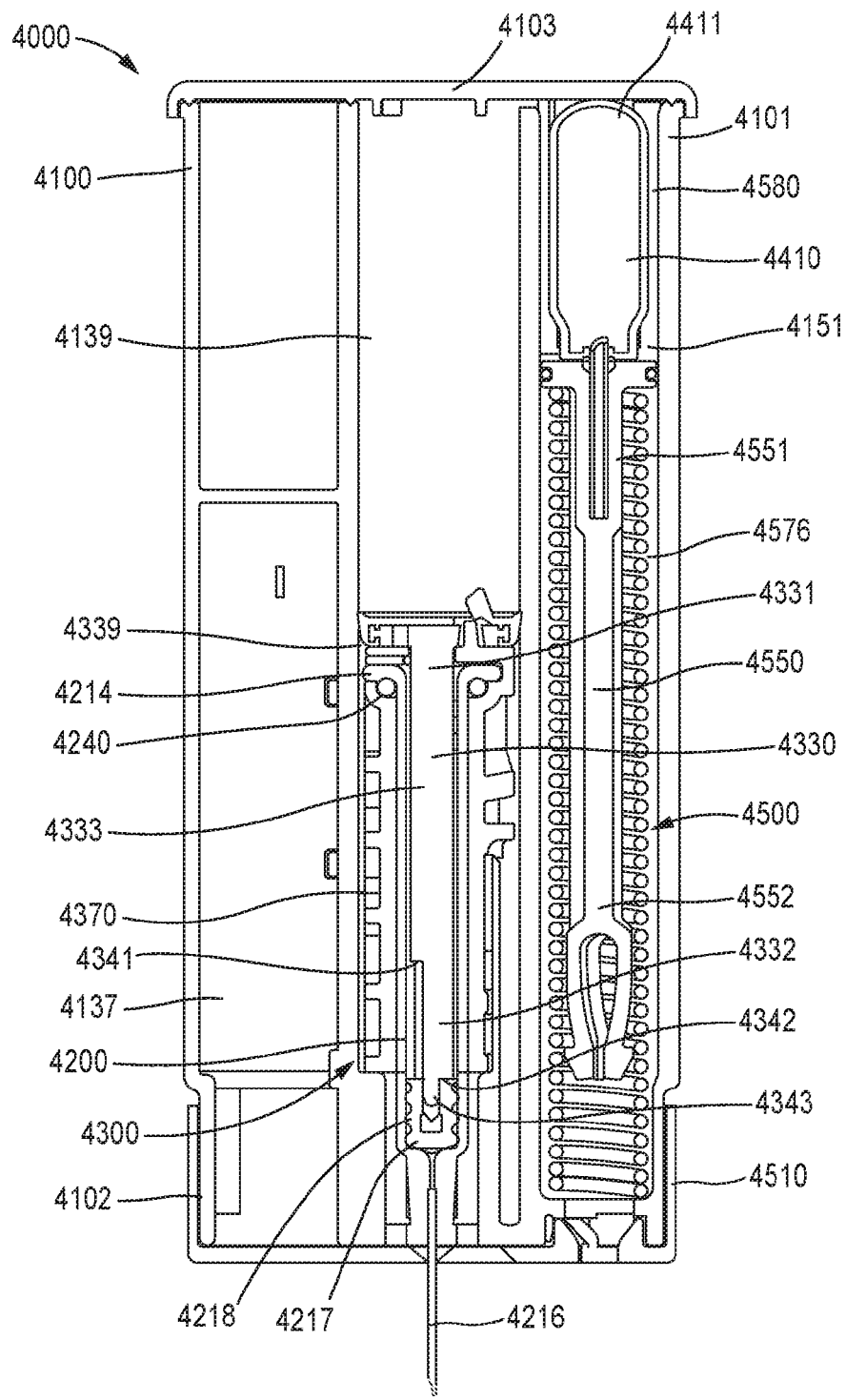
FIG. 57 is a cross-sectional front view of the medical injector illustrated in FIG. 56, in a second configuration.

The medical injector 4000 is similar to the medical injector 3000 described above. As shown in FIGS. 56 and 57, the medical injector 4000 includes a housing 4100, the cover 4190 (FIG. 56), a safety lock 4700 (FIG. 56), a base 4510, a system actuator assembly 4500, a delivery mechanism 4300, a medicament container 4200 and a needle guard assembly 4800. The structure and operation of the cover 4190, the safety lock 4700 and the base 4510 are similar to the structure and operation of the cover 3190, the safety lock 3700 and the base 3510, respectively. Accordingly, only the delivery mechanism 4300, the system actuator assembly 4500 and the needle guard assembly 4800 are described in detail below.

As shown in FIG. 56, the housing 4100 has a proximal end portion 4101 and a distal end portion 4102. The housing 4100 defines a gas cavity 4151, a medicament cavity 4139 and the electronic circuit system cavity 4137. The gas cavity 4151, medicament cavity 4139 and the electronic circuit system cavity 4137 of the housing 4100 of the medical injector 4000 are similar to the gas cavity 3151, the medicament cavity 3139 and the electronic circuit system cavity 3137, shown and described above with reference to FIGS. 15 and 16.

The distal end portion 4102 of the housing 4100 is similar to the distal end portion 3102 of the housing 3100, described above in reference to FIG. 15. The proximal end portion 4101 includes a proximal cap 4103. The proximal cap 4103 includes a gas container retention member 4580 and defines a gas passageway (not shown in FIGS. 56 and 57). The gas container retention member 4580 is configured to receive a gas container 4410. The gas container retention member 4580 extends from a distal surface of the proximal cap 4103 and is configured to place a proximal end 4411 of the gas container adjacent to the proximal cap 4103. Similarly stated, the gas container retention member 4580 extends a given distance from the proximal cap 4103 such that the gas container 4410 is disposed adjacent to the proximal cap 4103 within a proximal end of the gas cavity 4151. In this manner, the gas container retention member 4580 differs from the gas container retention member 3580, which positions the gas container 3410 apart from the proximal cap 3103.

The system actuator assembly 4500 includes the base 4510, a release member 4550 and a spring 4576. The release member 4550 has a proximal end portion 4551 and a distal end portion 4552, and is movably disposed within the gas cavity 4151. The proximal end portion 4551 and the distal end portion 4552 of the release member 4550 are similar to the corresponding structure of the release member 3550 of the medical injector 3000, described above with reference to FIGS. 18-21. The release member 4550 differs from the release member 3550, however, in that the release member 4550 is substantially longer than the length of the release member 3550 of the medical injector 3000. In this manner, the release member 4550 is able to engage the gas container 4410 disposed at the proximal end of the gas cavity 4151. Similarly stated, with the gas container 4410 disposed at the proximal end of the gas cavity 4151, the length of the release member 4550 is increased, compared to the release member 3550 of the medical injector 3000, so that the release member 4550 can engage the gas container 4410. Consequently, the length of the spring 4576 (in the compressed state) is longer than the length of the spring 3576 included in the medical injector 3000, described above with reference to FIGS. 18-21.

The arrangement of the system actuator assembly 4500, the gas container 4410 and the gas container retention member 4580 function similar to the system actuator assembly 3500, the gas container 3410 and the gas container retention member 3580, respectively, to activate the delivery mechanism 4300. In some embodiments, the gas container retention member 4580 can be configured to place the gas container 4410 at any suitable position within the gas cavity 4151. In this manner, the length of the release member 4550 and the spring 4576 can be any given length such that the proximal end portion 4551 of the release member can engage the gas container 4410, as shown in FIG. 57.

The medicament delivery mechanism 4300 includes a carrier 4370 (also referred to herein as the "first movable member" 4370) and a piston member 4330 (also referred to herein as the "second movable member" 4330). The carrier 4370 is similar to the carrier 3370 included in the medical injector 3000 and is movably disposed within the medicament cavity 4139. Therefore, the carrier 4370 is not described in detail herein.

The piston member 4330 includes a proximal end portion 4331, a distal end portion 4332 and a piston rod 4333. The piston portion 4330 is movably disposed within the medicament cavity 4139. The proximal end portion 4331 includes a sealing member 4339 and is similar in form and function to the proximal end portion 3331 of piston member 3330 of the medical injector 3000 described above. The distal end portion 4332 includes a first surface 4341, a second surface 4342 and an elongate protrusion 4343. The second surface 4342 and the elongate protrusion 4343 are disposed within a portion of the carrier 4370 and within the medicament container 4200. The first surface 4341 is configured to contact an engagement portion 4379 of the carrier 4370 when the medicament container 4200 is in a first configuration to maintain a given distance between the second surface 4342 and an elastomeric member 4217 of the medicament container 4200 (see e.g., FIG. 56), in a similar manner as described above. The elongate protrusion 4343 is configured to be disposed within a channel 4218 defined by the elastomeric member 4217. Similarly stated, the piston portion 4330 includes a portion and/or surface in contact with the elastomeric member 4217 and a portion and/or surface not in contact with the elastomeric member 4217, when the carrier 4370 is in the first configuration. In some embodiments, the elongate protrusion 4343 can be used to align the piston rod 4333 with the elastomeric member 4217 disposed within the medicament container 4200.

The piston member 4330 is configured to move within the housing 4100 (e.g., in response to the release of a pressurized gas). When the piston member 4330 moves, the first surface 4341 of the piston portion 4330 can apply a force to a portion of the carrier 4370 such that the carrier 4370 and the piston portion 4330 move together within the medicament cavity 4139. As described above, after the carrier 4370 is placed in its second (or deformed) configuration, the piston rod 4333 can move relative to the carrier 4370 and the elongate 4343 and the second surface 4342 can engage the elastomeric member 4217 to convey the medicament 4220 contained in the medicament container 4200 (see e.g., FIG. 57).

Figure 58:
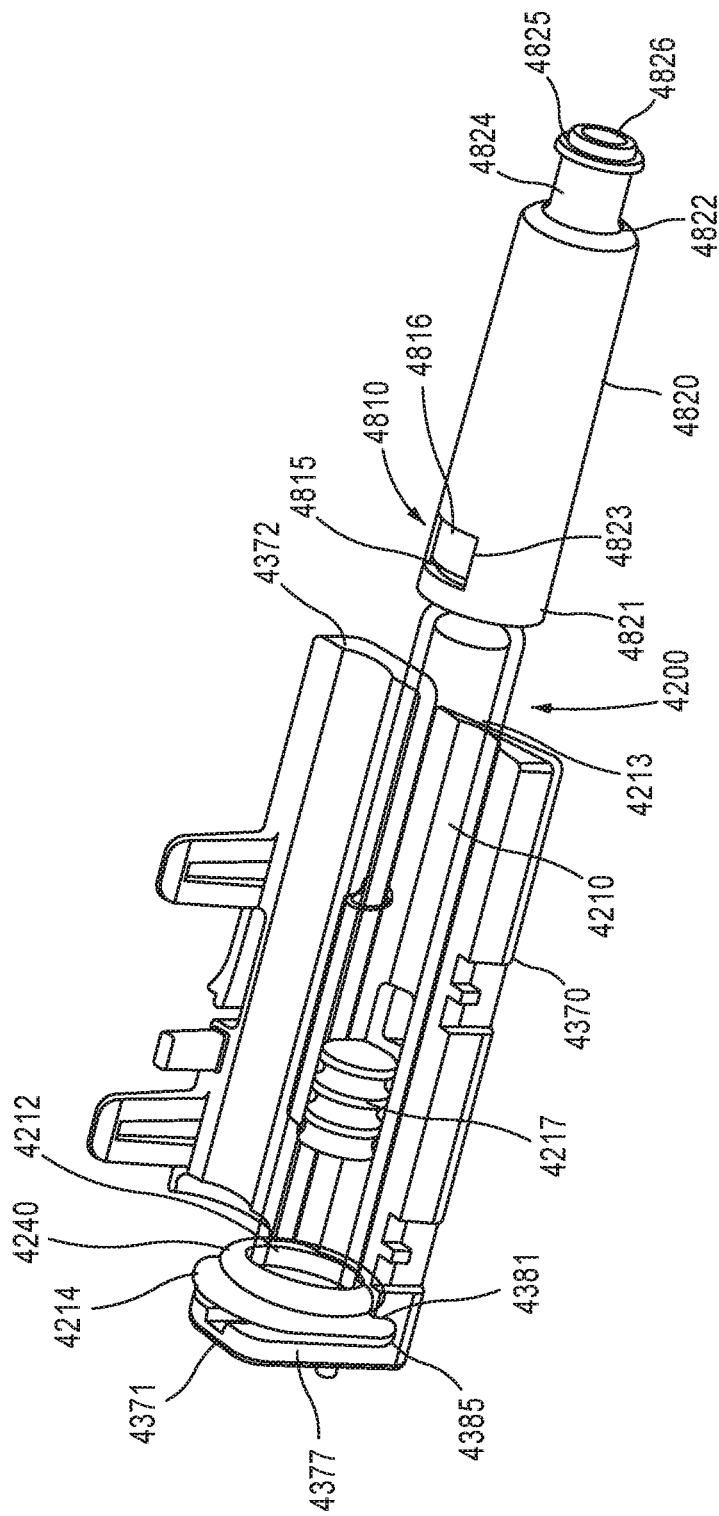
FIG. 58 is a perspective view of a portion of the medical injector illustrated in FIG. 56, in a first configuration.
Figure 59:
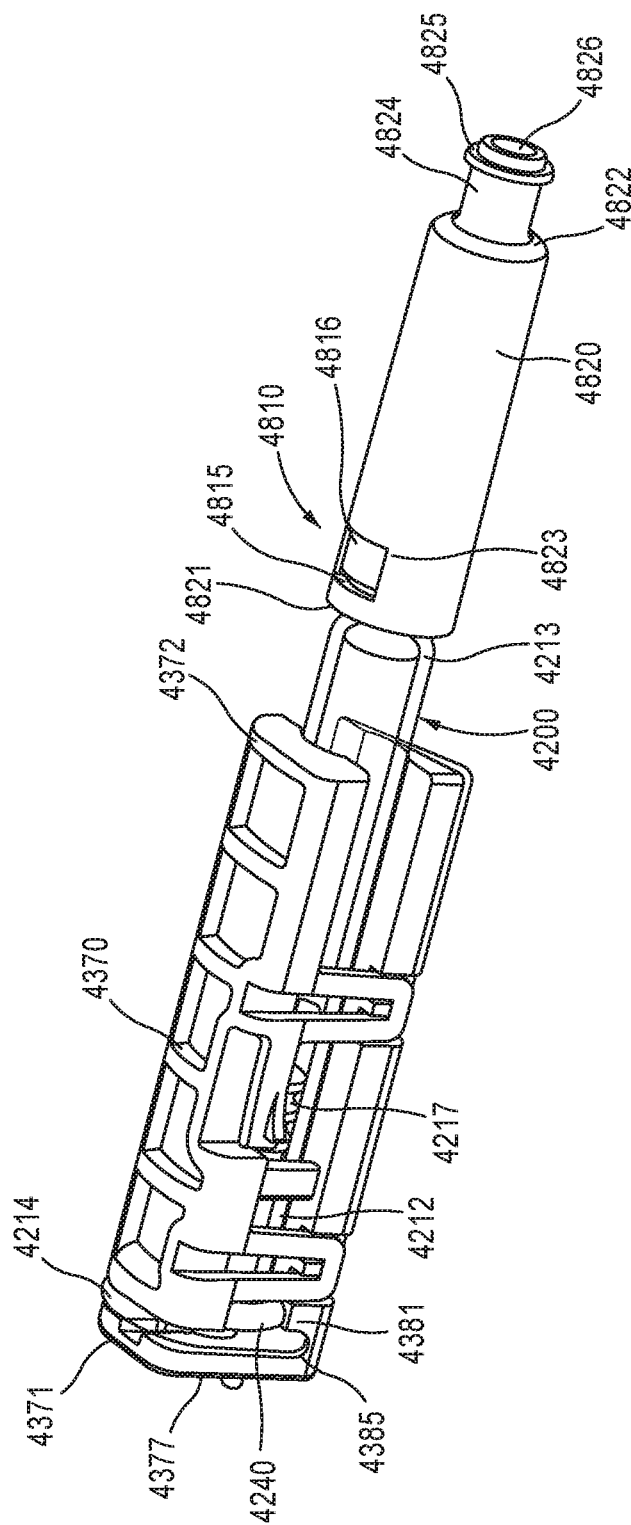
FIG. 59 is a perspective view of a portion of the medical injector illustrated in FIG. 56, in a second configuration.

As shown in FIGS. 58 and 59, the medicament container 4200 is configured to be disposed within the carrier 4370. The medicament container 4200 includes a proximal end portion 4212 and a distal end portion 4213. The proximal end portion 4212 includes a flange 4214. The distal end portion 4213 is in fluid communication with a needle 4216 (see e.g., FIG. 59). The form and function of the medicament container 4200 is similar to the form and function of the medicament container 3200 of the medical injector 3000. The medicament container 4200 also includes a damping member 4240 disposed at a distal surface of the flange 4214.

The flange 4214 of the medicament container 4200 is disposed with in a flange groove 4385 defined by a first shoulder 4377 and a second shoulder 4381 of the carrier 4370. The flange groove 4385 includes a portion configured to receive the damping member 4240. In this manner, the damping member 4240 is configured to dampen a portion of a retraction force applied to the flange 4214 of the medicament container 4200 by the second shoulder 4381. The arrangement of the damping member 4240 within the flange groove 4381 reduces the likelihood of the flange 4214 breaking under the force applied by the second shoulder 4381, which can prevent the retraction of the medicament container 4200.

The needle guard assembly 4800 includes an inner needle sheath 4810 and an outer needle sheath 4820. The inner needle sheath 4810 includes an outer surface 4815 that has a ring 4816. The inner needle sheath 4810 is disposed within the outer needle sheath 4820 (see e.g., FIGS. 58 and 59). The inner needle sheath 4810 is similar to the needle sheath 3810 of the medical injector 3000, described above with reference to FIG. 46. Therefore, details of the inner needle sheath 4810 are not described in detail herein.

The outer needle sheath 4820 includes a proximal end portion 4821 and a distal end portion 4822, and defines a lumen 4826 therebetween. The lumen 4826 is configured to receive the inner needle sheath 4810. The proximal end portion 4821 includes an inner sheath aperture 4823 configured to receive the ring 4816 of the inner needle sheath 4810. The ring 4816 extends from the outer surface 4815 of the inner needle sheath 4810 and a portion of the ring is disposed within the inner sheath aperture 4823. The arrangement of the ring 4816 of the inner needle sheath 4810 and the inner sheath aperture 4823 prevent the movement of the inner needle sheath 4810 within the outer needle sheath 4810.

The distal end portion 4822 includes a neck 4824 that has a rib 4825. The neck 4824 of the distal end portion 4822 is configured to contact engagement members 4721 of the safety lock 4700. Similarly stated, the neck 4824 of the distal end portion 4822 is disposed within a space defined between the engagement members 4721 of the safety lock 4700. The engagement members 4721 allow the distal end portion 4822 of the outer needle sheath 4820 to move between the engagement members 4721 in a distal direction, but not in a proximal direction. Similarly stated, the engagement members 4721 include an edge that contacts the rib 4825 of the outer needle sheath 4820 such as to prevent the safety lock 4700 from moving in a distal direction relative to the outer needle sheath 4820. Said another way, the needle guard assembly 4800 is removed from the needle 4216 when the safety lock 4700 is moved in a distal direction with respect to the housing 4100 (similar to the result as shown for the medical injector 3000 in FIG. 50).

The function of the medical injector 4000 is substantially similar to the function of the medical injector 3000, described with reference to FIGS. 9-55. In this manner, the user of the medical injector 4000 can actuate the medical injector 4000 to inject a medicament, disposed within the medicament container 4200, into an injection site of a patient.

Figure 60:
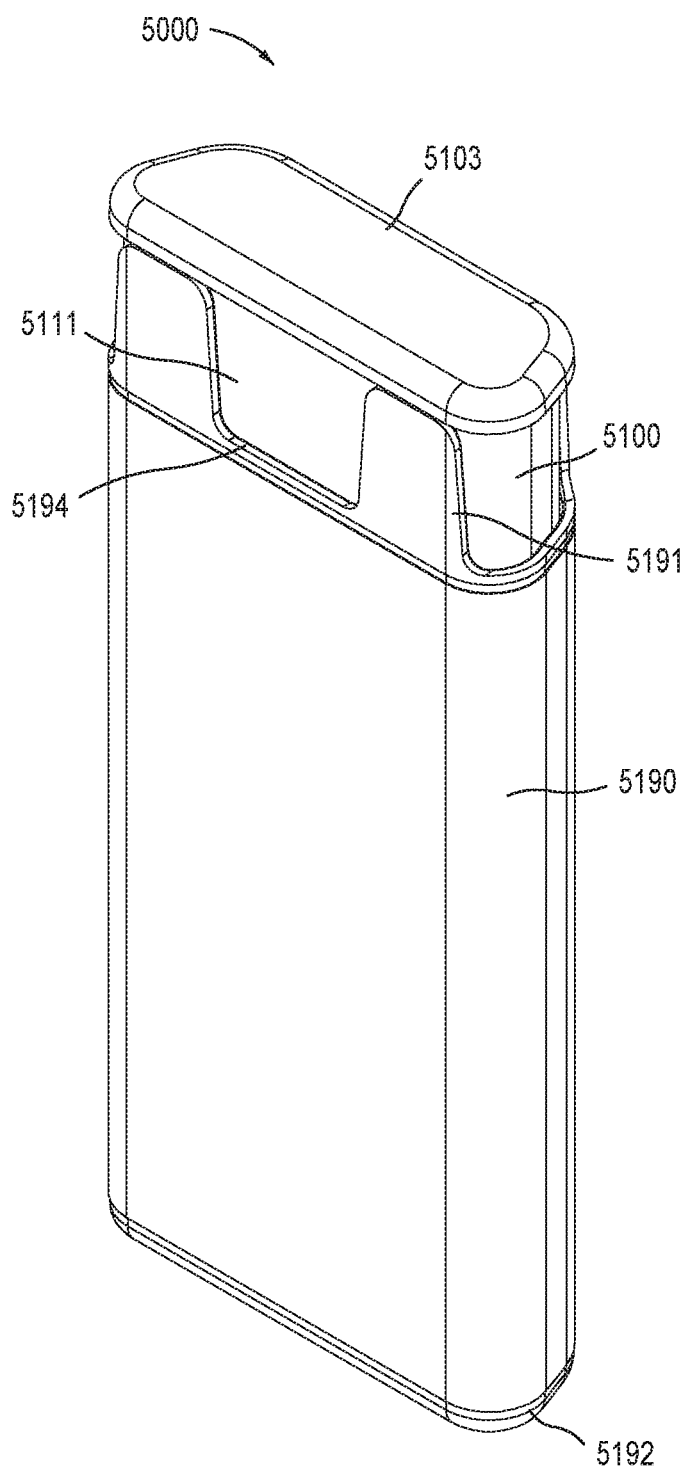
FIGS. 60 and 61 are perspective views of a medical injector according to an embodiment, in a first configuration.
Figure 61:
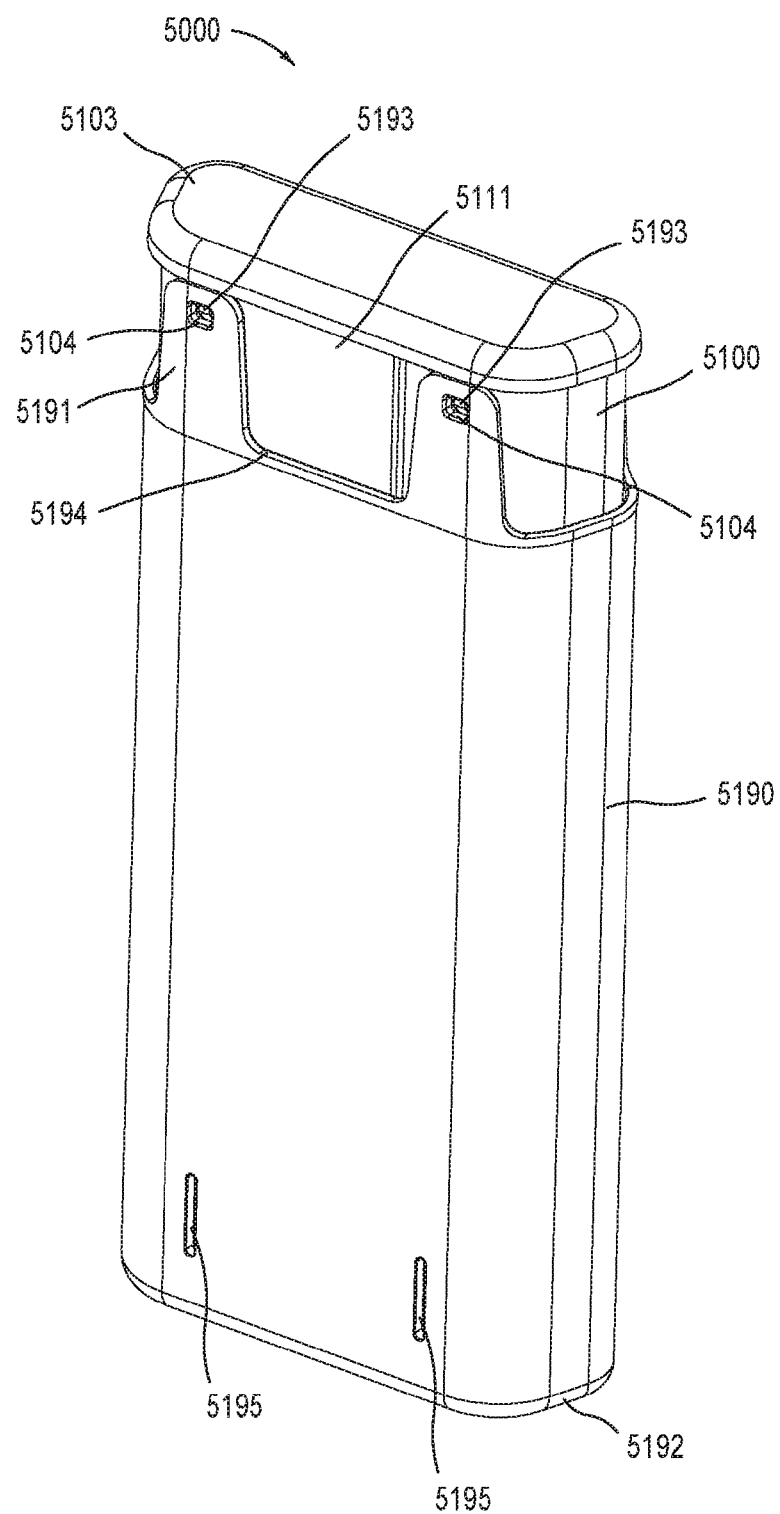
Figure 62:
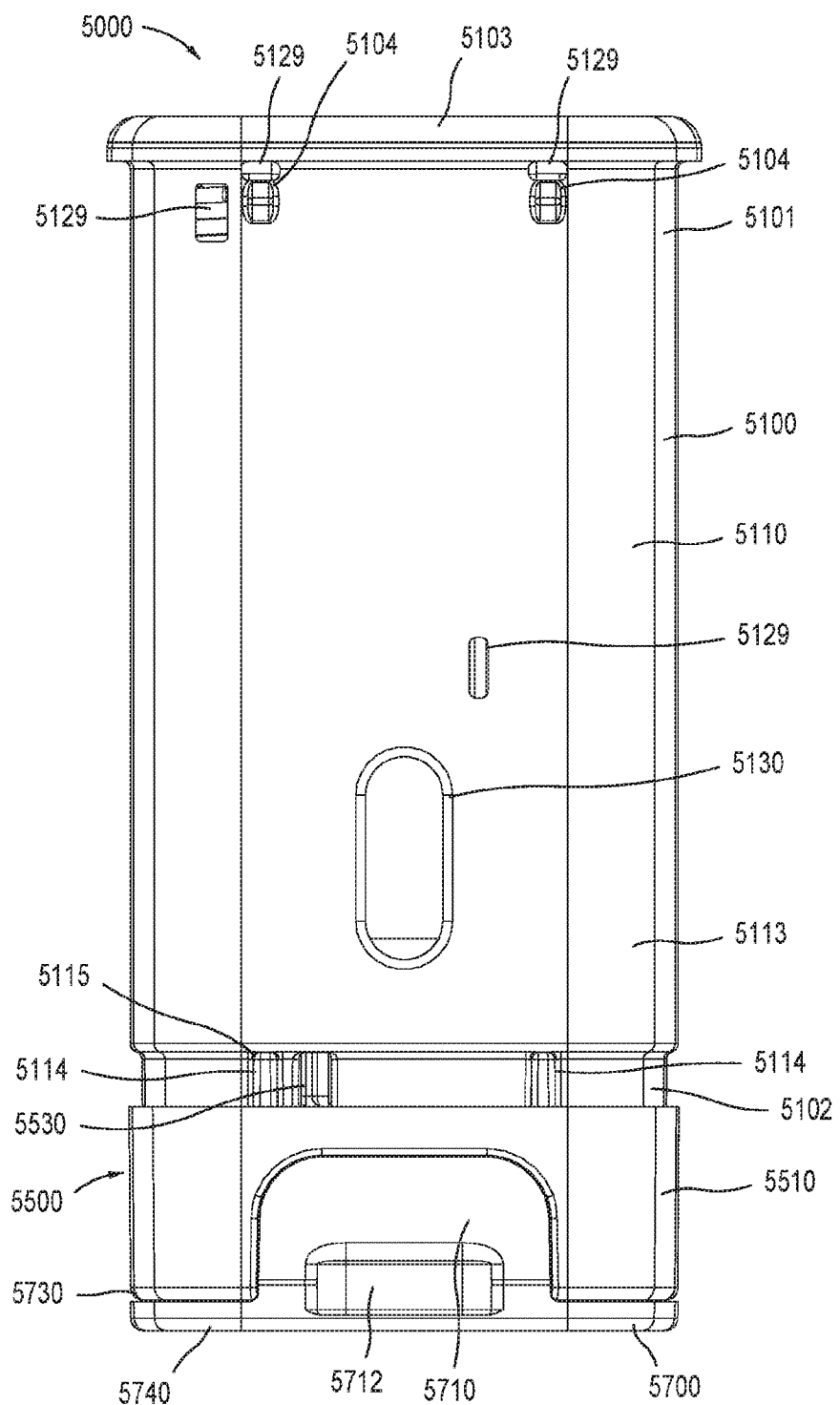
FIG. 62 is a front view of the medical injector illustrated in FIG. 60 with a cover removed.
Figure 63:
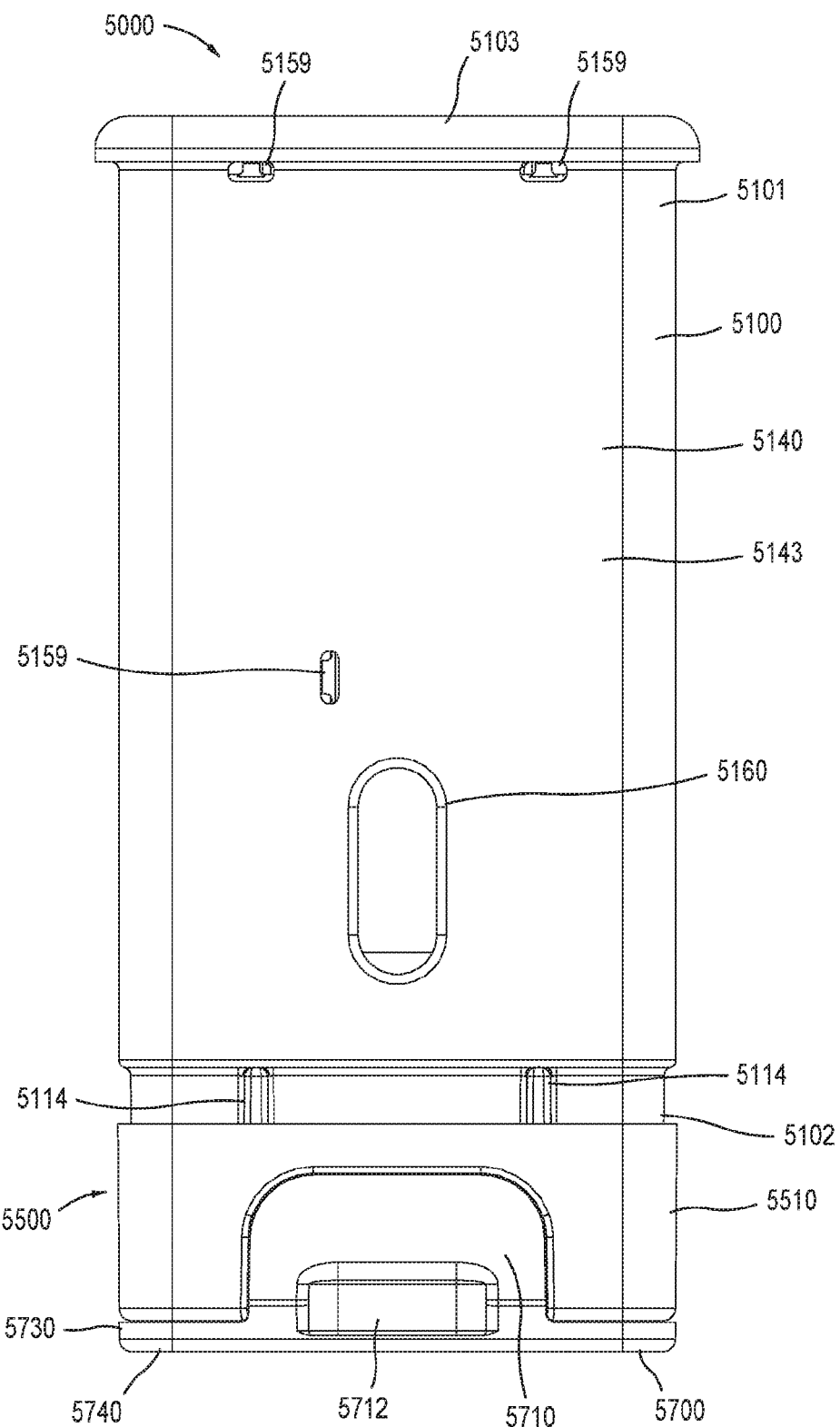
FIG. 63 is a back view of the medical injector illustrated in FIG. 60 with the cover removed.
Figure 64:
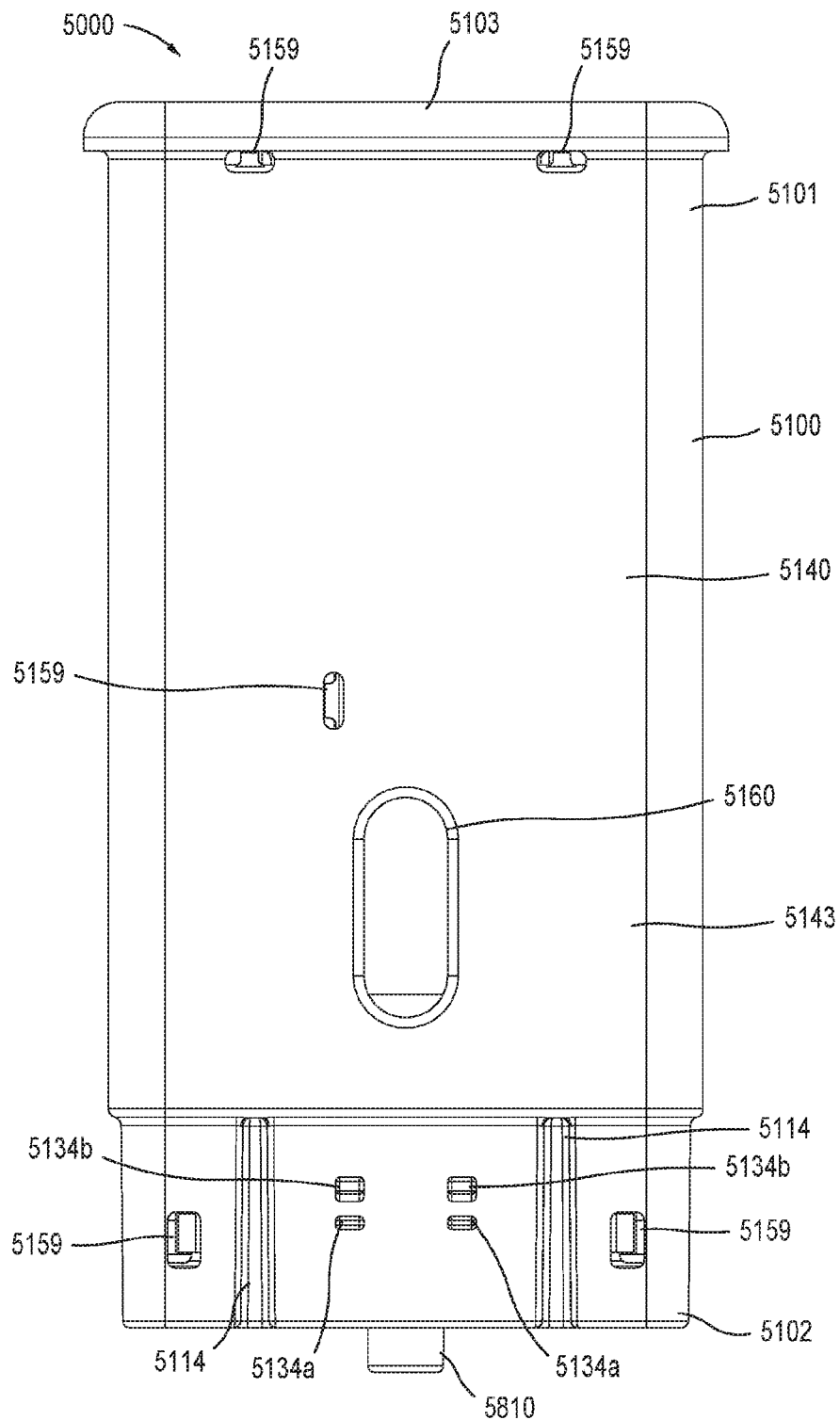
FIG. 64 is a back view of a portion of the medical injector illustrated in FIG. 60.

Although the medicament injector 3000 and the medical injector 4000 are shown and described above as including a system actuation including the release of a pressurized gas, in other embodiments, a medicament delivery device can include any suitable method of delivery of a medicament disposed within. For example, FIGS. 60-98 show a medical injector 5000, according to an embodiment that includes a mechanical energy storage member, rather than a compressed gas container. FIGS. 60-61 are perspective views of the medical injector 5000 in a first configuration (i.e., prior to use). The medical injector 5000 includes a housing 5100 (see e.g., FIGS. 62-70), a system actuator 5500 (see e.g., FIGS. 71-73), a medicament container 5200 containing a medicament 5220 (see e.g., FIG. 74), a medicament delivery mechanism 5300, a transfer member 5600 (see e.g., FIG. 75-80), a cover 5190 (see e.g., FIGS. 81-82), and a safety lock 5700 (see e.g., FIGS. 83-87). A discussion of the components of the medical injector 5000 will be followed by a discussion of the operation of the medical injector 5000.

As shown in FIGS. 62-70, the housing 5100 includes a first housing member 5110 (FIGS. 66 and 67) and a second housing member 5140 (FIGS. 68 and 69) that can couple to form the housing 5100. The housing 5100 has a proximal end portion 5101 and a distal end portion 5102. The housing 5100 defines a first status indicator aperture 5130 (defined by the first housing member 5110) and a second status indicator aperture 5160 (defined by the second housing member 5140). The status indicator apertures 5130, 5160 can allow a patient to monitor the status and/or contents of the medicament container 5200 contained within the housing 5100. For example, by visually inspecting the status indicator aperture 5130 and/or 5160, a patient can determine whether the medicament container 5200 contains a medicament 5220 and/or whether the medicament 5220 has been dispensed.

Figure 66:
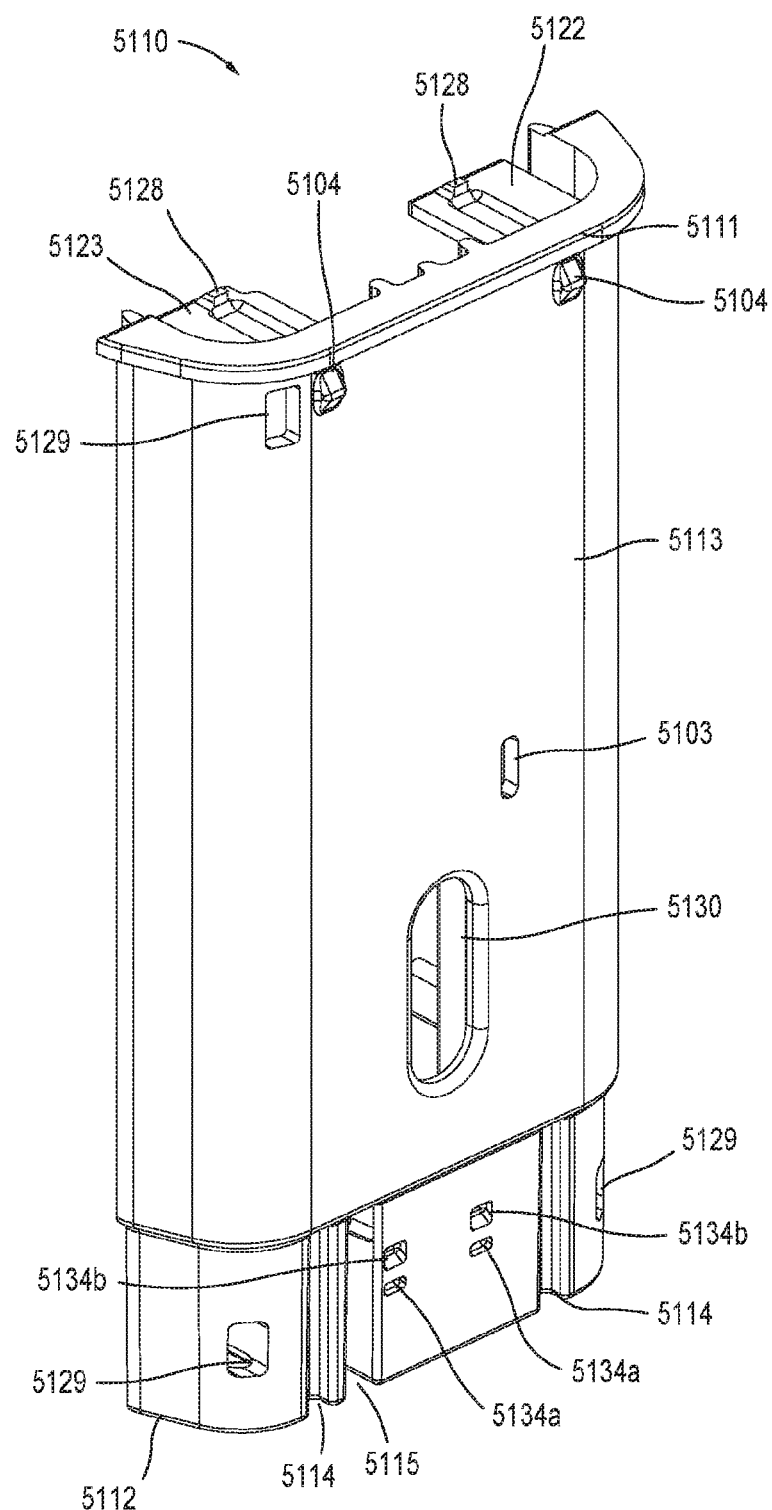
FIG. 66 is a front perspective views of a first portion of the housing of the medical injector illustrated in FIGS. 62 and 63.
Figure 67:
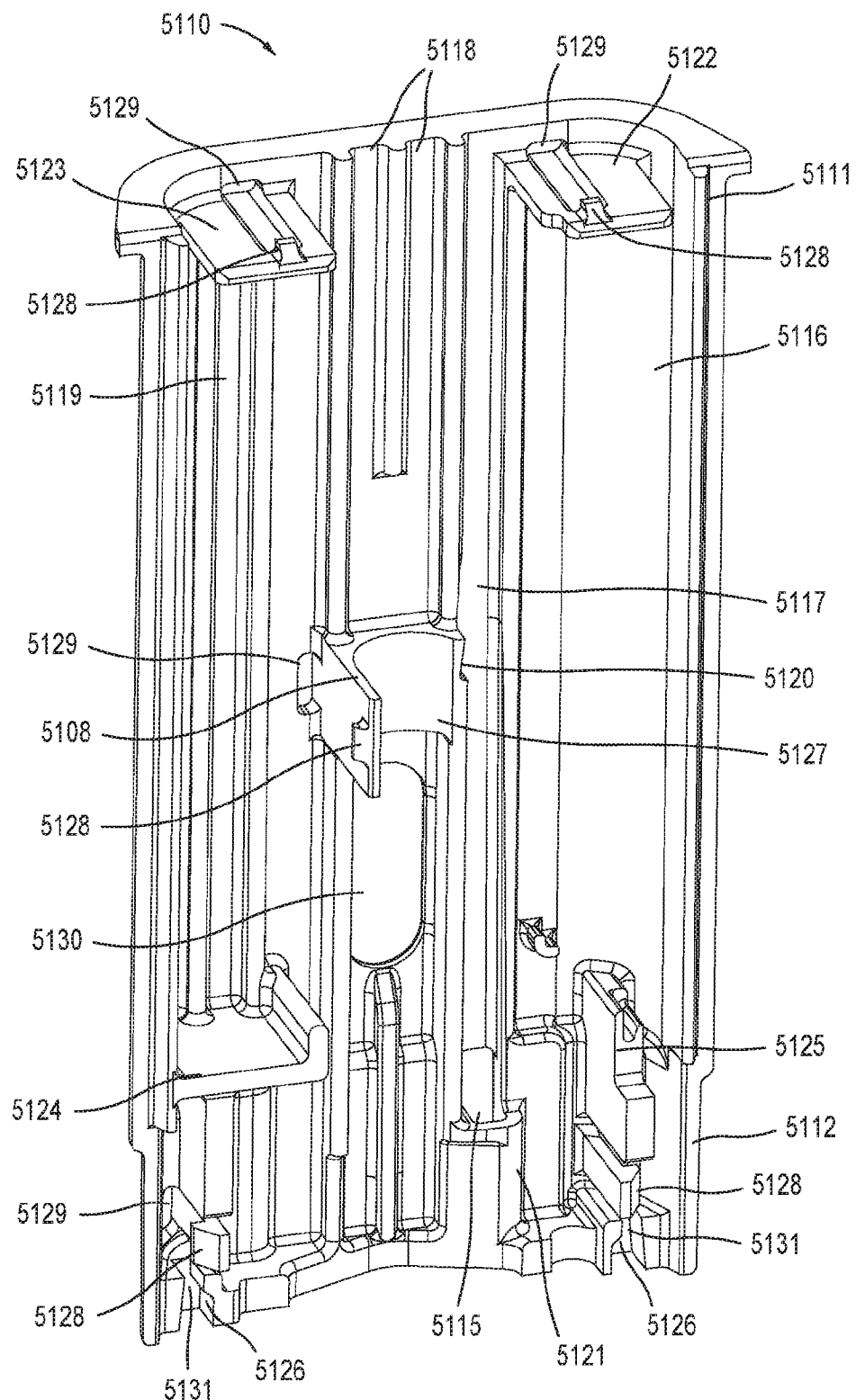
FIG. 67 is a rear perspective views of the first portion of the housing of the medical injector illustrated in FIG. 66.

As shown in FIGS. 66-67, the first housing member 5110 includes an outer surface 5113 and an inner surface 5116, and a proximal end portion 5111 and a distal end portion 5112. The outer surface 5113 includes cover retention protrusions 5104 at the proximal end portion 5111 of the first housing member 5110 (see e.g., FIGS. 61, 62 and 66). The cover retention protrusions 5104 are configured to be received within corresponding openings 5193 defined by the cover 5190 to retain the cover 5190 about the housing 5100. In this manner, as described in more detail herein, the cover 5190 is removably coupled to and disposed about at least a portion of the housing 5100.

The outer surface 5113 defines base retention recesses 5134A and 5134B, an activation rod groove 5115, and base rail grooves 5114, at the distal end portion 5112 of the first housing member 5110. The distal base retention recesses 5134A are configured to receive base connection knobs 5518 of an actuator 5510 (also referred to herein as "base 5510," see e.g., FIG. 88) when the base 5510 is in a first position relative to the housing 5100. The proximal base retention recesses 5134B are configured to receive the base connection knobs 5518 of the base 5510 when the base 5510 is in a second position relative to the housing 5100. The base retention recesses 5134A, 5134B have a tapered proximal sidewall and a non-tapered distal sidewall. This allows the base retention recesses 5134A, 5134B to receive the base connection knobs 5518 such that the base 5510 can move proximally relative to the housing 5100, but cannot move distally relative to the housing 5100. Said another way, the distal base retention recesses 5134A are configured to prevent the base 5510 from moving distally when the base 5510 is in a first position and the proximal base retention recesses 5134B are configured to prevent the base 5510 from moving distally when the base 5510 is in a second position. Similarly stated, the proximal base retention recesses 5134B and the base connection knobs 5518 cooperatively to limit movement of the base 5510 to prevent undesirable movement of the base 5510 after the medical injector 5000 is actuated. The proximal base retention recesses 5134B and the base connection knobs 5518 also provide a visual cue to the user that the medical injector 5000 has been used.

The activation rod groove 5115 is configured to receive an activator 5530 (also referred to herein as "release member 5530," see e.g., FIG. 88) of the base 5510. As described in more detail herein, the release member 5530 of the base 5510 is configured to engage a portion of the medicament delivery mechanism 5300 when the base 5510 is moved with respect to the housing 5100. The base rail grooves 5114 are configured to receive guide members 5517 of the base 5510. The guide members 5517 of the base 5510 and the base rail grooves 5114 of the housing 5100 engage each other in a way that allows the guide members 5517 of the base 5510 to slide in a proximal and/or distal direction within the base rail grooves 5114 while limiting lateral movement of the guide members 5517. This arrangement allows the base 5510 to move in a proximal and/or distal direction with respect to the housing 5100 but prevents the base 5510 from moving in a lateral direction with respect to the housing 5100.

The inner surface 5116 of the first housing member 5110 includes a medicament container holder 5127, an upper spring plate 5122 and an upper bias member plate 5123. The inner surface 5166 also includes a series of protrusions that define a transfer member groove 5117, piston portion grooves 5118 and a bias portion groove 5119 (see e.g., FIG. 67). The medicament container holder 5127 is configured to receive a body 5210 of the medicament container 5200 (e.g., a prefilled syringe). The medicament container holder 5127 defines a latch member notch 5120 that includes an engagement surface 5109 (see e.g. FIG. 72) configured to engage a latch protrusion 5315 of a latch portion 5310 of the medicament delivery mechanism 5300. The medicament container holder 5127 includes a proximal end surface 5108. The proximal end surface 5108 is configured to contact a portion of the medicament container 5200 (either directly or via intervening structure, such as an o-ring or damping member) when the medicament container 5200 is in a second position, as described in further detail herein.

The upper spring plate 5122 is disposed at the proximal end portion 5111 of the first housing member 5110. The upper spring plate 5122 extends from the inner surface 5116 and is configured to contact a proximal end portion 5421 of a spring 5420 (see FIG. 91). In this manner, when activated, the upper spring plate 5122 limits proximal movement of the spring 5420 such that the spring expands distally to move the medicament delivery mechanism 5300 in a distal direction (see e.g., FIG. 93). Similarly stated, the upper spring plate 5122 receives a force from the spring 5420 and applies an equal and opposite reaction force to the proximal end portion 5421 of the spring 5420 such that a distal end portion 5422 of the spring 5420 expands in a distal direction, as described in further detail herein.

The upper bias plate 5123 is disposed at the proximal end portion 5111 of the first housing member 5110 and extends from the inner surface 5116. The upper bias plate 5123 is configured to selectively engage a bias portion 5350 of the medicament delivery mechanism 5300 (see FIG. 91). In this manner, the upper bias plate 5123 is configured to limit the proximal movement of the bias portion 5350 of the medicament delivery mechanism 5300, as described in further detail herein.

As described above, the inner surface 5116 includes protrusions that define the transfer member groove 5117, the piston portion grooves 5118 and the bias portion groove 5119. The transfer member groove 5117 is configured to receive a guide protrusion 5619 of the transfer member 5600 (see FIG. 80). The guide protrusion 5619 of the transfer member 5600 and the transfer member groove 5117 defined by the inner surface 5116 of the first housing member 5110 engage each other in a way that allows the guide protrusion 5619 of the transfer member 5600 to slide in a proximal and/or distal direction within the transfer member groove 5117 while limiting lateral movement of the guide protrusion 5619. This arrangement allows the transfer member 5600 to move in a proximal and/or distal direction with respect to the housing 5100 but prevents the transfer member 5600 from moving in a lateral direction with respect to the housing 5100. Similarly, the piston portion grooves 5118 are configured to receive the guide protrusions 5302 of the piston portion 5330 of the medicament delivery mechanism 5300 (see FIG. 76). The bias portion groove 5119 is configured to receive the guide protrusion 5354 of the bias portion 5350 of the medicament delivery mechanism 5300 (see FIG. 76). In this manner, the piston portion grooves 5118 and the bias member groove 5119 engage the guide protrusions 5302 of the piston portion 5330 and the guide protrusion 5354 of the bias portion 5350, respectively, to prevent the medicament delivery mechanism 5300 from moving in a lateral direction with respect to the housing 5100 and/or rotating within the housing 5100.

The inner surface 5116 of the first housing member 5110 further includes a transfer member release protrusion 5121, a transfer member release support protrusion 5125, a lower bias plate 5124, and base lock protrusions 5126. The transfer member release protrusion 5121 is configured to engage a latch arm 5618 of the transfer member 5600 to place the transfer member 5600 in a second configuration when the transfer member 5600 moves to a second position (see e.g., FIG. 97). Contemporaneously, the transfer member release support protrusion 5125 supports the latch arm 5618 of the transfer member 5600 as the transfer member is placed in the second configuration, as described in further detail herein.

The lower bias plate 5124 engages a distal end portion 5353 of the bias portion 5350 of the delivery mechanism 5300 (see e.g., FIG. 95), as described in further detail herein. The base lock protrusions 5126 are configured to engage base locks 5515 of the base 5510 when the safety lock 5700 is in contact with the medical injector 5000 (see FIG. 73). Similarly stated, the safety lock 5700, the base lock protrusions 5126, and the base locks 5515 collectively prevent the base 5510 from moving in a proximal direction relative to the housing 5100 when the base locks 5515 of the base 5510 are in contact with the base lock protrusions 5126 of the first housing portion 5110, as described in further detail herein.

The first housing member 5110 further includes a set of tabs 5128 and a set of openings 5129. The tabs 5128 extend from portions of the inner surface 5116 of the first housing member 5110. The first housing member 5110 can include any number of tabs 5128 that can have any suitable shape or size. For example, in some embodiments, the tabs 5128 vary in size. The tabs 5128 are configured to engage portions of the second housing member 5140 to couple the first housing member 5110 to the second housing member 5140, as described in further detail herein.

Figure 68:
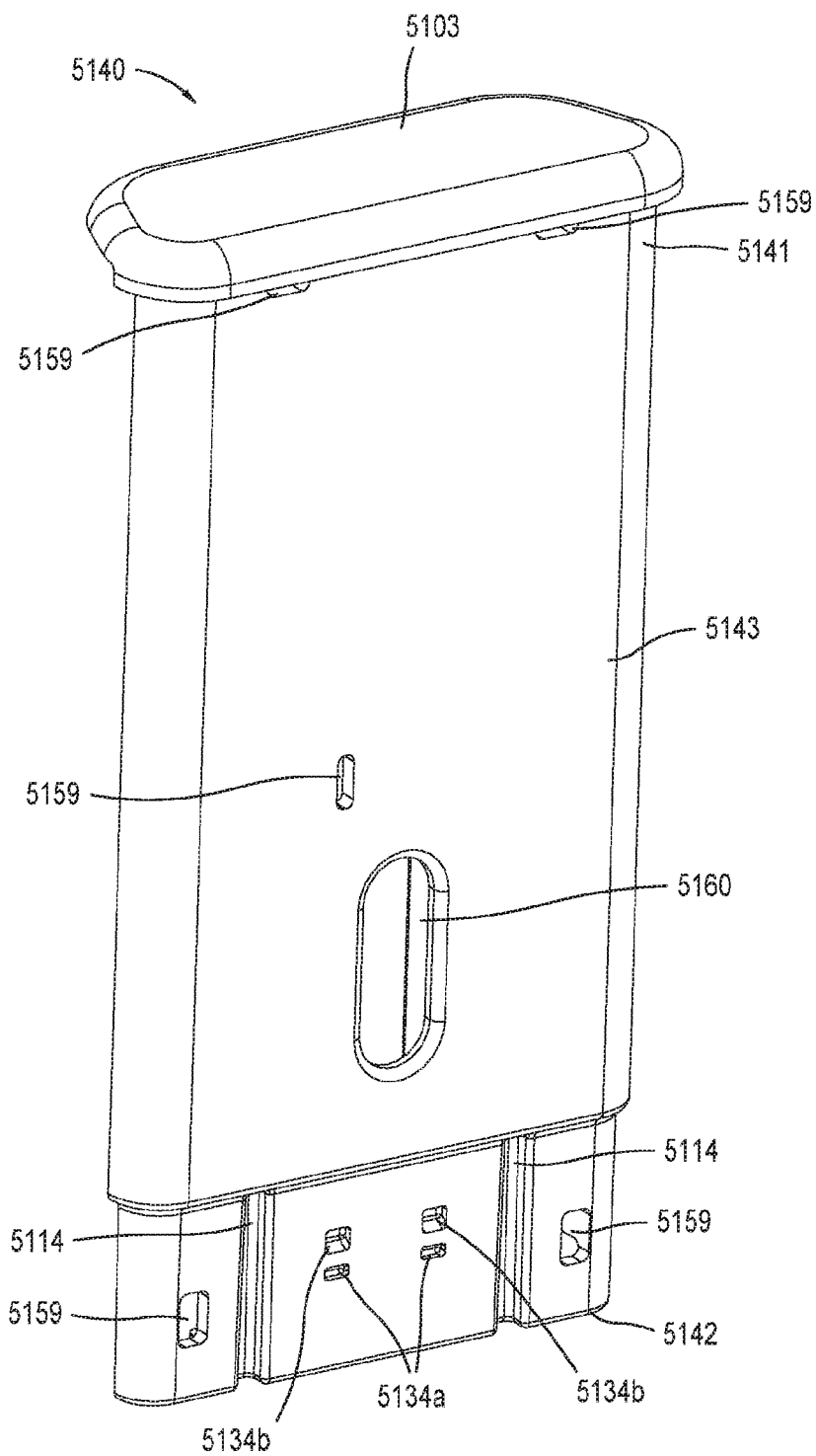
FIG. 68 is a front perspective views of a second portion of the housing of the medical injector illustrated in FIGS. 62 and 63.
Figure 69:
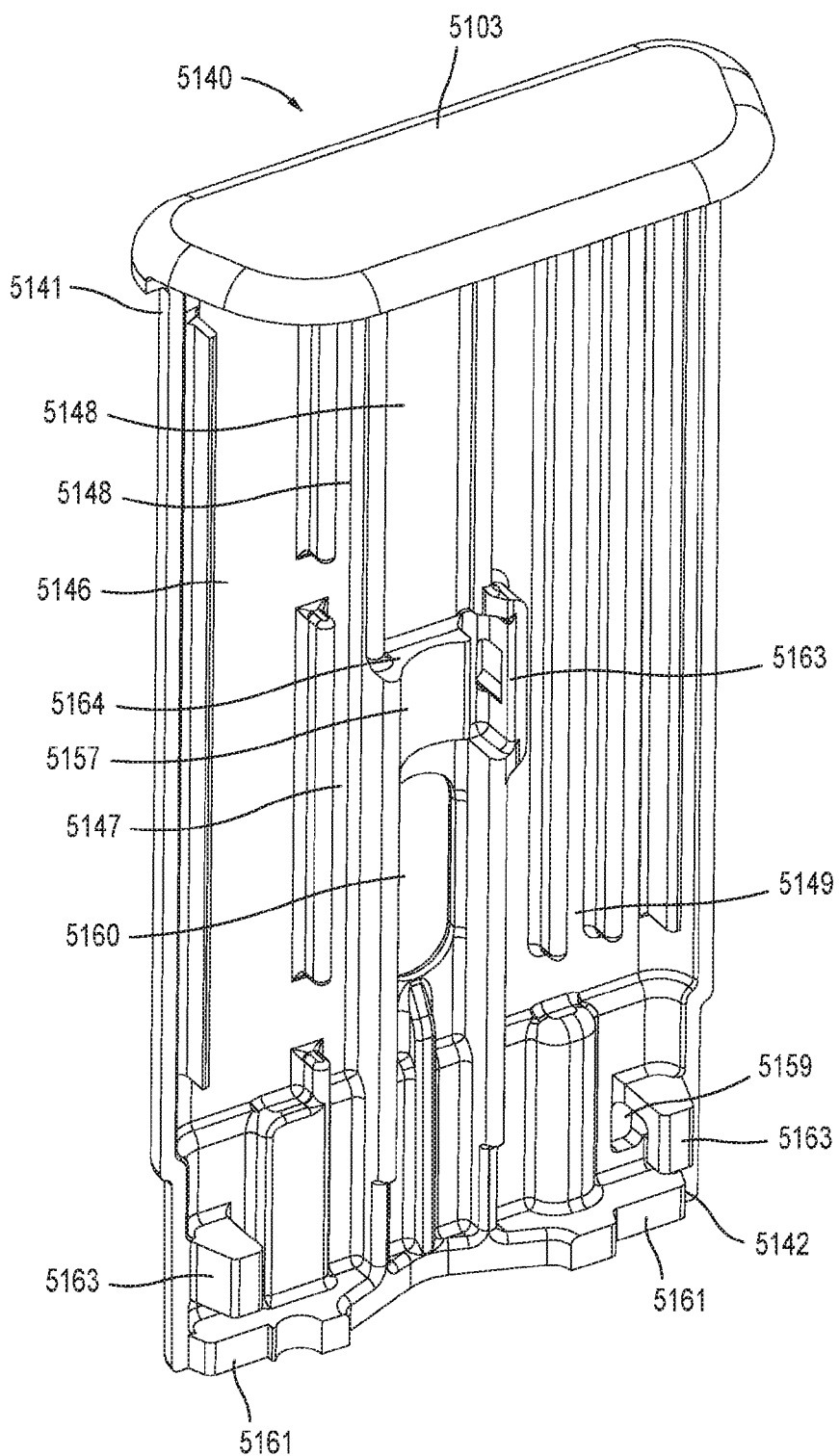
FIG. 69 is a rear perspective views of the second portion of the housing of the medical injector illustrated in FIG. 68.
Figure 70:
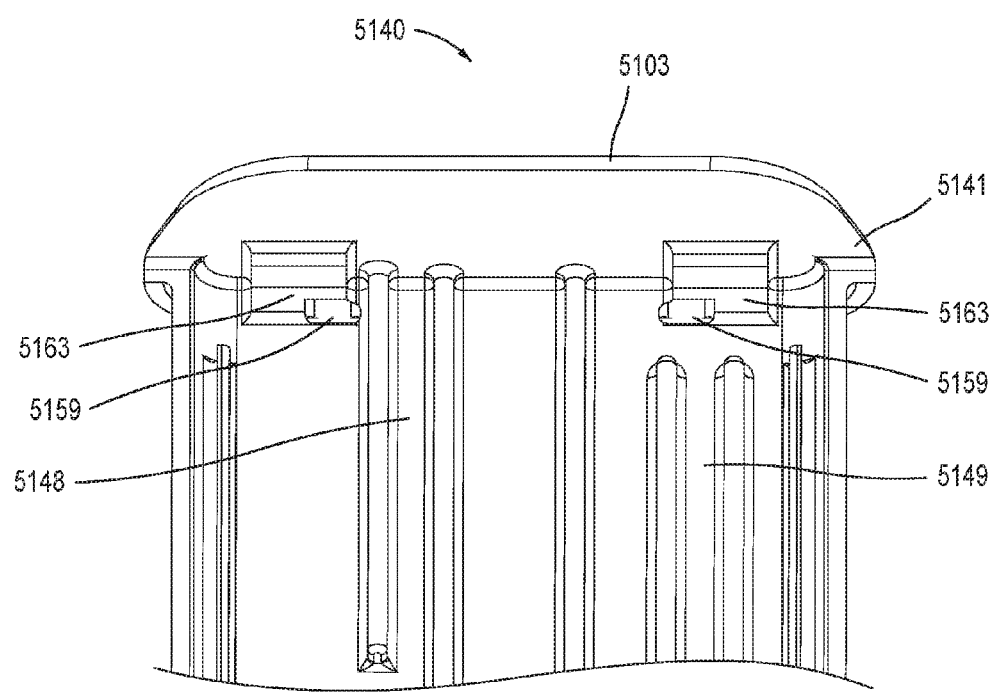
FIG. 70 is an enlarged view of a portion of the second portion of housing of the medical injector illustrated in FIG. 69.

As shown in FIGS. 68-70, the second housing member 5140 includes an outer surface 5143 and an inner surface 5146. The second housing member 5140 also includes a proximal end portion 5141, a proximal cap 5103, and a distal end portion 5142. The outer surface 5143 defines base retention recesses 5134A and 5134B and base rail grooves 5114, at the distal end portion 5142 of the second housing member 5140. The distal base retention recesses 5134A are configured to receive base connection knobs 5518 of the base 5510 when the base 5510 is in a first position relative to the housing 5100. The proximal base retention recesses 5134B are configured to receive the base connection knobs 5518 of the base 5510 when the base 5510 is in a second position relative to the housing 5100. The base retention recesses 5134A, 5134B have a tapered proximal sidewall and a non-tapered distal sidewall. This allows the base retention recesses 5134A, 5134B to receive the base connection knobs 5518 such that the base 5510 can move proximally relative to the housing 5100, but cannot move distally relative to the housing 5100. Said another way, the distal base retention recesses 5134A are configured to prevent the base 5510 from moving distally when the base 5510 is in a first position and the proximal base retention recesses 5134B are configured to prevent the base 5510 from moving distally when the base 5510 is in a second position. Similarly stated, the proximal base retention recesses 5134B and the base connection knobs 5518 cooperatively limit movement of the base 5510 to prevent undesirable movement of the base 5510 after the medical injector 5000 is actuated. The proximal base retention recesses 5134B and the base connection knobs 5518 also provide a visual cue to the user that the medical injector 5000 has been used.

The base rail grooves 5114 are configured to receive guide members 5517 of the base 5510. The guide members 5517 of the base 5510 and the base rail grooves 5114 of the second housing member 5140 engage each other in a way that allows the guide members 5517 of the base 5510 to slide in a proximal and/or distal direction within the base rail grooves 5114 while limiting lateral movement of the guide members 5517. This arrangement allows the base 5510 to move in a proximal and/or distal direction with respect to the housing 5100 but prevents the base 5510 from moving in a lateral direction with respect to the housing 5100.

The proximal cap 5103 extends from the proximal end portion 5141 of the second housing member 5140 and encloses the proximal end portion 5101 of the housing 5100 when the first housing member 5110 is coupled to the second housing member 5140.

The inner surface 5146 of the second housing member 5140 includes a medicament container holder 5157. The inner surface further includes protrusions that define a transfer member groove 5147, piston portion grooves 5148, and a bias portion groove 5149. The medicament container holder 5157 is configured to receive a body 5210 of the medicament container 5200 (e.g., a prefilled syringe). Moreover, the medicament container holder 5157 is configured to be coupled to a portion of the medicament container holder 5127 of the first housing member 5110 to define a space in which the medicament container 5200 is disposed. The medicament container holder 5157 includes a proximal end surface 5164. The proximal end surface 5164 is configured to contact a portion of the medicament container 5200 (either directly or via intervening structure) when the medicament container 5200 is in the second position, as described in further detail herein.

Figure 80:
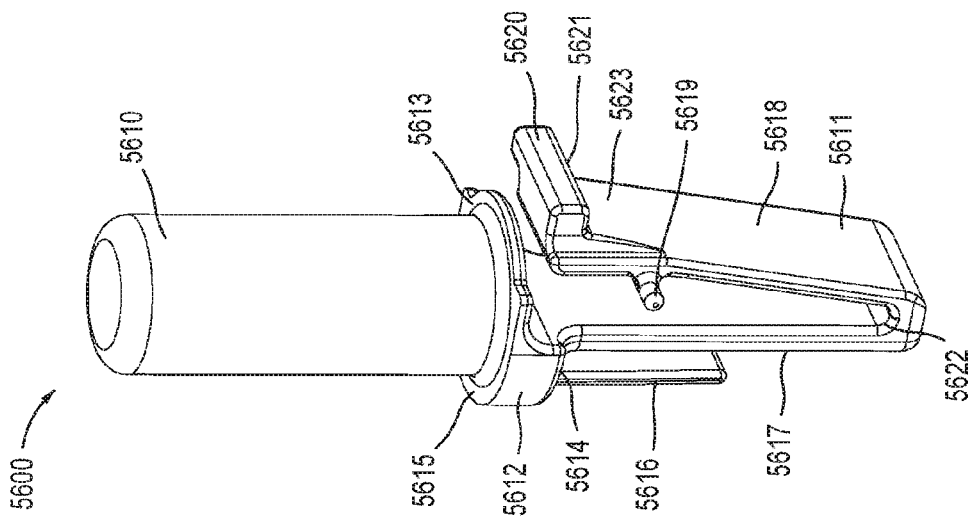
FIG. 80 is a rear perspective view of the second movable member of the medical injector illustrated in FIG. 79 in a first configuration.
Figure 79:
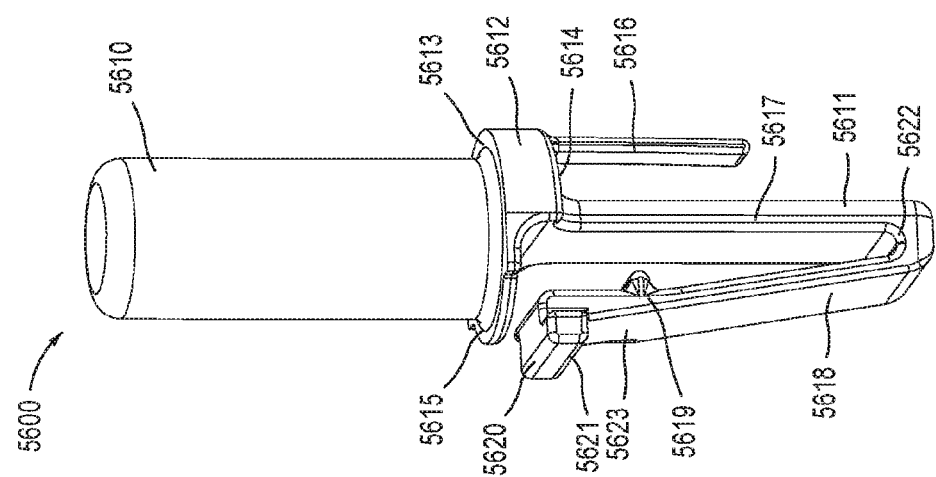
FIG. 79 is a front perspective view of a second movable member of the medical injector illustrated in FIG. 60, in a first configuration.

The transfer member groove 5147 receives a latch 5620 of the transfer member 5600 (see FIGS. 79 and 80). The latch 5620 of the transfer member 5600 and the transfer member groove 5147 defined by the inner surface 5146 of the second housing member 5140 engage each other in a way that allows the latch 5620 of the transfer member 5600 to slide in a proximal and/or distal direction within the transfer member groove 5147 while limiting lateral movement of the guide protrusion 5619. Similarly, the piston portion grooves 5148 are configured to receive the guide protrusions 5302 of the piston portion 5330 of the medicament delivery mechanism 5300. The bias portion groove 5149 is configured to receive the guide protrusion 5354 of the bias portion 5350 of the medicament delivery mechanism 5300. In this manner, the piston portion grooves 5148 and the bias member groove 5149 engage the guide protrusions 5302 of the piston portion 5330 and the guide protrusion 5354 of the bias portion 5350, respectively, to prevent the medicament delivery mechanism 5300 from moving in a lateral direction with respect to the housing 5100 and/or rotating within the housing 5100.

The second housing member 5140 further includes a set of tab latches 5163 and defines a set of openings 5159. The second housing member 5140 can include any number of tab latches 5163 such that the number of tab latches 5163 correspond to the number of tabs 5128 of the first housing member 5110. Collectively, the tabs 5128 of the first housing member 5110 and the tab latches 5163 of the second housing member 5140 couple the first housing member 5110 to the second housing member 5140. Similarly stated, the tabs 5128 are configured to engage the tab latches 5163 to define a lock fit. Moreover, a surface of the tabs 5128 is in contact with a surface of the tab latches 5163 to define a lock fit such that the first housing member 5110 and the second housing member 5140 couple together to define the housing 5100. The openings 5129 of the first housing member 5110 and the openings 5159 of the second housing member 5140 allow access to the tabs 5128 of the first housing member 5110 and the tab latches 5163 of the second housing member 5140, respectively. In this manner, the first housing member 5110 can be decoupled from the second housing member 5140.

Figure 65:
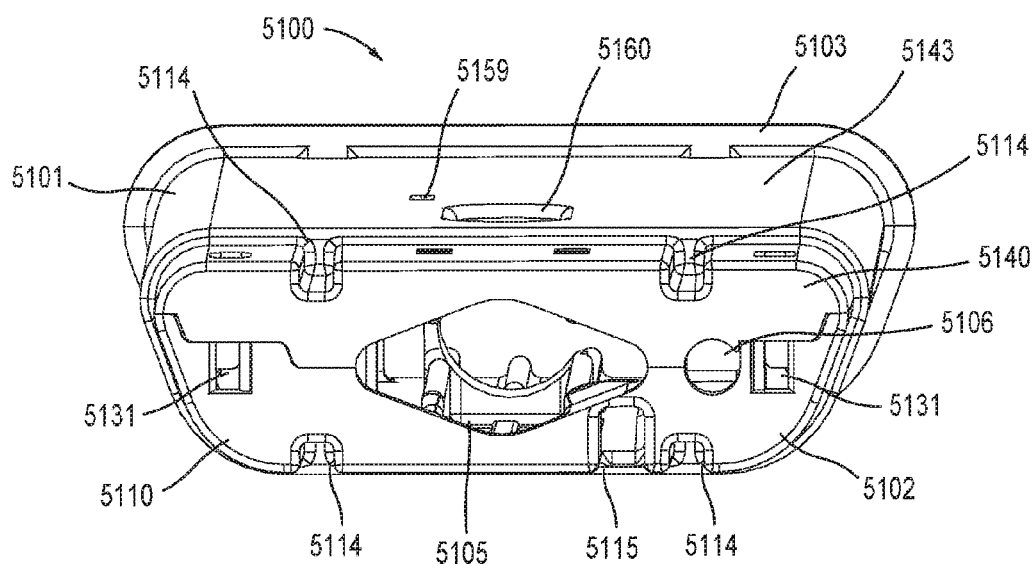
FIG. 65 is a bottom perspective view of a housing of the medical injector illustrated in FIG. 64.

As shown in FIG. 65, when the first housing member 5110 and the second housing member 5140 are assembled, the distal end portion 5102 of the housing 5100 defines a needle aperture 5105, a transfer member access opening 5106 and base lock openings 5131. Similarly stated, the first housing member 5110 and the second housing member 5140 collectively define the needle aperture 5105, the transfer member access opening 5106 and the base lock openings 5131. The needle aperture 5105 is configured to allow the needle 5216 (see e.g., FIGS. 74, 92 and 93) to exit the housing 5100 when the medical injector 5000 is actuated, as described in further detail herein.

The transfer member access opening 5106 is configured to provide access to the transfer member 5600 when the transfer member 5600 is disposed within the housing 5100. For example, in some embodiments, the transfer member 5600 can be disengaged from the medicament delivery mechanism 5300 without moving the medicament delivery mechanism 5300 in the distal direction. In this manner, the medical injector 5000 can be disabled such that the medicament delivery mechanism 5300 cannot engage the medicament container 5200 to convey a medicament 5220. For example, in some embodiments, a user, manufacturer and/or operator can disengage the transfer member 5600 from the medicament delivery mechanism 5300, via the transfer member access opening 5106, to safely dispose of an unused medical injector 5000 whose medicament 5220 expired. In other embodiments, an operator can manipulate the transfer member within the housing 5100 via the transfer member access opening 5106 during the assembly of the medical injector 5000.

Figure 73:
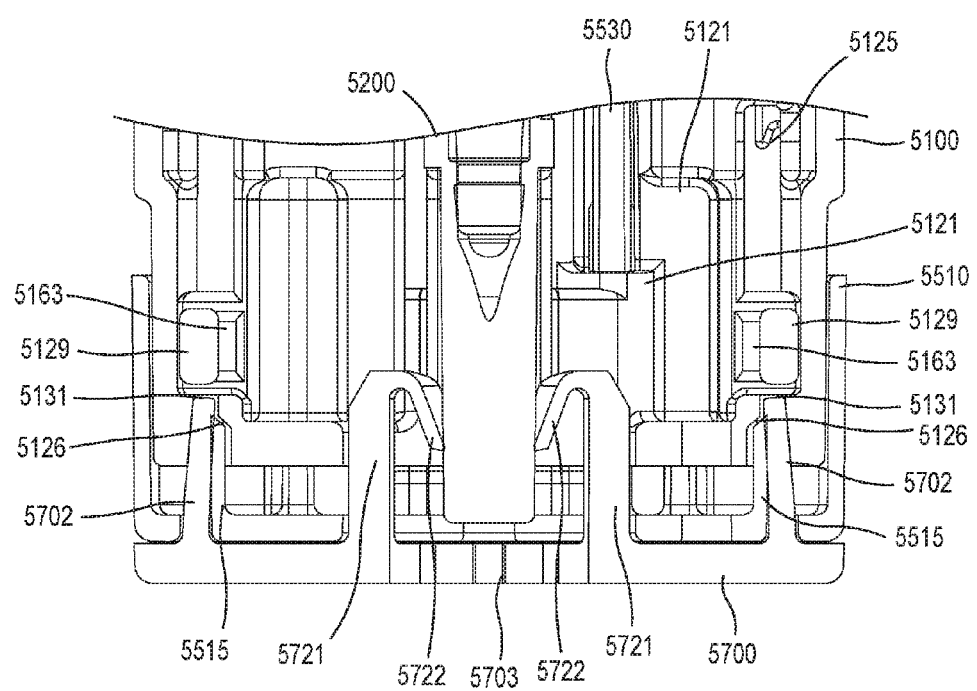
FIG. 73 is an enlarged view of a portion of the medicament delivery mechanism on the medical injector illustrated in FIG. 71.

The base lock openings 5131 are configured to receive the base locks 5515 and the safety lock protrusions 5702, as shown in the cross-sectional view of FIG. 73. The base lock openings 5131 receive the base locks 5515 and the safety lock protrusions 5702 such that the base locks 5515 of the base 5510 are in contact with the base lock protrusions 5126 of the first housing member 5110 when the safety lock protrusions 5702 are disposed within the base lock openings 5131. In this manner, the safety lock protrusions 5702 and the base lock protrusion 5126 prevent the base from moving in a proximal direction by placing the proximal surface of the base locks 5515 in contact with a distal surface of the base lock protrusions 5126. When the safety lock protrusions 5702 are removed from the base lock openings 5131, the proximal surface of the tapered surface of the base locks 5515 allow movement in a proximal direction past the corresponding tapered surfaces of the base lock protrusions 5126 when the base 5510 is moved in the proximal direction.

Figure 78:
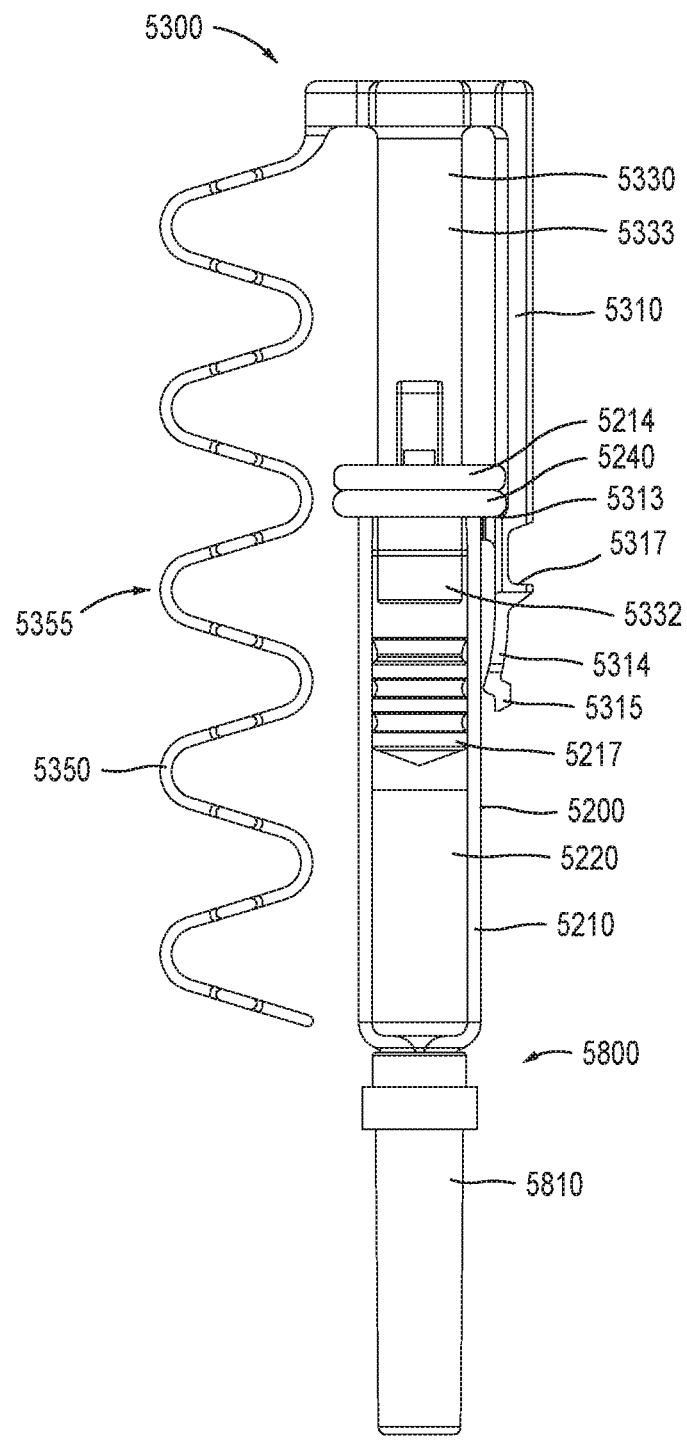
FIG. 78 is a front view of a portion of the medical injector illustrated in FIG. 60.

FIGS. 71-80 show the medicament container 5200, the system actuator 5500, the transfer member 5600 and the medicament delivery mechanism 5300 of the medical injector 5000. The medicament container 5200 has a body 5210 with a distal end portion 5213 and a proximal end portion 5212. The body 5210 defines a volume 5211 that contains (i.e., is filled with or partially filled with) a medicament 5220 (see, e.g., FIG. 74). The distal end portion 5213 of the medicament container 5200 includes a neck 5215 that is coupled to the needle 5216, as described below. The proximal end portion 5212 of the medicament container 5200 includes an elastomeric member 5217 (i.e., a plunger) that seals the medicament 5220 within the body 5210. The elastomeric member 5217 is configured to move within the body 5210 to inject the medicament 5220 from the medicament container 5200. More particularly, as shown in FIG. 78, the elastomeric member 5217 receives a piston rod 5333 of a piston portion 5330 included in the medicament delivery mechanism 5300. The proximal end portion 5212 includes a flange 5214 and a damping member 5240 (see FIG. 78) configured to engage the piston portion 5330 and the latch portion 5310 of the medicament delivery mechanism 5300. The flange 5214 and the damping member 5240 are also configured to engage and/or contact the medicament container holders 5127 and 5157 of the housing 5100.

The elastomeric member 5217 can be of any design or formulation suitable for contact with the medicament 5220. For example, the elastomeric member 5217 can be formulated to minimize any reduction in the efficacy of the medicament 5220 that may result from contact (either direct or indirect) between the elastomeric member 5217 and the medicament 5220. For example, in some embodiments, the elastomeric member 5217 can be formulated to minimize any leaching or out-gassing of compositions that may have an undesired effect on the medicament 5220. In other embodiments, the elastomeric member 5217 can be formulated to maintain its chemical stability, flexibility and/or sealing properties when in contact (either direct or indirect) with the medicament 5220 over a long period of time (e.g., for up to six months, one year, two years, five years or longer). In some embodiments, the elastomeric member 5217 is similar to the elastomeric member 3217 of the medical injector 3000, described with reference to FIG. 22.

Figure 74:
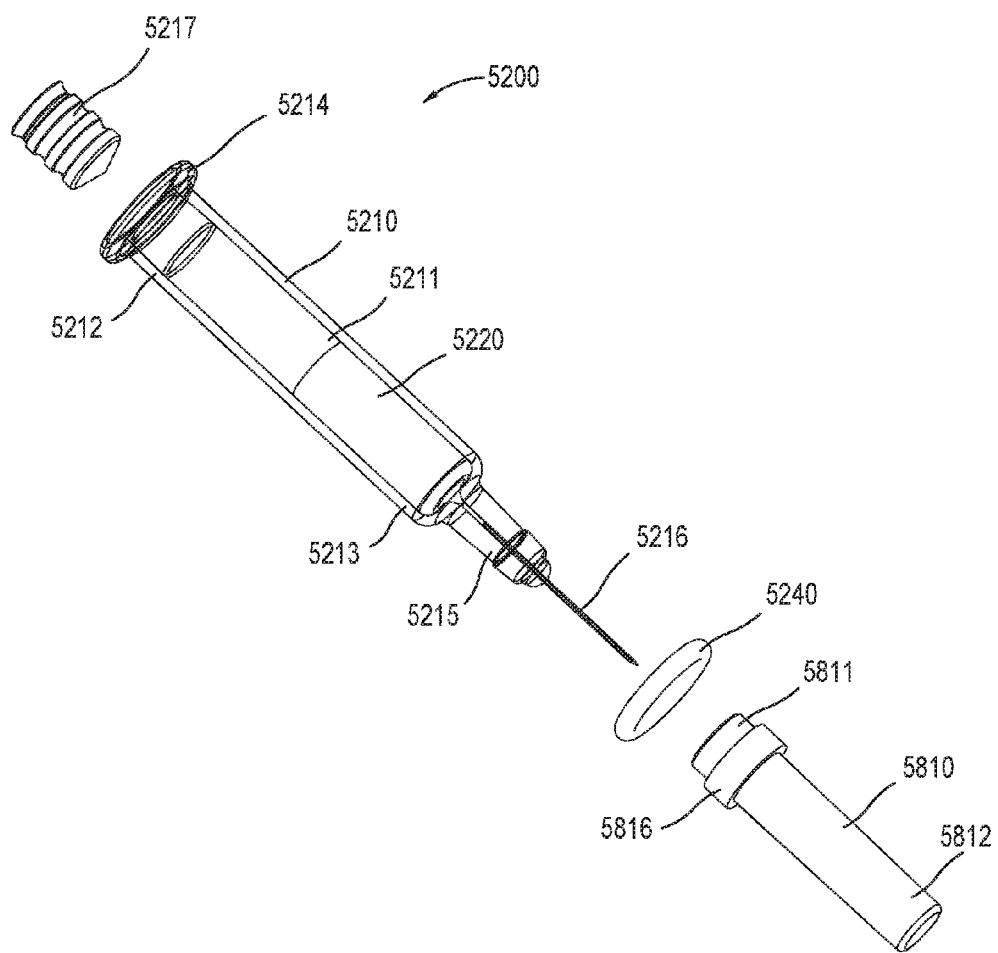
FIG. 74 is an exploded view of a medicament container of the medical injector illustrated in FIG. 60.
Figure 75:
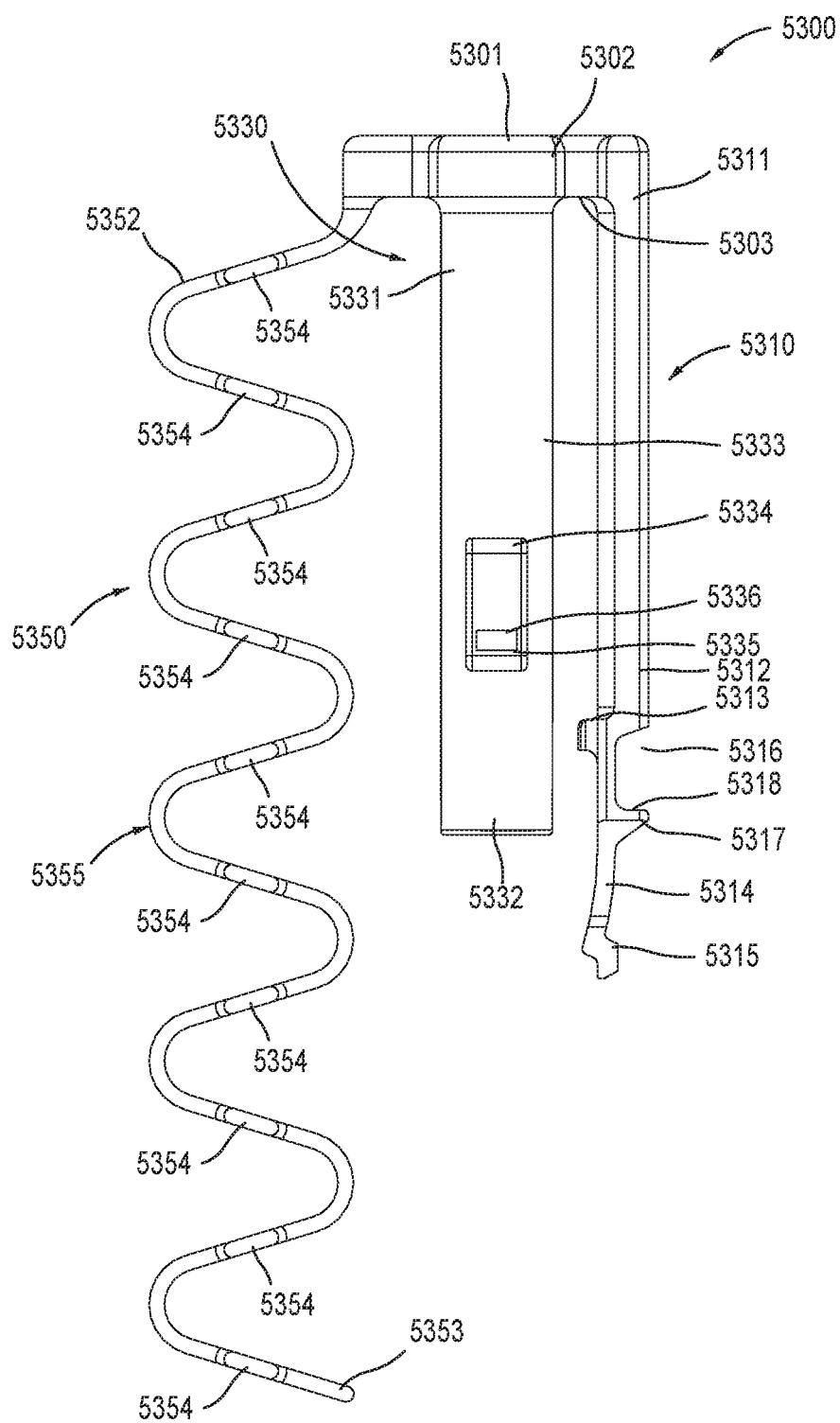
FIG. 75 is a front view of a first movable member of the medical injector illustrated in FIG. 60, in a first configuration.
Figure 76:
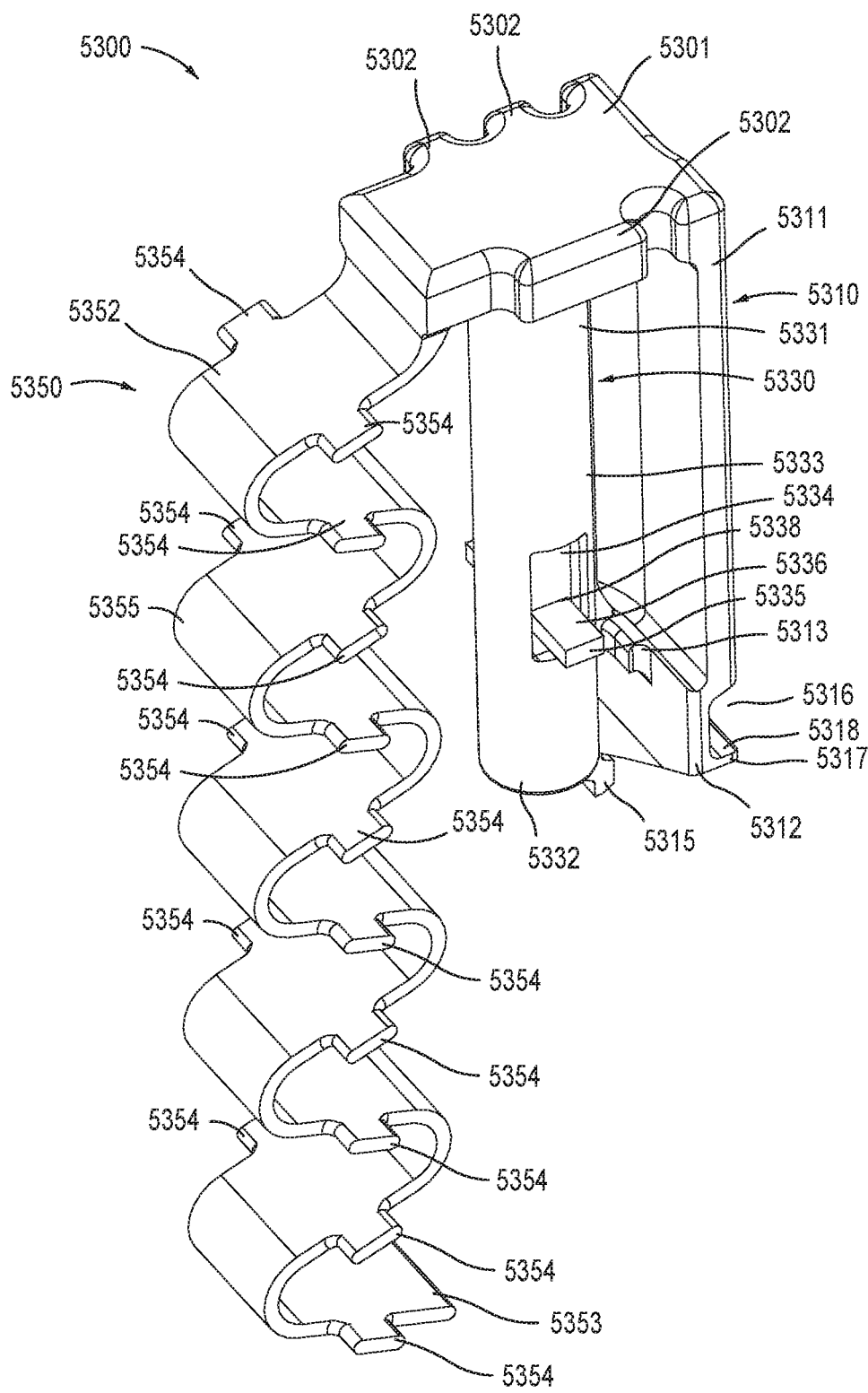
FIG. 76 is a front perspective view of the first movable member of the medical injector illustrated in FIG. 75, in a first configuration.
Figure 77:
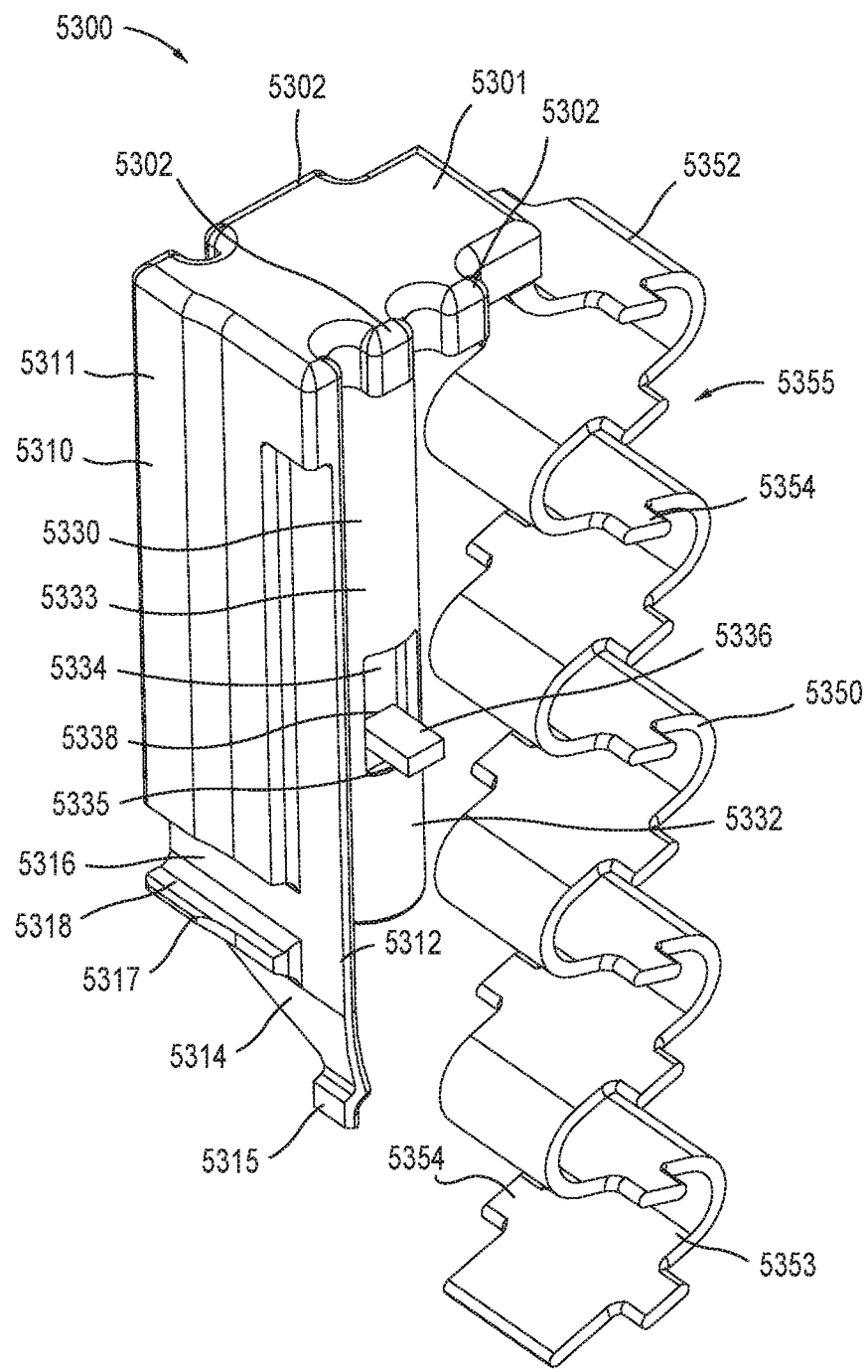
FIG. 77 is a rear perspective view of the first movable member of the medical injector illustrated in FIG. 75, in a first configuration.

The medicament container 5200 can have any suitable size (e.g., length and/or diameter) and can contain any suitable volume of the medicament 5220. Moreover, the medicament container 5200 and the piston portion 5330 can be collectively configured such that the piston portion 5330 travels a desired distance within the medicament container 5200 (i.e., the "stroke") during an injection event. In this manner, the medicament container 5200, the volume of the medicament 5220 within the medicament container 5200 and the piston portion 5330 can be collectively configured to provide a desired fill volume and delivery volume. For example, the medicament container 5200, as shown in FIG. 74, is a prefilled syringe and can be purchased and/or acquired with a given fill volume. In this manner, the piston portion 5330 can be configured to provide a desired delivery volume.

Moreover, the length of the medicament container 5200 and the length of the piston portion 5330 can be configured such that the medicament delivery mechanism 5300 can fit in the same housing 5100 regardless of the fill volume, the delivery volume and/or the ratio of the fill volume to the delivery volume. In this manner, the same housing and production tooling can be used to produce devices having various dosages of the medicament 5220. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

As shown in FIGS. 71-74, the system actuator 5500 includes the base 5510 and a release member 5530, and is configured to move in the proximal and distal direction relative to the housing 5100. Although the base 5510 and the release member 5530 are shown as being monolithically constructed to form the system actuator 5500, in other embodiments the system actuator 5500 can include a base that is constructed separately from (and later joined to) a release member. As described above, when the medical injector 5000 is in its first configuration (i.e., the storage configuration), the base locks 5515 and the safety lock protrusions 5702 are disposed within the base lock opening 5131 such that the base locks 5515 are urged by the safety lock protrusions 5702 into contact with the base lock protrusions 5126. Therefore, the system actuator 5500 and/or the base 5510 cannot move in the proximal direction to actuate the medicament delivery mechanism 5300. Similarly stated, as shown in FIG. 73, when the medical injector 5000 is in its first configuration (i.e., the storage configuration), the safety lock protrusions 5702 and the base lock protrusions 5126 cooperatively limit the proximal movement of the base 5510.

Figure 72:
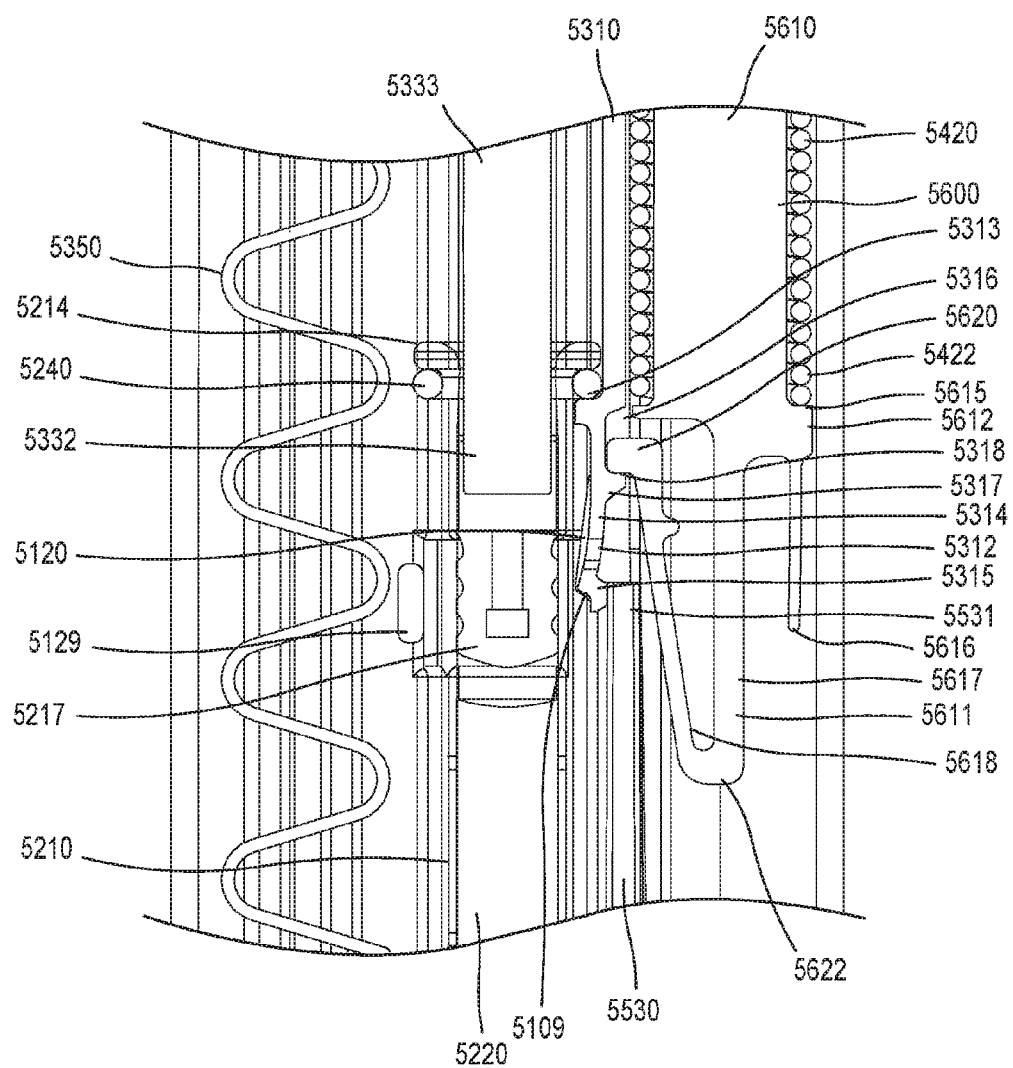
FIG. 72 is an enlarged view of a portion of the medicament delivery mechanism on the medical injector illustrated in FIG. 71.

The release member 5530 has a proximal end portion 5531 and a distal end portion 5532. The release member 5530 extends from a proximal surface 5511 of the base 5510. The proximal end portion 5531 of the release member 5530 is configured to engage that latch portion 5310 of the medicament delivery mechanism 5300 when the medical injector is in its first (or storage) configuration. More particularly, as shown in FIG. 72, the proximal end portion 5531 of the release member 5530 maintains a first latch protrusion 5315 of the latch portion 5310 in contact with the engagement surface 5109 of the latch member notch 5120 of the housing 5100. When the engagement surface 5109 is in contact with the first latch protrusion 5315, the engagement surface 5109 applies a reaction force to the first latch protrusion 5315 in response to the force applied by the spring 5420, which urges the transfer member 5600 and the medicament delivery mechanism 5300 in a distal direction. Similarly stated, when the first latch protrusion 5315 is in contact with the engagement surface 5109, the engagement surface 5109 limits distal movement of the first latch protrusion 5315, and thus, the medicament delivery mechanism 5300. In this manner, when the system actuator 5500 is in a first position (i.e., coupled to the distal end portion of the housing 5100), the release member 5530 maintains the first latch protrusion 5315 within the latch member notch 5120 and maintains the medical injector 5000 in the first configuration (e.g., non-actuated configuration).

The medicament delivery mechanism 5300 (all or portions of which can also be referred to as a "first movable member") includes the latch portion 5310, the piston portion 5330 and the bias portion 5350 (see e.g., FIGS. 75-78). The latch portion 5310 is operably coupled to the spring 5420 via the transfer member 5600 (i.e., the second movable member 5600). The medicament delivery mechanism 5300 includes a proximal end portion 5301. The proximal end portion 5301 includes the guide protrusions 5302, described above with reference to FIGS. 67-70.

The latch portion 5310 includes a proximal end portion 5311 and a distal end portion 5312. The proximal end portion 5311 is disposed at and/or joined with the proximal end portion 5301 of the medicament delivery mechanism 5300. Similarly stated, the latch portion 5310 is configured to extend from the proximal end portion 5301 of the medicament delivery mechanism 5300 in the distal direction. The distal end portion 5312 of the latch portion 5310 includes a latch arm 5314 having a first latch protrusion 5315, a second latch protrusion 5317, and a second shoulder 5313, and defines a channel 5316. As described above, the first latch protrusion 5315 is configured to engage the release member 5530 and the engagement surface 5109 of the latch member notch 5120. In particular, as shown in FIG. 72, the release member 5530 urges, bends and/or deforms the latch arm 5314 to maintain the first latch protrusion 5315 within the latch member notch 5120. Thus, the latch arm 5314 can be constructed from a flexible material such that the release member 5530 can urge, bend and/or deform the latch arm 5314 to engage the first latch protrusion 5315 with the latch member notch 5120.

The channel 5316 of the latch portion 5310 is defined between a surface of the distal end portion 5312 of the latch portion 5310 and a proximal surface 5318 of the second latch protrusion 5317. The channel 5316 is configured to receive the latch 5620 of the transfer member 5600. More particularly, when the medical injector 5000 is in the first configuration, the proximal surface 5318 of the second latch protrusion 5317 is in contact with a distal surface 5621 of the latch 5620 of the transfer member 5600. In this manner, the transfer member 5600 can transfer a force produced by the actuation of the spring 5420 to the latch portion 5310 of the medicament delivery mechanism 5300 to move the medicament delivery mechanism 5300 in the distal direction. Similarly stated, this arrangement allows the medicament delivery mechanism 5300 to move with and/or remain coupled to the transfer member 5600 (which can be referred to as a "second movable member") during the insertion and/or injection operation.

The piston portion 5330 includes a proximal end portion 5331 and a distal end portion 5332 and defines a piston rod 5333 therebetween. The proximal end portion 5331 is disposed at and/or joined with the proximal end portion 5301 of the medicament delivery mechanism 5300. Similarly stated, the piston portion 5330 is configured to extend from the proximal end portion 5301 of the medicament delivery mechanism 5300 in the distal direction. The distal end portion 5332 is configured to be disposed at least partially within the proximal end portion 5212 of the medicament container 5200. The piston rod 5333 defines recesses 5334.

The piston portion 5330 includes two engagement members 5336 that have a first shoulder 5335 and a deformable portion 5338. The engagement members 5336 are at least partially disposed within the recesses 5334 defined by the piston rod 5333, and extend in a lateral direction relative to the piston portion 5330. Similarly stated, the engagement members 5336 extend from the corresponding recess 5334 and are substantially perpendicular to a longitudinal axis defined by the piston portion 5330 between the proximal end portion 5331 and the distal end portion 5332. In this manner, as described in more detail herein, when the engagement members 5336 are deformed (e.g., at the deformable portion 5338), the engagement members 5336 fold into and/or are contained within the recesses 5334. The engagement members 5336 can be any suitable size or shape. In some embodiments, the engagement members 5336 can be monolithically formed with the piston portion 5330. In other embodiments, the engagement members 5336 can be formed separately from a brittle material and later coupled to the piston portion 5330. In still other embodiments, the engagement members 5336 can be formed separately from a flexible material and coupled to the piston portion 5330. In some embodiments, for example, the engagement members 5336 can be a single pin that is disposed through an opening within the piston portion 5330 such that the ends of the pins protrude from the recesses 5334.

Figure 91:
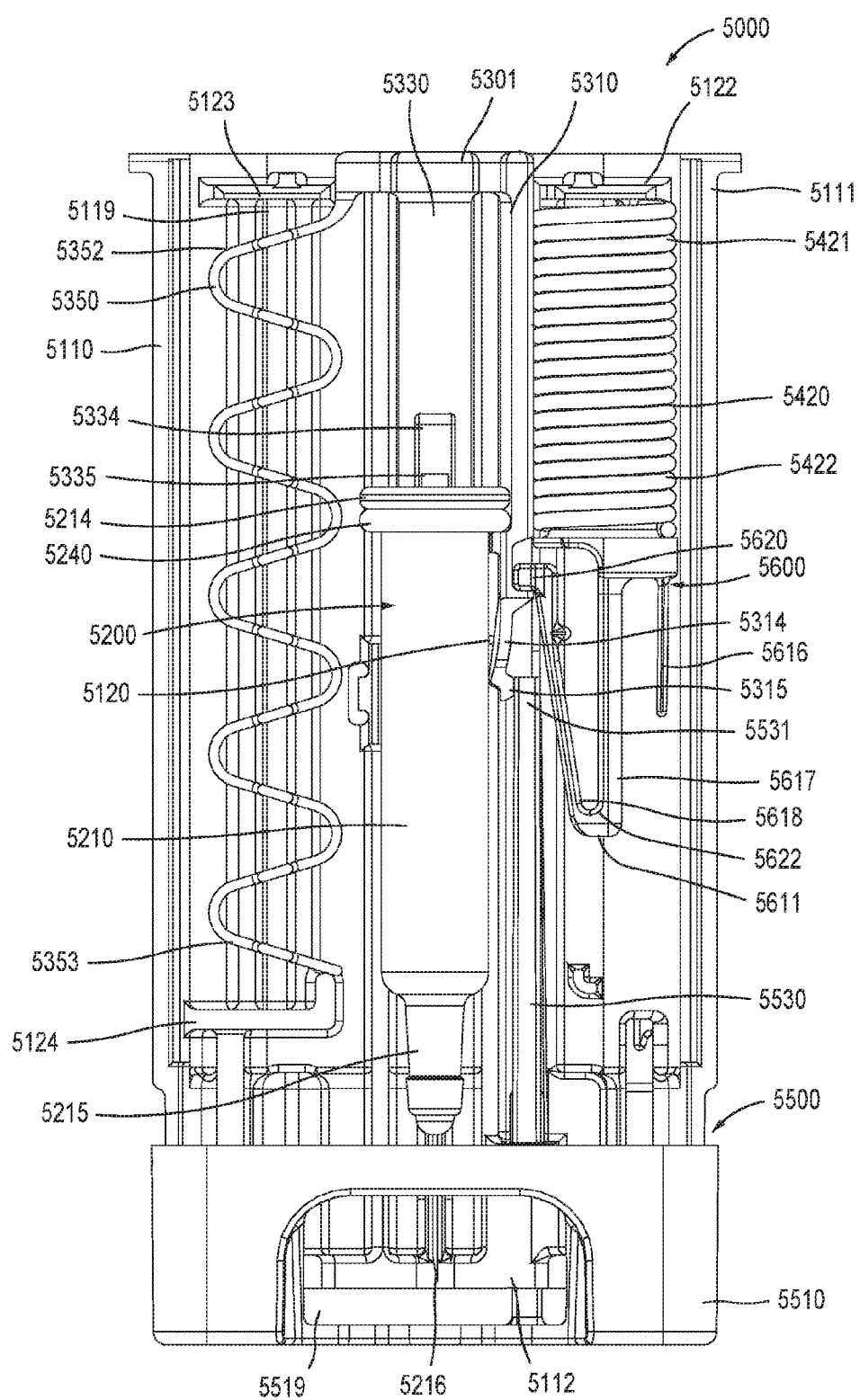
FIG. 91 is a front view of a portion of the medical injector illustrated in FIG. 60 in the third configuration.

The first shoulder 5335 of the engagement member 5336 is disposed at a distal surface of the engagement member 5336. As shown in FIG. 91, the first shoulder 5335 is configured to engage a proximal surface of the flange 5214 of the medicament container 5200. In this manner, the piston portion 5330 of the medicament delivery mechanism 5300 is configured to move the medicament container 5200 in response to a force applied by the spring 5420 when the medical injected 5000 is actuated. Similarly stated, when the release member 5530 actuates the medical injector 5000, the transfer member 5600 transfers a force from the spring 5420 to the medicament delivery mechanism 5300 such that the first shoulder 5335 of the piston portion 5330 moves the medicament container 5200 from the first position to the second position.

The deformable portion 5338 of the engagement member 5336 is configured to deform during and/or to initiate an injection event. The deformable portion 5338 can be any suitable structure that deforms (e.g., either plastically or elastically, including bending, breaking, stretching or the like) when the force applied thereto exceeds a value. For example, in some embodiments, the deformable portion 5338 can include a fillet configured to act as a stress concentration riser configured to deform under a given force. In use within the medical injector 5000, the deformable portion 5338 is configured to deform during and/or to initiate an injection event when the medicament container 5200 is in the second position. After deformation of the deformable portion 5338 and/or movement of the engagement members 5336, the first shoulder 5335 is no longer in contact with the flange 5214 of the medicament container 5200 and the piston portion 5330 is allowed to move in a distal direction, relative to the medicament container 5200.

The bias portion 5350 includes a proximal end portion 5352 and a distal end portion 5353. The proximal end portion 5352 is disposed at and/or joined with the proximal end portion 5301 of the medicament delivery mechanism 5300. Similarly stated, the bias portion 5350 is configured to extend from the proximal end portion 5301 of the medicament delivery mechanism 5300 in the distal direction.

Figure 95:
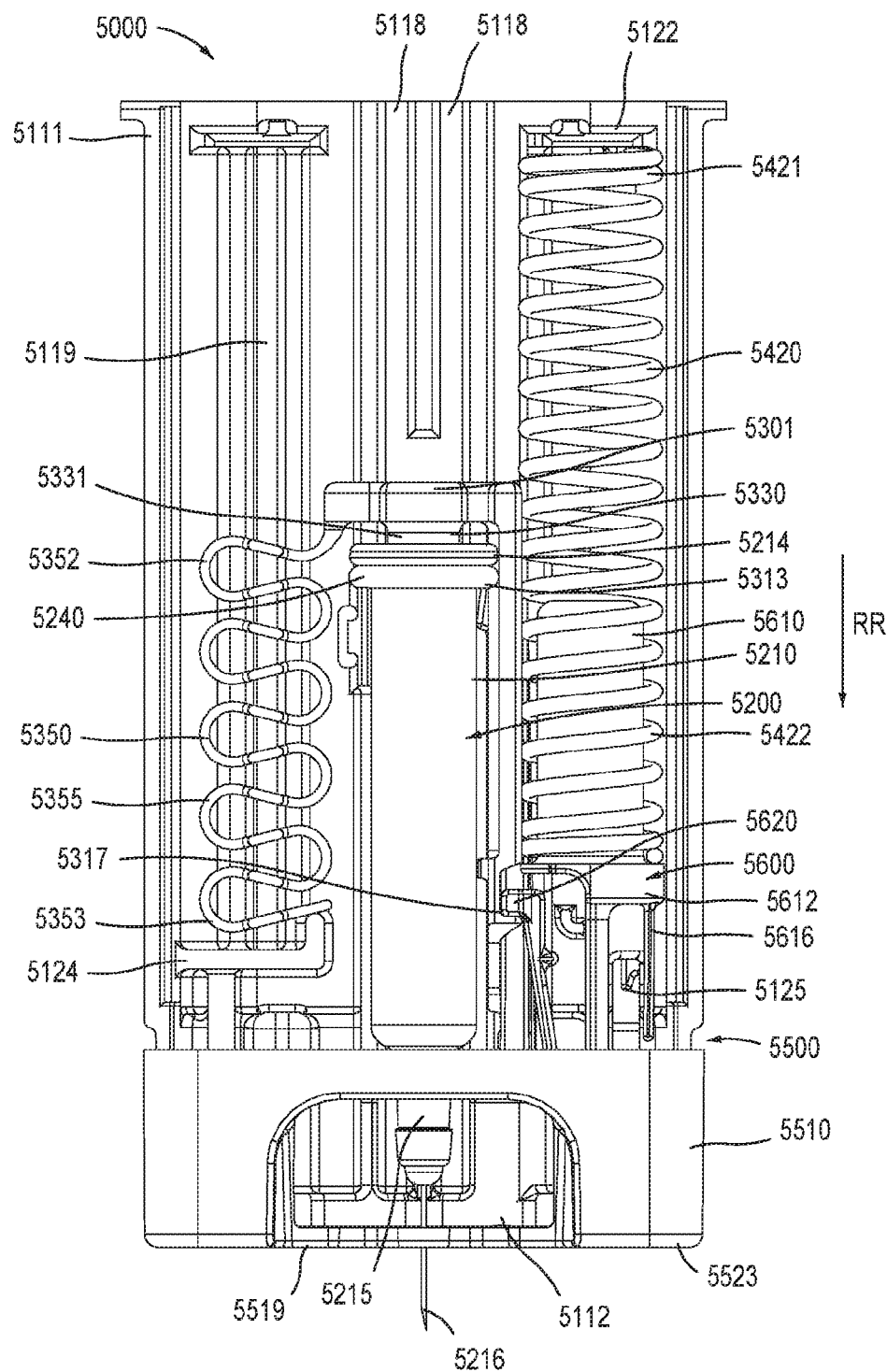
FIG. 95 is a front view of the medical injector illustrated in FIG. 60 in a fifth configuration (i.e., the injection configuration).
Figure 96:
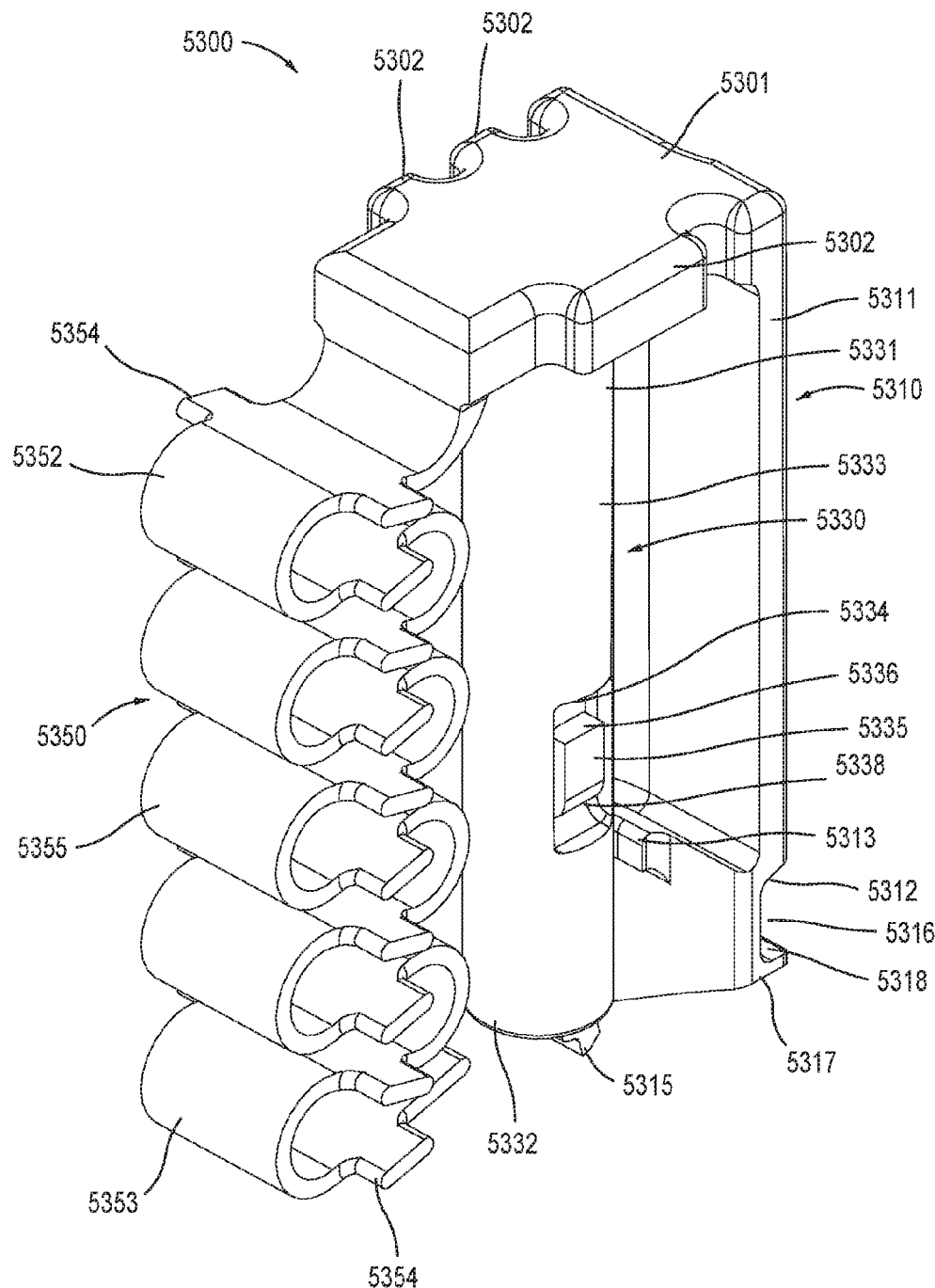
FIG. 96 is a perspective view of a first movable member of the medical injector illustrated in FIG. 60 in a second configuration.

The bias portion 5350 includes a serpentine portion 5355 constructed from any suitable material and having suitable dimensions such that the bias portion 5350 and/or the serpentine portion 5355 produce a force when the serpentine portion 5355 is compressed (see e.g., FIG. 95). As described above, the bias portion 5350 includes guide protrusions 5354 (see e.g., FIG. 76) configured to engage the bias member grooves 5119 defined by the first housing member 5110 and the bias member grooves 5149 defined by the second housing member 5140 to prevent the bias portion 5350 from moving in a lateral direction with respect to the housing 5100 and/or rotating within the housing 5100. The distal end portion 5353 of the bias portion 5350 is configured to engage the lower bias plate 5124. In this manner, a proximal surface of the lower bias plate 5124 prevents the distal end portion 5353 of the bias portion 5350 from moving in the distal direction as the medicament delivery device 5300 moves in the distal direction in response to the distal force applied by the spring 5420 when the medical injector 5000 is actuated. Therefore, the serpentine portion 5355 of the bias portion 5350 is compressed between the proximal end portion 5352 and the distal end portion 5353.

Figure 97:
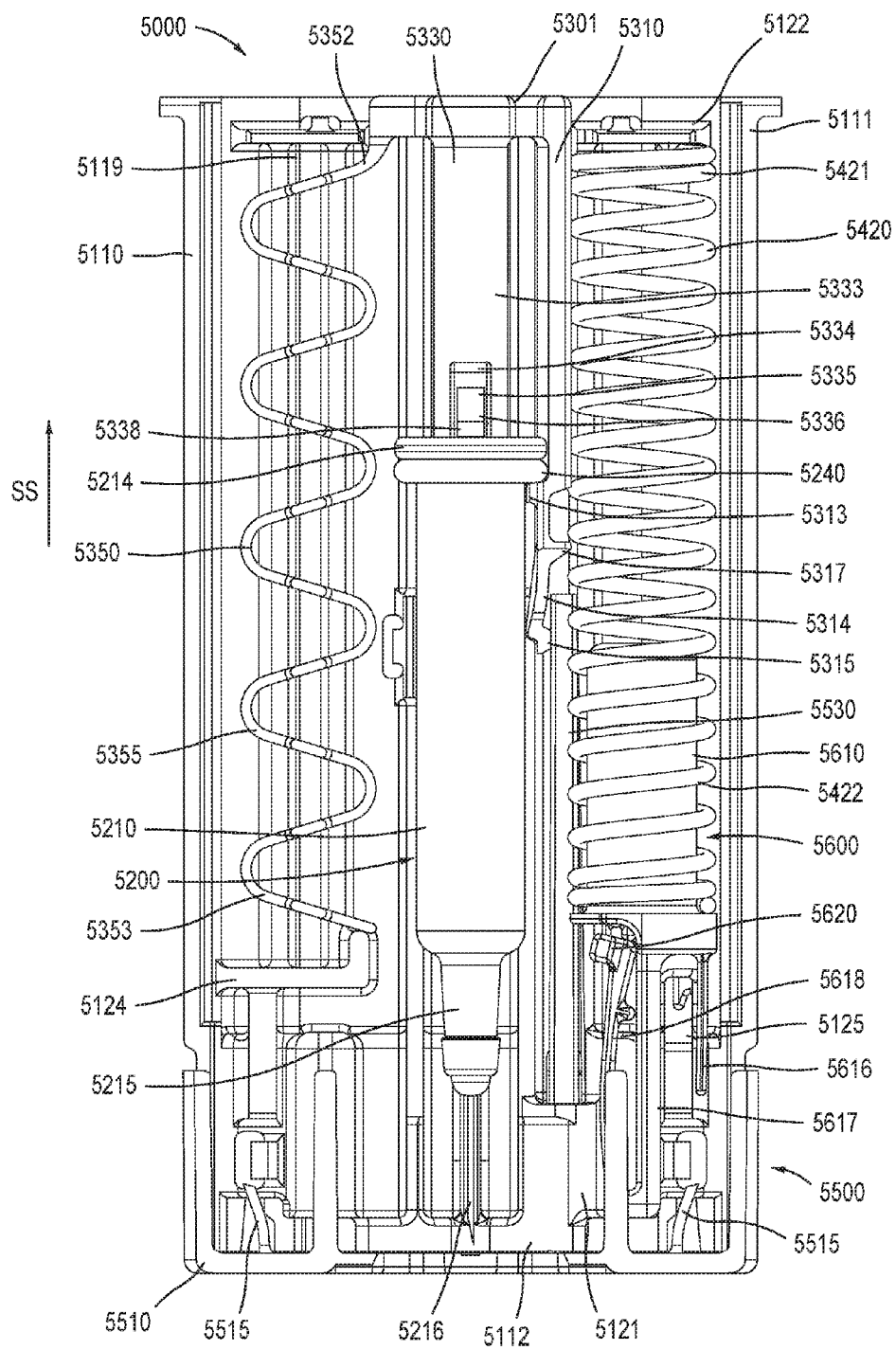
FIG. 97 is a front view of the medical injector illustrated in FIG. 60 in a sixth configuration (i.e., the retraction configuration).
Figure 98:
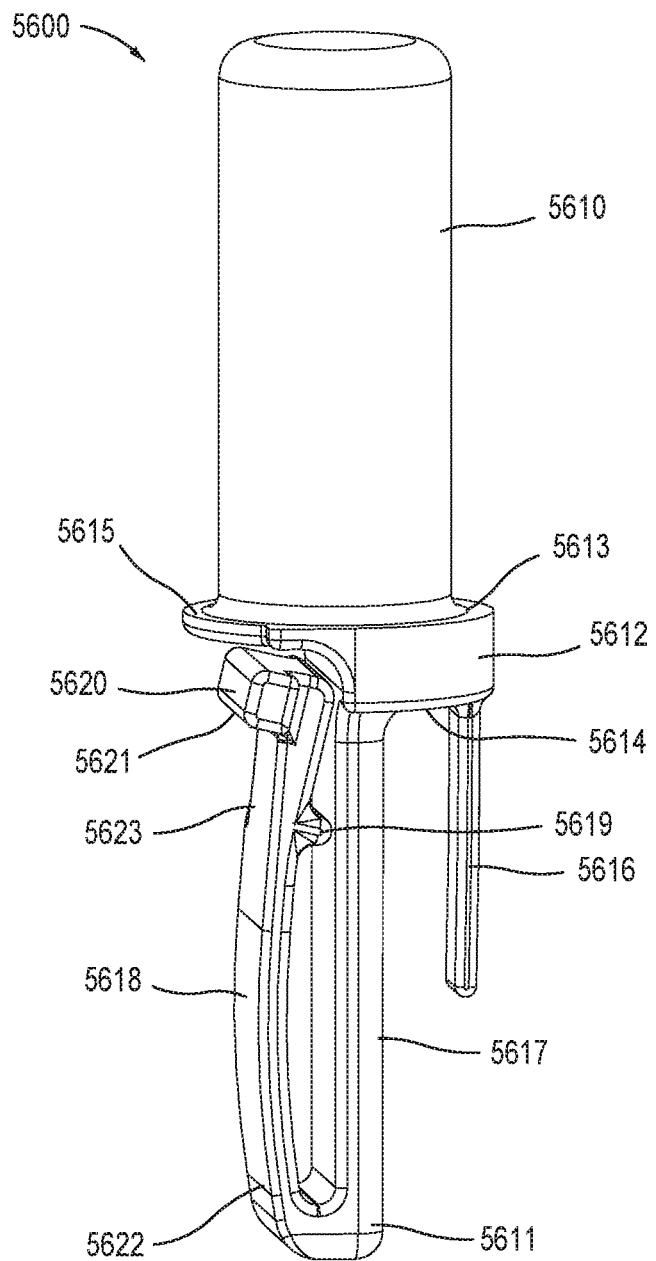
FIG. 98 is a front perspective view of a second movable member of the medical injector illustrated in FIG. 60 in a second configuration.

The transfer member 5600 (also referred to as the "second movable member") includes a proximal end portion 5610 and a distal end portion 5611, and is configured to move between a first configuration (see e.g., FIGS. 79 and 80) and a second configuration (see e.g., FIGS. 97 and 98). The proximal end portion 5610 is substantially cylindrical and is configured to engage and/or contact the spring 5420. Moreover, the transfer member 5600 includes a ring protrusion 5612 that includes a proximal surface 5613 defining a spring seat 5615. As shown in FIG. 72, the distal end portion 5422 of the spring 5420 is disposed about the proximal end portion 5610 of the transfer member 5600, and is configured to engage the spring seat 5615 defined by the ring protrusion 5612.

The transfer member 5600 further includes a guide arm 5616 and the latch extension 5617 that extends from a distal surface 5614 of the ring protrusion 5612. The guide arm 5616 is configured to guide the transfer member 5600 as it moves in the distal direction and provide support to the latch extension 5617 when the transfer member 5600 is placed in the second configuration, as described in further detail herein.

The latch extension 5617 includes the latch arm 5618 and a bendable portion 5622. The latch arm 5618 includes the guide protrusion 5619 and the latch 5620. As described above, the latch extension 5617 extends in a distal direction from the ring protrusion 5612 of the transfer member 5600. The latch arm 5618 is configured to extend from the distal end portion 5611 of the transfer member 5610. Similarly stated, the latch arm 5618 extends from a distal end portion of the latch extension 5617. Moreover, the latch arm 5618 extends from the distal end portion of the latch extension 5617 at a suitable angle such that the latch 5620 is received within the channel 5316 (see e.g., FIG. 72). For example, in some embodiments, the latch arm 5618 extends from the distal end portion of the latch extension 5617 at an acute angle. The guide protrusion 5619 is configured to engage the transfer member groove 5117, as described above.

The latch 5620 extends from a proximal end portion 5623 of the latch arm 5618. The latch 5620 is configured to engage the second latch protrusion 5317 of the latch portion 5310 of the medicament delivery mechanism 5300. As described above, the distal surface 5621 of the latch 5620 is configured to be in contact with a proximal surface 5318 of the second latch protrusion 5317 when the transfer member 5600 is in the first configuration. In this manner, the transfer member 5600 transfers a force from the actuation of the spring 5420 to the medicament delivery mechanism 5300 via the transfer member 5600 to move the medicament delivery mechanism 5300 in the distal direction within the housing 5100. Therefore, the force produced by the spring 5420 results in both the insertion of the needle 5216 and injection of the medicament 5220 within the medicament container 5200, which occur as separate and distinct operations, as described herein.

Furthermore, when the transfer member 5600 has moved a desired distance in the distal direction, in response to the force produced by the actuation of the spring 5420, the latch arm 5618 engages the transfer member release protrusion 5121 of the housing 5100 (see e.g., FIG. 67) to place the transfer member 5600 in the second configuration. Similarly stated, the latch arm 5618 engages and/or contacts the transfer member release protrusion 5121 when the transfer member 5600 is in the second position. The bendable portion 5622 of the latch extension 5617 is configured to bend, relative to the latch extension 5617. Thus, when the latch arm 5618 engages the transfer member release protrusion 5121, the bendable portion 5622 of the transfer member 5600 bends, thereby placing the transfer member 5600 in its second configuration (see FIGS. 97 and 98). When the transfer member 5600 is in its second configuration, the latch 5620 is disengaged from the second latch protrusion 5317 of the medicament delivery mechanism 5300. Said another way, when the latch arm 5618 engages the transfer member release protrusion 5121, the bendable portion 5622 of the transfer member bends such that the angle between the latch arm 5618 and the latch extension 5617 is reduced, thus disengaging the transfer member 5600 from the medicament delivery mechanism 5300. Said yet another way, when the transfer member 5600 is in its second configuration, the medicament delivery mechanism 5300 is isolated and/or no longer operably coupled to the spring 5420. In this manner, as described below, the retraction force exerted by the biasing portion 5350 moves the medicament delivery mechanism 5300 proximally within the housing 5100 to retract the needle 5216.

Figure 81:
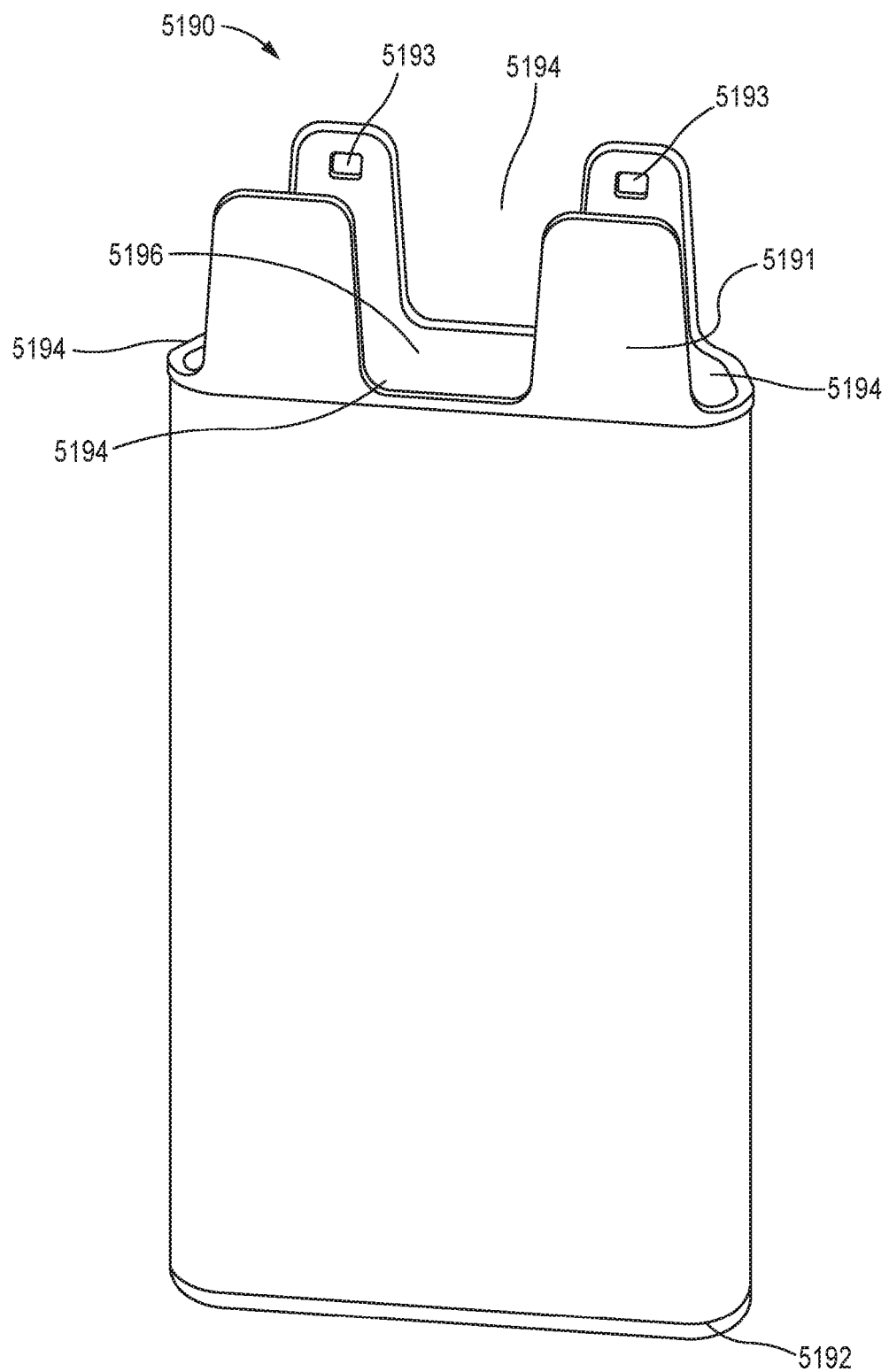
FIGS. 81 and 82 are perspective views of a cover of the medical injector illustrated in FIG. 60.
Figure 82:
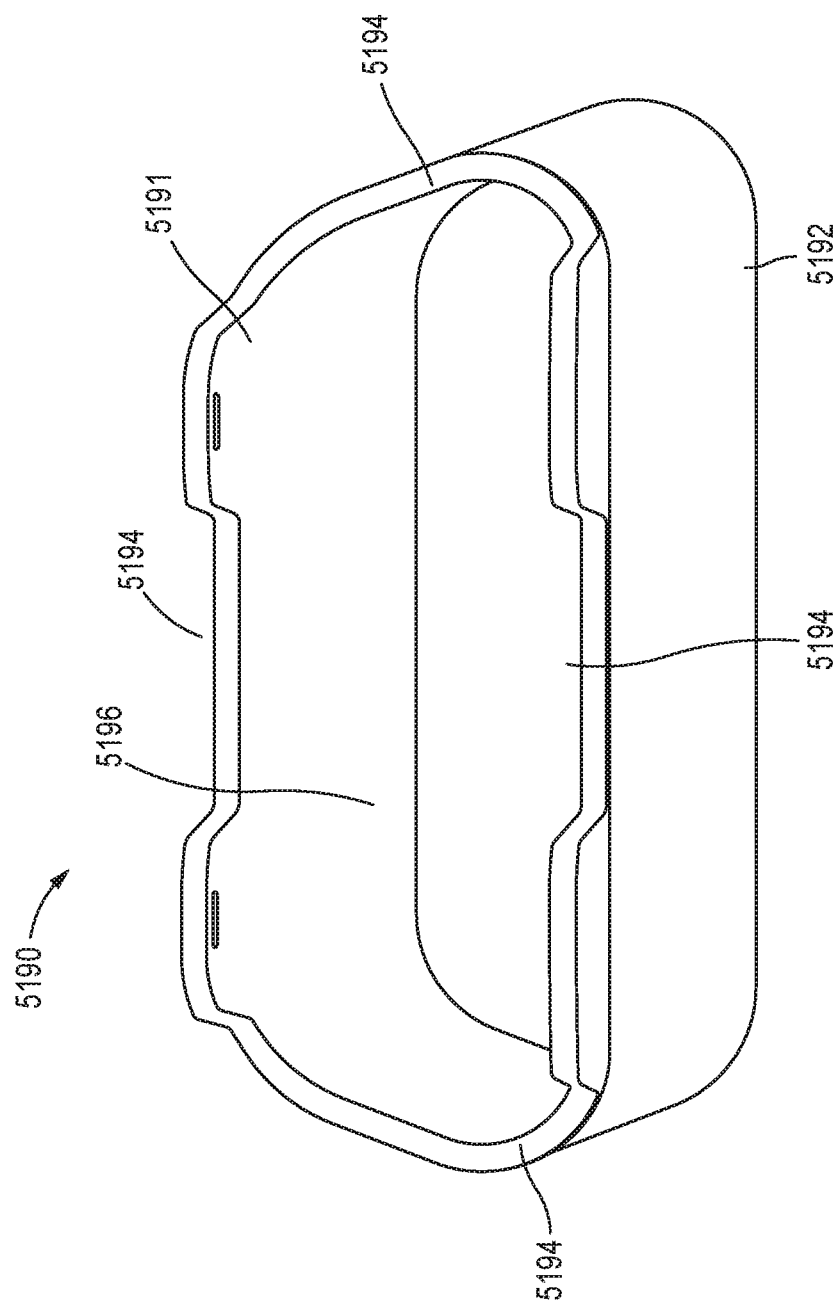
Figure 83:
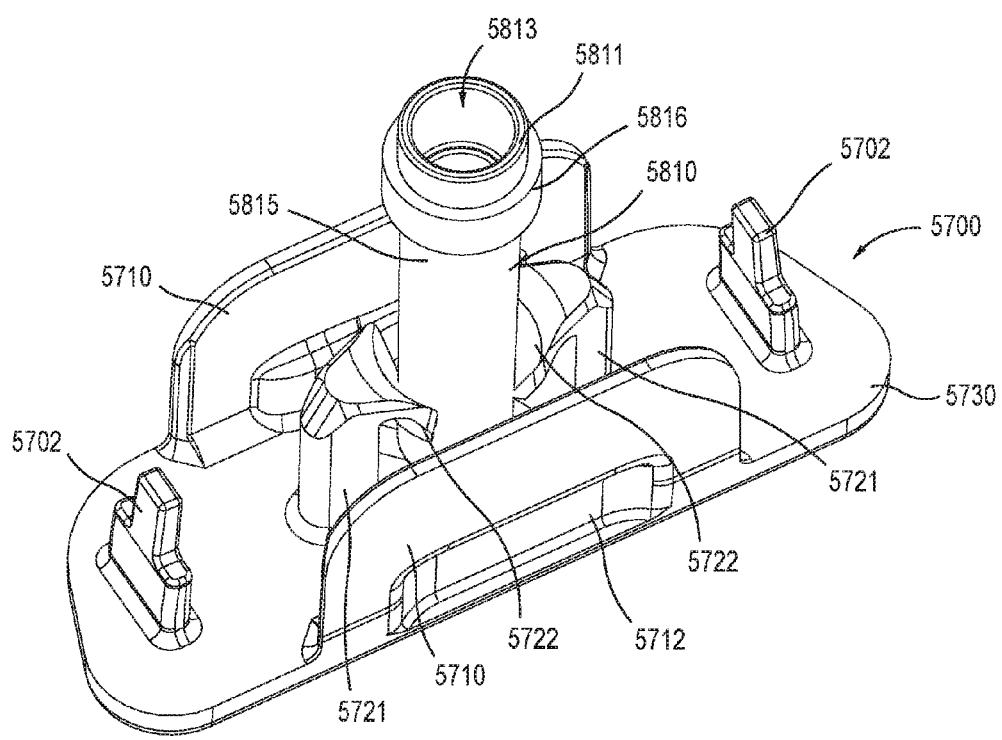
FIG. 83 is a perspective view of a safety lock of the medical injector illustrated in FIG. 60.
Figure 84:
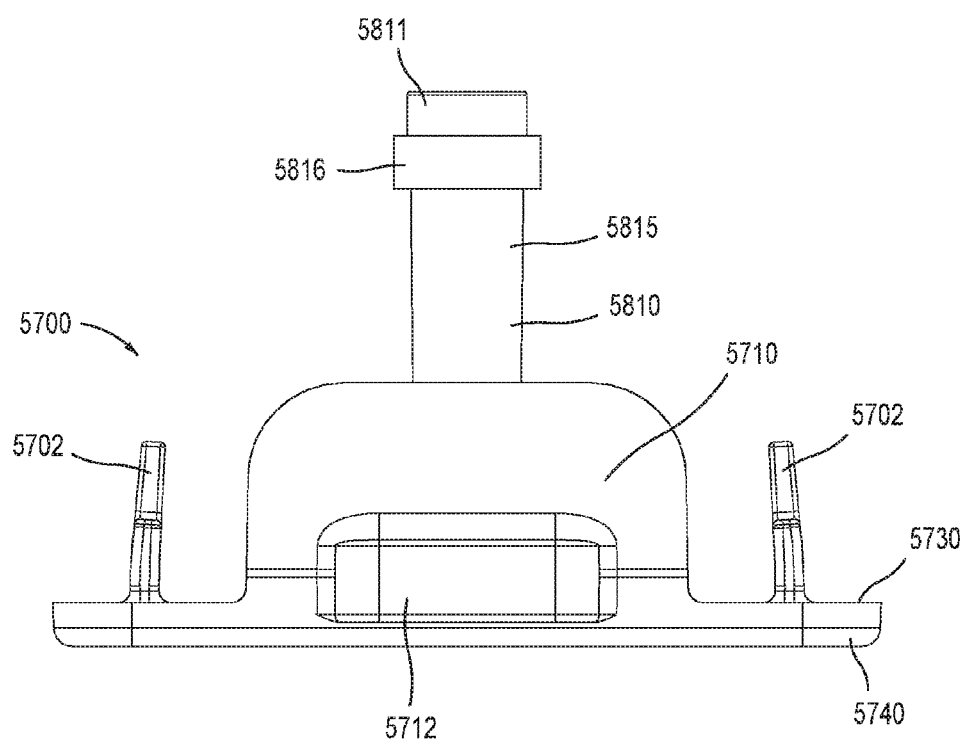
FIG. 84 is a front view of the safety lock of the medical injector illustrated in FIG. 83.
Figure 85:
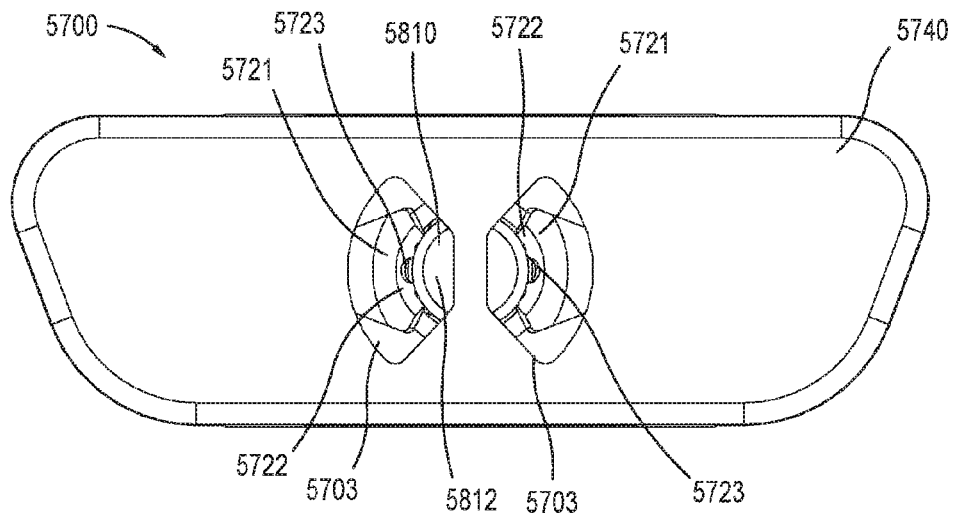
FIG. 85 is a bottom view of the safety lock of the medical injector illustrated in FIG. 83.

FIGS. 81 and 82 show the cover 5190 of the medical injector 5000. The cover 5190 includes a proximal end portion 5191 and a distal end portion 5192, and defines a cavity 5196. The cavity 5196 of the cover 5190 is configured to receive at least a portion of the housing 5100. Thus, when the portion of the housing 5100 is disposed within the cover 5190, the cover 5190 blocks an optical pathway between the medicament container 5200 and a region outside of the housing 5100. Similarly stated, when the portion of the housing 5100 is disposed within the cover 5190, the cover 5190 is obstructs the first status indicator aperture 5130 and/or the second status indicator aperture 5160 of the housing 5100 to reduce the amount of light transmitted to the medicament 5220 within the medicament container 5200. In this manner, the life of the medicament 5220 can be extended by the prevention and/or reduction of degradation to the medicament 5220 that may be caused by ultra-violet radiation.

The proximal end portion 5191 of the cover 5190 defines apertures 5193. The apertures 5193 configured to receive the cover retention protrusions 5104 of the housing 5100 (shown in FIGS. 10 and 12). In this manner, the apertures 5193 and the cover retention protrusions 5104 of the housing 5100 removably retain the cover 5190 about at least a portion of the housing 5100. Said another way, the apertures 5193 and the cover retention protrusions 5104 of the housing 5100 are configured such that the cover 5190 can be removed from a portion of the housing 5100 and then replaced about the portion of the housing 5100.

The cover 5190 can be any suitable configuration and can include any suitable feature. For example, the cover 5190 includes openings 5195 and notches 5194. In some embodiments, the openings 5195 can receive inserts (not shown). The inserts can be flexible inserts and can be configured to increase friction between the cover 5190 and a surface. For example, the inserts can increase the friction between the cover 5190 and a surface on which the medical injector 5000 is placed, to prevent sliding. The notches 5194 are disposed at the proximal end of the cover 5190. In some embodiments, the notches 5194 can be used to reduce the material needed to manufacture the cover 5190.

FIGS. 83-87 show the safety lock 5700 of the medical injector 5000. The safety lock 5700 of the medical injector 5000 includes a proximal surface 5730, a distal surface 5740 opposite the proximal surface 5730 and a needle sheath 5810. The safety lock 5700 defines a needle sheath aperture 5703. The proximal surface 5730 of the safety lock 5700 includes two safety lock protrusions 5702, two opposing pull-tabs 5710 and an engagement portion 5720. As described above, when the safety lock 5700 is in a first (locked) position, the safety lock protrusions 5702 are configured to be disposed through the safety lock protrusion apertures 5514 defined by the base 5510 (see e.g., FIG. 88) and within the base lock openings 5131 defined by the distal end portion 5102 of the housing 5100 (see e.g., FIG. 73). Accordingly, the safety lock protrusions 5702 are configured to prevent the base locks 5515 of the base 5510 from moving past the base lock protrusion 5126 of the first housing member 5110, thereby preventing proximal movement of the base 5510 and/or delivery of the medicament 5220. Similarly stated, when the medical injector 5000 is in its first configuration (i.e., the storage configuration), the safety lock protrusions 5702 are disposed adjacent and/or in contact with the base lock protrusions 5126, thereby preventing lateral deformation (e.g., a outward flexing motion) of the base lock protrusions 5126. Thus, the arrangement of the safety lock protrusions 5702 prevents the system actuator 5500 and/or the base 5510 from moving in the proximal direction to actuate the medicament delivery mechanism 5300.

The pull-tabs 5710 of the safety lock 5700 include a grip portion 5712. The grip portion 5712 of the pull-tabs 5710 provides an area for the user to grip and/or remove the safety lock 5700 from the rest of the medicament delivery system 5700. In some embodiments, the pull-tabs 5710 can include indicia, such as, for example, an indicia similar to that included in the pull tabs 3710 of the safety lock 3700, described with reference to FIG. 43.

The engagement portion 5720 of the safety lock 5700 includes engagement members 5721. The engagement members 5721 extend in a proximal direction from the proximal surface 5730. The engagement members 5721 have tabs 5722 that extend from a surface of the engagement members 5721. The tabs 5722 are configured to engage an outer surface 5815 of a distal end portion 5812 of the needle sheath 5810.

Figure 86:
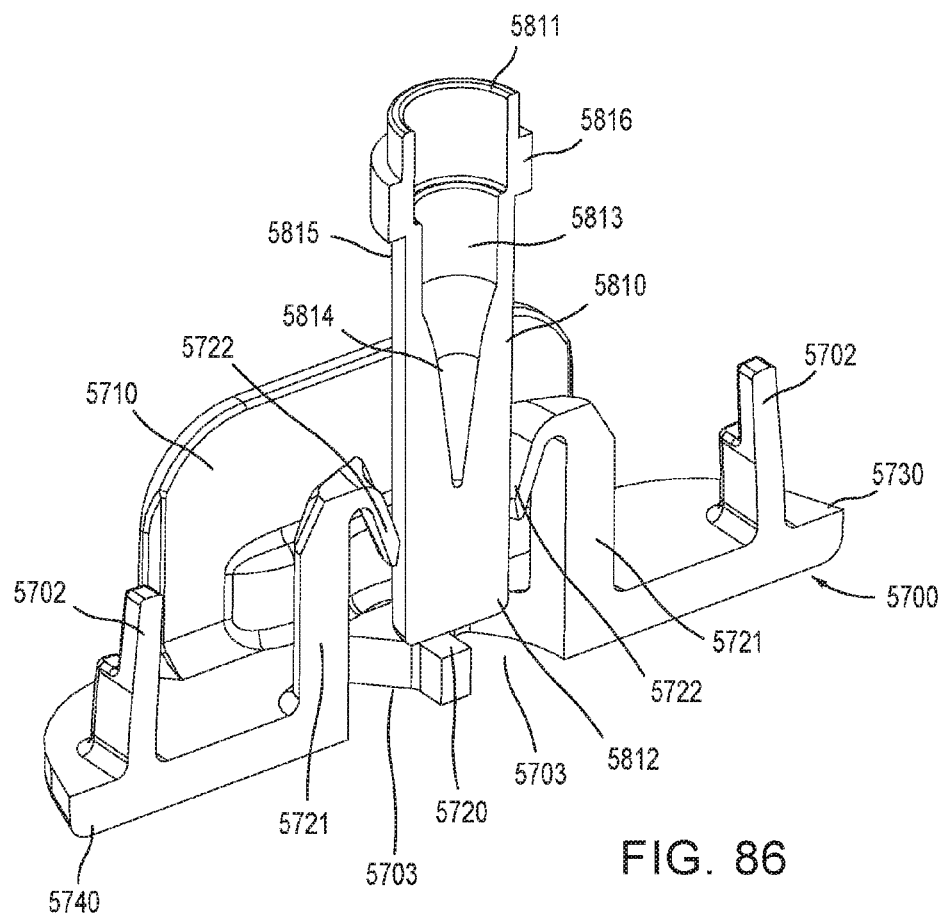
FIG. 86 is a cross-section view of the safety lock of the medical injector illustrated in FIG. 83.
Figure 87:
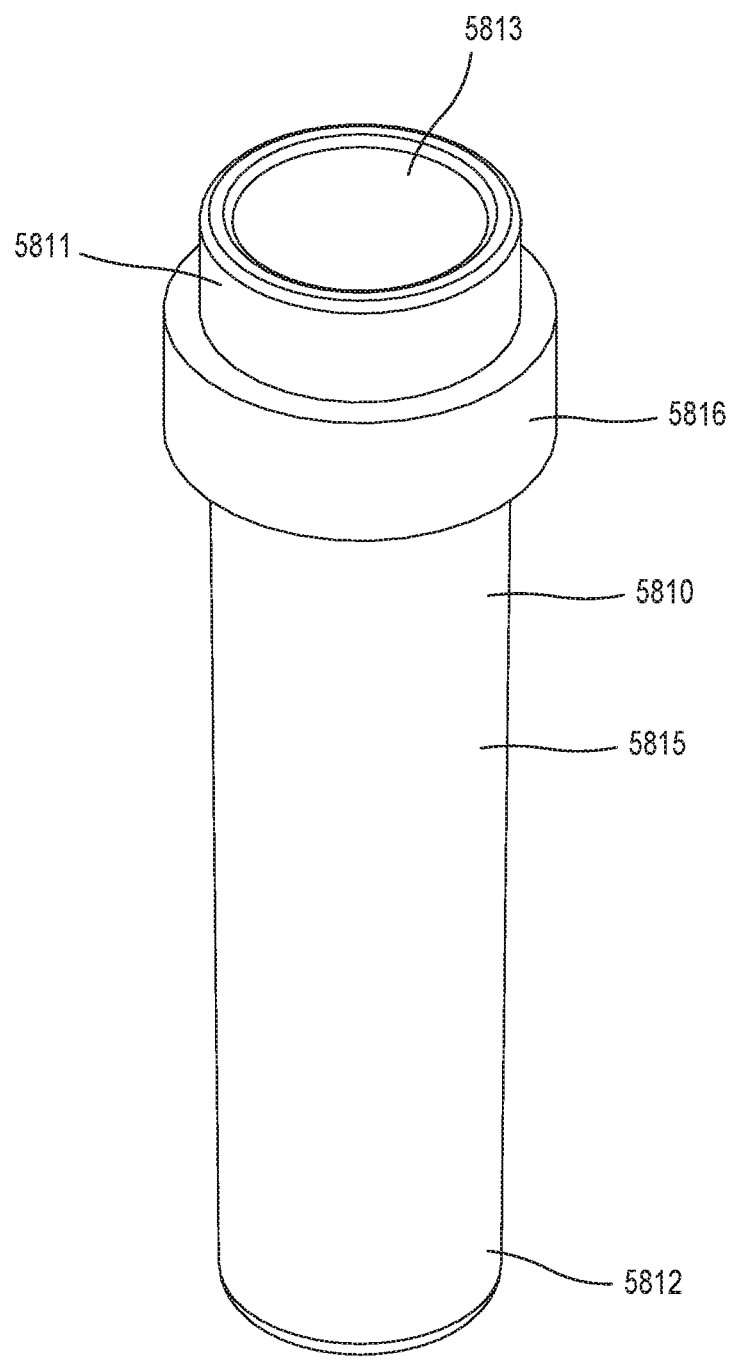
FIG. 87 is a perspective view of a needle sheath of the safety lock of the medical injector illustrated in FIG. 83.

As shown in FIGS. 86 and 87, the needle sheath 5810 includes the distal end portion 5812, a proximal end portion 5811 and a rib 5816. The needle sheath 5810 further includes a contoured portion 5814 that defines a bore 5813. The bore 5813 of the needle sheath 5810 is configured to receive the needle 5216 and/or a distal end portion of the 5213 of the medicament container 5200. The contoured portion 5814 of the needle sheath 5810 defines a friction fit with the distal end portion 5213 of the medicament container 5200. In this manner, the needle sheath 5810 can protect the user from the needle 5216 and/or can keep the needle 5216 sterile before the user actuates the medical injector 5000. The proximal end portion 5811 of the needle sheath is configured to contact the body 5210 of the medicament container 5200.

The distal end portion 5812 of the needle sheath 5810 is configured to be inserted into a space defined between the tabs 5722 of the engagement members 5721 of the safety lock 5700. The tabs 5722 are angled and/or bent towards the distal direction to allow the distal end portion 5812 of the needle sheath 5810 to move between the engagement members 5721 in a distal direction, but not in a proximal direction. Similarly stated, the tabs 5722 include an edge that contacts the outer surface 5815 of the needle sheath 5810 to prevent the safety lock 5700 from moving in a distal direction relative to the needle sheath 5810. Said another way, the needle sheath 5810 is removed from the needle 5216 when the safety lock 5700 is moved in a distal direction with respect to the housing 5100 (see e.g., FIG. 90).

Figure 88:
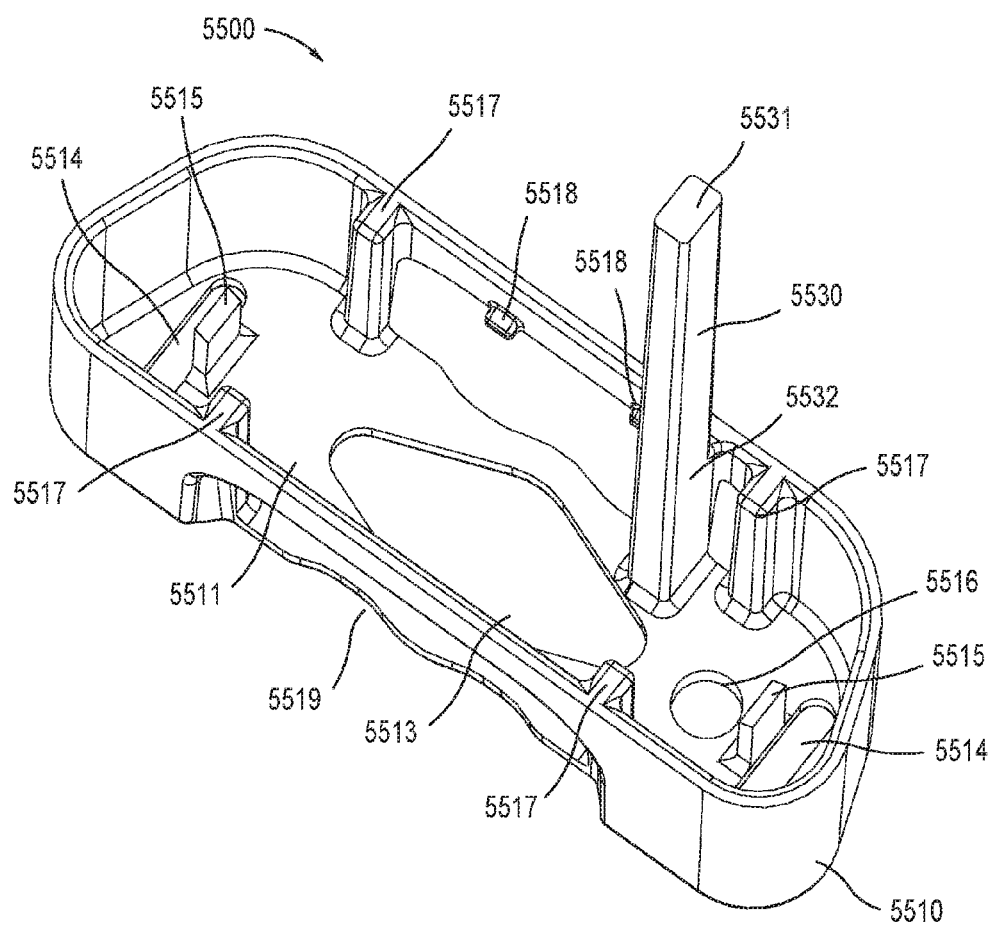
FIG. 88 is a perspective view of a base of the medical injector illustrated in FIG. 60.
Figure 89:
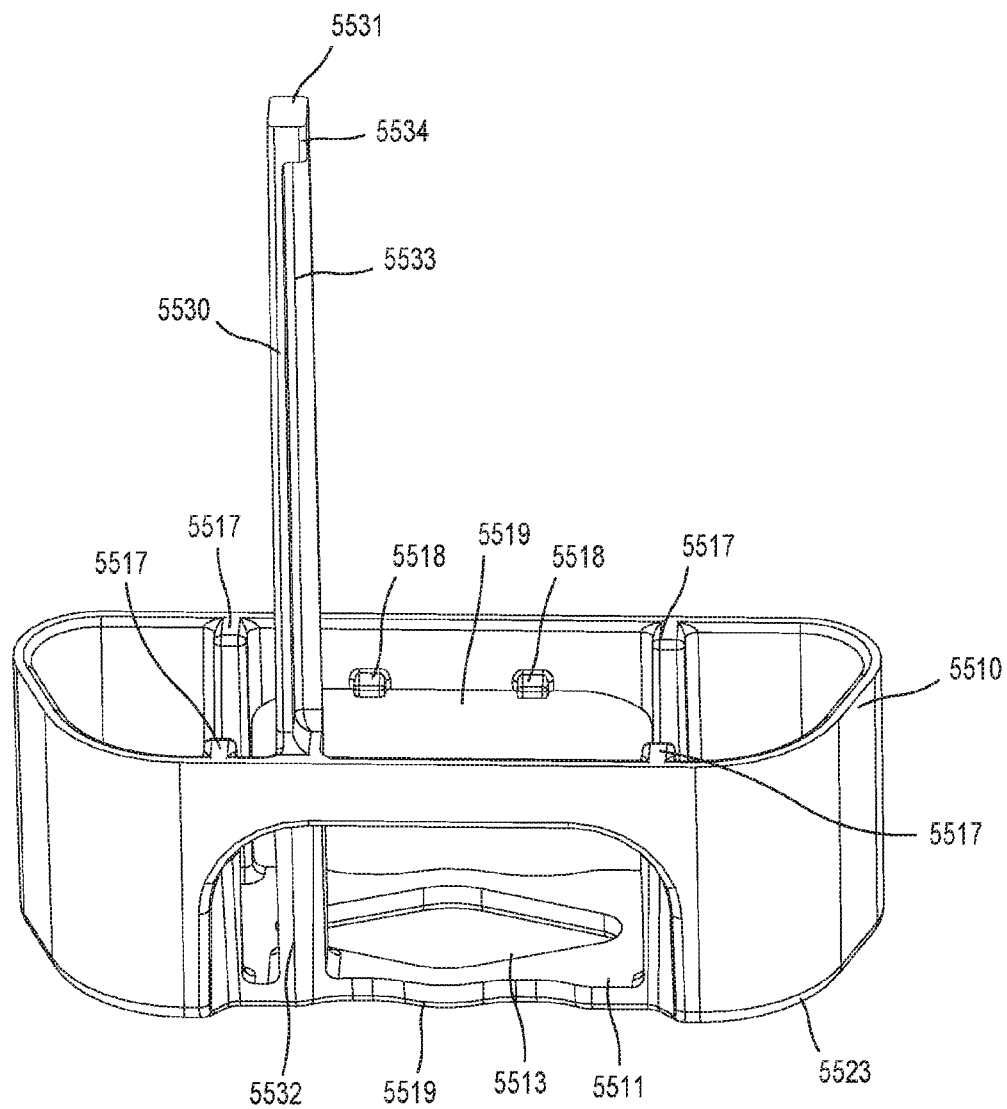
FIG. 89 is a front view of the base of the medical injector illustrated in FIG. 88.
Figure 90:
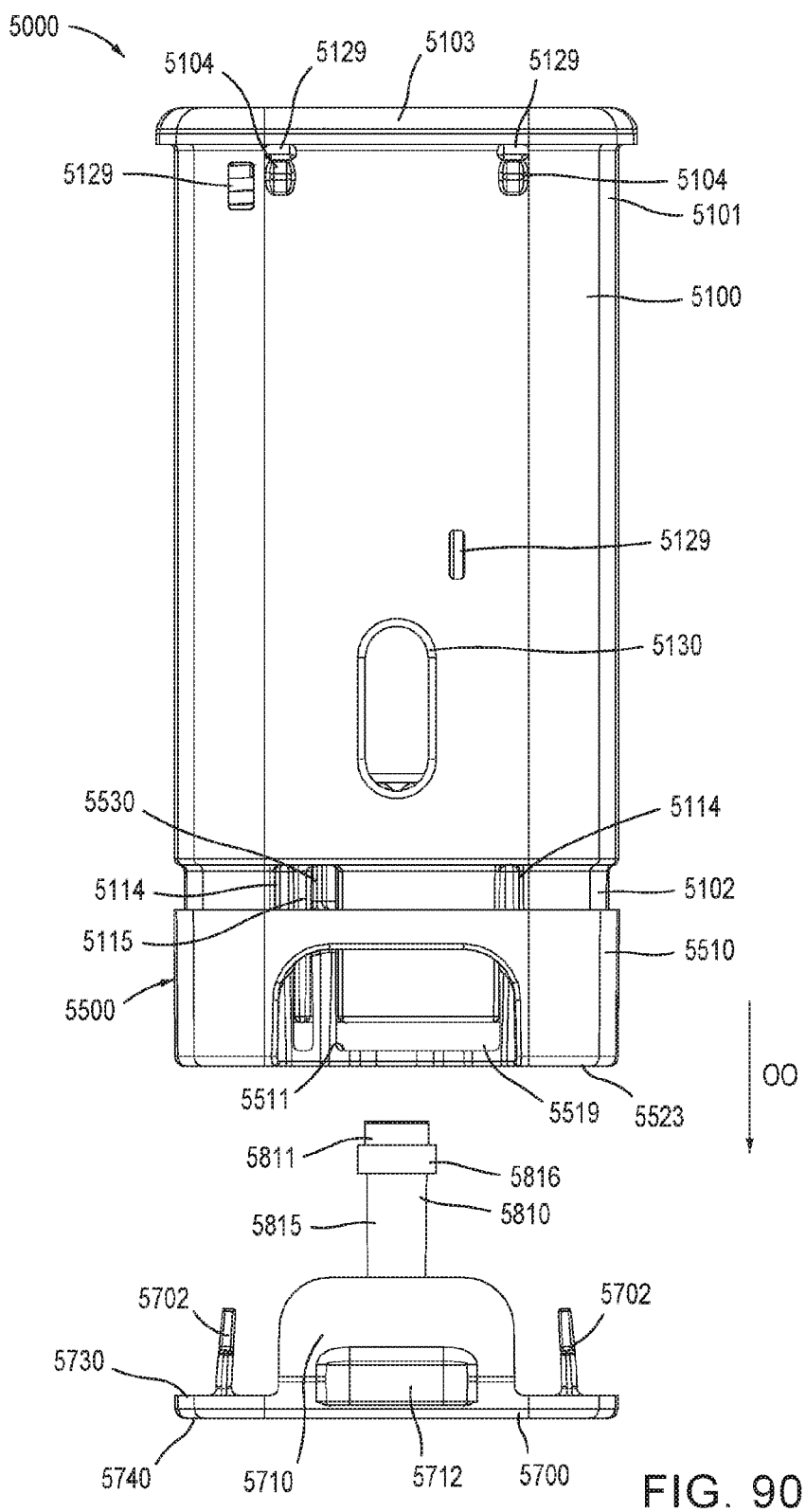
FIG. 90 is a front view of the medical injector illustrated in FIG. 60 in a third configuration.

FIGS. 88 and 89 show the base 5510 (or actuator) of the medical injector 5000. The base 5510 includes the proximal surface 5511, a distal surface 5523 and base connection knobs 5518. The base 5510 defines a needle aperture 5513, safety lock protrusion apertures 5514, transfer member access opening 5516 and pull-tab openings 5519. The needle aperture 5513 is configured to receive the needle 5216 when the medical injector 5000 is actuated. The safety lock protrusion apertures 5514 of the base 5510 receive the safety lock protrusions 5702 of the safety lock 5700 when the medical injector 5000 is in the first configuration, as described above. The transfer member access opening 5516 provides access to the transfer member 5600 when the transfer member 5600 is disposed within the housing 5100. The pull-tab openings 5519 are configured to receive the pull-tabs 5710 of the safety lock 5700 when the medical injector 5000 is in the first configuration.

Figure 71:
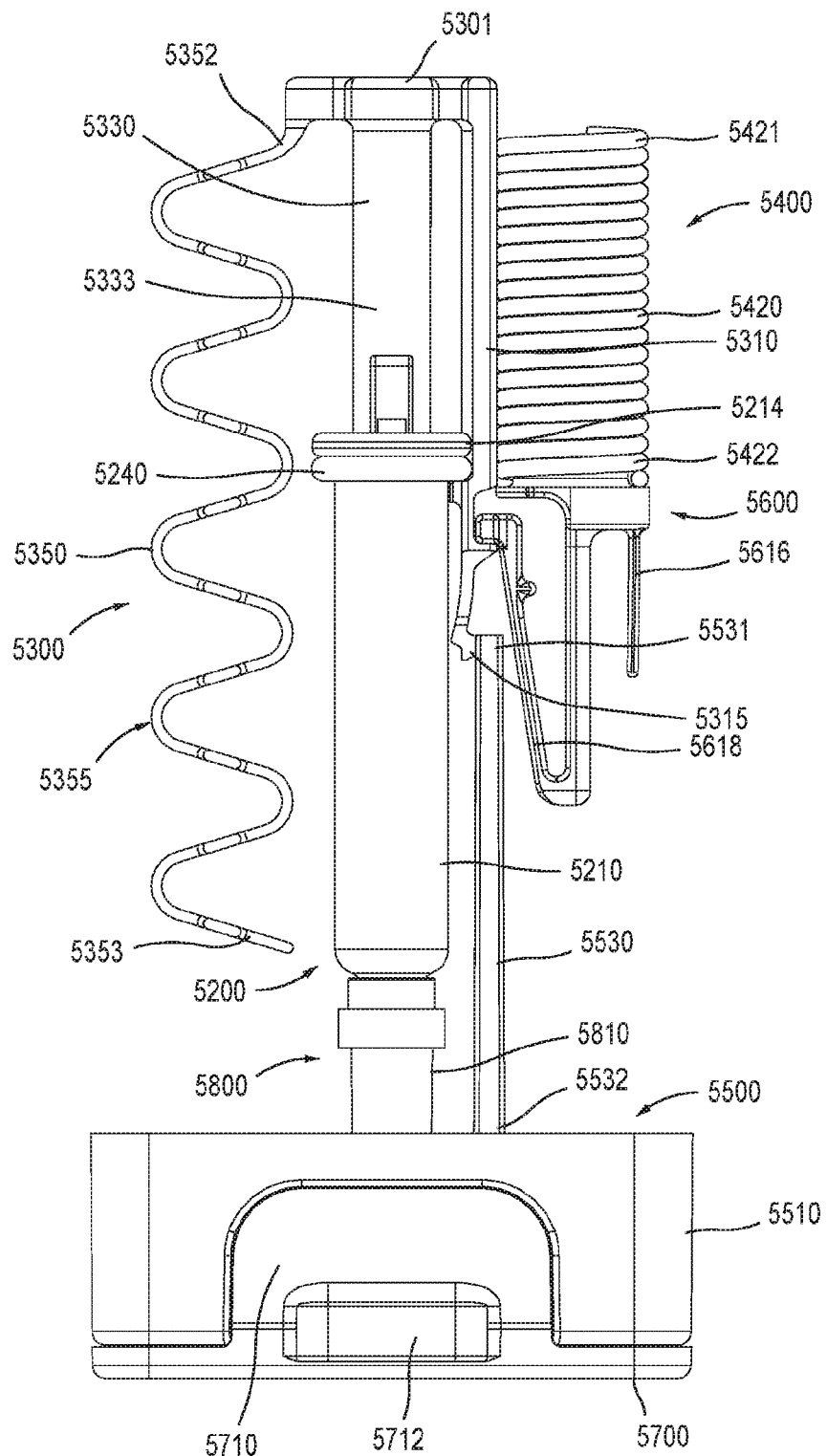
FIG. 71 is a front view of a medicament delivery mechanism of the medical injector illustrated in FIG. 60.

The proximal surface 5511 of the base 5510 includes and/or is coupled to the release member 5530, guide members 5517 and base locks 5515. The release member 5530 includes a proximal end portion 5531 and a distal end portion 5532 and defines a channel 5533 between a system lock surface 5534 and the distal end portion 5532 (see e.g., FIG. 89). As shown in FIG. 71, the system lock surface 5534 is disposed at the proximal end portion 5531 and is configured to engage the first latch protrusion 5315 of the medicament delivery mechanism 5300. Moreover, the system lock surface 5534 engages the first latch protrusion 5315 such that the system lock surface 5534 maintains the engagement of the first latch protrusion 5315 and the latch member notch 5120, as described above and shown in FIG. 72. Similarly stated, the system lock surface 5534 of the release member 5530 applies a force to the first latch protrusion 5315 to maintain the first latch protrusion 5315 within the latch member notch 5120. When the system actuator 5500 is moved in a proximal direction, as described in further detail herein, the system lock surface 5534 moves in the proximal direction to disengage the first latch protrusion 5315. In response, the first latch protrusion 5315 moves within the channel 5533 of the release member 5530 in a distal direction, as described in further detail herein. Similarly stated, upon actuation of the medicament injector 5000, a portion of the medicament delivery mechanism 5300 moves within the release member 5530.

The guide members 5517 of the base 5510 are configured to engage and/or slide within the base rail grooves 5114 of the housing 5100, as described above. The base locks 5515 of the base 5510 are configured to engage the base lock protrusions 5126 of the first housing member 5110. As described in further detail herein, when the safety lock 5700 is removed and the base 5510 is moved in a proximal direction with respect to the housing 5100, the base locks 5515 of the base 5510 are configured to disengage from the base lock protrusions 5126 and move in the proximal direction, relative to the base lock protrusions 5126. As described above, the base connection knobs 5518 are configured to engage the base retention recesses 5134A, 5134B in a way that allows proximal movement of the base 5510 but limits distal movement of the base 5510.

The medical injector 5000 is first enabled by moving the medicament delivery device 5000 from a first configuration to a second configuration by moving the cover 5190 from a first position to a second position. The cover 5190 is moved from the first position to the second position by moving it with respect to the housing 5100 in the distal direction. For example, the cover 5190 can be moved similarly to the cover 3190 of the medical injector 3000 described with reference to FIG. 49.

After the cover 5190 is removed from the housing 5100, the medical injector 5000 can be moved from the second configuration to a third configuration by moving the safety lock 5700 from a first position to a second position. The safety lock 5700 is moved from a first position to a second position by moving the safety lock 5700 with respect to the housing 5100 in the direction shown by the arrow OO in FIG. 90. Similarly stated, the medical injector 5000 can be moved from the second configuration to a third configuration by removing the safety lock 5700 from the distal end portion 5102 of the housing 5100. When the safety lock 5700 is moved from the first position to the second position, the safety lock protrusions 5702 are removed from within the base lock openings 5131 of the first housing member 5110, thereby enabling the system actuator 5500 and/or the base 5510. Similarly stated, when the safety lock 5700 is in the second position, the safety lock protrusions 5702 no longer maintain the engagement of the base locks 5515 with the base lock protrusions 5126 and/or the base locks 5515 can slide proximally relative to the base lock protrusion 5126 of the housing 5100. In this manner, the base 5510 can be moved from a first position to a second position. Moreover, with the safety lock 5700 removed, the needle sheath 5810 is removed from the medicament container 5200, as shown in FIG. 91.

After the safety lock 5700 is moved from the first position to the second position, the medical injector 5000 can be moved from the third configuration to a fourth configuration (i.e., the needle insertion configuration) by moving the base 5510 from the first position to the second position. Similarly stated, the medical injector 5000 can be actuated by the system actuator 5500 by moving the base 5510 proximally relative to the housing 5100. The base 5510 is moved from its first position to its second position by placing the medical injector 5000 against the body of the patient and moving the base 5510 with respect to the housing 5100 in the direction shown by the arrow PP in FIG. 92. With the base locks 5515 disengaged from the base lock protrusions 5126, the system actuator 5500 can move in the proximal direction causing the base locks 5515 move proximally past the base lock protrusions 5126.

Figure 92:
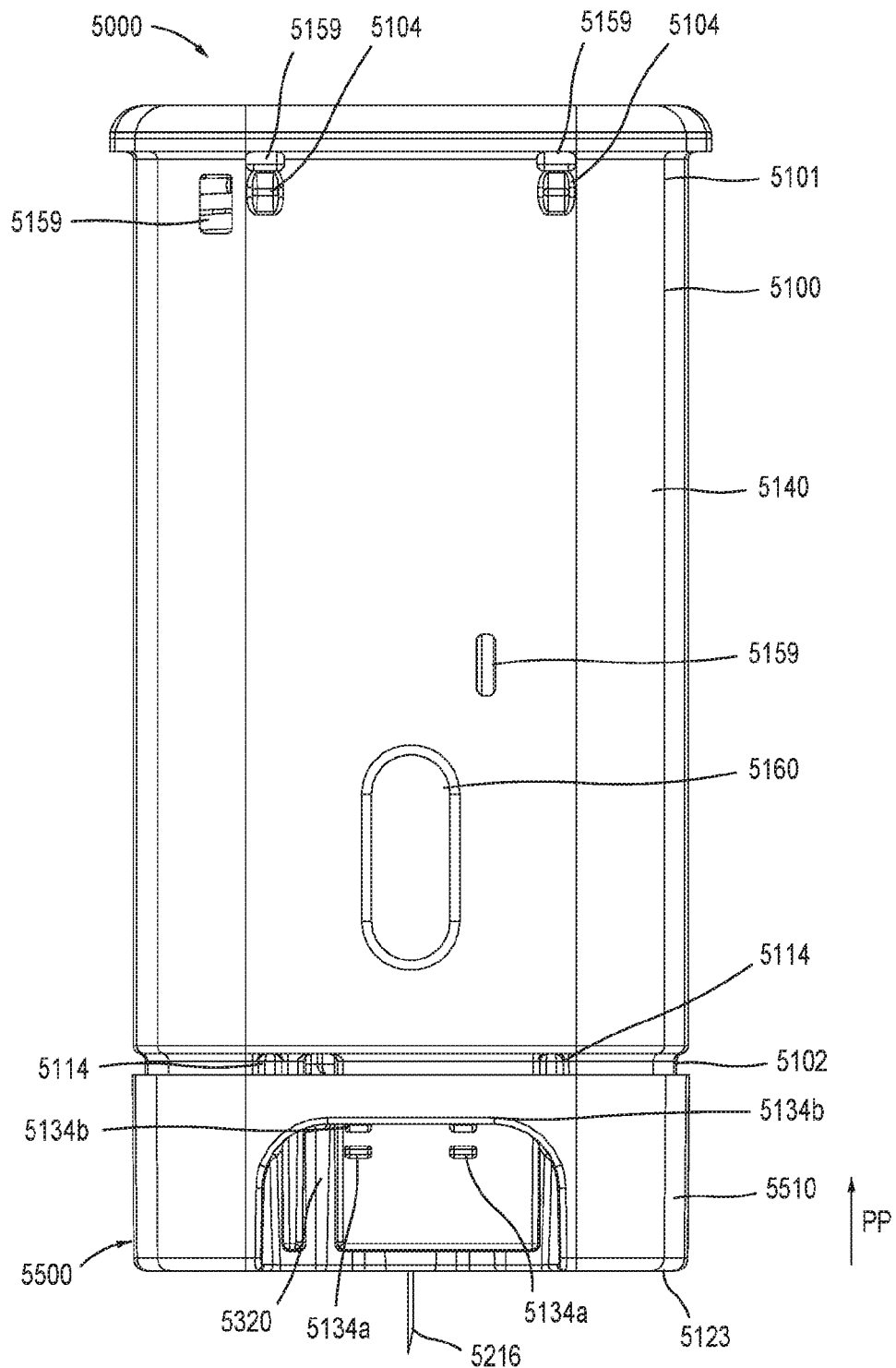
FIG. 92 is a front view of the medical injector illustrated in FIG. 60 in a fourth configuration (i.e., the needle insertion configuration).
Figure 93:
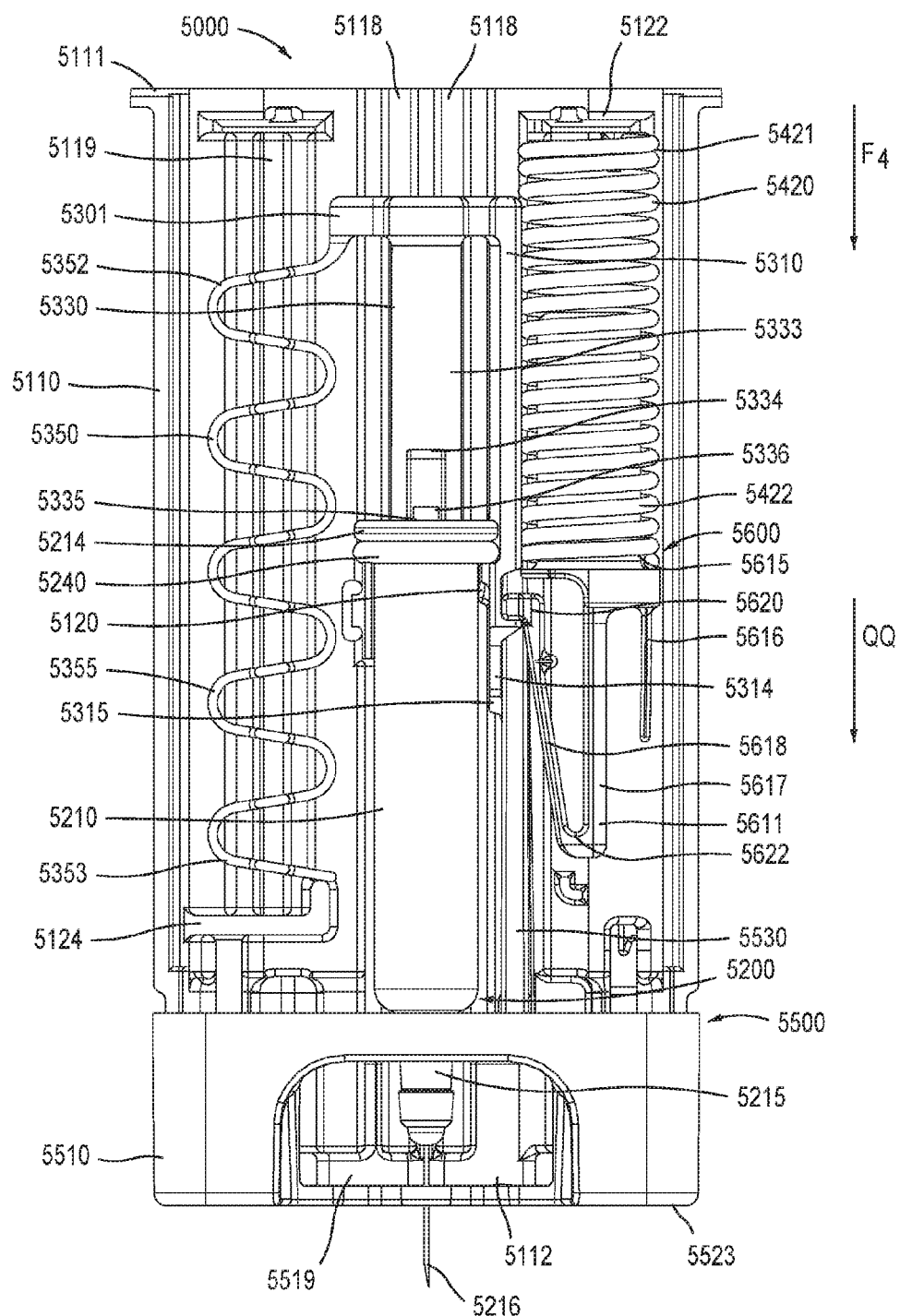
FIG. 93 is a front view of a portion of the medical injector illustrated in FIG. 60 in the fourth configuration (i.e., the needle insertion configuration).
Figure 94:
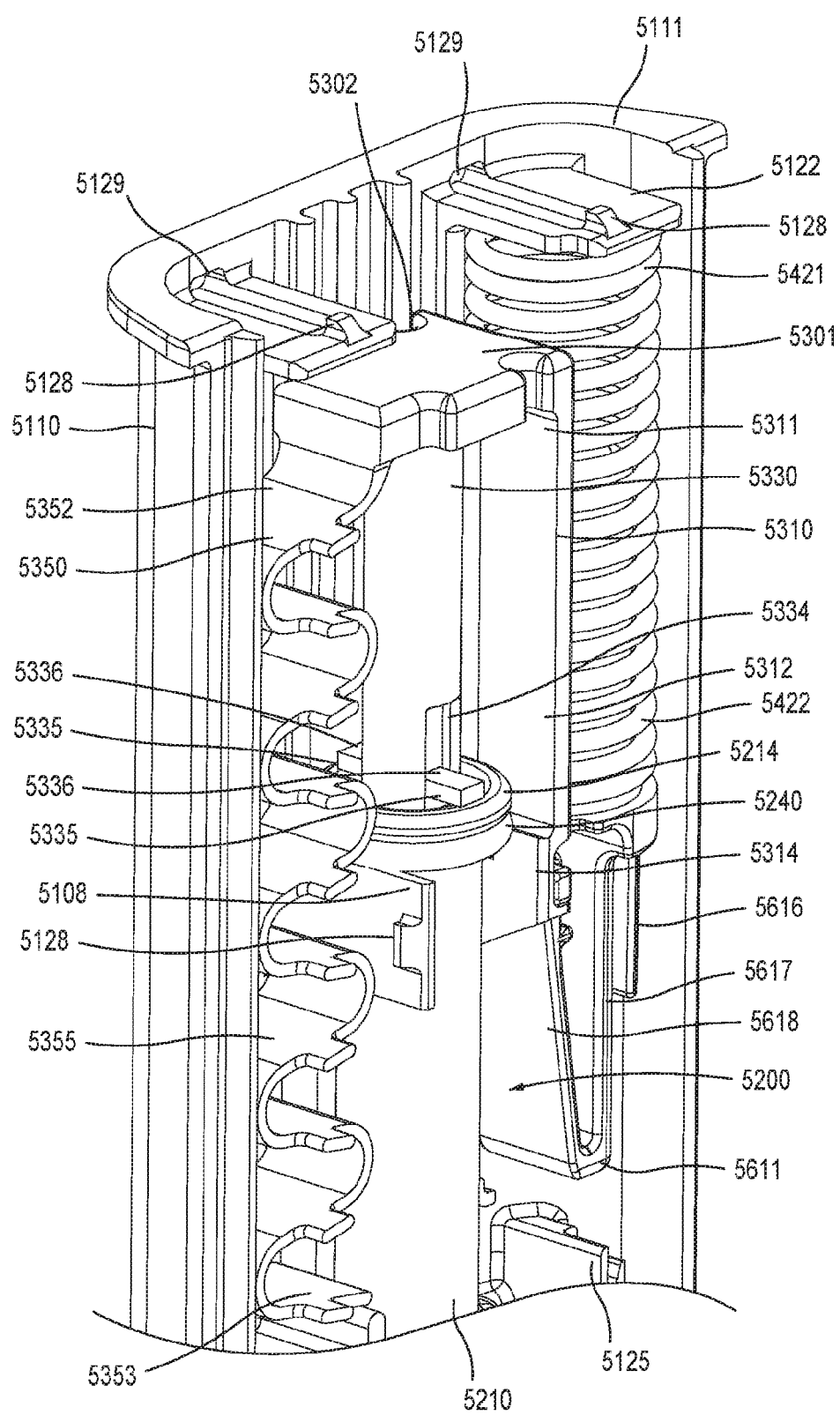
FIG. 94 is an enlarged perspective view of a portion of the medical injector illustrated in FIG. 60 in the fourth configuration (i.e., the needle insertion configuration).

When the base 5510 is moved from the first position to the second position, the system actuator 5500 actuates the medicament delivery mechanism 5300, thereby placing the medical injector 5000 in its fourth configuration (i.e., the needle insertion configuration), as shown in FIGS. 92-94. More specifically, the proximal movement of the system actuator 5500 and/or the base 5510 moves the release member 5530 in the proximal direction within the housing 5100, thereby allowing the first latch protrusion 5315 to be disengaged from the system lock surface 5534 of the proximal end portion 5533 of the release member 5530. Similarly stated, when the system actuator 5500 is moved in the proximal direction, the system lock surface 5534 disengages the first latch protrusion 5315. Moreover, when the system lock surface 5534 moves in the proximal direction relative to the first latch protrusion 5315, the first latch protrusion 5315 moves into the channel 5533 defined by the release member 5530.

When the first latch protrusion 5315 is disposed within the channel 5533, the force applied by the system lock surface 5534 of the base 5510 to maintain the first latch protrusion 5315 within the latch member notch 5120 is removed and the first latch protrusion 5315 is allowed to disengage the latch member notch 5120. Therefore, the engagement surface 5109 of the latch member notch 5120 no longer applies the reaction force to the first latch protrusion 5315; thus, the spring 5420 is allowed to expand. As described above, the proximal end portion 5421 of the spring 5420 is in contact with the upper spring plate 5122 of the first housing member 5110 such that the spring 5420 expands in the direction shown be the arrow QQ in FIG. 93. With the distal end portion 5422 of the spring 5420 in contact with the spring seat 5615 of the transfer member 5600, a force F4 produced by the expansion of the spring 5420 is applied to the transfer member 5600, which moves the transfer member 5600 in the direction shown by the arrow QQ. In this manner, the latch 5620 of the transfer member 5600 transfers at least a portion of the force F4 to the second latch protrusion 5317 of the latch portion 5310 of the medicament delivery mechanism 5300 such that the portion of the force moves the medicament delivery mechanism 5300 in the distal direction, shown by the arrow QQ in FIG. 93. Thus, the medicament delivery mechanism 5300 (the first movable member) and the transfer member 5600 (the second movable member) move together distally within the housing.

When the medicament delivery mechanism 5300 is moving distally, the piston portion 5330 of the medicament delivery mechanism 5300 applies a portion of the force F4 to the medicament container 5200. More specifically, as shown in FIG. 94, the first shoulder 5335 of each engagement member 5336 contacts the flange 5214 of the medicament container 5200. The movement of the medicament delivery mechanism 5300 moves the piston portion 5330 in the distal direction. Therefore, with the first shoulder 5335 of each engagement member 5336 in contact with the flange 5214 of the medicament container 5200, the first shoulder 5335 transfers a portion of the force F4 to the medicament container 5200 to move the medicament container 5200 in the distal direction. The movement of the medicament container 5200 within the housing 5100 results in the needle insertion operation.

As shown in FIG. 78, the distance between the end surface of the piston rod 5333 and the engagement members 5336 is such that when the first shoulder 5335 of each engagement member 5336 contacts the flange 5214, the distal end portion 5332 of the piston rod 5333 is spaced apart from the elastomeric member 5217 within the medicament container 5200. This arrangement prevents any portion of the force F4 from being applied or transferred to the plunger 5217. Said another way, during the needle insertion operation (i.e., when the medical injector is being moved to its fourth configuration) the plunger 5217 is isolated from the piston portion 5330. Accordingly, this arrangement reduces and/or eliminates leakage and/or injection of medicament 5220 from the medicament container 5200 during the needle insertion operation.

After the transfer member 5600, the medicament delivery mechanism 5300 and the medicament container 5200 move in the distal direction a given distance, the damping member 5240 of the medicament container 5200 contacts the proximal surface 5108 of the medicament container holder 5127 and 5157 of the first housing portion 5110 and the second housing portion 5140, respectively. The proximal surface 5108 prevents the medicament container 5200 from moving further in the distal direction. Thus, when the flange 5214 and/or the damping member 5240 contact the proximal surface 5108, the needle 5216 is fully inserted into the target location of a patient. At this point, the medical injector 5000 can be moved from the fourth configuration to the fifth configuration (i.e., the medicament delivery configuration), shown in FIGS. 95 and 96.

When the damping member 5240 of the medicament container 5200 is in contact with the proximal surface 5108 of the medicament container holders 5127 and 5157, the medicament container 5200 is prevented from moving in the distal direction. The portion of the force F4 applied by the spring 5420, however, continues to urge the transfer member 5600 and the medicament delivery mechanism 5300 in the direction shown by the arrow RR in FIG. 95. More specifically, when the medicament container 5200 is in contact with the medicament container holders 5127 and 5157, the force F4 applied by the spring 5420 moves the transfer member 5600 and the medicament delivery mechanism 5300 in the distal direction, relative to the medicament container 5200. In this manner, the portion of the force F4 applied to the medicament delivery mechanism 5300 causes the deformable portion 5338 of the engagement members 5336 to deform and/or bend inward (see e.g., FIG. 96). Similarly stated, the deformable portion 5338 of each of the engagement members 5336 is configured to deform when the damping member 5240 of the medicament container 5200 is in contact with the proximal surface 5108 of the medicament container holders 5127 and 5157. When the deformable portion 5338 is deformed, the engagement members 5336 are disposed within the recesses 5334 defined by the piston rod 5333 (see e.g., FIG. 96). In this manner, the piston rod 5333 is configured to move within the medicament container 5200 into contact with the elastomeric member 5217 to deliver the medicament 5220. Similarly stated, the piston portion 5330 is moved from its first configuration, in which the engagement members 5336 collectively have a size that is greater than the size (i.e., diameter) of the inner bore of the medicament container 5200 to its second configuration, in which the engagement members 5336 collectively have a size that is less than the size (i.e., diameter) of the inner bore of the medicament container 5200. This decrease in size (or diameter) allows the piston rod 5333 to move within the medicament container 5200.

When the medicament delivery mechanism 5300 moves in the distal direction to move the elastomeric member 5217 and inject the medicament 5220, the serpentine portion 5355 and/or the bias portion 5350 is also compressed. More specifically, a portion of the force F4 compresses the serpentine portion 5355 and/or the bias portion 5350 between the proximal end portion 5301 of the medicament delivery mechanism 5300 and the lower bias plate 5124. Similarly stated, the bias portion 5350 is configured to compress as the serpentine portion 5355 elastically deforms (e.g., bending, squeezing, or compressing such that the bias portion 5350 returns to a non-deformed configuration when the deforming force is removed). In this manner, the space defined between adjacent portions of the serpentine portion 5355 is reduced.

As the spring 5420 fully expands, the medicament delivery mechanism 5300 moves in the distal direction to fully inject the medicament 5220 within the medicament container 5200 through the needle 5216. Additionally, when the spring 5420 is fully expanded and/or when the medicament delivery mechanism 5300 has moved a desired distance within the housing 5100, the latch arm 5618 of the transfer member 5600 engages the transfer member release protrusion 5121 of the housing 5100. As described above, the transfer member release protrusion 5121 contacts the latch arm 5618 of the transfer member 5600 such that the bendable portion 5622 disposed at the distal end of the latch extension 5617 bends. In this manner, the latch 5620 of the latch arm 5618 is disengaged from the second latch protrusion 5318 of the latch portion 5310 of the medicament delivery mechanism 5300 (see e.g., FIGS. 97 and 98). Similarly stated, the spring 5240 and/or the transfer member 5600 are decoupled from the medicament delivery mechanism 5300. With the latch arm 5618 disengaged from the latch portion 5310, the medical injector 5000 can be moved from the fifth configuration to the sixth configuration (i.e., the retraction configuration).

As shown in FIG. 98, the transfer mechanism 5600 is deformed such that the transfer member 5600 and/or the spring 5420 are no longer engaged with the medicament delivery mechanism 5300. Therefore, the medicament delivery mechanism 5300 is configured to move within the housing 5100 in the direction shown by the arrow SS in FIG. 97 in response to the force produced by the bias portion 5350. Similarly stated, with the medicament delivery mechanism 5300 disengaged from the transfer member 5600 and/or the spring 5420, the force F4 is no longer applied to the medicament delivery mechanism 5300. In this manner, the bias portion 5350 is configured to expand in the direction of the arrow SS shown in FIG. 97 to apply a retraction force to the medicament delivery mechanism 5300. Similarly stated, with the portion of the force F4 configured to compress the bias portion 5350 removed, the bias portion 5350 expands, returning to its uncompressed (i.e., non-deformed) configuration.

During the retraction operation, the second shoulder 5313 included in the latch portion 5310 is configured to engage a distal surface of the damping member 5240 and/or the flange 5214. The second shoulder 5313 is further configured to transmit the retraction force produced by the expansion of the bias portion 5350 to the flange 5214, thereby moving the medicament container 5200 proximally. Similarly stated, the medicament container 5200 is moved in the proximal direction towards the first position of the medicament container 5200. This motion, removes the needle 5216 from the target location of the patient and retracts the needle into the housing 5100, as shown in FIG. 97.

Any of the devices and/or medicament containers shown and described herein can include any suitable medicament or therapeutic agent. In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a rabies vaccine and/or a meningococcus vaccine. In other embodiments, the medicament contained within any of the medicament containers shown herein can be a catecholamine, such as epinephrine. In yet other embodiments, the medicament contained within any of the medicament containers shown herein can include peptide hormones such as insulin and glucagon, human growth hormone (HGH), erythropoiesis-stimulating agents (ESA) such as darbepoetin alfa, monoclonal antibodies such as denosumab and adalimumab, interferons, etanercept, pegfilgrastim, and other chronic therapies, or the like. In yet other embodiments, the medicament contained within any of the medicament containers shown herein can be a placebo substance (i.e., a substance with no active ingredients), such as water.

In other embodiments, the medicament contained within any of the medicament containers shown herein can be an opioid receptor antagonist, such as naloxone, including any of the naloxone formulations described in U.S. patent application Ser. No. 13/036,720, entitled "Medicament Delivery Device for Administration of Opioid Antagonists Including Formulation for Naloxone," filed on Feb. 28, 2011, incorporated by reference above. In one aspect, the present disclosure relates to compositions comprising naloxone or a pharmaceutically acceptable salt thereof suitable for use in the medicament delivery devices disclosed herein. Accordingly, the present naloxone compositions may be adapted for various administration routes, depending on the apparatus in which such composition(s) are to be employed. For example, in some embodiments, the present compositions may be adapted for transmucosal administration as, e.g., a nasal spray, or alternatively as a sublingual or buccal spray. In other embodiments, the present naloxone compositions may be adapted for parenteral administration as, e.g., an injectable solution.

The present compositions generally comprise an effective amount of naloxone, i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. For example, as described herein, the present naloxone compositions may be useful in treating respiratory depression and/or other indications associated with opioid toxicity. Accordingly, an effective amount of naloxone in the present compositions may be an amount sufficient to treat such respiratory depression and/or other indications associated with opioid toxicity. The present naloxone compositions typically have a concentration of 4,5-epoxy-3,14-dihydroxy-17-(2-propenyl)morphinan-6-one (or a salt and/or ester thereof) between about 0.01 mg/mL and about 10 mg/mL (e.g., between about 0.05 mg/mL and about 2 mg/mL, or any other value or range of values therein, including about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, or about 1.9 mg/mL).

In some embodiments, the present naloxone compositions comprise a pH-adjusting agent. In some embodiments, the pH-adjusting agent includes at least one of hydrochloric acid, citric acid, acetic acid, phosphoric acid, or combinations thereof. The pH-adjusting agent may comprise an organic and/or inorganic acid or salt thereof (e.g., alkali metal salts [Li, Na, K, etc.], alkaline earth metal [e.g., Ca, Mg, etc.] salts, ammonium salts, etc.). In other embodiments, the pH-adjusting agent includes mixtures of one or more acids and one or more salts thereof, e.g., citric acid and citrate salts, acetic acid and acetate salts, phosphoric acid and phosphate salts, etc. In certain embodiments, the pH-adjusting agent is added in an amount sufficient to provide a pH of the present naloxone compositions of from about 3 to about 5 (for example a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0). Accordingly, the present compositions may comprise naloxone salts of the pH-adjusting agent employed. For example, in one embodiment, the pH-adjusting agent is dilute aqueous hydrochloric acid, and the naloxone salt is naloxone.HCl (e.g., 4,5-epoxy-3,14-dihydroxy-17-(2-propenyl)-morphinan-6-one hydrochloride).

Solvents suitable for use in the present compositions are not particularly limited, provided they are pharmaceutically acceptable. Accordingly, any pharmaceutically acceptable solvent in which the components of the present compositions are soluble, and which does not adversely affect the stability of the present compositions and/or the naloxone and/or naloxone salts contained therein may be employed. For example, in a typical composition, the solvent is sterile water (e.g., USP grade water for injection [WFI]).

In some embodiments, the present compositions may also comprise one or more tonicity-adjusting agents. For example, the tonicity-adjusting agent may include at least one of dextrose, glycerin, mannitol, potassium chloride, sodium chloride, or combinations thereof. The tonicity-adjusting agent(s) may be present in an amount of from about 0.1 mg/mL to about 50 mg/mL (e.g., including about 0.5 mg/mL, about 1.0 mg/mL, about 2.0 mg/mL, about 3.0 mg/mL, about 4.0 mg/mL, about 5.0 mg/mL, about 10 mg/mL, about 15 mg/mL, about 20 mg/mL, about 25 mg/mL, about 30 mg/mL, about 35 mg/mL, about 40 mg/mL, or about 45 mg/mL). In one embodiment, the tonicity-adjusting agent is sodium chloride, and the concentration thereof is between about 0.1 mg/mL and about 20 mg/mL. Generally, in naloxone compositions as described herein which are adapted for injection and/or intranasal delivery, tonicity-adjusting agents are added to provide a desired osmolality. In some embodiments, the osmolality of the naloxone compositions described herein is from about 250 to about 350 mOsm.

Because the naloxone compositions disclosed herein may be stored in the medicament container of the devices described herein for extended periods of time under varying storage conditions, in some embodiments the present compositions may further comprise stabilizers to prevent or inhibit decomposition of the naloxone during storage. Various types of pharmaceutically acceptable stabilizers can be used, including antioxidants (e.g. substituted phenols such as BHT, TBHQ, BHA, or propyl gallate; ascorbates such as ascorboyl palmitate, sodium ascorbate, ascorbic acid), complexing agents (e.g., cyclodextrins); or chelating agents such as EDTA (and its salts), D-gluconic acid δ-lactone, sodium or potassium gluconate, sodium triphosphate, and sodium hexametaphosphate.

Examples

The chemical stability of several exemplary naloxone hydrochloride compositions was evaluated at various pH and temperature conditions. The formulation of six development lots was performed to evaluate pH and order of addition parameters for naloxone hydrochloride. Assay testing was performed on aliquots of bulk formulation solution sampled prior to the filtration process to determine if the filtration process contributed to any API losses.

Exemplary naloxone compositions were prepared according to the formulations set forth in Table 1, below:

TABLE 1

Exemplary Naloxone Formulations.

| Lot | Intial WFI (g) | Order of Addition | API Added (mg) | API Mix Time (seconds) | NaCl Added (g) | NaCl Mix Time (seconds) | Intial pH | Adjusted pH | Final pH | Volume of pH Adjuster (mL) | Final Weight (g) |
|---|---|---|---|---|---|---|---|---|---|---|---|
| 1 | 400.01 | A | 554.73 | 110 | 4.5000 | 98 | 5.52 | 3.01 | 2.99 | 4.1 | 500.00 |
| 2 | 400.15 | B | 555.10 | 86 | 4.5269 | 69 | 5.41 | 6.51 | 6.51 | 0.5 | 502.14 |
| 3 | 400.13 | A | 554.95 | 104 | 4.5033 | 58 | 5.39 | 4.47 | 4.47 | 0.2 | 502.17 |
| 4 | 400.00 | B | 554.58 | 82 | 4.4999 | 87 | 5.37 | 3.01 | 3.01 | 4.0 | 502.15 |
| 5 | 399.99 | A | 554.59 | 85 | 4.5513 | 74 | 5.40 | 6.49 | 6.49 | 0.2 | 502.16 |
| 6 | 400.02 | B | 554.81 | 68 | 4.5020 | 70 | 5.45 | 4.50 | 4.49 | 0.2 | 502.19 |

Final Formulation Solution Density = 1.0043 g/mL (Determined daring the formulation process for Lot 1)
Order of Addition:
A = Water, NACl, naloxone hydrochloride, pH adjuster
B = Water, naloxone hydrochloride, NaCl, pH adjuster There were no noticeable differences between the formulations from lot to lot. The order of addition of the components had no observable impact on the dissolution times for either the API (Naloxone Hydrochloride) or the NaCl. Initial solution pH values indicated no observable differences between the solutions prior to final pH adjustment. The volumes required for the final pH adjustment were also consistent, indicating no significant differences between the lots.

Solutions were filtered after formulation to determine if filtration after formulation impacts overall solution API concentration. Pre-filtration assay values were consistent with the post-filtration (initial) assay results for each lot, as shown in Table 2, below:

TABLE 2

Filtration of Naloxone Formulations.

| Lot | Pre-Filtration Naloxone Hydrochloride (mg/mL) | Post-Filtration Naloxone Hydrochloride (mg/mL) |
|---|---|---|
| 1 | 1.02 | 1.02 |
| 2 | 1.00 | 1.00 |
| 3 | 1.01 | 1.00 |
| 4 | 1.02 | 1.01 |
| 5 | 1.00 | 0.99 |
| 6 | 1.01 | 0.99 |

Because the naloxone compositions described herein may be stored in the medicament container of the devices described herein for extended periods of time under varying storage conditions, initial testing was performed to support a stability study for the development lots of naloxone hydrochloride. Initial appearance, pH and assay results are shown in Table 3, below:

TABLE 3

Initial Appearance, pH and Assay Results

| Lot | Replicate | Appearance | Osmolality (mOsm) | pH | Assay (mg/mL) |
|---|---|---|---|---|---|
| 1 | 1 | Clear, colorless solution free of visible particulate matter | 295 | 3.09 | 1.02 |
|  | 2 | Clear, colorless solution free of visible particulate matter | 295 | 3.09 | 1.02 |
|  |  | Mean (n = 2) | 295 | 3.09 | 1.02 |
| 2 | 1 | Clear, colorless solution free of visible particulate matter | 294 | 6.54 | 1.00 |
|  | 2 | Clear, colorless solution free of visible particulate matter | 295 | 6.55 | 1.00 |
|  |  | Mean (n = 2) | 295 | 6.55 | 1.00 |
| 3 | 1 | Clear, colorless solution free of visible particulate matter | 292 | 4.92 | 1.00 |
|  | 2 | Clear, colorless solution free of visible particulate matter | 289 | 4.96 | 1.00 |
|  |  | Mean (n = 2) | 291 | 4.94 | 1.00 |
| 4 | 1 | Clear, colorless solution free of visible particulate matter | 294 | 3.13 | 1.01 |
|  | 2 | Clear, colorless solution free of visible particulate matter | 294 | 3.14 | 1.01 |
|  |  | Mean (n = 2) | 294 | 3.14 | 1.01 |
| 5 | 1 | Clear, colorless solution free of visible particulate matter | 295 | 6.57 | 0.99 |
|  | 2 | Clear, colorless solution free of visible particulate matter | 295 | 6.57 | 0.99 |
|  |  | Mean (n = 2) | 295 | 6.57 | 0.99 |
| 6 | 1 | Clear, colorless solution free of visible particulate matter | 292 | 4.95 | 0.99 |
|  | 2 | Clear, colorless solution free of visible particulate matter | 290 | 4.99 | 0.99 |
|  |  | Mean (n = 2) | 291 | 4.97 | 0.99 |

The pH analysis of Lots 3 and 6 exhibited increases of 0.4 and 0.5, respectively, in comparison to the pH values obtained during the formulation process. To verify the initial bulk pH, an aliquot of bulk formulation solution for Lot 6 was removed from storage at 5° C. and allowed to equilibrate to room temperature. The determined pH was 4.52, confirming the final pH obtained during the formulation process. Analysis of related substances was performed for each individual sample, as shown in Table 4, below:

TABLE 4

Initial Related Substance Screening Results

| Lot | Replicate | Unknown (Identified by RRT) | % Related Substance | Total Related Substances (%) | Mean of Total Related Substances (%) |
|---|---|---|---|---|---|
| 1 | 1 | NR | NR | NR | NR |
|  | 2 | NR | NR | NR |  |
| 2 | 1 | NR | NR | NR | NR |
|  | 2 | 0.559 | 0.05 | 0.05 |  |
| 3 | 1 | NR | NR | NR | NR |
|  | 2 | NR | NR | NR |  |
| 4 | 1 | NR | NR | NR | NR |
|  | 2 | NR | NR | NR |  |
| 5 | 1 | 0.160 | 0.11 | 0.17 | 0.09 |
|  |  | 0.559 | 0.06 |  |  |
|  | 2 | NR | NR | NR |  |
| 6 | 1 | NR | NR | NR | NR |
|  | 2 | NR | NR | NR |  |

NR = Not Reportable (<0.05% Impurity)

In Table 4, % Related Substance=(Related Substance Peak Area/Total Integrated Area)×100. Peaks greater than or equal to 0.05% were reported. Replicates that exhibited levels of related substances that were not reportable were treated as 0.00% for determination of mean total related substances.

One month stability testing was conducted as previously described, with the following additional analyses:
  pH analysis for all lots at the 25° C./60% RH condition
  pH analysis for lots 1 and 4 at the 40° C./75% RH condition
  Assay and Related Substances analysis for lots 1 and 4 at the 25° C./60% RH and 40° C./75% RH conditions

TABLE 5

One-Month Stability Results - 70° C./75% RH

| Lot | Replicate | Appearance | pH | Assay (mg/mL) |
|---|---|---|---|---|
| 1 | 1 | Clear, colorless solution free of visible particulate matter | 3.28 | 1.02 |
|  | 2 | Clear, colorless solution free of visible particulate matter | 3.25 | 1.01 |
|  |  | Mean (n = 2) | 3.27 | 1.02 |

TABLE 5-continued

One-Month Stability Results - 70° C./75% RH

| Lot | Replicate | Appearance | pH | Assay (mg/mL) |
|---|---|---|---|---|
| 2 | 1 | Clear, colorless solution free of visible particulate matter | 6.05 | 0.94 |
|   | 2 | Clear, colorless solution free of visible particulate matter | 6.05 | 0.94 |
|   | Mean (n = 2) |  | 6.05 | 0.94 |
| 3 | 1 | Clear, colorless solution free of visible particulate matter | 5.32 | 0.97 |
|   | 2 | Clear, colorless solution free of visible particulate matter | 5.44 | 0.97 |
|   | Mean (n = 2) |  | 5.38 | 0.97 |
| 4 | 1 | Clear, colorless solution free of visible particulate matter | 3.28 | 1.01 |
|   | 2 | Clear, colorless solution free of visible particulate matter | 3.28 | 0.99 |
|   | Mean (n = 2) |  | 3.28 | 1.00 |
| 5 | 1 | Clear, colorless solution free of visible particulate matter | 6.06 | 0.94 |
|   | 2 | Clear, colorless solution free of visible particulate matter | 6.05 | 0.93 |
|   | Mean (n = 2) |  | 6.06 | 0.93 |
| 6 | 1 | Clear, colorless solution free of visible particulate matter | 5.41 | 0.95 |
|   | 2 | Clear, colorless solution free of visible particulate matter | 5.27 | 0.96 |
|   | Mean (n = 2) |  | 5.34 | 0.95 |

TABLE 6a

One Month Related Substances Results - 70° C./75% RH - Lots 1-3

| Lot | Replicate | Unknown (Identified by RRT) | % Related Substance | Total Related Substances (%) | Mean of Total Related Substances (%) |
|---|---|---|---|---|---|
| 1 | 1 | 0.038 | 0.11 | 0.42 | 0.46 |
|   |   | 0.404 | 0.19 |   |   |
|   |   | 0.597 | 0.12 |   |   |
|   | 2 | 0.038 | 0.13 | 0.50 |   |
|   |   | 0.404 | 0.23 |   |   |
|   |   | 0.597 | 0.14 |   |   |
| 2 | 1 | 0.034 | 0.08 | 4.94 | 4.77 |
|   |   | 0.038 | 0.21 |   |   |
|   |   | 0.089 | 0.08 |   |   |
|   |   | 0.118 | 0.08 |   |   |
|   |   | 0.136 | 4.23 |   |   |
|   |   | 0.403 | 0.11 |   |   |
|   |   | 1.029 | 0.15 |   |   |
|   | 2 | 0.034 | 0.07 | 4.59 |   |
|   |   | 0.038 | 0.17 |   |   |
|   |   | 0.089 | 0.08 |   |   |
|   |   | 0.136 | 4.04 |   |   |
|   |   | 0.403 | 0.10 |   |   |
|   |   | 1.028 | 0.13 |   |   |
| 3 | 1 | 0.038 | 0.19 | 2.79 | 2.94 |
|   |   | 0.118 | 0.06 |   |   |
|   |   | 0.136 | 2.17 |   |   |
|   |   | 0.403 | 0.15 |   |   |
|   |   | 0.596 | 0.06 |   |   |
|   |   | 1.026 | 0.17 |   |   |
|   | 2 | 0.038 | 0.19 | 3.09 |   |
|   |   | 0.117 | 0.05 |   |   |
|   |   | 0.136 | 2.46 |   |   |
|   |   | 0.403 | 0.15 |   |   |
|   |   | 0.596 | 0.05 |   |   |
|   |   | 1.024 | 0.19 |   |   |

TABLE 6b

One Month Related Substances Results - 70° C./75% RH - Lots 4-6

| Lot | Replicate | Unknown (Identified by RRT) | % Related Substance | Total Related Substances (%) | Mean of Total Related Substances (%) |
|---|---|---|---|---|---|
| 4 | 1 | 0.038 | 0.11 | 0.44 | 0.79 |
|   |   | 0.403 | 0.20 |   |   |
|   |   | 0.596 | 0.13 |   |   |
|   | 2 | 0.039 | 0.22 | 1.13 |   |
|   |   | 0.116 | 0.09 |   |   |
|   |   | 0.135 | 0.09 |   |   |
|   |   | 0.403 | 0.46 |   |   |
|   |   | 0.596 | 0.28 |   |   |
| 5 | 1 | 0.039 | 0.18 | 4.60 | 4.80 |
|   |   | 0.089 | 0.07 |   |   |
|   |   | 0.115 | 0.05 |   |   |
|   |   | 0.133 | 4.20 |   |   |
|   |   | 0.403 | 0.10 |   |   |
|   | 2 | 0.039 | 0.18 | 5.00 |   |
|   |   | 0.089 | 0.09 |   |   |
|   |   | 0.132 | 4.64 |   |   |
|   |   | 0.402 | 0.08 |   |   |
| 6 | 1 | 0.038 | 0.17 | 2.85 | 2.76 |
|   |   | 0.132 | 2.55 |   |   |
|   |   | 0.403 | 0.13 |   |   |
|   | 2 | 0.038 | 0.17 | 2.66 |   |
|   |   | 0.114 | 0.06 |   |   |
|   |   | 0.132 | 2.31 |   |   |
|   |   | 0.402 | 0.13 |   |   |

TABLE 7

One-Month Stability Results - 40° C./75% RH

| Lot | Replicate | pH | Assay (mg/mL) |
|---|---|---|---|
| 1 | 1 | 3.14 | 1.01 |
|   | 2 | 3.13 | 1.01 |
|   | Mean (n = 2) | 3.14 | 1.01 |
| 4 | 1 | 3.16 | 1.01 |
|   | 2 | 3.16 | 1.00 |
|   | Mean (n = 2) | 3.16 | 1.00 |

TABLE 8

One Month Related Substances Results - 40° C./75% RH

| Lot | Replicate | Unknown (Identified by RRT) | % Related Substance | Total Related Substances (%) | Mean of Total Related Substances (%) |
|---|---|---|---|---|---|
| 1 | 1 | NR | NR | NR | NR |
|   | 2 | NR | NR | NR |   |
| 4 | 1 | 0.592 | 0.05 | 0.05 | 0.22 |
|   | 2 | 0.040 | 0.12 | 0.38 |   |
|   |   | 0.115 | 0.06 |   |   |
|   |   | 0.592 | 0.19 |   |   |

TABLE 9

One-Month Stability Results - 25° C./60% RH

| Lot | Replicate | pH | Assay (mg/mL) |
|---|---|---|---|
| 1 | 1 | 3.11 | 1.01 |
|   | 2 | 3.16 | 1.01 |
|   | Mean (n = 2) | 3.14 | 1.01 |
| 2 | 1 | 6.33 | No analysis performed |
|   | 2 | 6.41 |   |
|   | Mean (n = 2) | 6.37 |   |

TABLE 9-continued

One-Month Stability Results - 25° C./60% RH

| Lot | Replicate | pH | Assay (mg/mL) |
|---|---|---|---|
| 3 | 1 | 5.20 | No analysis performed |
|   | 2 | 5.21 |  |
|   | Mean (n = 2) | 5.21 |  |
| 4 | 1 | 3.19 | 1.01 |
|   | 2 | 3.17 | 1.01 |
|   | Mean (n = 2) | 3.18 | 1.01 |
| 5 | 1 | 6.32 | No analysis performed |
|   | 2 | 6.40 |  |
|   | Mean (n = 2) | 6.36 |  |
| 6 | 1 | 5.23 | No analysis performed |
|   | 2 | 5.24 |  |
|   | Mean (n = 2) | 5.24 |  |

TABLE 10

One Month Related Substances Results - 25° C./60% RH

| Lot | Replicate | Unknown (Identified by RRT) | % Related Substances | Total Related Substances (%) | Mean of Total Related Substances (%) |
|---|---|---|---|---|---|
| 1 | 1 | NR | NR | NR | NR |
|   | 2 | NR | NR | NR |  |
| 4 | 1 | NR | NR | NR | NR |
|   | 2 | NR | NR | NR |  |

Three month stability testing was conducted as previously described, including the following measurements:

pH analysis for all lots at the 25° C./60% RH condition pH analysis for lots 1 and 4 at the 40° C./75% RH condition Assay and Related Substances analysis for lots 1 and 4 at the 25° C./60% RH and 40° C./75% RH conditions

TABLE 11

Three-Month Stability Results - 70° C./75% RH

| Lot | Replicate | Appearance | pH | Assay (mg/mL) |
|---|---|---|---|---|
| 1 | 1 | Clear, colorless solution free of visible particulate matter | 3.70 | 1.00 |
|   | 2 | Clear, colorless solution free of visible particulate matter | 3.70 | 1.00 |
|   | Mean (n = 2) |  | 3.70 | 1.00 |
| 4 | 1 | Clear, colorless solution free of visible particulate matter | 3.74 | 0.96 |
|   | 2 | Clear, colorless solution free of visible particulate matter | 3.77 | 0.94 |
|   | Mean (n = 2) |  | 3.76 | 0.95 |

TABLE 12a

Three Month Related Substances Results - 70° C./75% RH - Lot 1

| Lot | Replicate | Unknown (Identified by RRT) | % Related Substance | Total Related Substances (%) | Mean of Total Related Substances (%) |
|---|---|---|---|---|---|
| 1 | 1 | 0.039 | 0.36 | 1.70 | 1.74 |
|   |   | 0.096 | 0.14 |  |  |
|   |   | 0.136 | 0.05 |  |  |
|   |   | 0.165 | 0.34 |  |  |
|   |   | 0.364 | 0.50 |  |  |
|   |   | 0.384 | 0.06 |  |  |
|   |   | 0.555 | 0.19 |  |  |
|   |   | 1.112 | 0.06 |  |  |
|   | 2 | 0.039 | 0.39 | 1.79 |  |
|   |   | 0.096 | 0.15 |  |  |
|   |   | 0.136 | 0.05 |  |  |
|   |   | 0.165 | 0.41 |  |  |
|   |   | 0.364 | 0.47 |  |  |
|   |   | 0.384 | 0.06 |  |  |
|   |   | 0.555 | 0.18 |  |  |
|   |   | 1.112 | 0.07 |  |  |

TABLE 12b

Three Month Related Substances Results - 70° C./75% RH - Lot 4

| Lot | Replicate | Unknown (Identified by RRT) | % Related Substance | Total Related Substances (%) | Mean of Total Related Substances (%) |
|---|---|---|---|---|---|
| 4 | 1 | 0.039 | 0.78 | 3.44 | 4.34 |
|   |   | 0.095 | 0.38 |  |  |
|   |   | 0.112 | 0.06 |  |  |
|   |   | 0.135 | 0.13 |  |  |
|   |   | 0.155 | 0.06 |  |  |
|   |   | 0.164 | 0.66 |  |  |
|   |   | 0.312 | 0.07 |  |  |
|   |   | 0.363 | 0.76 |  |  |
|   |   | 0.383 | 0.10 |  |  |
|   |   | 0.554 | 0.29 |  |  |
|   |   | 1.111 | 0.14 |  |  |
|   | 2 | 0.039 | 1.16 | 5.23 |  |
|   |   | 0.096 | 0.58 |  |  |
|   |   | 0.112 | 0.11 |  |  |
|   |   | 0.135 | 0.21 |  |  |
|   |   | 0.155 | 0.07 |  |  |
|   |   | 0.164 | 0.96 |  |  |
|   |   | 0.312 | 0.11 |  |  |
|   |   | 0.363 | 1.19 |  |  |
|   |   | 0.383 | 0.14 |  |  |
|   |   | 0.553 | 0.46 |  |  |
|   |   | 1.110 | 0.24 |  |  |

TABLE 13

Three-Month Stability Results - 40° C./75% RH

| Lot | Replicate | Appearance | pH | Assay (mg/mL) |
|---|---|---|---|---|
| 1 | 1 | Clear, colorless solution free of visible particulate matter | 3.21 | 1.01 |
|   | 2 | Clear, colorless solution free of visible particulate matter | 3.23 | 1.01 |
|   | Mean (n = 2) |  | 3.22 | 1.01 |
| 4 | 1 | Clear, colorless solution free of visible particulate matter | 3.31 | 1.01 |
|   | 2 | Clear, colorless solution free of visible particulate matter | 3.33 | 1.01 |
|   | Mean (n = 2) |  | 3.32 | 1.01 |

TABLE 14

Three Month Related Substances Results - 40° C./75% RH

| Lot | Rep-licate | Unknown (Identified by RRT) | % Related Substance | Total Related Substances (%) | Mean of Total Related Substances (%) |
|---|---|---|---|---|---|
| 1 | 1 | 0.039 | 0.06 | 0.23 | 0.17 |
|   |   | 0.364 | 0.06 |      |      |
|   |   | 0.555 | 0.11 |      |      |
|   | 2 | 0.555 | 0.10 | 0.10 |      |
| 4 | 1 | 0.039 | 0.08 | 0.25 | 0.20 |
|   |   | 0.363 | 0.06 |      |      |
|   |   | 0.554 | 0.11 |      |      |
|   | 2 | 0.039 | 0.05 | 0.14 |      |
|   |   | 0.554 | 0.09 |      |      |

TABLE 15

Three-Month Stability Results - 25° C./60% RH

| Lot | Replicate | Appearance | pH | Assay (mg/mL) |
|---|---|---|---|---|
| 1 | 1 | Clear, colorless solution free of visible particulate matter | 3.18 | 1.01 |
|   | 2 | Clear, colorless solution free of visible particulate matter | 3.18 | 1.01 |
|   |   | Mean (n = 2) | 3.18 | 1.01 |
| 4 | 1 | Clear, colorless solution free of visible particulate matter | 3.21 | 1.01 |
|   | 2 | Clear, colorless solution free of visible particulate matter | 3.19 | 1.01 |
|   |   | Mean (n = 2) | 3.20 | 1.01 |

TABLE 16

Three Month Related Substances Results - 25° C./60% RH

| Lot | Rep-licate | Unknown (Identified by RRT) | % Related Substance | Total Related Substances (%) | Mean of Total Related Substances (%) |
|---|---|---|---|---|---|
| 1 | 1 | NR | NR | NR | NR |
|   | 2 | NR | NR | NR |    |
| 4 | 1 | NR | NR | NR | NR |
|   | 2 | NR | NR | NR |    |

Medicament Delivery Devices

The naloxone compositions described herein can be included in any suitable medicament delivery device. For example, in some embodiments, a medicament delivery device configured for self-administration (or administration by an untrained user, such a person accompanying the patient) can include any of the naloxone compositions described herein. Such medicament delivery devices can include, for example, an auto-injector, an intranasal delivery device, a pre-filled syringe, an inhaler or the like. In this manner, the medicament delivery device (including the naloxone composition) can be used by the patient (or an untrained user) in any setting (e.g., the patient's home, in a public venue or the like).

In some embodiments, a medicament delivery device can be configured to automatically deliver any of the naloxone compositions described herein. Similarly stated, in some embodiments, a medicament delivery device, after being actuated by the user, can automatically produce (i.e., produce without any further human intervention) a force to deliver the naloxone composition. In this manner, the force with which the naloxone composition is delivered is within a desired range, and is repeatable between different devices, users or the like.

Figure 99:
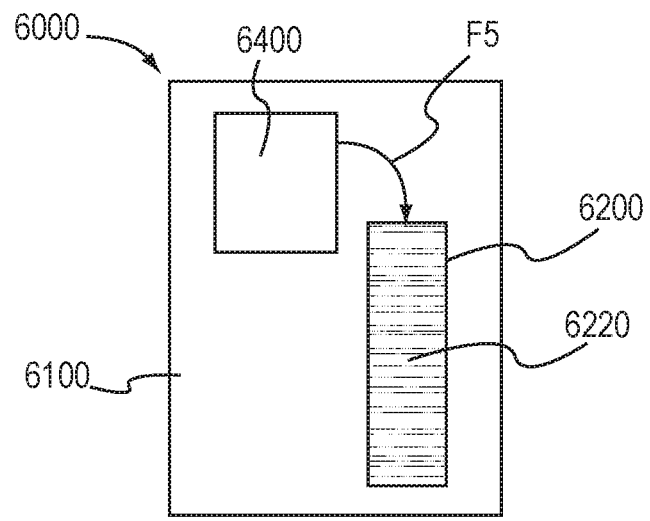
FIG. 99 is a schematic illustration of a medicament delivery device according to an embodiment.

One example of such a medicament delivery device is provided in FIG. 99, which is a schematic illustration of a medicament delivery device 6000 according to an embodiment. The medicament delivery device 6000 includes a housing 6100, a medicament container 6200 and an energy storage member 6400. The medicament container 6200 is disposed within the housing 6100, and contains (i.e., is filled or partially filled with) a naloxone composition 6220. The energy storage member 6400 is disposed within the housing 6100, and is configured to produce a force F5 to deliver the naloxone composition 6220 (e.g., from the medicament container 6200 to a body).

The naloxone composition 6220 can be any of the naloxone compositions described herein. In particular, the naloxone composition 6220 can include an effective amount of naloxone or salts thereof, a tonicity-adjusting agent, and a pH-adjusting agent. The naloxone composition 6220 can be formulated such that the osmolality of the naloxone composition 6220 ranges from about 250-350 mOsm and the pH ranges from about 3-5.

In some embodiments, the naloxone composition 6220 can include any suitable concentration of 4,5-epoxy-3,14-dihydroxy-17-(2-propenyl) morphinan-6-one. In some embodiments, for example, the naloxone composition 6220 has a concentration of 4,5-epoxy-3,14-dihydroxy-17-(2-propenyl)morphinan-6-one between approximately 0.01 mg/mL and approximately 10 mg/mL. In other embodiments, the naloxone composition 6220 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 6220 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH-adjusting agent can be any of the pH-adjusting agents described herein, and can be included within the naloxone composition 6220 in any suitable amount and/or concentration. For example, in some embodiments, the pH-adjusting agent includes at least one of hydrochloric acid, citric acid, citrate salts, acetic acid, acetate salts, phosphoric acid or phosphate salts. In other embodiments, the pH-adjusting agent includes a dilute hydrochloric acid.

The medicament container 6200 can be any container suitable for storing the naloxone composition 6220. In some embodiments, the medicament container 6200 can be, for example, a pre-filled syringe, a pre-filled cartridge, a vial, an ampule or the like. In other embodiments, the medicament container 6200 can be a container having a flexible wall, such as, for example, a bladder.

The energy storage member 6400 can be any suitable device or mechanism that, when actuated, produces a force F5 to deliver the naloxone composition 6220. Similarly stated, the energy storage member 6400 can be any suitable device or mechanism that produces the force F5 such that the naloxone composition 6220 is conveyed from the medicament container 6200 into a body of a patient. The naloxone composition 6220 can be conveyed into a body via any suitable mechanism, such as, for example, by injection, intranasally, via inhalation or the like. By employing the energy storage member 6400 to produce the force F5, rather than relying on a user to manually produce the delivery force, the naloxone composition 6220 can be delivered into the body at the desired pressure and/or flow rate, and with the desired characteristics. Moreover, this arrangement reduces the likelihood of partial delivery (e.g., that may result if the user is interrupted or otherwise rendered unable to complete the delivery).

In some embodiments, the energy storage member 6400 can be a mechanical energy storage member, such as a spring, a device containing compressed gas, a device containing a vapor pressure-based propellant or the like. In other embodiments, the energy storage member 6400 can be an electrical energy storage member, such as a battery, a capacitor, a magnetic energy storage member or the like. In yet other embodiments, the energy storage member 6400 can be a chemical energy storage member, such as a container containing two substances that, when mixed, react to produce energy.

As shown in FIG. 99, the energy storage member 6400 can be in any position and/or orientation relative to the medicament container 6200. In some embodiments, for example, the energy storage member 6400 can be positioned within the housing 6100 spaced apart from the medicament container 6200. Moreover, in some embodiments, the energy storage member 6400 can be positioned such that a longitudinal axis of the energy storage member 6400 is offset from the medicament container 6200. In other embodiments, the energy storage member 6400 can substantially surround the medicament container 6200.

Moreover, the energy storage member 6400 can be operably coupled to the medicament container 6200 and/or the naloxone composition 6220 therein such that the force F5 delivers the naloxone composition 6220. In some embodiments, for example, the force F5 can be transmitted to the naloxone composition 6220 via a piston or plunger (not shown in FIG. 99). In other embodiments, the force F5 can be transmitted to the naloxone composition 6220 via a hydraulic or pneumatic coupling. In yet other embodiments, the force F5 can be transmitted to the naloxone composition 6220 electrically. In still other embodiments, the force F5 can be transmitted to the naloxone composition 6220 via a combination of any of the above.

Figure 100:
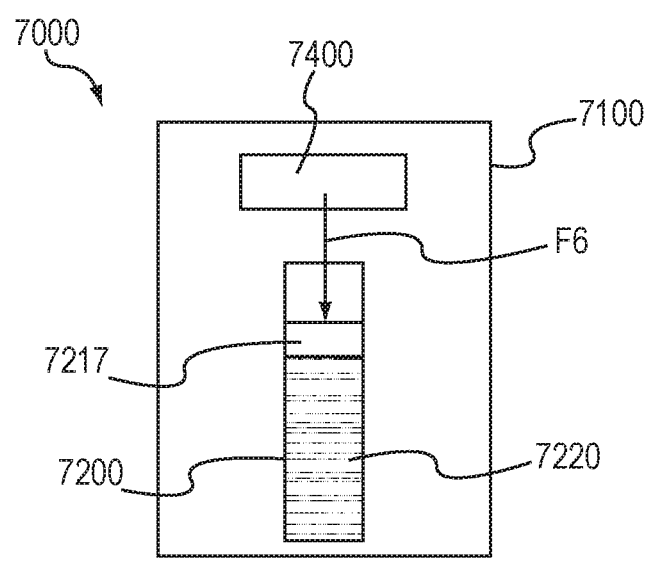
FIG. 100 is a schematic illustration of a medicament delivery device according to an embodiment.

In some embodiments, a medicament container can include an elastomeric member, such that the force produced by an energy storage member is transferred to the naloxone composition by the elastomeric member. For example, FIG. 100 is a schematic illustration of a medicament delivery device 7000 according to an embodiment. The medicament delivery device 7000 includes a housing 7100, a medicament container 7200, an elastomeric member 7217 and an energy storage member 7400. The medicament container 7200 is disposed within the housing 7100, and contains (i.e., is filled or partially filled with) a naloxone composition 7220. The naloxone composition 7220 can be any of the naloxone compositions described herein. The energy storage member 7400 is disposed within the housing 7100, and is configured to produce a force F6 to deliver the naloxone composition 7220, as described herein.

The elastomeric member 7217 is disposed within the medicament container 7200 to seal an end portion of the medicament container 7200. The elastomeric member 7217 can be disposed within the medicament container 7200 during the fill process, and can form a substantially fluid-tight seal to prevent leakage of the naloxone composition 7220 from the medicament container 7200. Moreover, the elastomeric member 7217 is operatively coupled to the energy storage member 7400 such that, in use the force F6 acts upon the elastomeric member 7217 to deliver the naloxone composition 7220 from the medicament container 7200.

The elastomeric member 7217 is formulated to be compatible with the naloxone composition 7220. Similarly stated, the elastomeric member 7217 is formulated to minimize any reduction in the efficacy of the naloxone composition 7220 that may result from contact (either direct or indirect) between the elastomeric member 7217 and the naloxone composition 7220. For example, in some embodiments, the elastomeric member 7217 can be formulated to minimize any leaching or out-gassing of compositions that may have an undesired effect on the naloxone composition 7220. In other embodiments, the elastomeric member 7217 can be formulated to maintain its chemical stability, flexibility and/or sealing properties when in contact (either direct or indirect) with naloxone over a long period of time (e.g., for up to six months, one year, two years, five years or longer).

In some embodiments, the elastomeric member 7217 can be formulated to include a polymer and a curing agent. In such embodiments, the polymer can include at least one of bromobutyl or chlorobutyl. In such embodiments, the curing agent can include at least one of sulfur, zinc or magnesium.

In some embodiments, the elastomeric member 7217 can be constructed from multiple different materials. For example, in some embodiments, at least a portion of the elastomeric member 7217 can be coated. Such coatings can include, for example, polydimethylsiloxane. In some embodiments, at least a portion of the elastomeric member 7217 can be coated with polydimethylsiloxane in an amount of between approximately 0.02 mg/cm$^2$ and approximately 0.80 mg/cm$^2$.

Figure 101:
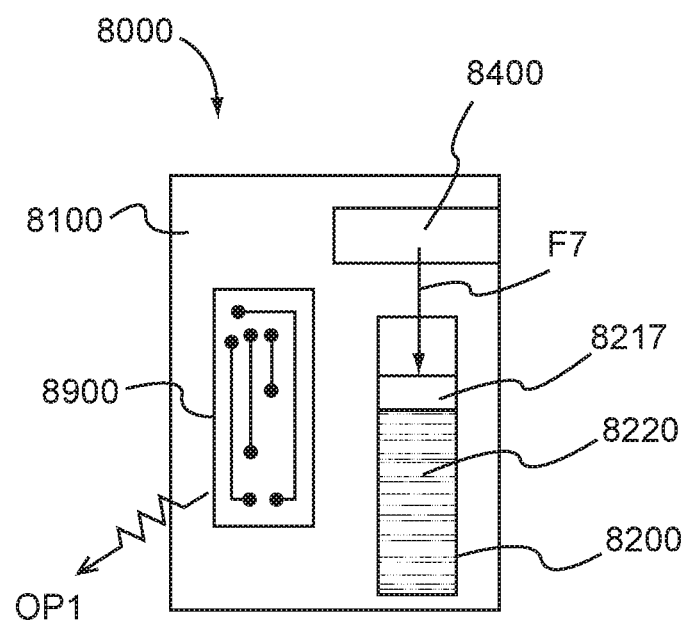
FIG. 101 is a schematic illustration of a medicament delivery device according to an embodiment.

A medicament delivery device configured for delivery of a naloxone composition can include an electronic circuit system that produces an output. Such output can include, for example, any output to assist the user and/or patient in administering the dose of the naloxone composition. For example, FIG. 101 is a schematic illustration of a medicament delivery device 8000 according to an embodiment. The medicament delivery device 8000 includes a housing 8100, a medicament container 8200, an elastomeric member 8217, an energy storage member 8400 and an electronic circuit system 8900. The medicament container 8200 is disposed within the housing 8100, and contains (i.e., is filled or partially filled with) a naloxone composition 8220. The naloxone composition 8220 can be any of the naloxone compositions described herein. For example, in some embodiments, the naloxone composition 8220 can include an effective amount of naloxone or salts thereof, a tonicity-adjusting agent, and a pH-adjusting agent. The naloxone composition can be formulated such that the osmolality of the naloxone composition ranges from about 250-350 mOsm and the pH ranges from about 3-5.

The energy storage member 8400 is disposed within the housing 8100, and is configured to produce a force F7 to deliver the naloxone composition 8220, as described herein. The elastomeric member 8217 is disposed within the medicament container 8200 to seal an end portion of the medicament container 8200. Moreover, the elastomeric member 8217 is operatively coupled to the energy storage member 8400 such that, in use the force F7 acts upon the elastomeric member 8217 to deliver the naloxone composition 8220 from the medicament container 8200.

The electronic circuit system 8900 is configured to produce an output OP1 when the electronic circuit system 8900 is actuated. The output can be, for example, an audible or visual output related to the naloxone composition (e.g., an indication of the expiration date, the symptoms requirement treatment with naloxone or the like), the use of the medicament delivery device, and/or post-administration procedures (e.g., a prompt to call 911, instructions for the disposal of the device or the like).

For example, in some embodiments, the electronic output OP1 can be associated with an instruction for using the medicament delivery device 8000. In other embodiments, the electronic output OP1 can be a post-use instruction, such as, for example, a recorded message notifying the user that the delivery of the naloxone composition 8220 is complete, instructing the user on post-use disposal of the medicament delivery device 8000 (e.g., post-use safety procedures), instructing the user to seek post-use medical treatment, and/or the like. In yet other embodiments, the electronic output OP1 can be associated with the patient's compliance in using medicament delivery device 8000.

The electronic output OP1 can be, for example, a visual output such as, for example, a text message to display on a screen (not shown), and/or an LED. In some embodiments, the electronic output OP1 can be an audio output, such as, for example, recorded speech, a series of tones, and/or the like. In other embodiments, the electronic output OP1 can be a wireless signal configured to be received by a remote device.

As described in more detail herein, the electronic circuit system 8900 can include any suitable electronic components operatively coupled to produce and/or output the electronic output OP1 and/or to perform the functions described herein. The electronic circuit system 8900 can be similar to the electronic circuit systems described in U.S. Pat. No. 7,731,686, entitled "Devices, Systems and Methods for Medicament Delivery," filed Jan. 9, 2007, which is incorporated herein by reference in its entirety.

The electronic circuit system 8900 can be actuated to produce the electronic output OP1 in any suitable manner. For example, in some embodiments, the electronic circuit system 8900 can be associated with an actuation of the medicament delivery device 8000. Said another way, the electronic circuit system 8900 can be configured to output the electronic output OP1 in response to actuation of the medicament delivery device 8000. In other embodiments, the electronic circuit system 8900 can be actuated manually by a switch (not shown in FIG. 101). Such a switch can be actuated (i.e., to actuated the electronic circuit system 8900) by a push button, by removing the medicament delivery device 8000 from a case or cover (not shown in FIG. 101), by receiving a signal from a remote electronic device, and/or any other suitable mechanism. In yet other embodiments, the electronic circuit system 8900 can be actuated by receiving input from the user via a voice prompt system.

The electronic circuit system 8900 can be coupled to and/or disposed within the housing 8100 in any suitable arrangement. For example, in some embodiments, the electronic circuit system 8900 can be coupled to an exterior or outer surface of the housing 8100. In other embodiments, at least a portion of the electronic circuit system 8900 can be disposed within the housing 8100. Moreover, in some embodiments, a portion of the electronic circuit system 8900 is disposed within the housing 8100 such that the portion of the electronic circuit system 8900 is fluidically and/or physically isolated from the medicament container 8200.

Figure 102:
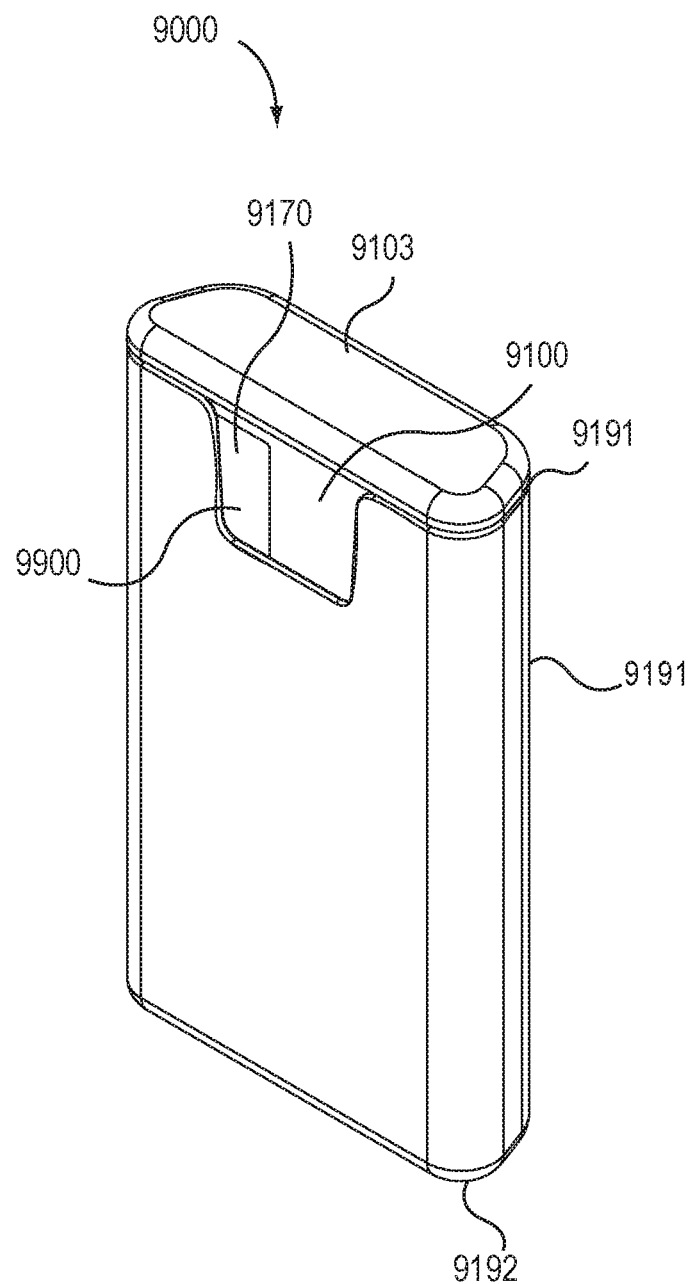
FIGS. 102 and 103 are perspective views of a medical injector according to an embodiment, in a first configuration.
Figure 103:
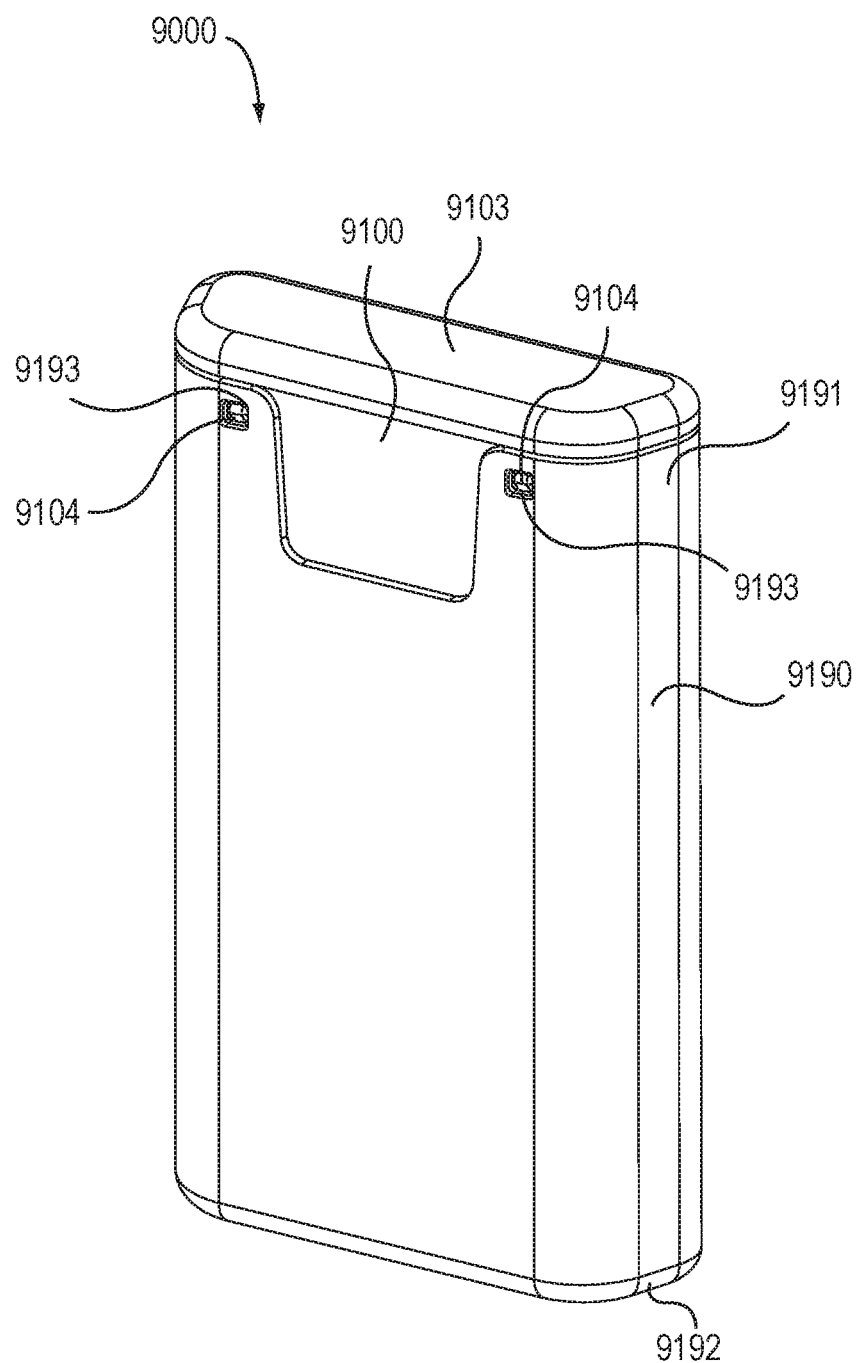
Figure 104:
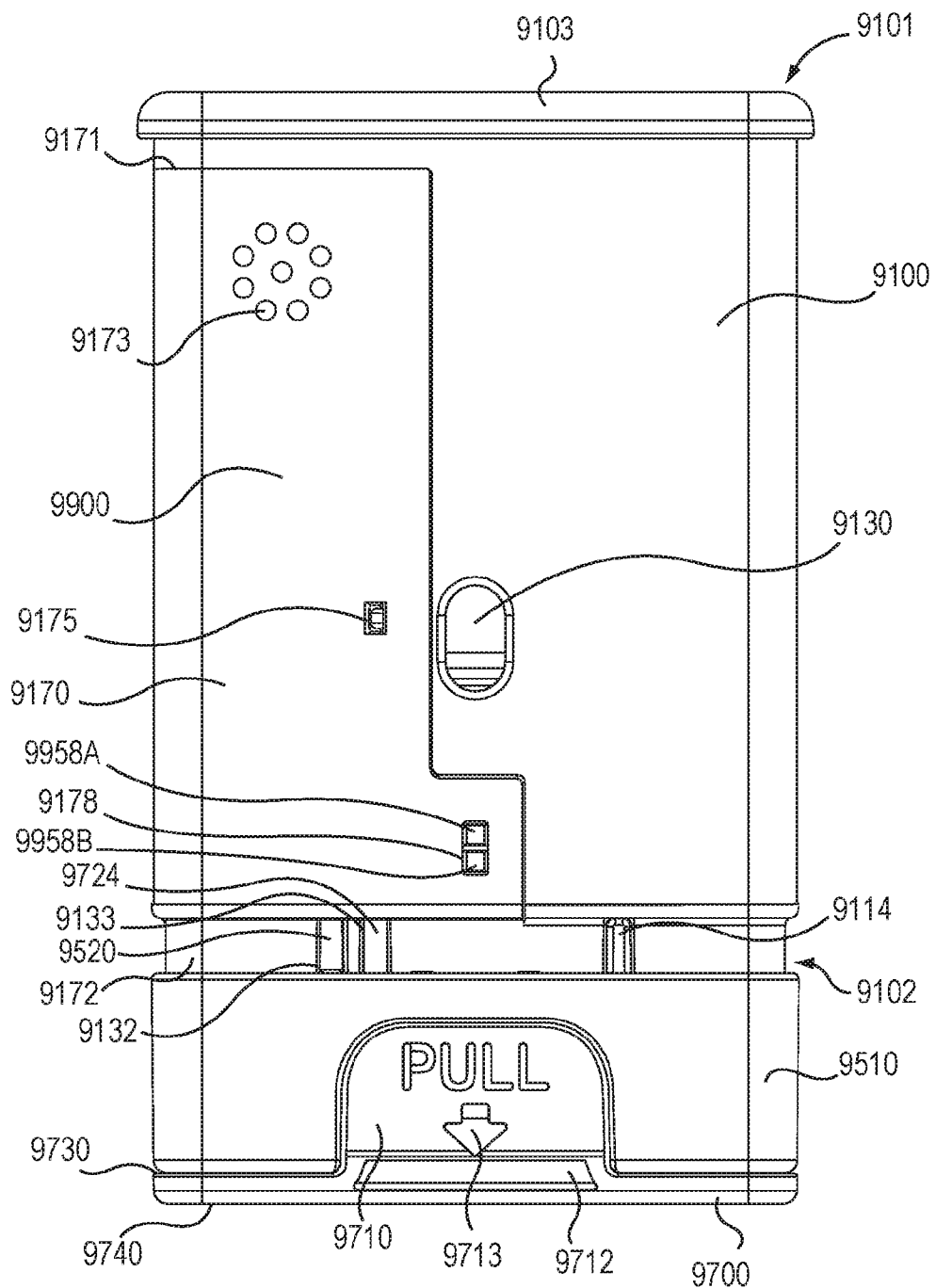
FIG. 104 is a front view of the medical injector illustrated in FIG. 102 with the cover removed.
Figure 119:
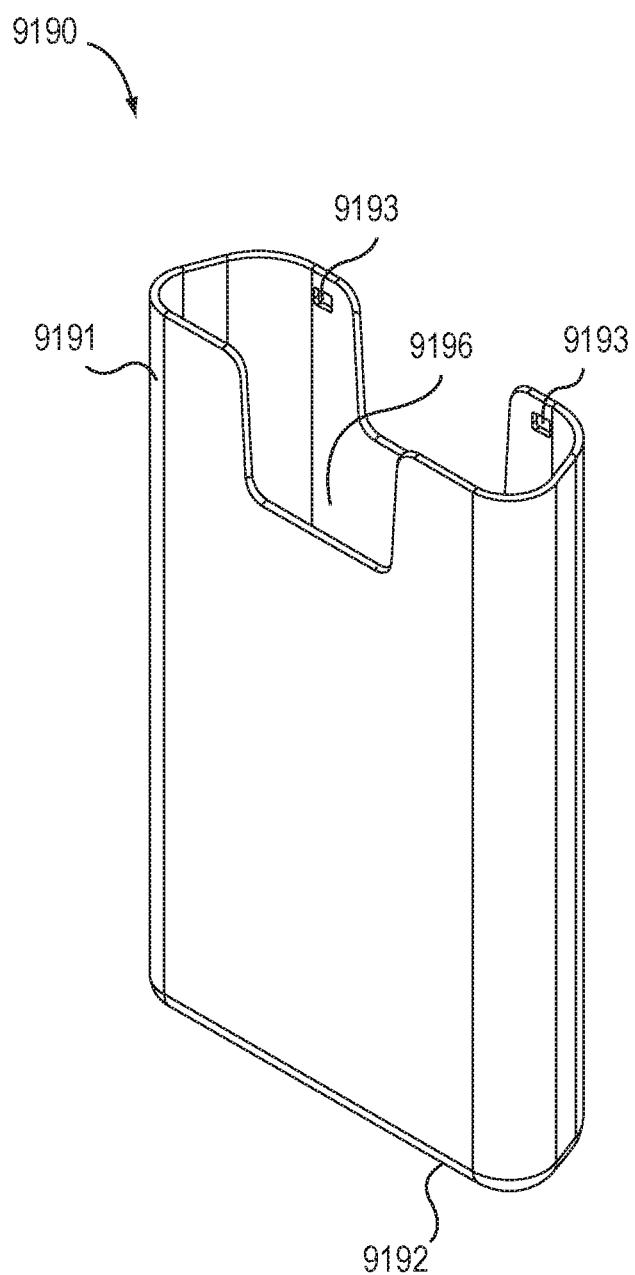
FIGS. 119 and 120 are perspective views of a cover of the medical injector illustrated in FIG. 102.

The medicament delivery device 8000 can be any suitable device for automatically delivering any of the naloxone compositions described herein. In some embodiments, the medicament delivery device can be a medical injector configured to automatically deliver a naloxone composition. For example, FIGS. 102-131 show a medical injector 9000, according to an embodiment. FIGS. 102-103 are perspective views of the medical injector 9000 in a first configuration (i.e., prior to use). The medical injector 9000 includes a housing 9100, a delivery mechanism 9300 (see e.g., FIGS. 110-112), a medicament container 9200 containing a naloxone composition 9220 (see e.g., FIG. 113), an electronic circuit system 9900 (see e.g., FIGS. 115-118), a cover 9190 (see e.g., FIGS. 119 and 120), a safety lock 9700 (see e.g., FIGS. 121-123) and a system actuation assembly 9500 (see e.g., FIGS. 110, 112, 124 and 125). A discussion of the components of the medical injector 9000 will be followed by a discussion of the operation of the medical injector 9000.

As shown in FIGS. 104-109, the housing 9100 has a proximal end portion 9101 and a distal end portion 9102. The housing 9100 defines a first status indicator aperture 9130 and a second status indicator aperture 9160. The first status indicator aperture 9130 defined by the housing 9100 is located on a first side of the housing 9100, and the second status indicator aperture 9160 of the housing 9100 is located on a second side of the housing 9100. The status indicator apertures 9130, 9160 can allow a patient to monitor the status and/or contents of the medicament container 9200 contained within the housing 9100. For example, by visually inspecting the status indicator apertures 9130, 9160, a patient can determine whether the medicament container 9200 contains a medicament and/or whether a medicament has been dispensed.

Figure 107:
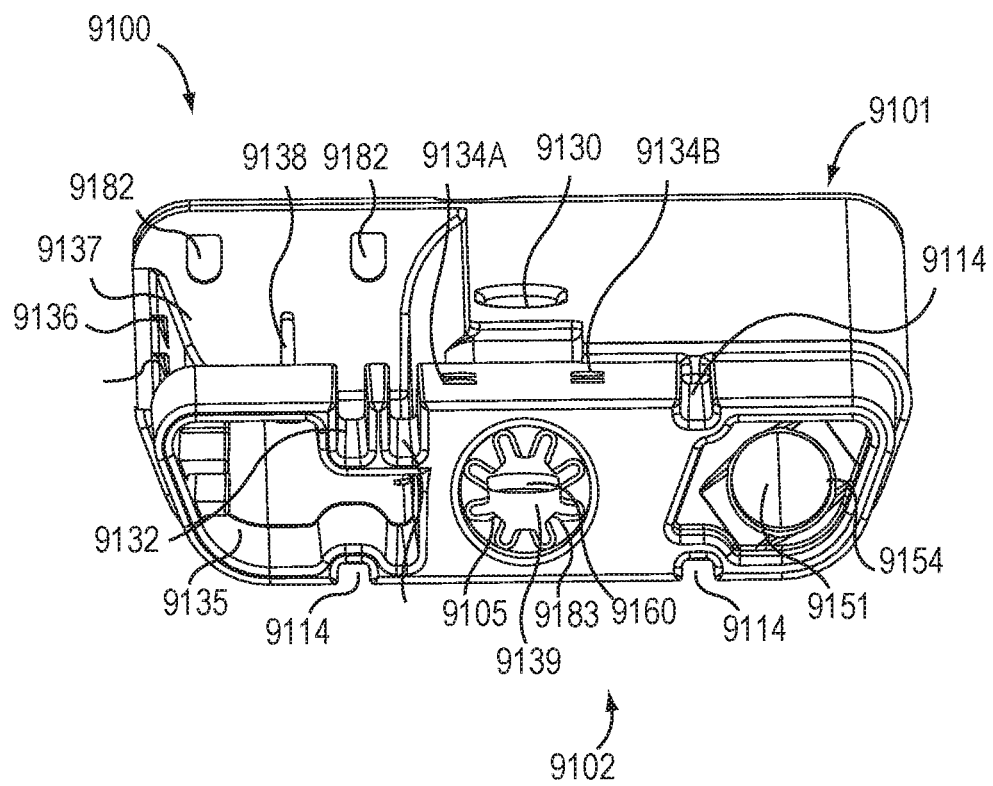
FIG. 107 is a bottom perspective view of a housing of the medical injector illustrated in FIG. 102.
Figure 108:
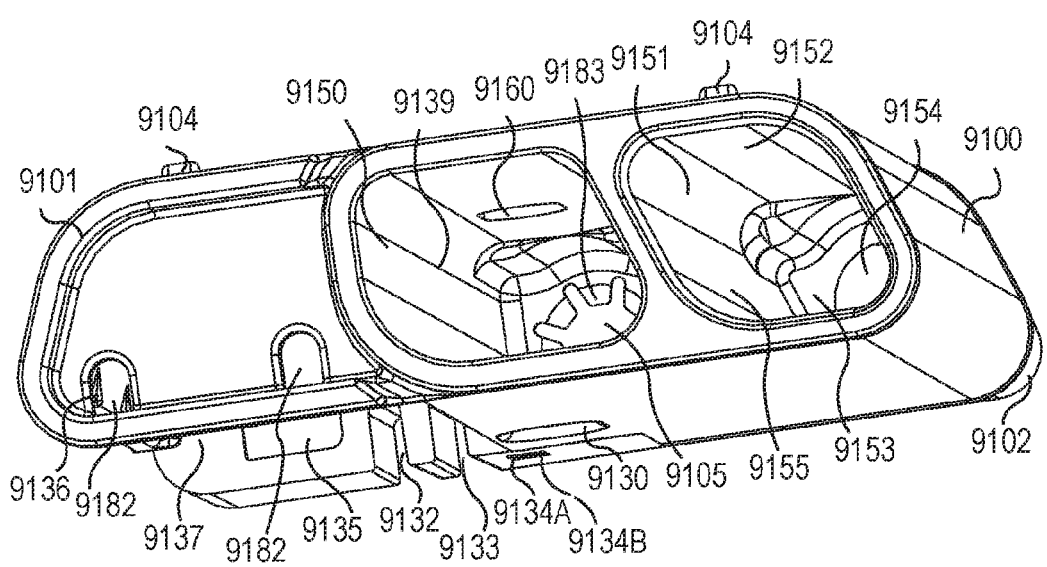
FIG. 108 is a top perspective view of a housing of the medical injector illustrated in FIG. 102.
Figure 110:
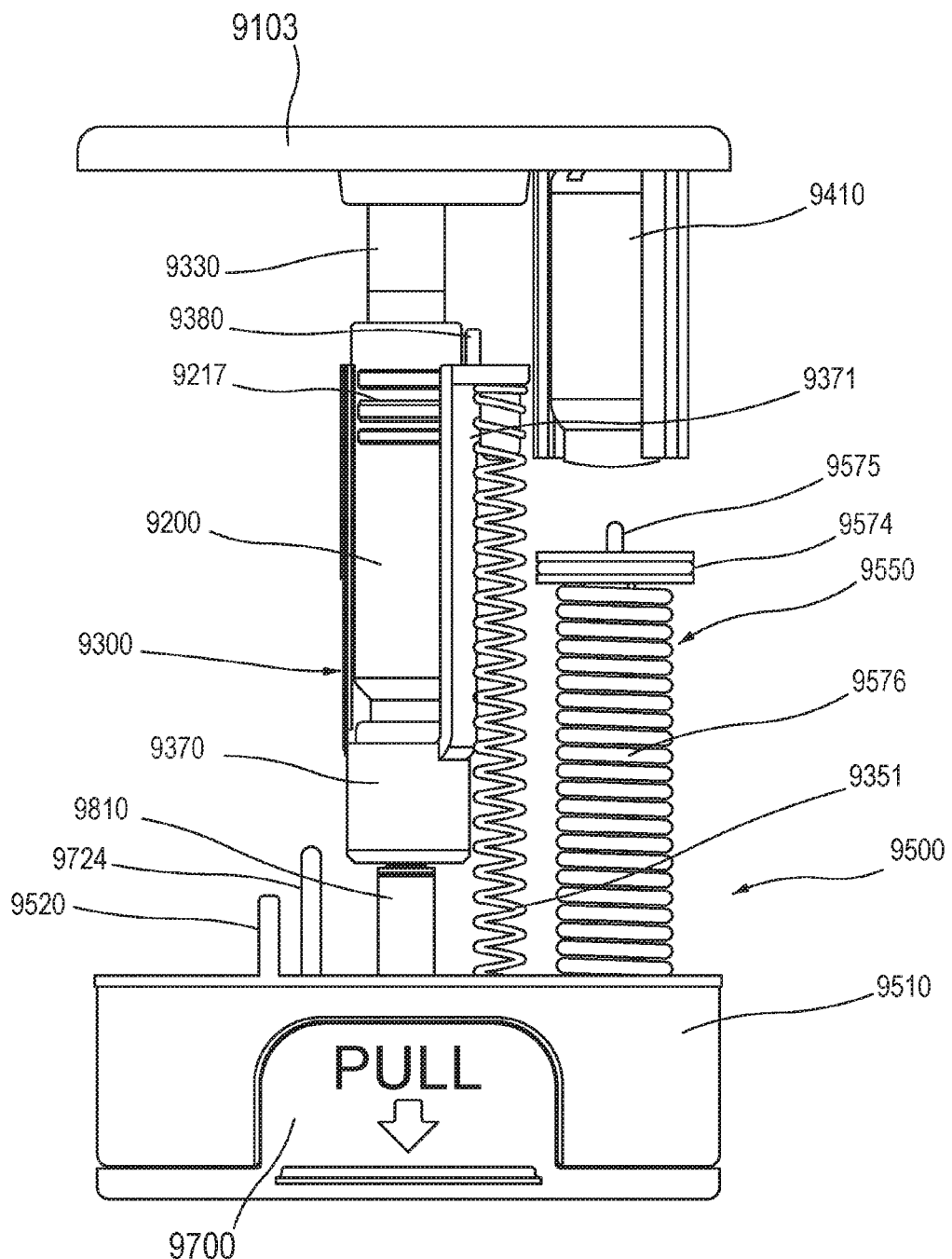
FIGS. 110 and 111 are front views of a medicament delivery mechanism of the medical injector illustrated in FIG. 102.
Figure 111:
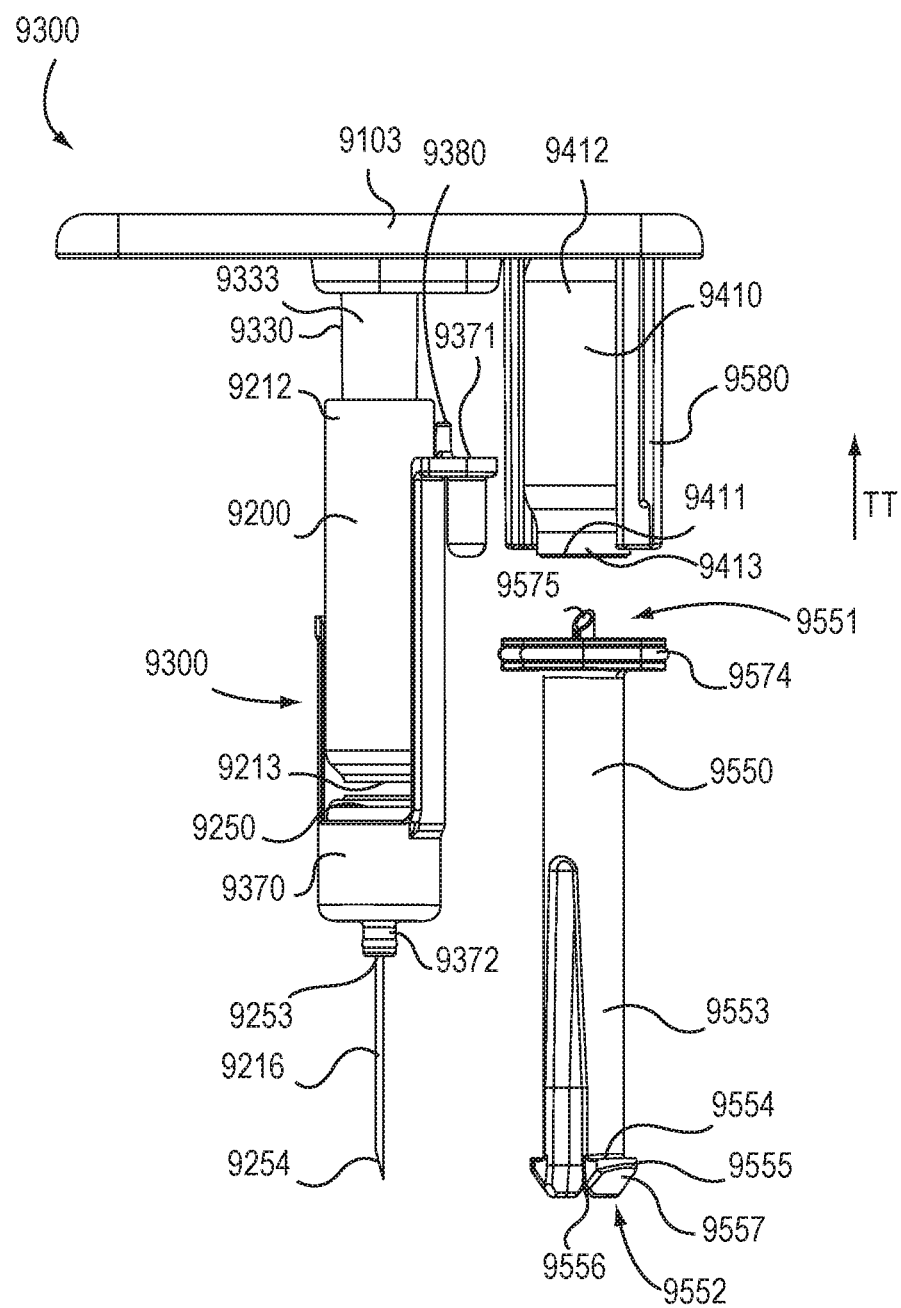
Figure 112:
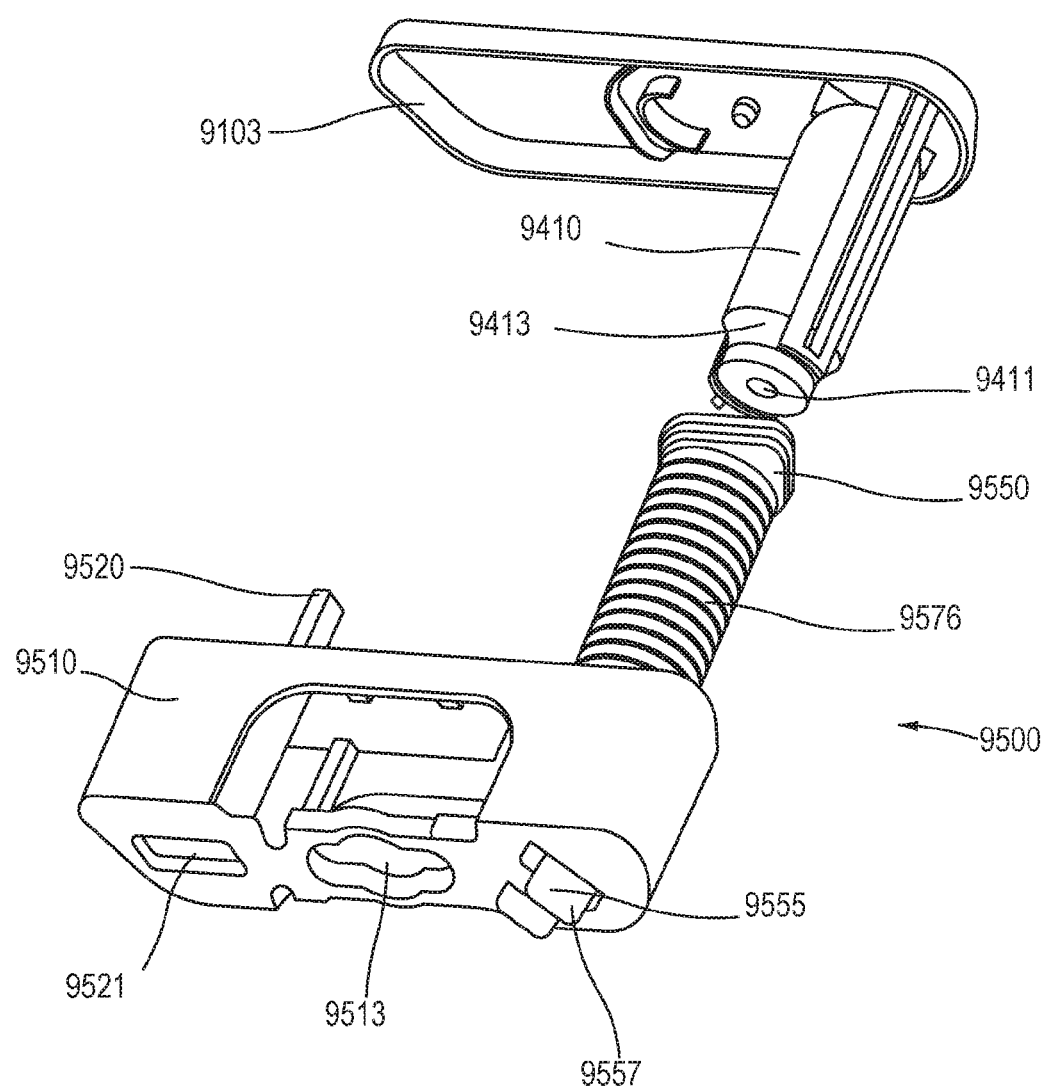
FIG. 112 is a perspective view of a portion of the medical injector illustrated in FIG. 102.

As shown in FIGS. 107 and 108, the housing 9100 defines a gas cavity 9151, a medicament cavity 9139 and an electronic circuit system cavity 9137. The gas cavity 9151 has a proximal end portion 9182 and a distal end portion 9153. The gas cavity 9151 is configured to receive the gas container 9410 and a portion of the system actuation assembly 9500 (e.g., the release member 9550 and the spring 9576, as shown in FIGS. 110-112) as described in further detail herein. The proximal end portion 9182 of the gas cavity 9151 is configured to receive the gas container retention member 9580 of the proximal cap 9103 of the housing 9100, as described in further detail herein. The gas cavity 9151 is in fluid communication with the medicament cavity 9139 via a gas passageway 9156 (see e.g., FIG. 109), as described in further detail herein, and the gas cavity 9151 is in fluid communication with a region outside the housing 9100 via a release member aperture 9154 (see e.g., FIGS. 107 and 108).

The medicament cavity 9139 is configured to receive the medicament container 9200 and a portion of the delivery mechanism 9300. In particular, the carrier 9370 and the piston 9330 of the medicament delivery mechanism 9300 are movably disposed in the medicament cavity 9139. The medicament cavity 9139 is in fluid communication with a region outside the housing 9100 via a needle aperture 9105 (see e.g., FIGS. 107 and 108).

The electronic circuit system cavity 9137 is configured to receive the electronic circuit system 9900. The housing 9100 has protrusions 9136 (see e.g., FIG. 106) configured to stabilize the electronic circuit system 9900 when the electronic circuit system 9900 is disposed within the electronic circuit system cavity 9137. The housing 9100 also defines connection apertures 9182 configured to receive connection protrusions 9174A of the electronic circuit system 9900, and aperture 9129 (see e.g., FIGS. 107 and 108) configured to receive a portion of a protrusion 9177 of the electronic circuit system 9900 (see e.g., FIG. 118). In this manner, the electronic circuit system 9900 can be coupled to the housing 9100 within the electronic circuit system cavity 9137. In other embodiments, the electronic circuit system 9900 can be coupled within the electronic circuit system cavity 9137 by other suitable means such as an adhesive, a clip, a label and/or the like.

The electronic circuit system cavity 9137 is fluidically and/or physically isolated from the gas cavity 9151 and/or the medicament cavity 9139 by a sidewall 9150. The sidewall 9150 can be any suitable structure to isolate the electronic circuit system cavity 9137 within the housing 9100 from the gas cavity 9151 and/or the medicament cavity 9139 within the housing 9100. Similarly, the gas cavity 9151 and the medicament cavity 9139 are separated by a sidewall 9155. In some embodiments, sidewall 9155 can be similar to the sidewall 9150, which isolates the gas cavity 9151 and the medicament cavity 9139 from the electronic circuit system cavity 9137. In other embodiments, the gas cavity 9151 can be fluidically and/or physically isolated from the medicament cavity 9139.

Figure 105:
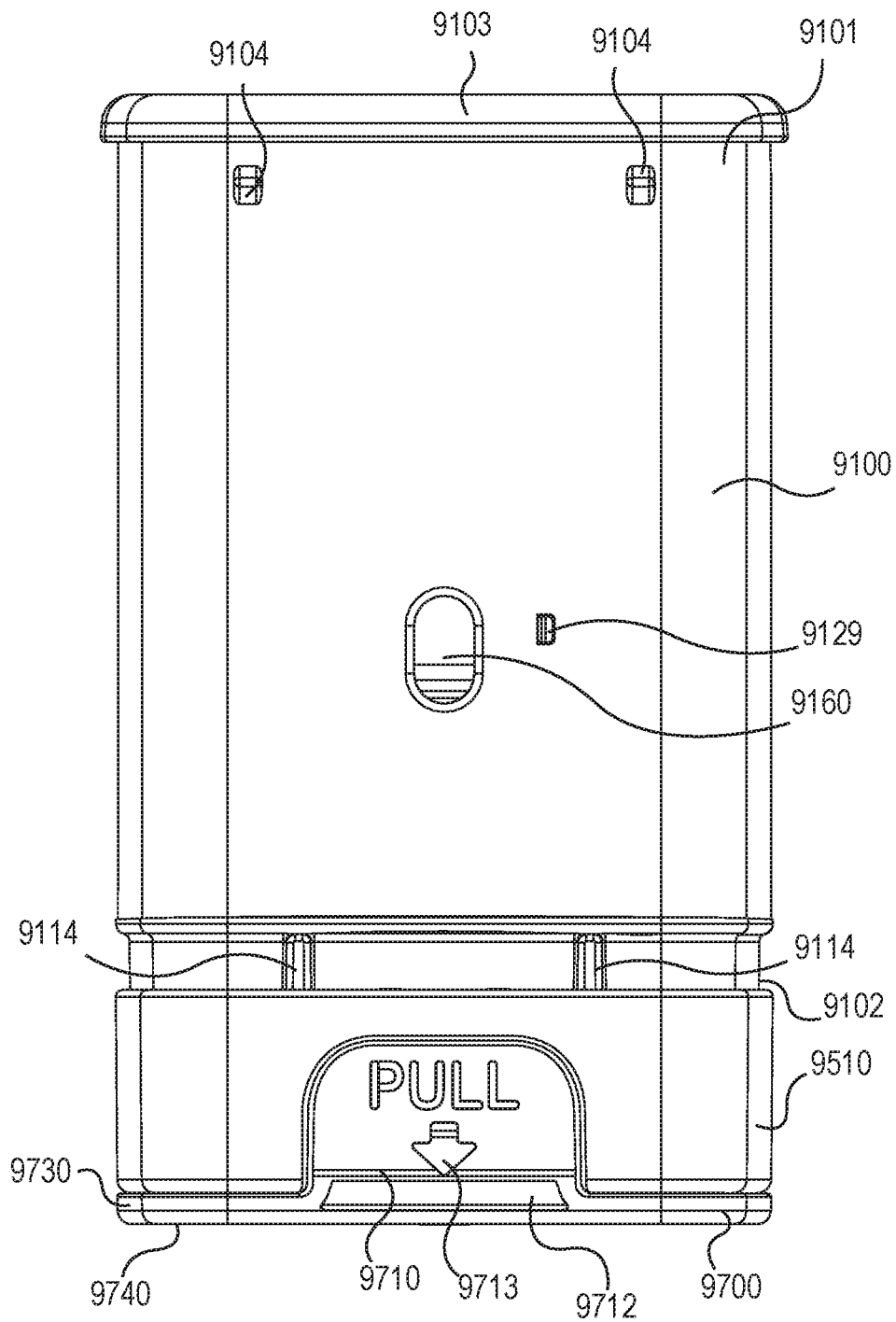
FIG. 105 is a back view of the medical injector illustrated in FIG. 102 with the cover removed.

The proximal end portion 9101 of the housing 9100 includes a proximal cap 9103, a speaker protrusion 9138 (see e.g., FIGS. 106 and 107), and cover retention protrusions 9104 (see e.g., FIGS. 103 and 105). The speaker protrusion 9138 is configured to maintain a position of an audio output device 9956 of the electronic circuit system 9900 relative to the housing 9100 when the electronic circuit system 9900 is attached to the housing 9100, as described herein. The cover retention protrusions 9104 are configured to be received within corresponding openings 9193 on the cover 9190. In this manner, as described in more detail herein, the cover 9190 can be removably coupled to and disposed about at least a portion of the housing 9100.

Figure 109:
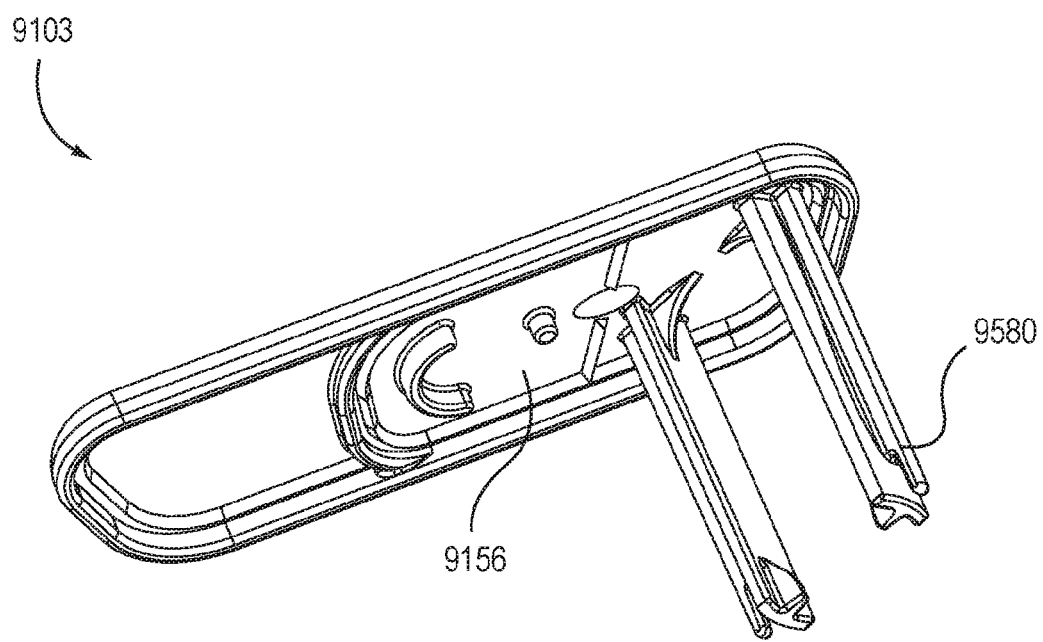
FIG. 109 is a perspective view of a proximal cap of the medical injector illustrated in FIG. 102.

As shown in FIG. 109, the proximal cap 9103 includes a gas container retention member 9580 and defines a gas passageway 9156. The gas container retention member 9580 is configured to receive and/or retain a gas container 9410 that can contain a pressurized gas. The gas passageway 9156 is configured to allow for the passage of gas contained in the gas container 9410 from the gas cavity 9151 to the medicament cavity 9139, as further described herein. Said another way, the gas passageway 9156 places the gas cavity 9151 in fluid communication with the medicament cavity 9139.

Figure 106:
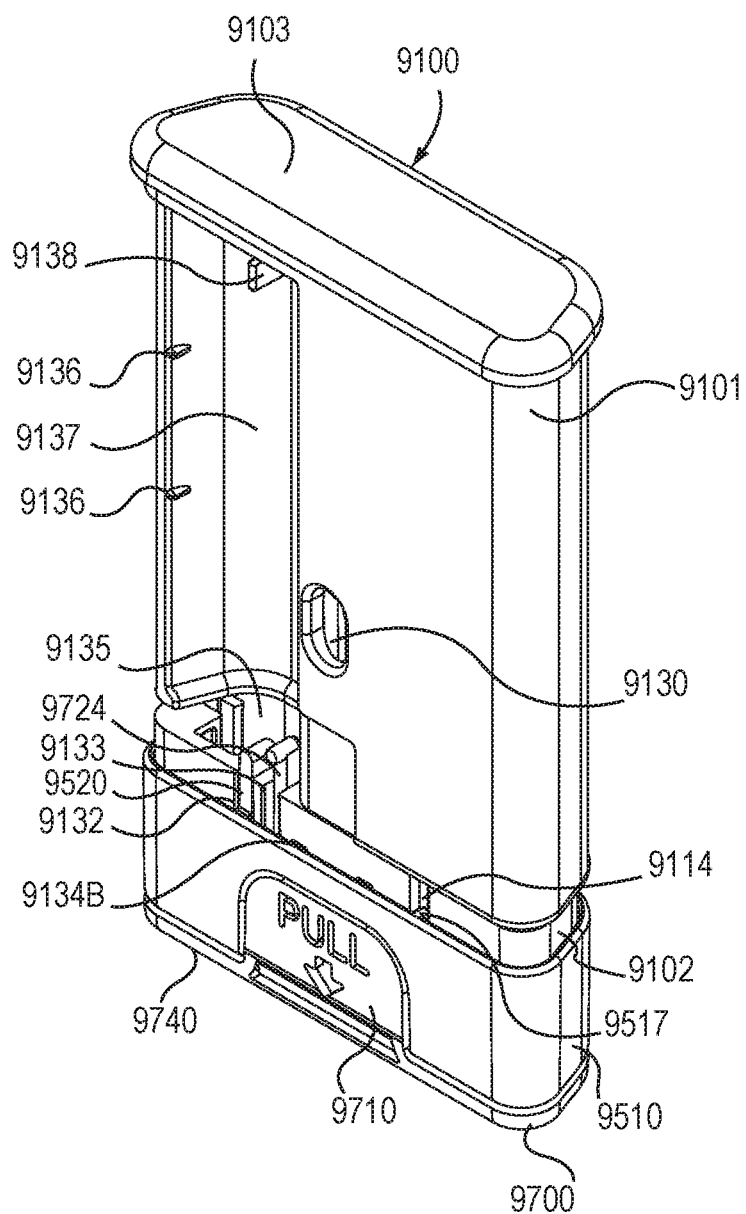
FIG. 106 is a perspective view of a portion of the medical injector illustrated in FIG. 102.

As shown in FIGS. 105-107, the distal end portion 9102 of the housing 9100 defines a battery isolation protrusion aperture 9135, a needle aperture 9105, a safety lock actuator groove 9133, a release member aperture 9154, a base actuator groove 9132, base retention recesses 9134A, 9134B, and base rail grooves 9114. The battery isolation protrusion aperture 9135 is configured to receive the battery isolation protrusion 9197 of the cover 9190 (see e.g., FIG. 120), as described in further detail herein.

The needle aperture 9105 is configured to allow the needle 9216 (see e.g., FIGS. 110, 128 and 129) to exit the housing 9100 when the medical injector 9000 is actuated. The portion of the sidewall of the housing 9100 that defines the needle aperture 9105 includes multiple sheath retention protrusions 9183. In some embodiments, the sheath retention protrusions can interact with the plurality of ribs 9825 of the needle sheath 9810 (see e.g. FIG. 123) to maintain a position of the needle sheath 9810 relative to the safety lock 9700 when the safety lock 9700 is coupled to the housing 9100 and/or when the safety lock 9700 is being removed from the housing 9100.

The safety lock actuator groove 9133 is configured to receive an actuator 9724 of the safety lock 9700. As described in more detail herein, the actuator 9724 is configured to engage and/or activate the electronic circuit system 9900 when the safety lock 9700 is moved with respect to the housing 9100. The release member aperture 9154 is configured to receive a safety lock protrusion 9702 (see e.g., FIG. 121). As described in more detail below, when the medical injector is in the first configuration (i.e., when the safety lock 9700 is in place prior to use), the safety lock protrusion 9702 is disposed within an opening 9556 between extensions 9553 of a release member 9550 (see e.g., FIGS. 111 and 112) such that activation of the medical injector 9000 is prevented. The safety lock 9700, its components and functions are further described herein.

The distal base retention recesses 9134A are configured to receive the base connection knobs 9518 of the actuator 9510 (also referred to herein as "base 9510," see e.g., FIG. 124) when the base 9510 is in a first position relative to the housing 9100. The proximal base retention recesses 9134B are configured to receive the base connection knobs 9518 of the base 9510 when the base 9510 is in a second position relative to the housing 9100. The base retention recesses 9134A, 9134B have a tapered proximal sidewall and a non-tapered distal sidewall. This allows the base retention recesses 9134A, 9134B to receive the base connection knobs 9518 such that the base 9510 can move proximally relative to the housing 9100, but cannot move distally relative to the housing 9100. Said another way, the distal base retention recesses 9134A are configured to prevent the base 9510 from moving distally when the base 9510 is in a first position and the proximal base retention recesses 9134B are configured to prevent the base 9510 from moving distally when the base 9510 is in a second position. Similarly stated, the proximal base retention recesses 9134B and the base connection knobs 9518 cooperatively prevent "kickback" after the medical injector 9000 is actuated.

The base actuator groove 9132 is configured to receive an actuator 9520 of the base 9510. As described in more detail herein, the actuator 9520 of the base 9510 is configured to engage the electronic circuit system 9900 when the base 9510 is moved with respect to the housing 9100. The base rail grooves 9114 are configured to receive the guide members 9517 of the base 9510. The guide members 9517 of the base 9510 and the base rail grooves 9114 of the housing 9100 engage each other in a way that allows the guide members 9517 of the base 9510 to slide in a proximal and/or distal direction within the base rail grooves 9114 while limiting lateral movement of the guide members 9517. This arrangement allows the base 9510 to move in a proximal and/or distal direction with respect to the housing 9100 but prevents the base 9510 from moving in a lateral direction with respect to the housing 9100.

FIGS. 110-111 show the medicament container 9200, the system actuation assembly 9500 and the medicament delivery mechanism 9300 of the medical injector 9000. The medical injector 9000 is similar to the auto-injectors described in U.S. Pat. No. 7,648,482, entitled "Devices. Systems and Methods for Medicament Delivery," filed Nov. 21, 2006, which is incorporated herein by reference in its entirety.

Figure 113:
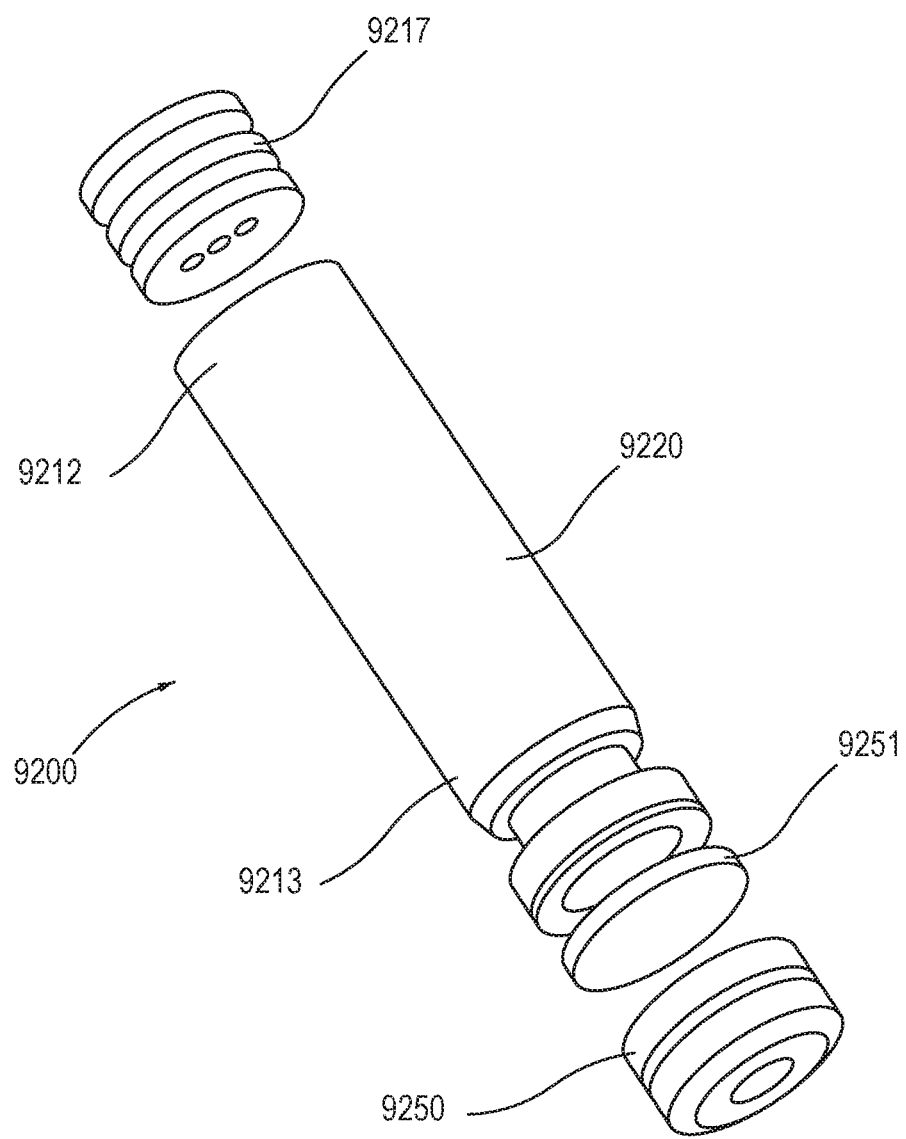
FIG. 113 is an exploded view of a medicament container of the medical injector illustrated in FIG. 102.
Figure 114:
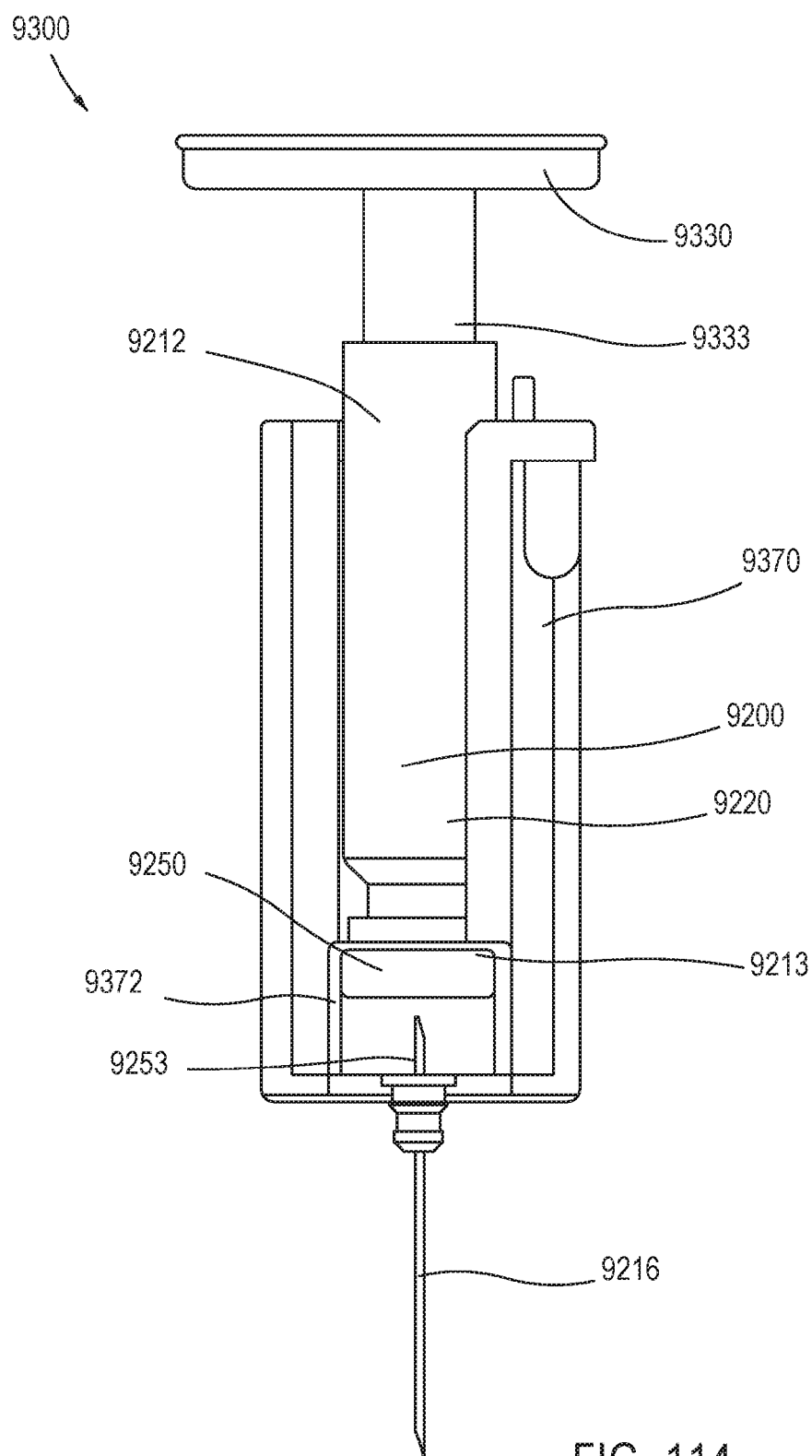
FIG. 114 is a front view of a portion of the medical injector illustrated in FIG. 102.
Figure 115:
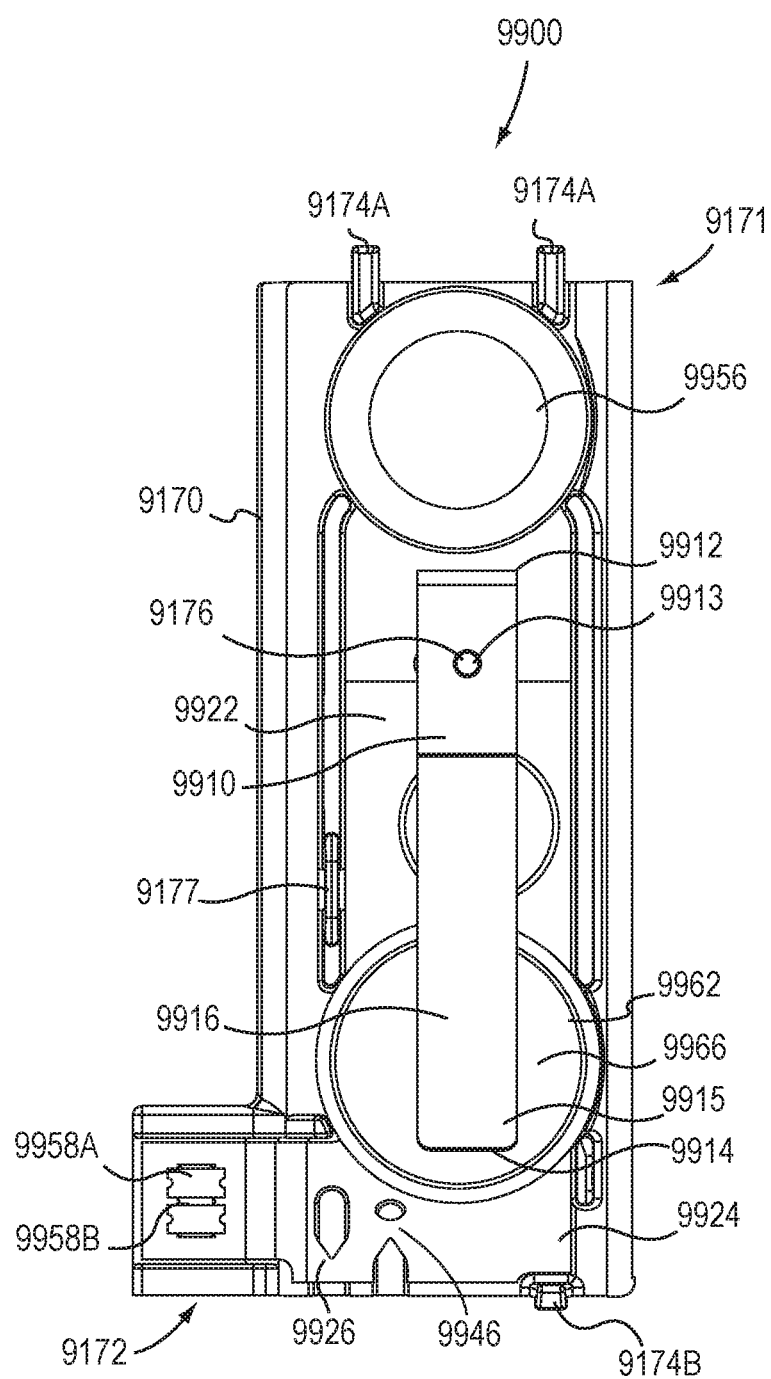
FIG. 115 is a back view of an electronic circuit system of the medical injector illustrated in FIG. 102.
Figure 116:
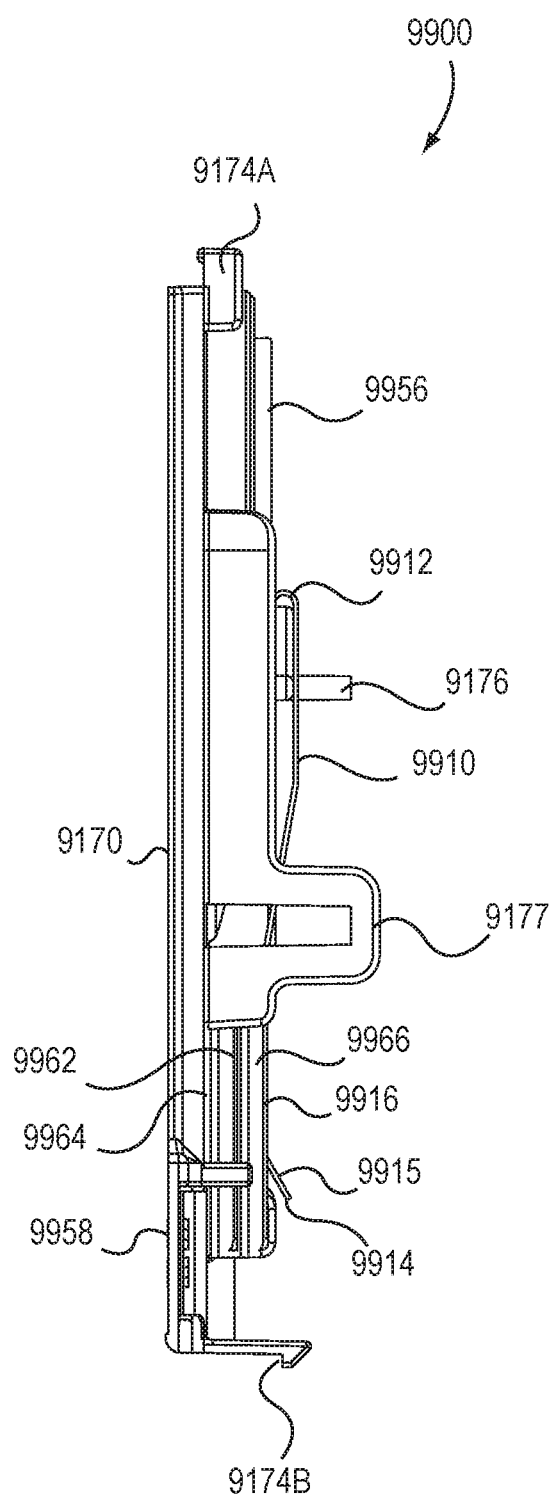
FIG. 116 is a side view of the electronic circuit system of the medical injector illustrated in FIG. 115.
Figure 117:
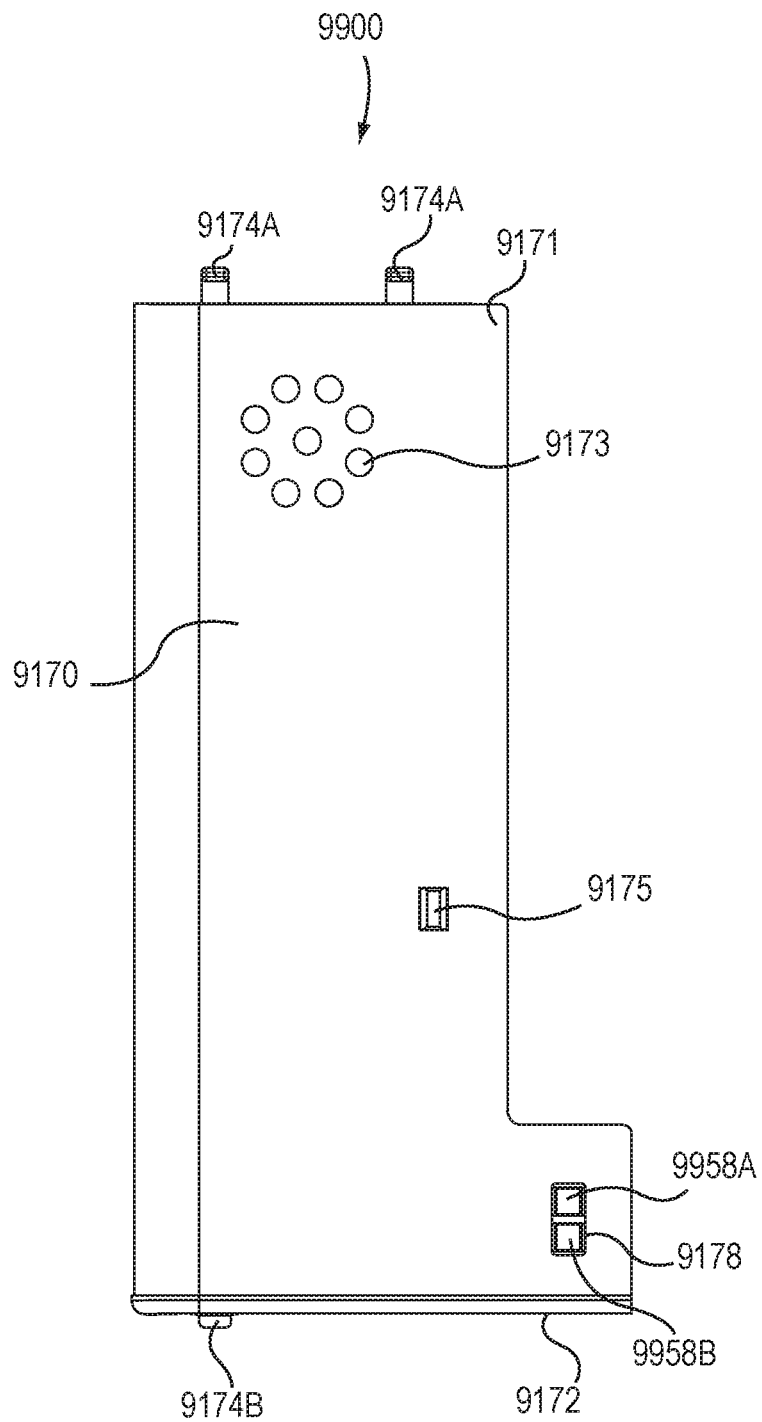
FIG. 117 is a front view of an electronic circuit system housing of the electronic circuit system illustrated in FIG. 115.
Figure 118:
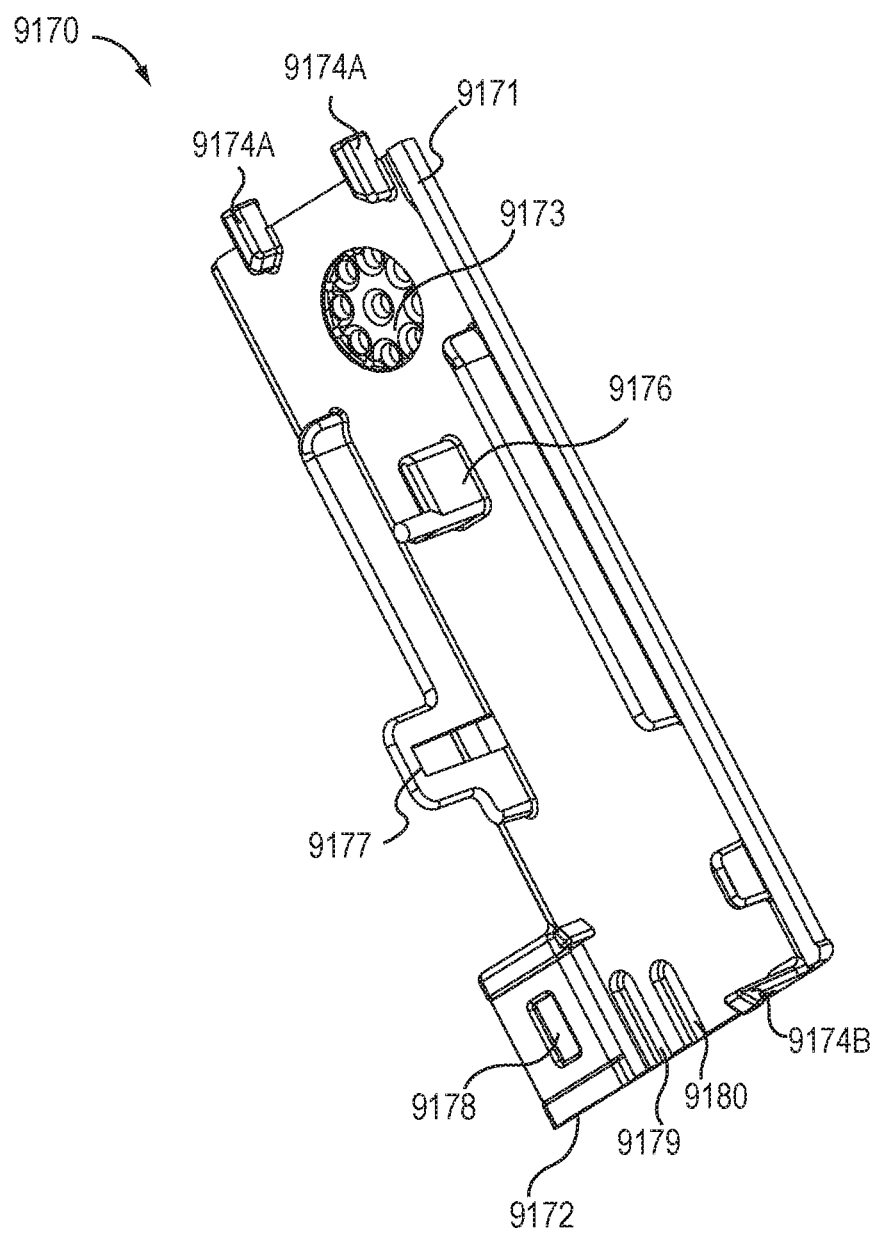
FIG. 118 is a perspective view of the electronic circuit system housing of the electronic circuit system illustrated in FIG. 117.

The medicament container 9200 of the medicament delivery mechanism 9300 has a distal end portion 9213 and a proximal end portion 9212, and contains (i.e., is filled with or partially filled with) a naloxone composition 9220 (see, e.g., FIG. 113). The distal end portion 9213 of the medicament container 9200 contains a seal 9250. The seal 9250, which can be, for example, an 8-I crimp seal, is configured to burst when punctured by the proximal end 9253 of the needle 9216, as described below. The proximal end portion 9212 of the medicament container 9200 includes an elastomeric member 9217, and is configured to receive a piston rod 9333 of the piston 9330. Although the medicament container 9200 is shown in FIG. 113 as including a liner 9251, in other embodiments, the medicament container 9200 need not include the liner 9251.

The medicament container 9200 can have any suitable size (e.g., length and/or diameter) and can contain any suitable volume of the naloxone composition 9220. Moreover, the medicament container 9200 and the piston 9330 can be collectively configured such that the piston 9330 travels a desired distance within the medicament container 9200 (i.e., the "stroke") during an injection event. In this manner, the medicament container 9200, the volume of the naloxone composition 9220 within the medicament container 9200 and the piston 9330 can be collectively configured to provide a desired fill volume and delivery volume. In some embodiments, for example, the size of the medicament container 9200 and the length of the piston 9330 can be such that the fill volume of the naloxone composition 9220 is approximately 0.76 ml and the delivery volume of the naloxone composition 9220 is approximately 0.30 ml (providing a delivery volume to fill volume ratio of approximately 0.4). In other embodiments, for example, the size of the medicament container 9200 and the length of the piston 9330 can be such that the fill volume of the naloxone composition 9220 is approximately 0.66 ml and the delivery volume of the naloxone composition 9220 is approximately 0.40 ml (providing a delivery volume to fill volume ratio of approximately 0.6).

Moreover, the length of the medicament container 9200 and the length of the piston 9330 can be configured such that the medicament delivery mechanism 9300 can fit in the same housing 9100 regardless of the fill volume, the delivery volume and/or the ratio of the fill volume to the delivery volume. In this manner, the same housing and production tooling can be used to produce devices having various dosages of the naloxone composition. For example, in a first embodiment (e.g., having a fill volume to delivery volume ratio of 0.4), the medicament container has a first length and the movable member has a first length. In a second embodiment (e.g., having a fill volume to delivery volume ratio of 0.6), the medicament container has a second length shorter than the first length, and the movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

The naloxone composition 9220 contained within the medicament container 9200 can be any of the naloxone compositions described herein. In particular, the naloxone composition 9220 can include an effective amount of naloxone or salts thereof, a tonicity-adjusting agent, and a pH-adjusting agent. The naloxone composition 9220 can be formulated such that the osmolality of the naloxone composition 9220 ranges from about 250-350 mOsm and the pH ranges from about 3-5.

In some embodiments, the naloxone composition 9220 can include any suitable concentration of 4,5-epoxy-3,14-dihydroxy-17-(2-propenyl) morphinan-6-one. In some embodiments, for example, the naloxone composition 9220 has a concentration of 4,5-epoxy-3,14-dihydroxy-17-(2-propenyl)morphinan-6-one between approximately 0.01 mg/mL and approximately 10 mg/mL. In other embodiments, the naloxone composition 9220 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 9220 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH-adjusting agent can be any of the pH-adjusting agents described herein, and can be included within the naloxone composition 9220 in any suitable amount and/or concentration. For example, in some embodiments, the pH-adjusting agent includes at least one of hydrochloric acid, citric acid, citrate salts, acetic acid, acetate salts, phosphoric acid or phosphate salts. In other embodiments, the pH-adjusting agent includes a dilute hydrochloric acid.

The elastomeric member 9217 can be of any design or formulation suitable for contact with the naloxone composition 9220. For example, the elastomeric member 9217 can be formulated to minimize any reduction in the efficacy of the naloxone composition 9220 that may result from contact (either direct or indirect) between the elastomeric member 9217 and the naloxone composition 9220. For example, in some embodiments, the elastomeric member 9217 can be formulated to minimize any leaching or out-gassing of compositions that may have an undesired effect on the naloxone composition 9220. In other embodiments, the elastomeric member 9217 can be formulated to maintain its chemical stability, flexibility and/or sealing properties when in contact (either direct or indirect) with naloxone over a long period of time (e.g., for up to six months, one year, two years, five years or longer).

In some embodiments, the elastomeric member 9217 can be formulated to include a polymer and a curing agent. In such embodiments, the polymer can include at least one of bromobutyl or chlorobutyl. In such embodiments, the curing agent can include at least one of sulfur, zinc or magnesium.

In some embodiments, the elastomeric member 9217 can be constructed from multiple different materials. For example, in some embodiments, at least a portion of the elastomeric member 9217 can be coated. Such coatings can include, for example, polydimethylsiloxane. In some embodiments, at least a portion of the elastomeric member 9217 can be coated with polydimethylsiloxane in an amount of between approximately 0.02 mg/cm$^2$ and approximately 0.80 mg/cm$^2$.

As shown in FIG. 110, the system actuator 9500 includes the base 9510, a release member 9550 and a spring 9576. FIG. 111 shows certain of the internal components of the medical injector 9000 without the base 9510 and the spring 9576 so that the release member 9550 can be more clearly shown.

The release member 9550 has a proximal end portion 9551 and a distal end portion 9552, and is movably disposed within the distal end portion 9153 of the gas cavity 9151. The proximal end portion 9551 of the release member 9550 includes a sealing member 9574 and a puncturer 9575. The sealing member 9574 is configured to engage the sidewall of the housing 9100 defining the gas cavity 9151 such that the proximal end portion 9152 of the gas cavity 9151 is fluidically isolated from the distal end portion 9153 of the gas cavity 9151. In this manner, when gas is released from the gas container 9410, the gas contained in the proximal end portion 9152 of the gas cavity 9151 is unable to enter the distal end portion 9153 of the gas cavity 9151. The puncturer 9575 of the proximal end portion 9551 of the release member 9550 is configured to contact and puncture a frangible seal 9411 on the gas container 9410 when the release member 9550 moves proximally within the gas cavity 9151, as shown by the arrow TT in FIG. 111.

The distal end portion 9552 of the release member 9550 includes extensions 9553. The extensions 9553 include projections 9555 that include tapered surfaces 9557 and engagement surfaces 9554. Further, the extensions 9553 define an opening 9556 between the extensions 9553. The engagement surfaces 9554 of the projections 9555 are configured to extend through the release member aperture 9154 of the housing 9100 and contact a distal surface of the housing 9100, as shown in FIG. 112. In this manner, the engagement surfaces 9554 of the projections 9555 limit proximal movement of the release member 9550 when the engagement surfaces 9554 are in contact with the distal surface of the housing 9100.

Figure 121:
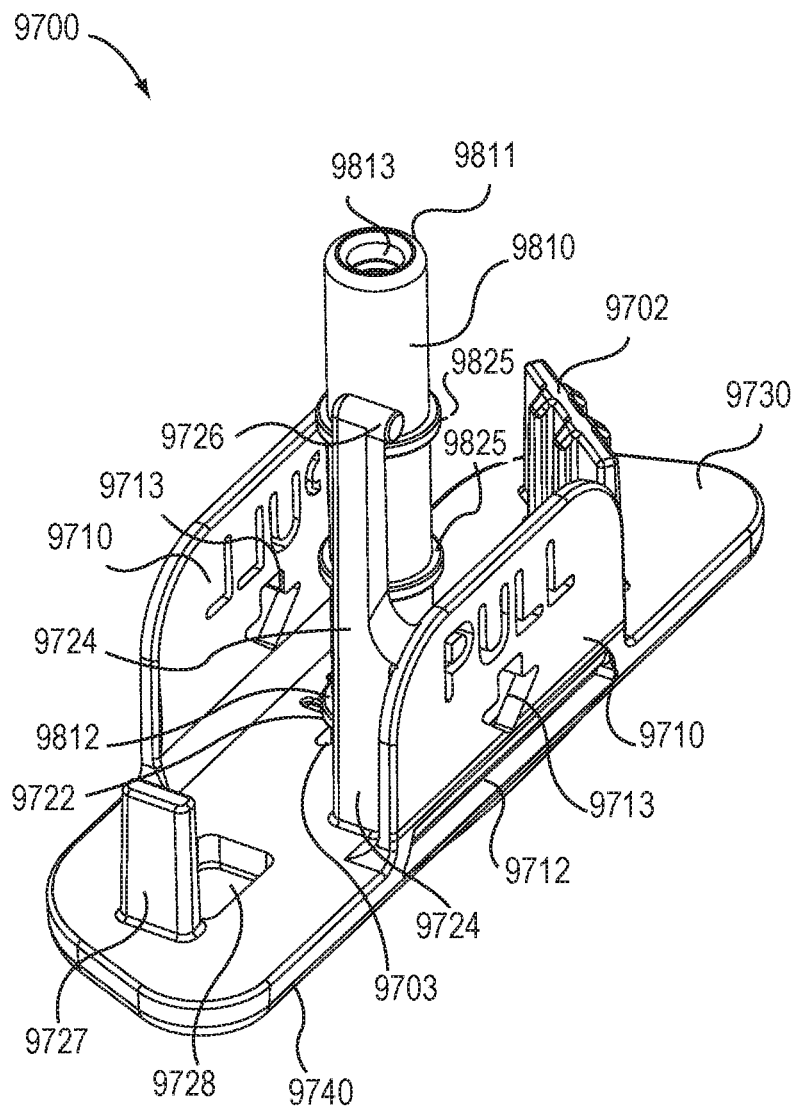
FIG. 121 is a perspective view of a safety lock of the medical injector illustrated in FIG. 102.

The opening 9556 defined by the extensions 9553 is configured to receive the safety lock protrusion 9702 of the safety lock 9700 (see e.g., FIGS. 112 and 121). The safety lock protrusion 9702 is configured to prevent the extensions 9553 from moving closer to each other. Said another way, the safety lock protrusion 9702 is configured to ensure that the extensions 9553 remain apart and the engagement surfaces 9554 of the projections 9555 remain in contact with the distal end portion 9102 of the housing 9100. In some embodiments, for example, the release member 9550 and/or the extensions 9553 can be constructed from any suitable material configured to withstand deformation that may occur when exposed to a load over an extended period of time. In some embodiments, for example, the release member 9550 and/or the extensions 9553 can be constructed from brass.

The tapered surfaces 9557 of the projections 9555 are configured to contact protrusions 9515 on a proximal surface 9511 of the base 9510 (see e.g., FIG. 124) when the base 9510 is moved proximally relative to the housing 9100. Accordingly, when the base 9510 is moved proximally relative to the housing 9100, the extensions 9553 are moved together by the contact protrusions 9515. The inward movement of the extensions 9553 causes the release member 9550 to become disengaged from the distal end portion of the housing 9100, thereby allowing the release member 9550 to be moved proximally along its longitudinal axis as the spring 9576 expands.

The medicament delivery mechanism 9300 includes a gas container 9410, a carrier 9370, a piston 9330, and a retraction spring 9351. As described above, the carrier 9370 and the piston 9330 are disposed within the medicament cavity 9139 of the housing 9100. The gas container 9410 is disposed within the gas cavity 9151 of the housing 9100.

The gas container 9410 includes a distal end portion 9413 and a proximal end portion 9412, and is configured to contain a pressurized gas. The distal end portion 9413 of the gas container 9410 contains a frangible seal 9411 configured to break when the puncturer 9575 of the proximal end portion 9551 of the release member 9550 contacts the frangible seal 9411. The gas container retention member 9580 of the proximal cap 9103 of the housing 9100 is configured to receive and/or retain the proximal end portion 9412 of the gas container 9410. Said another way, the position of the gas container 9410 within the gas cavity 9151 is maintained by the gas container retention member 9580.

The piston 9330 of the medicament delivery mechanism 9300 is movably disposed within the medicament cavity 9139. The piston 9330 includes a piston rod 9333 having a plunger at the distal end portion of the piston rod 9333. The piston rod 9333 is configured to move within the medicament container 9200. In this manner, the piston rod 9333 of the piston 9330 can apply a force to the elastomeric member 9217 to convey the naloxone composition 9220 contained in the medicament container 9200. The piston rod 9333 can be constructed of a resilient, durable, and/or sealing material, such as a rubber.

The carrier 9370 of the medicament delivery mechanism 9300 includes a distal end portion 9372 and a proximal end portion 9371. The medicament container 9200 is coupled to the carrier 9370 via a "snap-fit" connection (not shown) such that the medicament container 9200 can move relative to the carrier 9370 between a first configuration and a second configuration during an injection event. In the first configuration, the carrier 9370 is configured to move within the medicament cavity 9139 such that movement of the carrier 9370 within the medicament cavity 9139 causes contemporaneous movement of the medicament container 9200 within the medicament cavity 9139. The proximal end portion 9253 of the needle 9216 is spaced apart from the seal 9250 of the medicament container 9200 when the carrier 9370 and the medicament container 9200 are collectively in the first configuration (e.g., during needle insertion). When the carrier 9370 and the medicament container 9200 are moved to the second configuration, the medicament container 9200 releases from the "snap-fit" causing the medicament container 9200 to move distally with respect to the carrier 9370, causing the proximal end portion 9253 of the needle 9216 to pierce the seal 9250. In this manner, the needle 9216 can be selectively placed in fluid communication with the medicament container 9200 to define a medicament delivery path (not shown).

Figure 130:
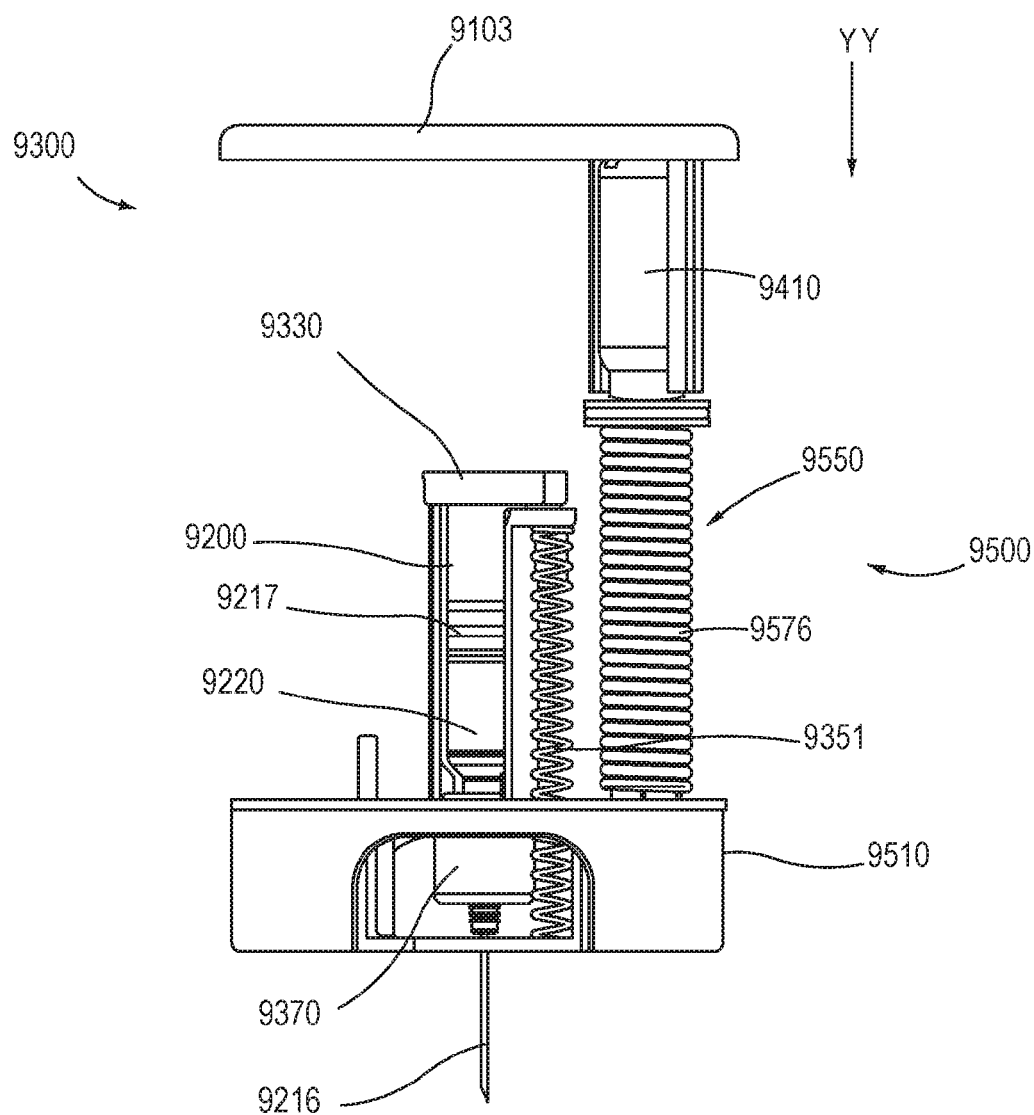
FIG. 130 is a front view of the medical injector illustrated in FIG. 102 in a fifth configuration (i.e., the injection configuration).

As shown in FIGS. 110, 111 and 130, the proximal end portion 9371 of the carrier 9370 includes a gas valve actuator 9380. The gas valve actuator 9380 is configured to engage a gas relief valve (not shown) of the piston 9330 to allow the pressurized gas contained within the gas chamber (i.e., the volume within the medicament cavity 9139 between the proximal end of the housing 9100 and the proximal end of the piston 9330) to escape when the injection event is complete. Thus, after the gas pressure within the medicament cavity 9139 decreases below a certain level, the force exerted by the retraction spring 9351 on the carrier 9370 can be sufficient to cause the carrier 9370 to move proximally within the housing 9100 (i.e., to retract). In addition, this arrangement results in there being substantially no residual force within the housing, which decreases stress on the components after the injection event.

FIGS. 115-118 show the electronic circuit system 9900. The electronic circuit system 9900 of the medical injector 9000 includes an electronic circuit system housing 9170, a printed circuit board 9922, a battery assembly 9962, an audio output device 9956, two light emitting diodes (LEDs) 9958A, 9958B and a battery clip 9910. The electronic circuit system 9900 is configured to fit within the electronic circuit system cavity 9137 of the housing 9100. Accordingly, as described above, the electronic circuit system 9900 is physically and/or fluidically isolated from the medicament cavity 9139, the gas cavity 9151 and/or the medicament delivery device 9300. As described herein, the electronic circuit system 9900 is configured to output an electronic output associated with the use of the medical injector 9000. Portions of the electronic circuit system 9900 are substantially similar to or the same as corresponding portions of the electronic circuit system 3900 included in the delivery device 3000 of FIGS. 9-59. Thus, similar portions are not described in further detail herein.

The electronic circuit system housing 9170 of the electronic circuit system 9900 includes a distal end portion 9172 and a proximal end portion 9171. The proximal end portion 9171 includes connection protrusions 9174A and a battery clip protrusion 9176. The connection protrusions 9174A extend from the proximal end portion 9171 of the electronic circuit system housing 9170, and are configured to be disposed within the connection apertures 9182 of the housing 9100, as described above. In this manner, the electronic circuit system 9900 can be coupled to the housing 9100 within the electronic circuit system cavity 9137. In other embodiments, the electronic circuit system 9900 can be coupled to the housing 9100 by other suitable means such as an adhesive, a clip, a label and/or the like. As described in more detail herein, the battery clip protrusion 9176 is configured to hold the battery clip 9910 in place.

As shown in FIGS. 115-118, the distal end portion 9172 of the electronic circuit system housing 9170 includes a connection protrusion 9174B, a stiffening protrusion 9177, and defines an LED aperture 9178, an aperture 9175, a safety lock actuator groove 9179, and a base actuator groove 9180. The LED aperture 9178 is configured to receive the LEDs 9958A, 9958B such that a user can view the LEDs 9958A, 9958B, which are described in more detail herein.

The connection protrusion 9174B extends from the distal end portion 9172 of the electronic circuit system housing 9170, and is configured to attach the electronic circuit system 9900 to the housing 9100, as described above. The stiffening protrusion 9177 is configured to have at least a portion received within and/or accessible via the aperture 9129 in the housing 9100 (see e.g., FIG. 105). The stiffening protrusion 9177 is configured to limit the bending (e.g., buckling) of the electronic circuit system housing 9170 when the electronic circuit system housing 9170 is coupled to the housing 9100. Moreover, a user can access the stiffening protrusion 9177 via the aperture 9175. In this manner, for example, the user can disengage the stiffening protrusion 9177 from the aperture 9129.

The safety lock actuator groove 9179 of the electronic circuit system housing 9170 is configured to be disposed adjacent the safety lock actuator groove 9133 of the distal end portion 9102 of the housing 9100. In this manner, the safety lock actuator groove 9179 of the electronic circuit system housing 9170 and the safety lock actuator groove 9133 of the distal end portion 9102 of the housing 9100 collectively receive the actuator 9724 of the safety lock 9700, which is described in more detail herein. Similarly, the base actuator groove 9180 of the electronic circuit system housing 9170 is configured to be disposed about the base actuator groove 9132 of the distal end portion 9102 of the housing 9100. The base actuator groove 9180 of the electronic circuit system housing 9170 and the base actuator groove 9132 of the distal end portion 9102 of the housing 9100 collectively receive the actuator 9520 of the base 9510, which is described in more detail herein.

The printed circuit board 9922 of the electronic circuit system 9900 includes a substrate 9924, a first actuation portion 9926 and a second actuation portion 9946. The substrate 9924 of the printed circuit board 9922 includes the electrical components necessary for the electronic circuit system 9900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board). The printed circuit board 9922 (including the first actuation portion 9926 and the second actuation portion 9946), the battery assembly 9962, and the audio output device 9956 are substantially similar in form and function as the printed circuit board 3922, the battery assembly 3962, and the audio output device 3956, respectively, included in the electronic circuit system 3900 of FIGS. 29-39. Therefore, the printed circuit board 992 and the battery assembly 9962 are not described in further detail herein.

The battery clip 9910 (shown in FIG. 115) includes a proximal end portion 9912 and a distal end portion 9914. The proximal end portion 9912 defines a retention aperture 9913. The retention aperture 9913 is configured to receive the battery clip protrusion 9176 of the electronic circuit system housing 9170. In this manner, the battery clip protrusion 9176 maintains the position of the battery clip 9910 with respect to the electronic circuit system housing 9170 and/or the battery assembly 9962.

The distal end portion 9914 of the battery clip 9910 includes a contact portion 9916 and an angled portion 9915. As described above, the contact portion 9916 is configured to contact the second surface 9966 of the battery assembly 9962 to place the battery assembly 9962 in electrical communication with the electronic circuit system 9900. The angled portion 9915 of the distal end portion 9914 of the battery clip 9910 is configured to allow a proximal end portion 9198 of a battery isolation protrusion 9197 (see e.g., FIG. 120) to be disposed between the second surface 9966 of the battery assembly 9962 and the contact portion 9916 of the distal end portion 9914 of the battery clip 9910. When the battery isolation protrusion 9197 is disposed between the second surface 9966 of the battery assembly 9962 and the contact portion 9916 of the distal end portion 9914 of the battery clip 9910, the electrical path between the battery assembly 9962 and the remainder of the electronic circuit system 9900 is severed, thereby removing power from the electronic circuit system 9900. The contact portion 9916 of the distal end portion 9914 of the battery clip 9910 is biased such that when the battery isolation protrusion 9197 is removed, the contact portion 9916 will move into contact the second surface 9966 of the battery assembly 9962, thereby restoring electrical communication between the battery assembly 9962 and the electronic circuit system 9900, as described above.

Figure 120:
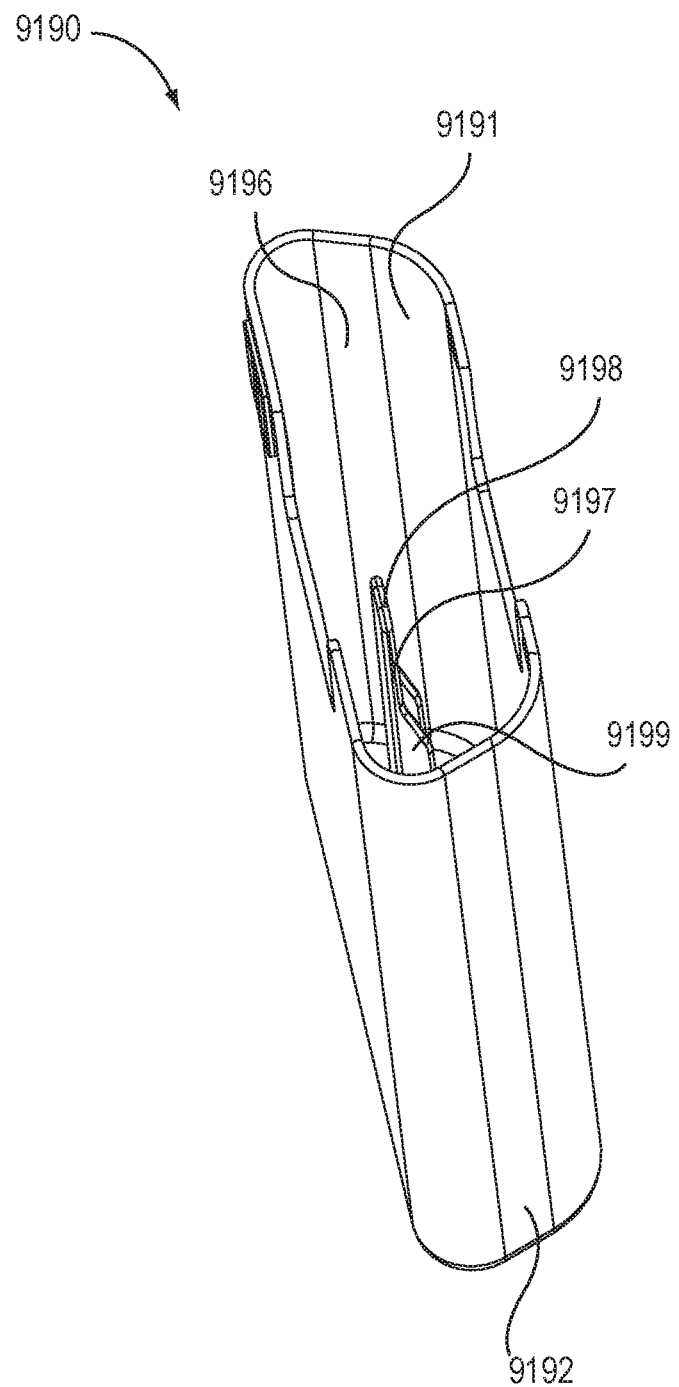

FIGS. 120 and 121 show the cover 9190 of the medical injector 9000. The cover 9190 includes a proximal end portion 9191 and a distal end portion 9192, and defines a cavity 9196. The cavity 9196 of the cover 9190 is configured to receive at least a portion of the housing 9100. Thus, when the portion of the housing 9100 is disposed within the cover 9190, the cover 9190 blocks an optical pathway between the medicament container 9200 and a region outside of the housing 9100. Similarly stated, when the portion of the housing 9100 is disposed within the cover 9190, the cover 9190 is obstructs the first status indicator aperture 9130 and/or the second status indicator aperture 9160 of the housing 9100 to reduce the amount of light transmitted to the naloxone composition 9220 within the medicament container 9200. In this manner, the life of the naloxone composition 9220 can extended by the prevention and/or reduction of degradation to the naloxone that may be caused by ultra-violet radiation.

The proximal end portion 9191 of the cover 9190 defines apertures 9193 configured to receive the cover retention protrusions 9104 of the housing 9100 (shown in FIGS. 103 and 105). In this manner, the apertures 9193 and the cover retention protrusions 9104 of the housing 9100 removably retain the cover 9190 about at least a portion of the housing 9100. Said another way, the apertures 9193 and the cover retention protrusions 9104 of the housing 9100 are configured such that the cover 9190 can be removed from a portion of the housing 9100 and then replaced about the portion of the housing 9100.

As described above, the electronic circuit system 9900 can be actuated when the housing 9100 is at least partially removed from the cover 9190. More particularly, the distal end portion 9192 of the cover 9190 includes a battery isolation protrusion 9197. The battery isolation protrusion 9197 includes a proximal end portion 9198 and a tapered portion 9199. The proximal end portion 9198 of the battery isolation protrusion 9197 is configured to be removably disposed between the second surface 9966 of the battery assembly 9962 and the contact portion 9916 of the distal end portion 9914 of the battery clip 9910, as described above.

Figure 122:
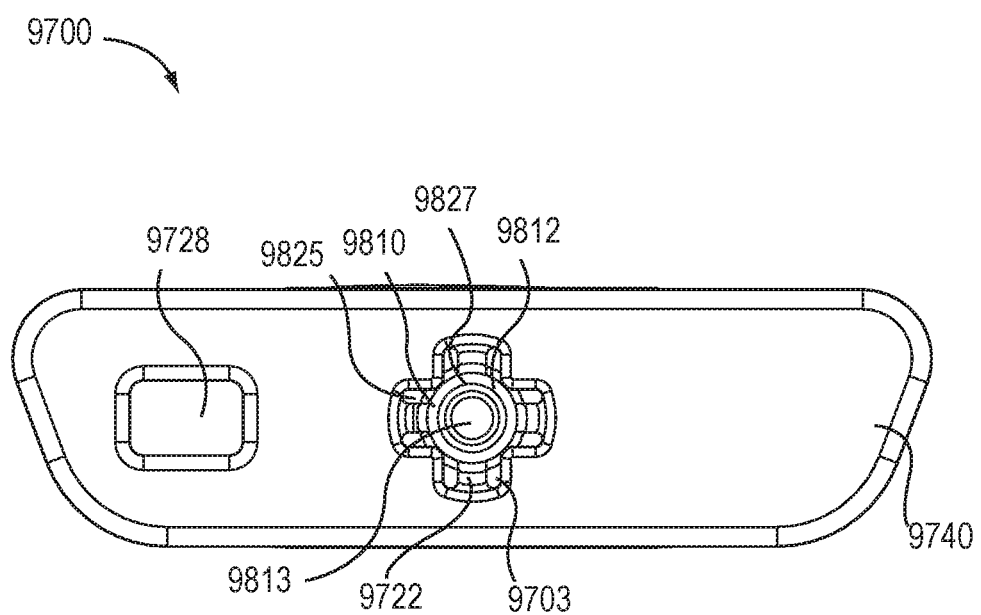
FIG. 122 is a bottom view of the safety lock of the medical injector illustrated in FIG. 121.
Figure 123:
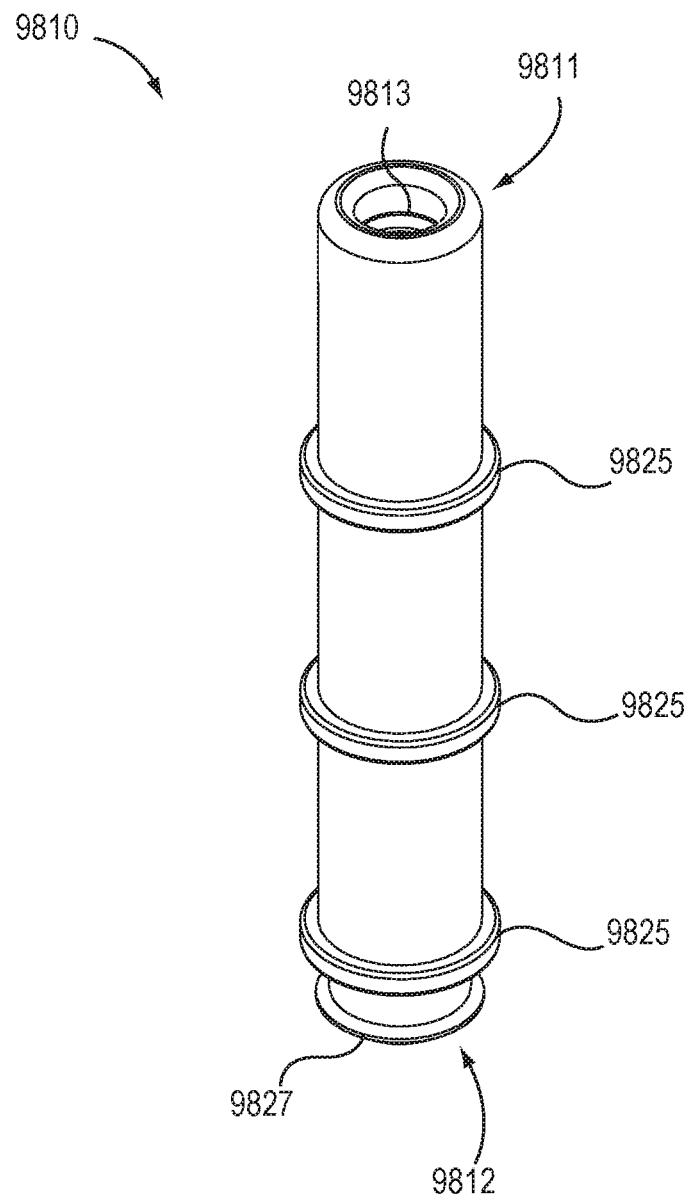
FIG. 123 is a perspective view of a needle sheath of the safety lock of the medical injector illustrated in FIG. 121.

FIGS. 121-123 show the safety lock 9700 of the medical injector 9000. The safety lock 9700 of the medical injector 9000 includes a proximal surface 9730, a distal surface 9740 opposite the proximal surface 9730 and a needle sheath 9810. The safety lock 9700 defines a needle sheath aperture 9703 and a battery isolation protrusion aperture 9728. The battery isolation protrusion aperture 9728 is configured to receive the battery isolation protrusion 9197 of the cover 9190 such that the battery isolation protrusion 9197 can be disposed within the electronic circuit system cavity 9137 or the electronic circuit system 9900, as described above. Similarly stated, the battery isolation protrusion aperture 9728 of the safety lock 9700 is aligned with the battery isolation protrusion aperture 9728 of the housing 9100, such that the battery isolation protrusion 9197 can be disposed within the electronic circuit system cavity 9137 when the cover 9190 is disposed about a portion of the housing 9100.

The proximal surface 9730 of the safety lock 9700 includes a safety lock protrusion 9702, a stopper 9727, an actuator 9724 and two opposing pull tabs 9710. As described above, when the safety lock 9700 is in a first (locked) position, the safety lock protrusion 9702 is configured to be disposed in the opening 9556 defined by the extensions 9553 of the distal end portion 9552 of the release member 9550 (see also FIG. 112). Accordingly, the safety lock protrusion 9702 is configured to prevent the extensions 9553 from moving closer to each other, thereby preventing proximal movement of the release member 9550 of the medicament delivery mechanism 9300 and/or delivery of the naloxone composition 9220. The stopper 9727 of the safety lock 9700 is a protrusion extending from the proximal surface 9730 of the safety lock 9700. The stopper 9727 is configured to contact a portion of the housing 9100 to limit the proximal movement of the safety lock 9700 relative to the housing 9100. In other embodiments, the stopper 9727 can be any structure configured to limit the proximal movement of the safety lock 9700.

The actuator 9724 of the safety lock 9700 has an elongated portion 9725 and a protrusion 9726. The elongated portion 9725 extends in a proximal direction from the proximal surface 9730. In this manner, the elongated portion 9725 can extend through a safety lock actuator opening 9524 of the base 9510 (see e.g., FIG. 35) and within the safety lock actuator groove 9133 of the housing 9100 and the safety lock actuator groove 9179 of the electronic circuit system housing 9170. The protrusion 9726 extends in a direction substantially transverse to the elongated portion 9725 and/or substantially parallel to the proximal surface 9730 of the safety lock 9700. As described above, the first actuation portion 9926 is configured to receive the protrusion 9726 of the actuator 9724 of the safety lock 9700.

The pull tabs 9710 of the safety lock 9700 include a grip portion 9712 and indicia 9741. The grip portion 9712 of the pull tabs 9710 provides an area for the user to grip and/or remove the safety lock 9700 from the rest of the medicament delivery system 9000. The indicia 9741 provides instruction on how to remove the safety lock 9700. In some embodiments, for example, the indicia 9741 can indicate the direction the user should pull the safety lock 9700 to remove the safety lock 9700.

As shown in FIGS. 122 and 123, the needle sheath 9810 of the safety lock 9700 includes a distal end portion 9811, a proximal end portion 9812 and a plurality of ribs 9825. The needle sheath 9810 can also define a lumen 9813. The lumen 9813 of the safety lock 9700 is configured to receive the needle 9216. In this manner, the needle sheath 9810 can protect the user from the needle 9216 and/or can keep the needle 9216 sterile before the user actuates the medical injector 9000. The proximal end portion 9812 of the needle sheath is configured to contact the distal end portion 9372 of the carrier 9370 of the medicament delivery mechanism 9300.

The distal end portion 9811 of the needle sheath 9810 has an angled ridge 9827. The angled ridge 9827 is configured to allow the proximal end portion 9812 of the needle sheath 9810 to irreversibly move through the needle sheath aperture 9703 of the safety lock 9700 in a distal direction. Said another way, the angled ridge 9827 can be configured in such a way as to allow the proximal end portion 9812 of the needle sheath 9810 to move through the needle sheath aperture 9703 in a distal direction, but not in a proximal direction. The needle sheath aperture 9703 has retaining tabs 9722 configured to engage the proximal end of the angled ridge 9827 when the needle sheath 9810 is moved in a proximal direction. In this manner, the retaining tabs 9722 prevent the proximal movement of the needle sheath with respect to the safety lock 9700. Further, the retaining tabs 9722 are configured to engage the proximal end of the angled ridge 9827 when the safety lock 9700 is moved in a distal direction. Said another way, the needle sheath 9810 is removed from the needle 9216 when the safety lock 9700 is moved in a distal direction with respect to the housing 9100.

Figure 124:
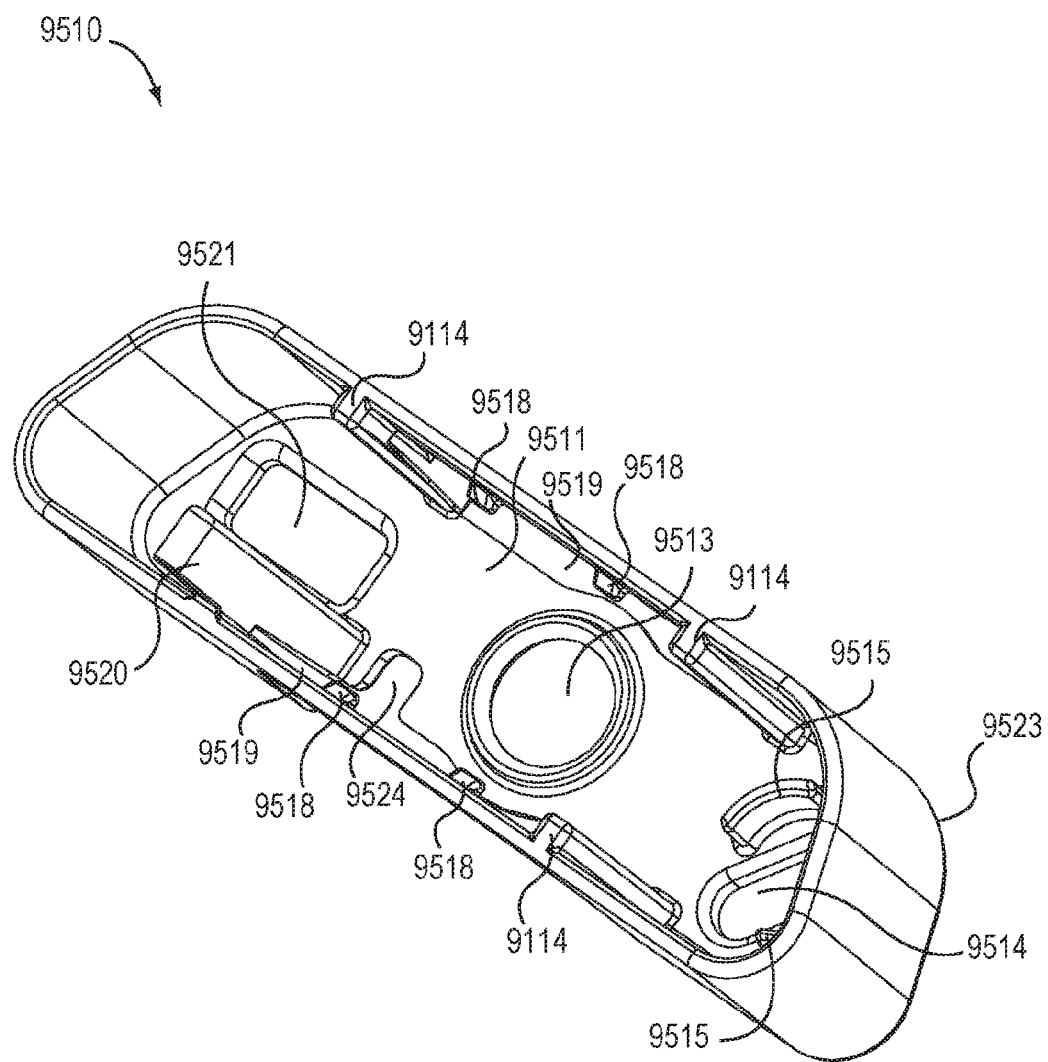
FIG. 124 is a perspective view of a base of the medical injector illustrated in FIG. 102.
Figure 125:
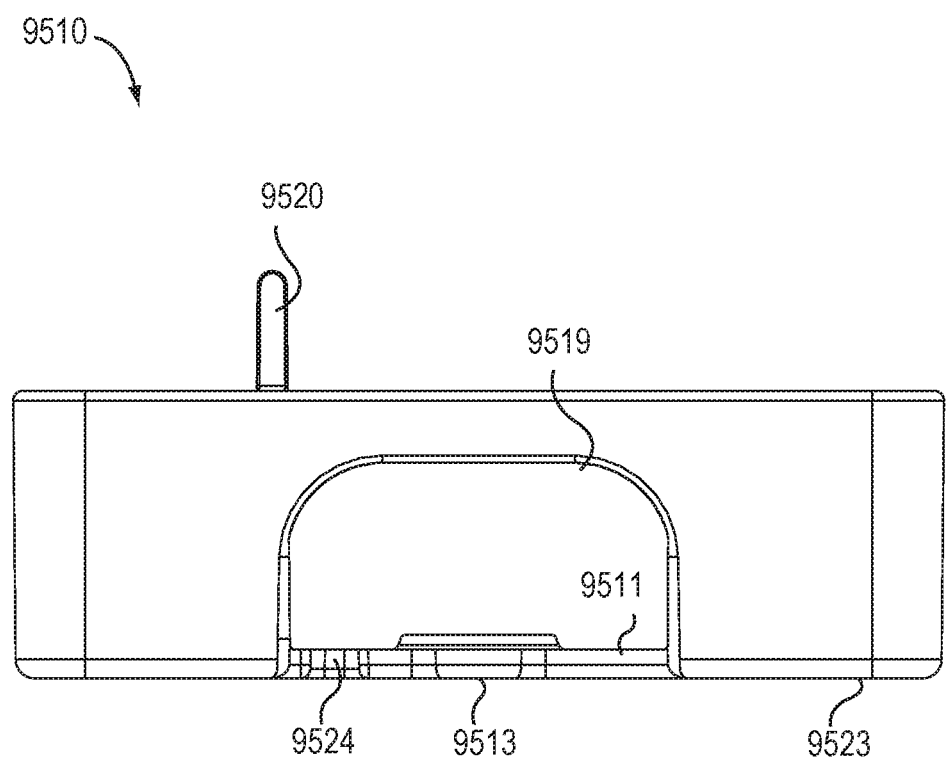
FIG. 125 is a front view of the base of the medical injector illustrated in FIG. 102.

FIGS. 124 and 125 show the base 9510 of the medical injector 9000. The base 9510 includes a proximal surface 9511, a distal surface 9523 and base connection knobs 9518. The base 9510 defines a needle aperture 9513, a safety lock protrusion aperture 9514, a battery isolation protrusion aperture 9521, a safety lock actuator opening 9524, and pull tab openings 9519. The needle aperture 9513 is configured to receive the needle 9216 when the medical injector 9000 is actuated. The safety lock protrusion aperture 9514 of the base 9510 receives the safety lock protrusion 9702 of the safety lock 9700. The battery isolation protrusion aperture 9521 of the base 9510 receives the battery isolation protrusion 9197 of the cover 9190 and the stopper 9727 of the safety lock 9700. The safety lock actuator opening 9524 receives the safety lock actuator 9724 of the safety lock 9700. The pull tab openings 9519 are configured to receive the pull tabs 9710 of the safety lock 9700.

The proximal surface 9511 of the base 9510 includes an actuator 9520, guide members 9517, and protrusions 9515. The actuator 9520 is an elongate member configured to engage the substrate 9924 of the electronic circuit system 9900. As described above, the opening 9945 of the second actuation portion 9946 is configured to receive the actuator 9520 of the base 9510. The guide members 9517 of the base 9510 are configured to engage and/or slide within the base rail grooves 9114 of the housing 9100, as described above. The protrusions 9515 of the base 9510 are configured to engage the tapered surfaces 9557 of the extensions 9553 of the release member 9550. As described in further detail herein, when the safety lock 9700 is removed and the base 9510 is moved in a proximal direction with respect to the housing 9100, the protrusion 9515 of the base 9510 are configured to move the extensions 9553 of the release member 9550 closer to each other, actuating the medicament delivery mechanism 9300. As described above, the base connection knobs 9518 are configured to engage the base retention recesses 9134A, 9134B in a way that allows proximal movement of the base 9510 but limits distal movement of the base 9510.

Figure 126:
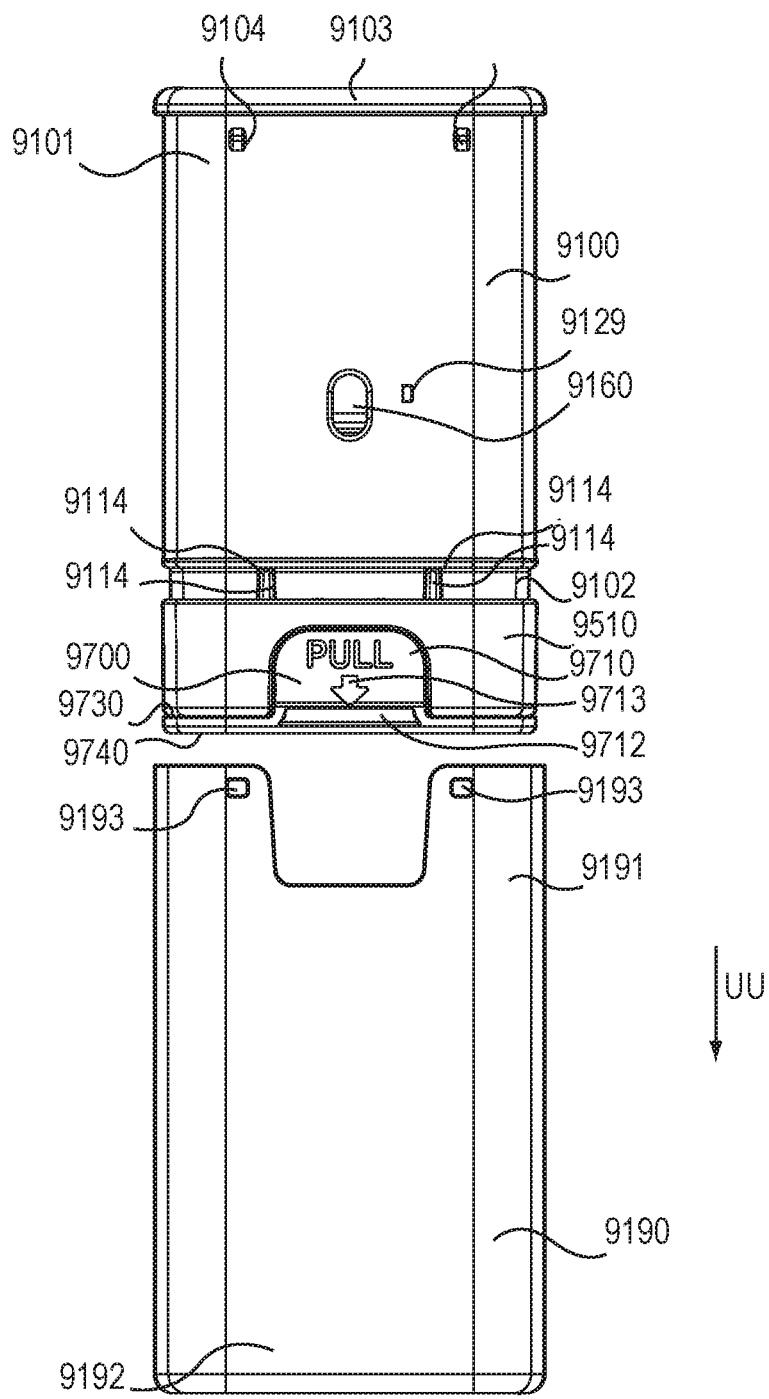
FIG. 126 is a back view of the medical injector illustrated in FIG. 102 in a second configuration.

As shown in FIG. 126, the medical injector 9000 is first enabled by moving the medicament delivery device 9000 from a first configuration to a second configuration by moving the cover 9190 from a first position to a second position. The cover 9190 is moved from the first position to the second position by moving it with respect to the housing 9100 in the direction shown by the arrow UU in FIG. 126. When the cover 9190 is moved with respect to the housing 9100 in the direction UU, the battery isolation protrusion 9197 is removed from the area between the battery clip 9910 and the second surface 9966 of the battery assembly 9962. In this manner, the battery assembly 9962 can be operatively coupled to the electronic circuit system 9900 when the cover 9190 is removed, thereby providing power to the electronic circuit system 9900. Similarly stated, this arrangement allows the electronic circuit system 9900 to be actuated when the cover 9190 is removed.

When power is provided, as described above, the electronic circuit system 9900 can output one or more predetermined electronic outputs. For example, in some embodiments, the electronic circuit system 9900 can output an electronic signal associated with recorded speech to the audible output device 9956. Such an electronic signal can be, for example, associated with a .WAV file that contains a recorded instruction instructing the user in the operation of the medical injector 9000. Such an instruction can state, for example, "remove the safety tab near the base of the auto-injector." The electronic circuit system 9900 can simultaneously output an electronic signal to one and/or both of the LEDs 9958A, 9958B thereby causing one and/or both of the LEDs 9958A, 9958B to flash a particular color. In this manner, the electronic circuit system 9900 can provide both audible and visual instructions to assist the user in the initial operation of the medical injector 9000.

In other embodiments, the electronic circuit system 9900 can output an electronic output associated with a description and/or status of the medical injector 9000 and/or the naloxone composition 9220 contained therein. For example, in some embodiments, the electronic circuit system 9900 can output an audible message indicating the symptoms for which the naloxone composition should be administered, the expiration date of the naloxone composition, the dosage of the naloxone composition or the like.

Figure 127:
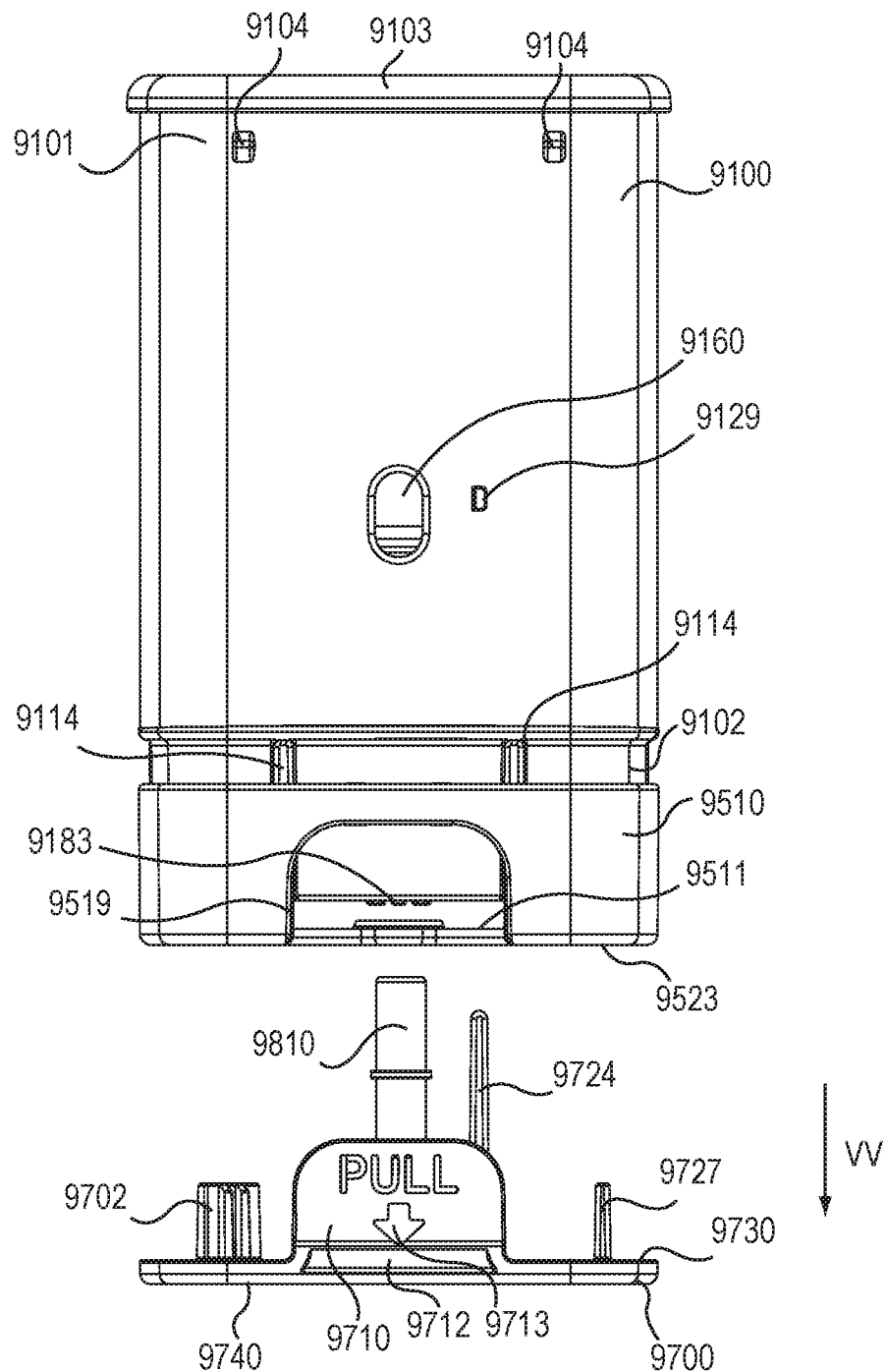
FIG. 127 is a back view of the medical injector illustrated in FIG. 102 in a third configuration.

After the cover 9190 is removed from the housing 9100, the medical injector 9000 can be moved from the second configuration to a third configuration by moving the safety lock 9700 from a first position to a second position. The safety lock 9700 is moved from a first position to a second position by moving the safety lock 9700 with respect to the housing 9100 in the direction shown by the arrow VV in FIG. 127. When the safety lock 9700 is moved from the first position to the second position, the safety lock protrusion 9702 is removed from between the extensions 9553 of the release member 9550, thereby enabling the medicament delivery mechanism 9300. Moreover, as shown in FIGS. 126 and 127, when the safety lock 9700 is moved from the housing 9100, the actuator 9724 of the safety lock 9700 actuates the first actuation portion 9926 of the electronic circuit system 9900, as described above with reference to the delivery device 3000 of FIGS. 9-59.

After the safety lock 9700 is moved from the first position to the second position, the medical injector 9000 can be moved from the third configuration to a fourth configuration by moving the base 9510 from a first position to a second position. Similarly stated, the medical injector 9000 can be actuated by the system actuation assembly 9500 by moving the base 9510 distally relative to the housing 9100. The base 9510 is moved from its first position to its second position by placing the medical injector 9000 against the body of the patient and moving the base 9510 with respect to the housing 9100 in the direction shown by the arrow WW in FIG. 128. Moving the base 9510 from the first position to the second position causes the protrusions 9515 on the proximal surface 9511 of the base 9510 to engage the tapered surfaces 9557 of the extensions 9553 of the release member 9550, thereby moving the extensions 9515 together. The inward movement of the extensions 9553 causes the release member 9550 to become disengaged from the distal end portion of the housing 9100, thereby allowing the release member 9550 to be moved proximally along its longitudinal axis as the spring 9576 expands.

Figure 128:
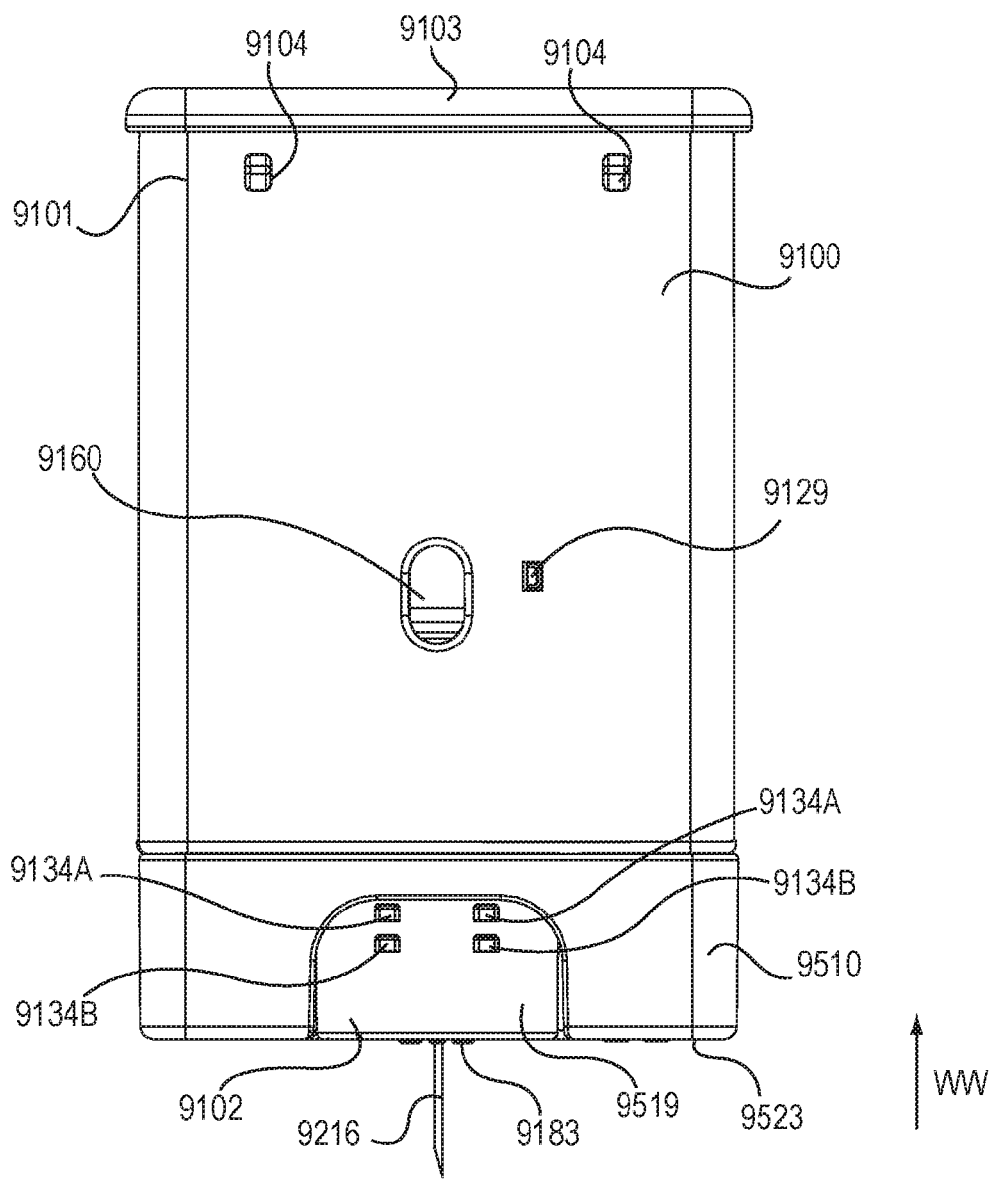
FIG. 128 is a back view of the medical injector illustrated in FIG. 102 in a fourth configuration (i.e., the needle insertion configuration).
Figure 129:
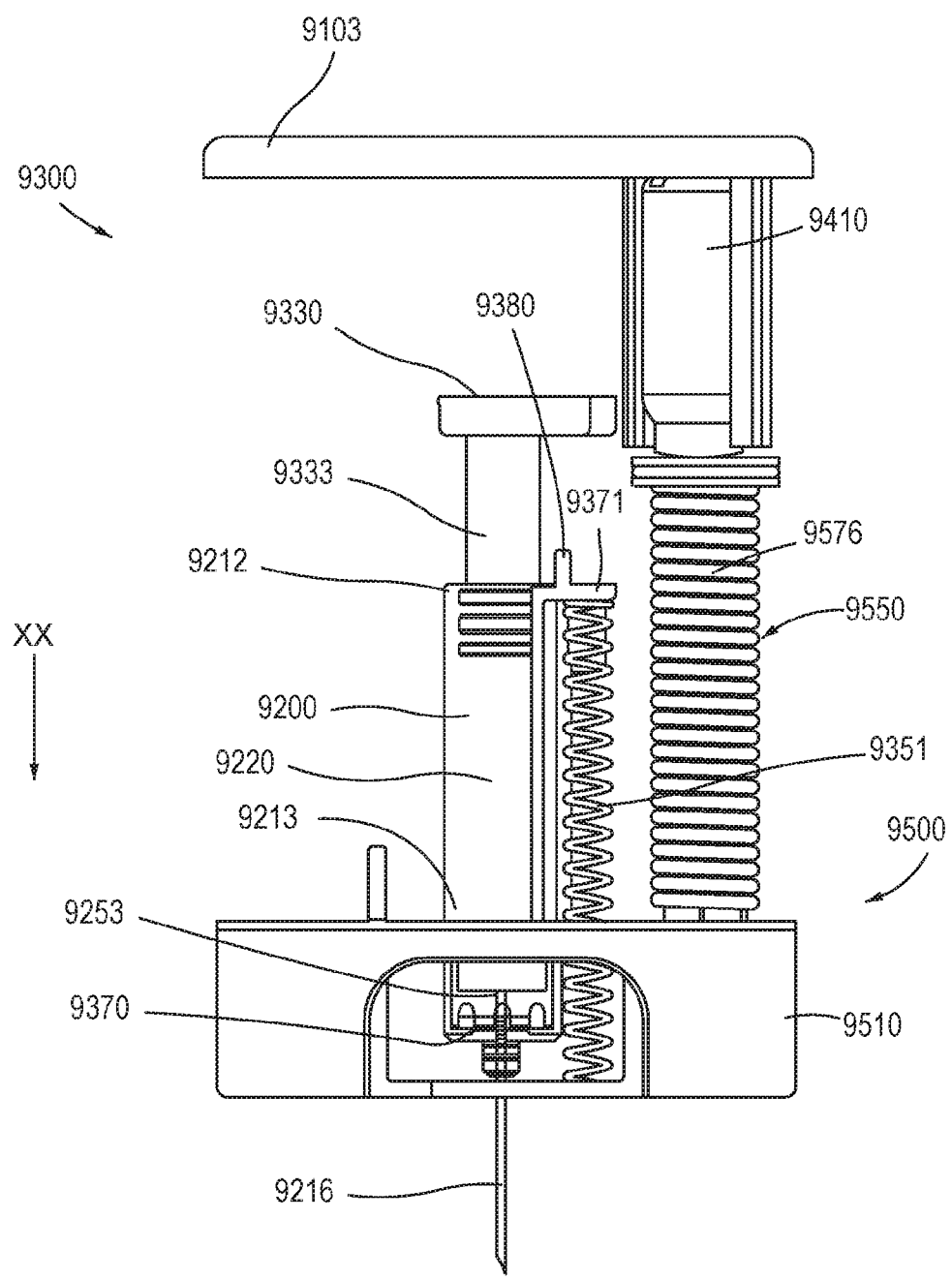
FIG. 129 is a front view of the medical injector illustrated in FIG. 102 in the fourth configuration (i.e., the needle insertion configuration).

When the base 9510 is moved from the first position to the second position, the system actuator 9500 actuates the medicament delivery mechanism 9300, thereby placing the medical injector 9000 in its fourth configuration (i.e., the needle insertion configuration), as shown in FIGS. 128 and 129. More particularly, when the medical injector is in its fourth configuration, the puncturer 9575 of the release member 9550 is in contact with and/or disposed through the frangible seal 9411 of the gas container 9410.

After the frangible seal 9411 has been punctured, an actuating portion of a compressed gas can escape from the gas container 9410 and flow via the gas passageway 9156 into the medicament cavity 9139. The gas applies gas pressure to the piston 9330 causing the piston 9330 and the carrier 9370 to move in a distal direction within the medicament cavity 9139, as shown by the arrow XX in FIG. 129. When the carrier 9370 moves distally within the medicament cavity 9139, the carrier 9370 and the medicament container 9200 are in a first configuration. Accordingly, as described above, the medicament container 9200 is connected to the carrier 9370 by a "snap fit" connection. In this manner, the medicament container 9200 and the needle 9216 contemporaneously move with piston 9330 and/or the carrier 9370 in a distal direction. As described above, the proximal end portion 9253 of the needle 9216 is connected to the distal end portion 9372 of the carrier 9370 and is spaced from the seal 9250 of the medicament container 9200 when the carrier 9370 is in its first configuration. Said another way, the medicament container 9200 and the needle 9216 do not define a medicament delivery path when the carrier 9370 is in the first configuration. The movement of the needle 9216 in a distal direction causes the distal end portion of the needle 9216 to exit the housing 9100 and enter the body of a patient prior to administering the naloxone composition 9220.

After the carrier 9370 and/or the needle 9216 have moved within the medicament cavity 9139 a predetermined distance, the carrier 9370 and the medicament container 9200 are moved from the first configuration to a second configuration. In the second configuration of the carrier 9370, the medicament container 9200 is released from the "snap-fit" allowing the medicament container 9200 and the piston 9330 to continue to move in a distal direction relative to the carrier 9370. Said another way, the medicament container 9200 is configured to slidably move within the carrier 9370 when the carrier is moved from the first configuration to the second configuration. As the medicament container 9200 continues to move within the carrier 9370, the proximal end portion 9253 of the needle 9216 contacts and punctures the seal 9250 of the medicament container 9200. This allows the medicament contained in the medicament container 9200 to flow into the lumen (not shown) defined by the needle 9216, thereby defining a medicament delivery path.

After the medicament container 9200 contacts the distal end of the carrier 9370, the medicament container 9200 stops moving within the carrier 9370 while the piston 9330 continues to move in a distal direction, as shown by the arrow YY in FIG. 130. This causes the piston 9330 to move within the medicament container 9200 containing the naloxone composition 9220. As the piston rod 9333 of the piston 9330 moves within the medicament container 9200, the piston rod 9333 contacts the elastomeric member 9217 and generates a pressure upon the naloxone composition 9220 contained within the medicament container 9200, thereby allowing at least a portion of the naloxone composition 9220 to flow out of the medicament container 9200 and into the lumen defined by the needle 9216. The medicament is delivered to a body of a user via the medicament delivery path defined by the medicament container 9200 and the needle 9216.

Figure 131:
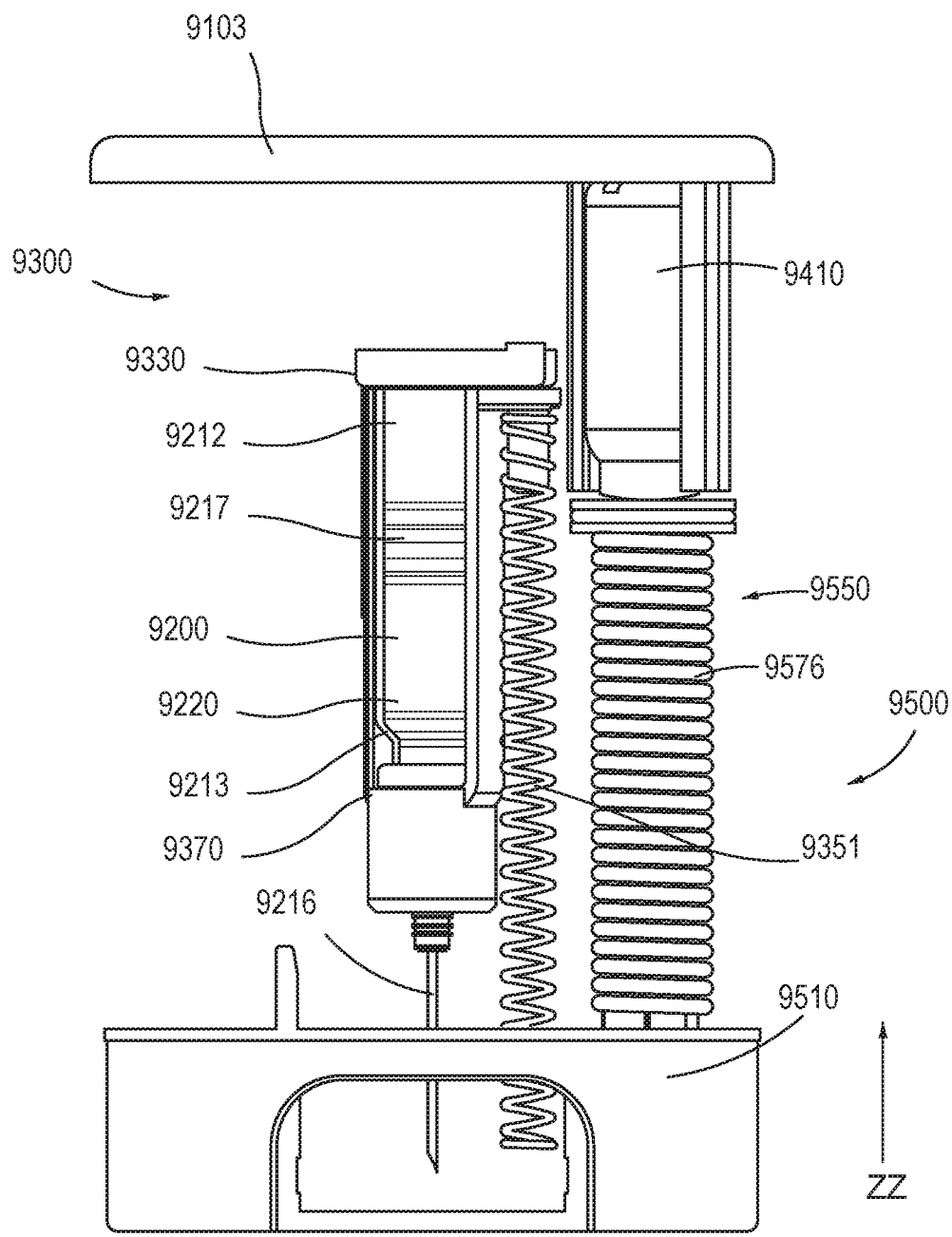
FIG. 131 is a front view of the medical injector illustrated in FIG. 102 in a sixth configuration (i.e., the retraction configuration).

As shown in FIG. 131, after the piston 9330 moves a predetermined distance within the medicament container 9200, the gas valve actuator 9380 of the carrier 9370 engages the gas relief valve (not shown in FIG. 131) of the piston 9330 thereby allowing the pressurized gas contained within the gas chamber (i.e., the volume within the medicament cavity 9139 between the proximal end of the housing 9100 and the proximal end of the piston 9330) to escape. Similarly stated, the gas valve actuator 9380 of the carrier 9370 engages the gas relief valve of the piston 9330, the pressure within the housing 9100 is reduced, thereby ending the injection event. In this manner, the pre-injection distance between the proximal end portion of the piston 9330 and the gas valve actuator 9380 of the carrier 9370 can be adjusted to control the amount of the naloxone composition 9220 to be injected. After the gas pressure within the medicament cavity 9139 decreases below a certain level, the force exerted by the retraction spring 9351 on the carrier 9370 can be sufficient to cause the carrier 9370 to move proximally within the housing 9100 (i.e., to retract), as shown by the arrow ZZ in FIG. 131.

As described above with reference to the delivery device 3000 of FIGS. 9-59, the actuator 9520 of the base 9510 actuates the second actuation portion 9946 of electronic circuit 9900 to trigger a predetermined output or sequence of outputs when the base 9510 is moved from its first position to its second position (see, e.g., FIGS. 37 and 39). For example, in some embodiments, the electronic circuit system 9900 can output an electronic signal associated with recorded speech to the audible output device 9956. Such an electronic signal can be, for example, associated with an audible countdown timer, instructing the user on the duration of the injection procedure, and/or the like (as described in detail above with reference to the delivery device 3000).

Although the electronic circuit system 9900 is shown and described above as having two irreversible switches (e.g., switch 9972 and switch 9973), in other embodiments, an electronic circuit system can have any number of switches. Moreover, such switches can be either reversible or irreversible. For example, FIGS. 132-137 show portions of a medicament delivery device 10000 having an electronic circuit system 10900 having three irreversible switches.

Figure 132:
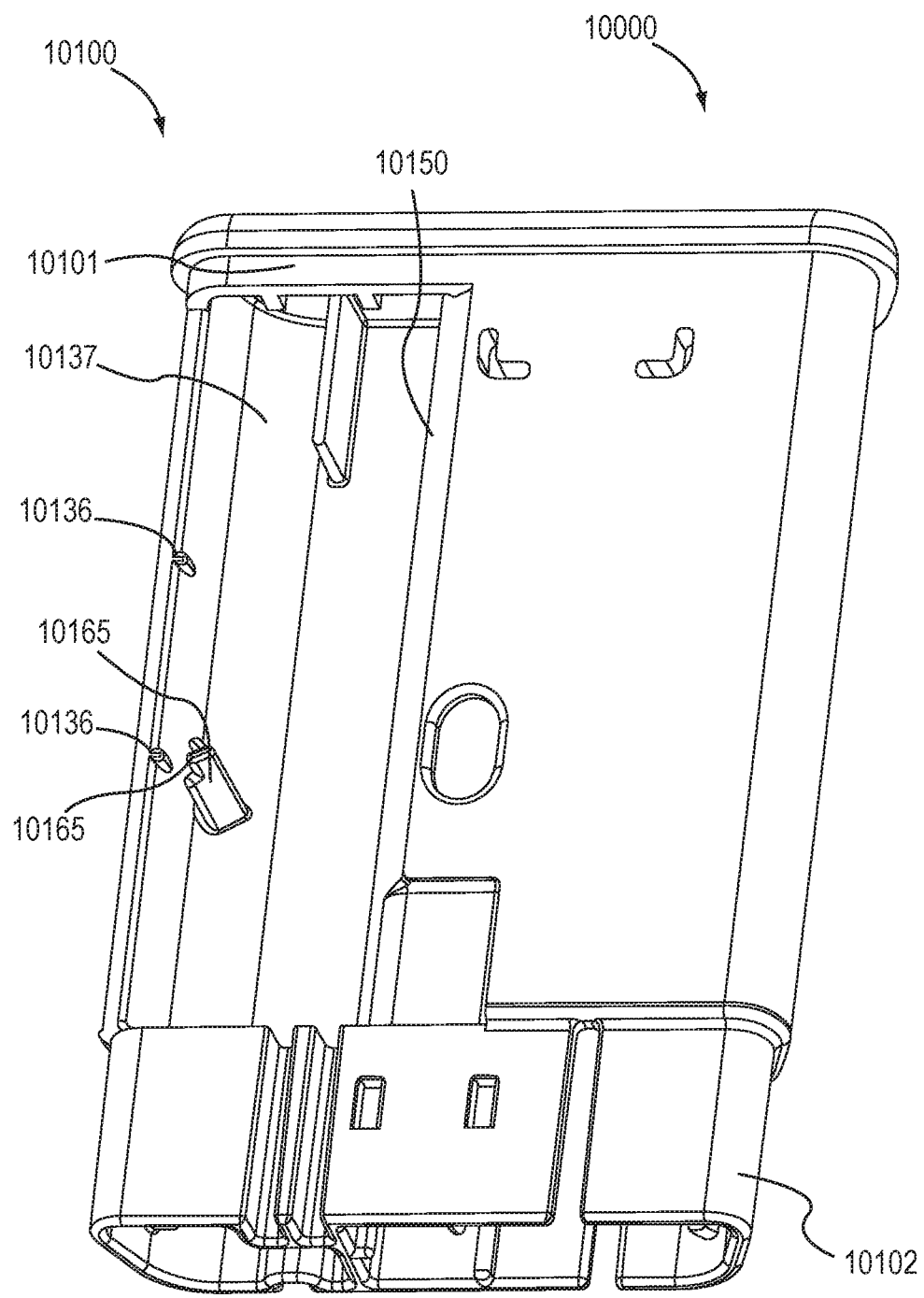
FIG. 132 is a perspective view of a housing of a medical injector according to an embodiment.
Figure 133:
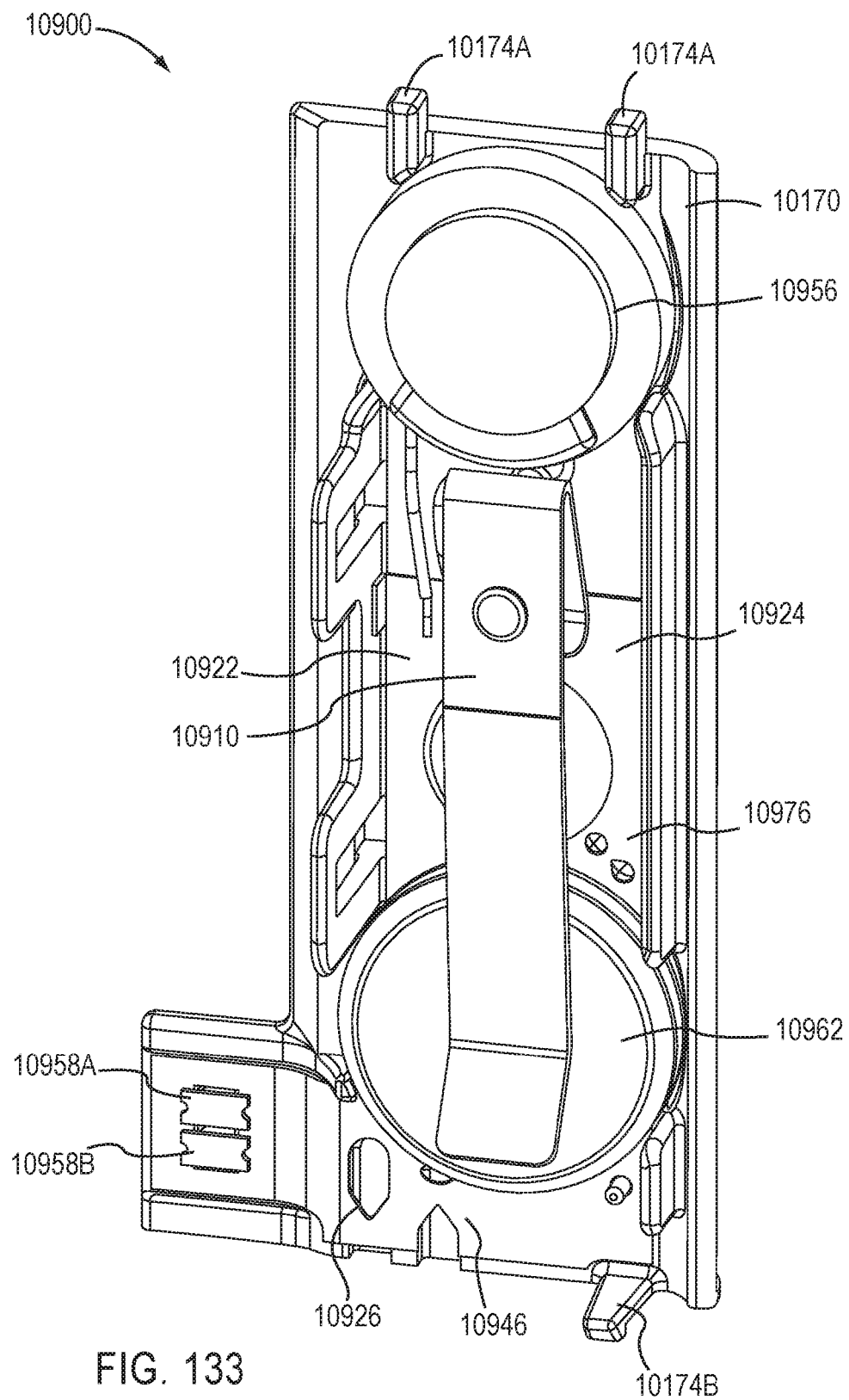
FIG. 133 is a perspective view of an electronic circuit system of a medical injector according to an embodiment.

The medicament delivery device 10000 is similar to the medical injector 9000 described above. As shown in FIGS. 132 and 133 (which show only portions of the medicament delivery device 10000), the medicament delivery device 10000 includes a housing 10100, a delivery mechanism (not shown), an electronic circuit system 10900, a cover (not shown), a safety lock (not shown, similar to safety lock 9700) and a base (not shown, similar to base 9510). The structure and operation of the delivery mechanism, the cover, the safety lock and the base are similar to the structure and operation of the delivery mechanism 9300, the cover 9190, the safety lock 9700 and the base 9510, respectively. Accordingly, only the electronic circuit system 10900 and the housing 10100 are described in detail below.

As shown in FIG. 132, the housing 10100 has a proximal end portion 10101 and a distal end portion 10102. The housing 10100 defines a gas cavity (not shown), a medicament cavity (not shown) and an electronic circuit system cavity 10137. The gas cavity and medicament cavity of the housing 10100 of the medicament delivery device 10000 are similar to the gas cavity 9151 and the medicament cavity 9139, shown and described above with reference to FIGS. 107 and 108.

The electronic circuit system cavity 10137 is configured to receive the electronic circuit system 10900. As described above, the electronic circuit system cavity 10137 is fluidically and/or physically isolated from the gas cavity and/or the medicament cavity by a sidewall 10150. The housing 10100 has protrusions 10136 configured to stabilize the electronic circuit system 10900 when the electronic circuit system 10900 is disposed within the electronic circuit system cavity 10137. The housing 10100 also defines connection apertures (not shown) configured to receive connection protrusions 10174A of the electronic circuit system 10900 (see e.g., FIG. 133). In this manner, the electronic circuit system 10900 can be coupled to the housing 10100 within the electronic circuit system cavity 10137 (see e.g., FIG. 136). In other embodiments, the electronic circuit system 10900 can be coupled within the electronic circuit system cavity 10137 by any other suitable means, such as an adhesive, a clip and/or the like.

The housing 10100 includes an actuation protrusion 10165 disposed within the electronic circuit system cavity 10137. As described in more detail herein, an angled end portion 10166 of the actuation protrusion 10165 of the housing 10100 is configured to engage a third actuation portion 10976 of a substrate 10924 of the electronic circuit system 10900 when the electronic circuit system 10900 is coupled to the housing 10100.

Figure 136:
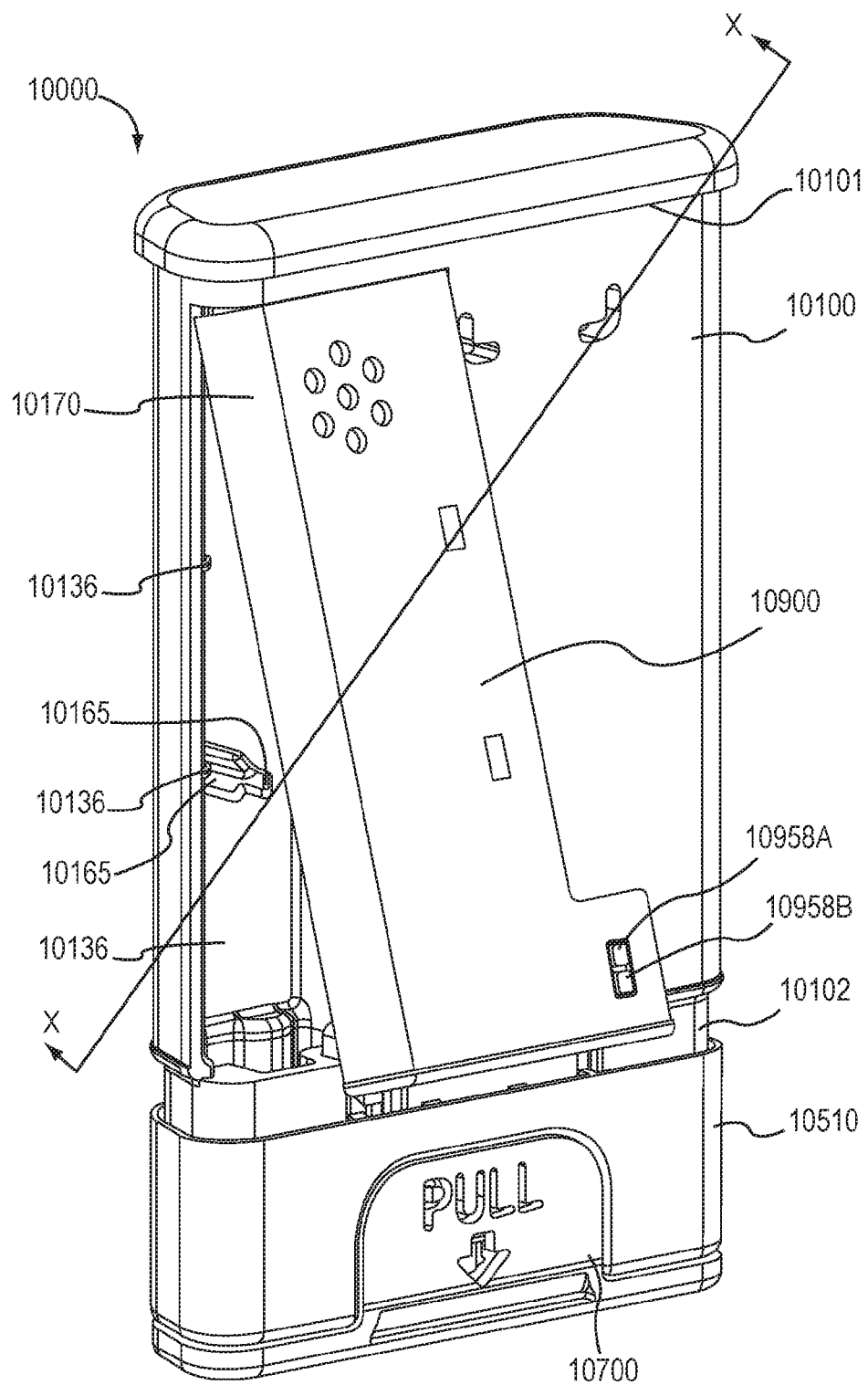
FIG. 136 is a perspective cross-sectional view of the housing and the electronic circuit system illustrated in FIG. 132 and FIG. 133 respectively.

As shown in FIG. 136, the electronic circuit system 10900 is configured to fit within the electronic circuit system cavity 10137 of the housing 10100. Accordingly, as described above, the electronic circuit system 10900 is physically and/or fluidically isolated from the medicament cavity, the gas cavity and/or the medicament delivery path within the medicament delivery device 10000 (not shown). As described herein, the electronic circuit system 10900 is configured to output an electronic output associated with a use of the medicament delivery device 10000.

As shown in FIG. 133, the electronic circuit system 10900 is similar to the electronic circuit system 9900 described above. The electronic circuit system 10900 of the medicament delivery device 10000 includes an electronic circuit system housing 10170, a printed circuit board 10922, a battery assembly 10962, an audio output device 10956, two light emitting diodes (LEDs) 10958A, 10958B and a battery clip 10910. The electronic circuit system housing 10170, the battery assembly 10962, the audio output device 10956, the two light emitting diodes (LEDs) 10958A, 10958B and the battery clip 10910 are similar to the electronic circuit system housing 9170, the battery assembly 9962, the audio output device 9956, the two light emitting diodes (LEDs) 9958A, 9958B and the battery clip 9910 of the electronic circuit system 9900 described above. Thus, a detailed discussion of these components is omitted.

The electronic circuit system 10900 also includes a processor 10950 configured to process electronic inputs (e.g., from input switches) and produce electronic outputs. As described herein, such electronic outputs can include audio or visual outputs associated with a use of the medicament delivery device 10000. The processor 10950 can be a commercially-available processing device dedicated to performing one or more specific tasks. For example, in some embodiments, the processor 10950 can be a commercially-available microprocessor, such as the Sonix SNC 17060 or the SNC 711120 voice synthesizers. Alternatively, the processor 10950 can be an application-specific integrated circuit (ASIC) or a combination of ASICs, which are designed to perform one or more specific functions. In yet other embodiments, the processor 10950 can be an analog or digital circuit, or a combination of multiple circuits.

The processor 10950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the processor 10950, for example, electronically-programmable read only memory (EPROM), erasable electronically-programmable read only memory (EEPROM), or flash memory.

Figure 134:
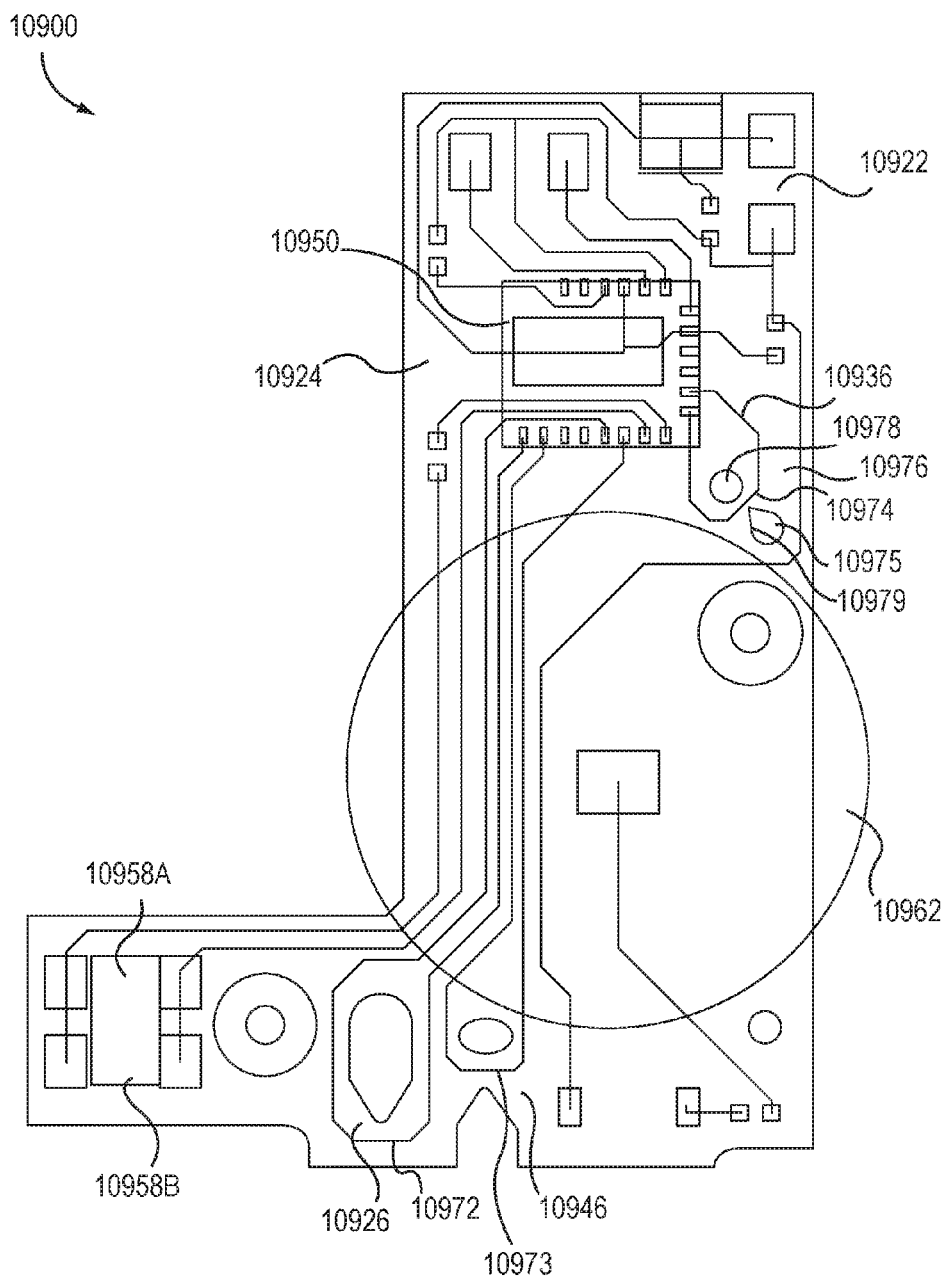
FIG. 134 is a back view of a printed circuit board of the electronic circuit system shown in FIG. 133.
Figure 135:
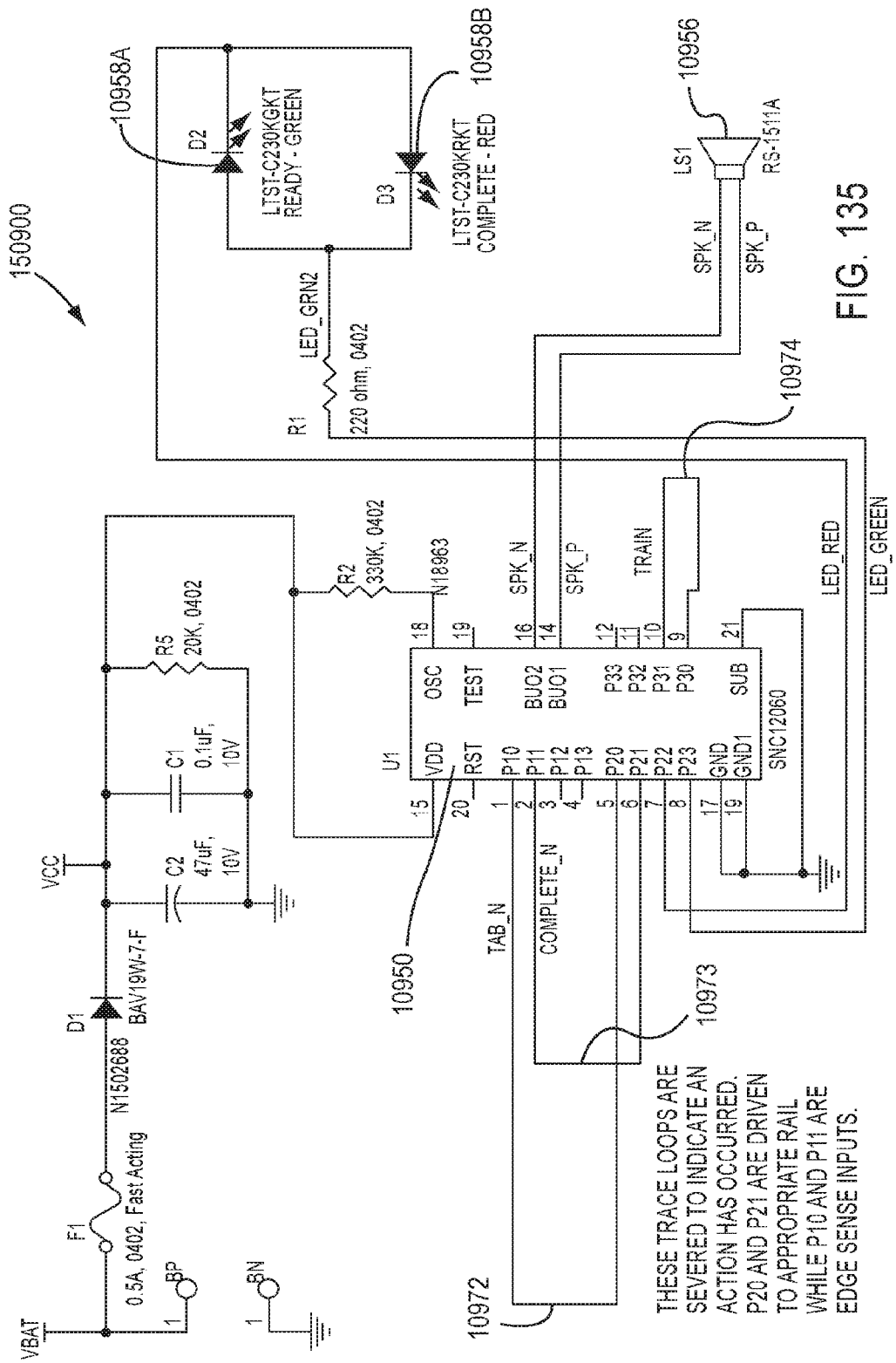
FIG. 135 is a schematic illustration of the electronic circuit system shown in FIG. 133.

FIG. 134 shows the printed circuit board 10922 of the electronic circuit system 10900. FIG. 135 is a schematic illustration of the electronic circuit system 10900. The printed circuit board 10922 of the electronic circuit system 10900 includes a substrate 10924, a first actuation portion 10926 (including a first switch 10972), a second actuation portion 10946 (including a second switch 10973), and a third actuation portion 10976 (including an electronic circuit system configuration switch 10974). The substrate 10924 of the printed circuit board 10922 includes the electrical components necessary for the electronic circuit system 10900 to operate as desired. For example, the electrical components can include resistors, capacitors, inductors, switches, microcontrollers, microprocessors and/or the like.

Figure 137:
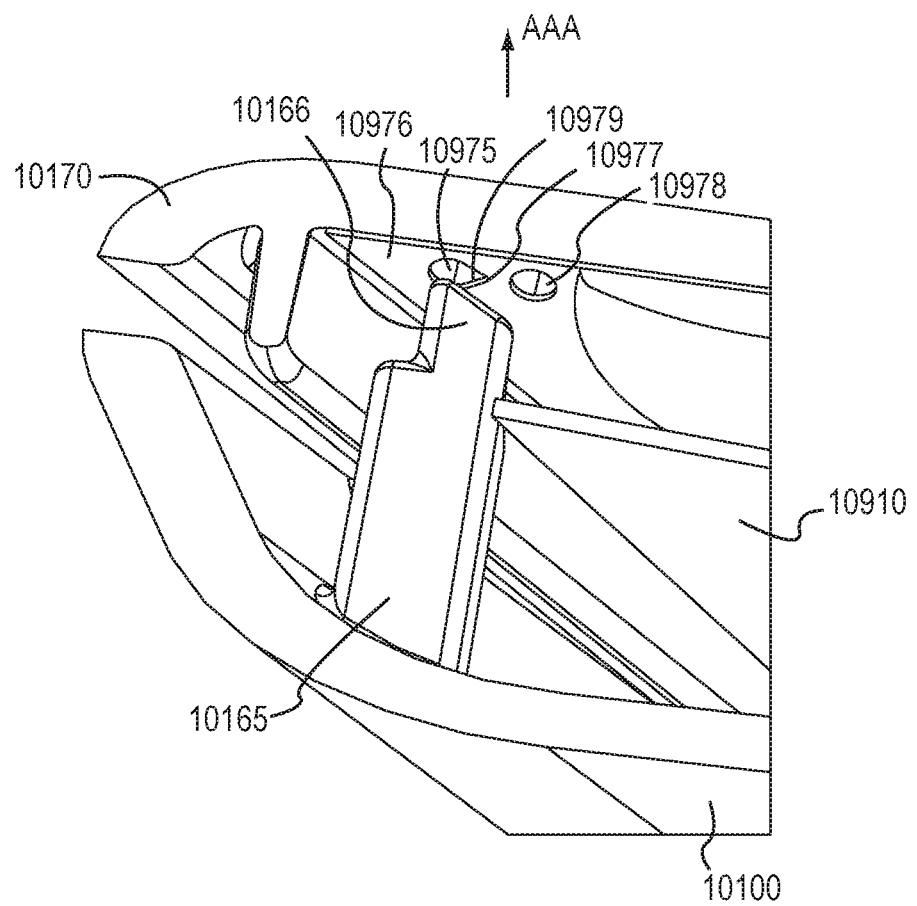

The first actuation portion 10926 and the second actuation portion 10946 are similar to the first actuation portion 9926 and the second actuation portion 9946 of the electronic circuit system 9900, described above (see e.g., FIG. 133), and are therefore not described or labeled in detail. The third actuation portion 10976 includes a third electrical conductor 10936 (see e.g., FIG. 134) and defines an actuation aperture 10975 having a boundary 10979, and a tear propagation limit aperture 10978. As shown in FIGS. 133 and 137, the actuation aperture 10975 of the third actuation portion 10976 is configured to receive the angled end portion 10166 of the actuation protrusion 10165 of the housing 10100 when the electronic circuit system 10900 is disposed within the electronic circuit system cavity 10137. The boundary 10979 of the actuation aperture 10975 has a discontinuous shape, such as, for example, a teardrop shape, that includes a stress concentration riser 10977. The discontinuity and/or the stress concentration riser 10977 of the boundary 10979 can be of any suitable shape to cause the substrate 10924 to deform in a predetermined direction when the angled end portion 10166 of the actuation protrusion 10165 of the housing 10100 is inserted into the actuation aperture 10975 (see e.g., FIG. 137), as described below.

The third electrical conductor 10936 includes the electronic circuit system configuration switch 10974 (see e.g., FIG. 134) disposed between the actuation aperture 10975 and the tear propagation limit aperture 10978, which can be, for example, a frangible portion of the third electrical conductor 10436. As shown in FIGS. 136 and 137, when the electronic circuit system 10900 is attached to the housing 10100, a portion of the angled portion 10166 of the actuation protrusion 10165 is disposed within the actuation aperture 10975 of the third actuation portion 10976, as shown by the arrow AAA in FIG. 137. Continued movement of the angled portion 10166 of the actuation protrusion 10165 within the third actuation portion 10976 of the substrate 10924 causes the third actuation portion 10976 of the substrate 10924 to tear, thereby separating the portion of the third electrical conductor 10936 including the electronic circuit system configuration switch 10974. Said another way, when the electronic circuit system 10900 is attached to the housing 10100, the actuation protrusion 10165 moves irreversibly the electronic circuit system configuration switch 10974 from a first state (e.g., a state of electrical continuity) to a second state (e.g., a state of electrical discontinuity).

The tear propagation limit aperture 10978 is configured to limit the propagation of the tear in the substrate 10924. Said another way, the tear propagation limit aperture 10978 is configured to ensure that the tear in the substrate 10924 does not extend beyond the tear propagation limit aperture 10978. The tear propagation limit aperture 10978 can be any shape configured to limit the propagation of a tear and/or disruption of the substrate 10924. For example, the tear propagation limit aperture 10978 can be oval shaped. In other embodiments, the boundary of the tear propagation limit aperture 10978 can be reinforced to ensure that the tear in the substrate 10924 does not extend beyond the tear propagation limit aperture 10978. The angled end portion 10166 of the actuation protrusion 10165 ensures that the tear in the substrate 10924 propagates in the desired direction. Said another way, the angled end portion 10166 of the actuation protrusion 10165 ensures that the tear in the substrate 10924 occurs between the actuation aperture 10975 and the tear propagation limit aperture 10978.

When the actuation protrusion 10165 of the housing 10100 moves irreversibly the electronic circuit system configuration switch 10974 of the electronic circuit system 10900 from the first state to the second state, the electronic circuit system 10900 can be moved between a first configuration and a second configuration. For example, in some embodiments, irreversibly moving the electronic circuit system configuration switch 10974 of the electronic circuit system 10900 to the second state places the electronic circuit system 10900 in the second configuration such that when power is applied to the electronic circuit system 10900, the electronic circuit system 10900 recognizes that the medicament delivery device 9000 is a certain type of medicament delivery device and/or is in a certain configuration. In some embodiments, the housing can be devoid of the actuation protrusion 10165, thus the electronic circuit system configuration switch 10974 is maintained in its first state when the electronic circuit system 10900 is attached to the housing 10100. In this manner, the electronic circuit system configuration switch 10974 can enable the electronic circuit system 10900 to be used in different types and/or configurations of medicament delivery devices. The dual functionality of the electronic circuit system 10900 enables production of the same electronic circuit system 10900 for multiple devices, thereby permitting mass production and decreasing the cost of production of the electronic circuit system 10900.

For example, in some embodiments the electronic circuit system 10900 can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

The actuation of the medicament delivery device configuration switch 10974 can configure the electronic circuit system 10900 to output a different electronic output when the medicament delivery device 10000 is a simulated medical injector than when the medicament delivery device 10000 is an actual medical injector. Said yet another way, the electronic circuit system 10900 can be configured to output a first series of electronic outputs when the electronic circuit system configuration switch 10974 is in the first state and a second series of electronic outputs when the electronic circuit system configuration switch 10974 is in the second state. In this manner, the electronic circuit system configuration switch 10974 can enable the same electronic circuit system 10900 to be used in both simulated medicament delivery devices and actual medicament delivery devices. When used on an actual medicament delivery device, for example, the housing can be devoid of the actuation protrusion 10165. The dual functionality of the electronic circuit system 10900 can decrease the cost of production of the electronic circuit system 10900 of the medicament delivery device 9000.

In other embodiments, moving the electronic circuit system configuration switch 10974 to the second state can place the electronic circuit system 10900 in any number of different functional configurations. For example, moving the electronic circuit system configuration switch 10974 from the first state to the second state can indicate the type of medicament in the medicament container, the dosage of the medicament and/or the language of the audible electronic outputs output by the electronic circuit system 10900.

In still other embodiments, any number of electronic circuit system configuration switches can be used. For example, multiple switches can be used to configure the electronic circuit system 10900 to output usage instructions in any number of languages. For example, if an electronic circuit system contained three configuration switches (e.g., switches A, B and C), switch A can correspond to English instructions, switch B to Spanish instructions and switch C to German instructions. Further, moving both switch A and B to the second state might correspond to French instructions. In this manner, a single electronic circuit system 10900 can be configured to output instructions in multiple languages.

The needle 9216, as well as any other needles shown and described herein, can have any diameter and/or length to facilitate the injection of the naloxone composition 9220. For example, the needle can have a length suitable to penetrate clothing and deliver the naloxone via a subcutaneous injection and/or an intramuscular injection. In some embodiments, the needle 9216 (and any needle disclosed herein) can have a length of greater than 1 inch, greater than 1.5 inches, greater than 2 inches, greater than 2.5 inches or greater than 3 inches. In some embodiments, the needle 9216 (and any needle disclosed herein) can have a lumen diameter of approximately between 19-gauge and 31-gauge.

Although the medical injectors 9000 and 10000 are shown and described above as being auto-injectors configured to deliver the naloxone compositions described herein via injection through a needle (e.g., needle 9216), in other embodiments, a medicament delivery device can be configured to deliver the naloxone compositions described herein via any suitable delivery member, and in any suitable manner. For example, in some embodiments, a medicament delivery device can include a delivery member that delivers the naloxone composition into the body via inhalation and/or intranasal delivery.

Figure 138:
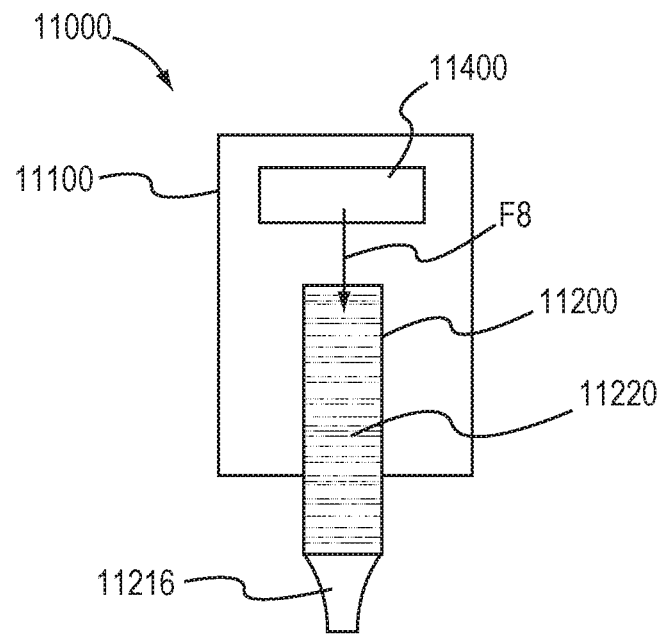

For example, FIG. 138 is a schematic illustration of a medicament delivery device 11000 according to an embodiment that is configured to deliver a naloxone composition intranasally and/or via inhalation. The medicament delivery device 11000 includes a housing 11100, a medicament container 11200, a delivery member 11300 and an energy storage member 11400. The medicament container 11200 is at least partially disposed within the housing 11100, and contains (i.e., is filled or partially filled with) a naloxone composition 11220. The delivery member 11300 is coupled to the medicament container 11200, and, as described herein, is configured to deliver the naloxone composition from the medicament container 11200 intranasally and/or via inhalation. The energy storage member 11400 is disposed within the housing 11100, and is configured to produce a force F8 to deliver the naloxone composition 11220 (e.g., from the medicament container 11200 to a body).

The naloxone composition 11220 can be any of the naloxone compositions described herein. In particular, the naloxone composition 11220 can include an effective amount of naloxone or salts thereof, a tonicity-adjusting agent, and a pH-adjusting agent. The naloxone composition 11220 can be formulated such that the osmolality of the naloxone composition 11220 ranges from about 250-350 mOsm and the pH ranges from about 3-5.

In some embodiments, the naloxone composition 11220 can include any suitable concentration of 4,5-epoxy-3,14-dihydroxy-17-(2-propenyl) morphinan-6-one. In some embodiments, for example, the naloxone composition 11220 has a concentration of 4,5-epoxy-3,14-dihydroxy-17-(2-propenyl)morphinan-6-one between approximately 0.01 mg/mL and approximately 60 mg/mL. In other embodiments, the naloxone composition 11220 has a concentration of 4,5-epoxy-3,14-dihydroxy-17-(2-propenyl)morphinan-6-one between approximately 0.05 mg/mL and approximately 2 mg/mL.

The tonicity-adjusting agent can be any of the tonicity-adjusting agents described herein, and can be included within the naloxone composition 11220 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH-adjusting agent can be any of the pH-adjusting agents described herein, and can be included within the naloxone composition 11220 in any suitable amount and/or concentration. For example, in some embodiments, the pH-adjusting agent includes at least one of hydrochloric acid, citric acid, citrate salts, acetic acid, acetate salts, phosphoric acid or phosphate salts. In other embodiments, the pH-adjusting agent includes a dilute hydrochloric acid.

The medicament container 11200 can be any container suitable for storing the naloxone composition 11220. In some embodiments, the medicament container 11200 can be, for example, a pre-filled syringe, a pre-filled cartridge, a vial, an ampule or the like. In other embodiments, the medicament container 11200 can be a container having a flexible wall, such as, for example, a bladder. Although shown and described as being partially disposed within the housing 11100, in other embodiments, the medicament container 11200 can be disposed entirely within the housing 11100. Moreover, in some embodiments, the medicament container 11200 can be movably disposed within the housing 11100, such as, for example, in a manner similar to the medicament container 9200 shown and described above.

The delivery member 11300 is coupled to the medicament container 11200 and defines, at least in part, a flow path through which the naloxone composition 11220 can be delivered into a body. Although shown as being directly coupled to a distal end portion of the medicament container 11200, in other embodiments, the delivery member 11300 can be indirectly coupled to the medicament container 11200, (e.g., via the housing 11100).

Moreover, in some embodiments, the delivery member 11300 can be coupled to, but fluidically isolated from, the medicament container 11200 prior to actuation of the energy storage member 11400. In this manner, the medicament delivery device 11000 can be stored for extended periods of time while maintaining the sterility of the naloxone composition 11220 contained within the medicament container 11200, reducing (or eliminating) any leakage of the naloxone composition 11220 from the medicament container 11200 or the like. This arrangement also reduces and/or eliminates the assembly operations (e.g., the operation of coupling the delivery member 11300 to the medicament container 11200) before the medicament delivery device 11000 can be used to administer the naloxone composition 11220. In this manner, the medicament delivery device 11000 produces a quick and accurate mechanism for delivering the naloxone composition 11220. Similarly stated by reducing and/or eliminating the assembly operations prior to use, this arrangement reduces likelihood that performance of medicament delivery device 11000 and/or the delivery member 11300 will be compromised (e.g., by an improper coupling, a leak or the like).

In some embodiments, the delivery member 11300 can be coupled to the medicament container 11200 via a coupling member (not shown in FIG. 138) having similar functionality to the carrier 9370 shown and described above with respect to the medicament delivery device 9000. In such an embodiment, the medicament container 11200 and/or the delivery member 11300 can be configured to move relative to the coupling member when the energy storage member 11400 is actuated. Such movement can fluidically couple the delivery member 11300 and the medicament container 11200, thereby defining a flow path through which the naloxone composition 11220 can be delivered to the patient.

In some embodiments, the delivery member 11300 can enhance the delivery of the naloxone composition 11220 thereby improving the efficacy of the naloxone composition 11220. Similarly stated, in some embodiments, the delivery member 11300 can produce a flow of the naloxone composition 11220 having desired characteristics to enhance the absorption rate of the naloxone composition 11220, to minimize the delivery of the naloxone composition 11220 to regions of the body in which such delivery is less effective (e.g., the throat, etc.) or the like.

For example, in some embodiments, the delivery member 11300 can produce a controlled flow rate of the naloxone composition 11220. In such embodiments, the delivery member 11300 can include one or more flow orifices, a tortuous flow path or the like, to produce a desired pressure drop and/or to control the flow through the delivery member 11300. For example, in some embodiments, the delivery member 11300 can be configured to minimize excessive delivery of the naloxone composition 11220. For example, for intranasal applications, the delivery member 11300 can reduce the likelihood of excess deposition of the naloxone composition 11220 on the mucosal membrane, which can result in a portion of the naloxone composition 11220 being nonabsorbed (e.g., running out of the nose or into the throat).

In some embodiments, the delivery member 11300 can be configured to atomize the naloxone composition 11220 to produce a spray for intranasal administration. For example, in some embodiments, the delivery member 11300 can produce an atomized spray of the naloxone composition having a desired spray geometry (e.g., spray angle and/or plume penetration) and/or droplet size distribution. In some embodiments, for example, the delivery member 11300 can include two chambers to allow substantially simultaneous deliver of the naloxone composition 11220 into both nostrils of a patient. Moreover, the delivery member 11300 can be cooperatively configured with the energy storage member 11400 to produce an atomized spray of the naloxone composition having a desired spray geometry and/or droplet size distribution. In this manner, the medicament delivery device 11000 can produce a consistent spray to enhance the efficacy of the naloxone composition 11220 under a wide variety of conditions.

In some embodiments, for example, the delivery member 11300 and the energy storage member 11400 can be cooperatively configured such that, when the energy storage member 11400 is actuated, the medicament delivery device 11000 produces an atomized spray of the naloxone composition 11220 having a substantial portion of the droplets therein having size distribution of between about 10 microns and about 20 microns. In this manner, the amount of the naloxone composition 11220 delivered to the lungs (e.g., the amount of smaller droplets that bypass the mucosal membrane) and/or the amount of the naloxone composition 11220 that runs into the throat (e.g., the amount of larger droplets) is minimized. In some embodiments, the delivery member 11300 and the energy storage member 11400 are cooperatively configured to produce a spray of the naloxone composition 11220 having a droplet size distribution wherein approximately 85 percent of the droplets have a size of between approximately 10 microns and 150 microns.

As described above, in some embodiments, the energy storage member 11400 is configured to "match" the delivery member 11300. Said another way, in some embodiments, the energy storage member 11400 is configured to produce the force F8 within a predetermined range to ensure the desired functionality of the delivery member 11300. Accordingly, the energy storage member 11400 can be any suitable device or mechanism that, when actuated, produces the desired force F8 to deliver the naloxone composition 11220 as described herein. By employing the energy storage member 11400 to produce the force F8, rather than relying on a user to manually produce the delivery force, the naloxone composition 11220 can be delivered into the body at the desired pressure and/or flow rate, and with the desired characteristics, as described above. Moreover, this arrangement reduces the likelihood of partial delivery (e.g., that may result if the user is interrupted or otherwise rendered unable to complete the delivery).

In some embodiments, the energy storage member 11400 can be a mechanical energy storage member, such as a spring, a device containing compressed gas, a device containing a vapor pressure-based propellant or the like. In other embodiments, the energy storage member 11400 can be an electrical energy storage member, such as a battery, a capacitor, a magnetic energy storage member or the like. In yet other embodiments, the energy storage member 11400 can be a chemical energy storage member, such as a container containing two substances that, when mixed, react to produce energy.

Figure 139:
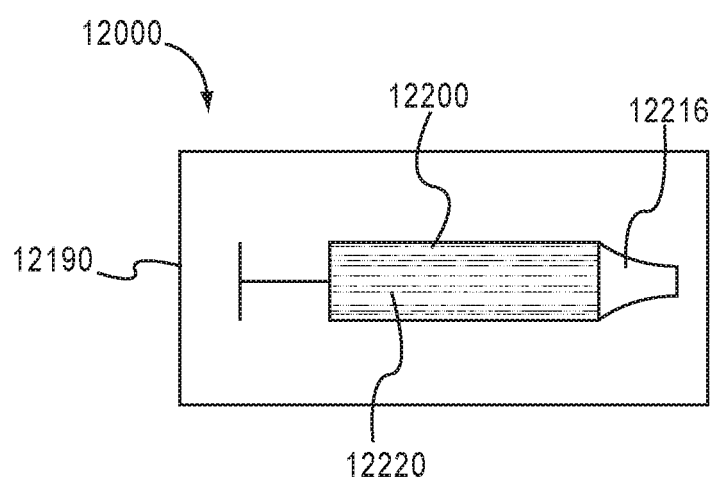

Although the medicament delivery device 11000 is shown and described above as including an energy storage member 11400, in other embodiments, a kit can include a medicament container containing a naloxone composition that is delivered by a manually-produced force. For example, FIG. 139 is a schematic illustration of a kit 12000 according to an embodiment. The kit 12000 includes a case 12190, a medicament container 12200 that contains (i.e., is filled or partially filled with) a naloxone composition 12220, and a delivery member 12300. The naloxone composition 12220 can be any of the naloxone compositions shown and described herein. The medicament container 12200 is movably disposed within the case 12190. More particularly, the medicament container 12200 can be removed from the case 12190 to deliver the naloxone composition 12220 contained therein.

Although the medicament container 12200 is shown as being substantially enclosed by and/or disposed within the case 12190, in other embodiments, the medicament container 12200 can be only partially enclosed by and/or disposed within the case 12190. In some embodiments, the case 12190 blocks an optical pathway between the medicament container 12200 and a region outside of the case 12190. Similarly stated, when the medicament container 12200 is disposed within the case 12190, the case 12190 is obstructs the medicament container 12200 to reduce the amount of light transmitted to the naloxone composition 12220 within the medicament container 12200.

The delivery member 12300, which can be a needle, an atomizer (e.g., for intranasal delivery, as described above), a mouthpiece or the like, is coupled to the medicament container 12200 and defines, at least in part, a flow path through which the naloxone composition 12220 can be delivered into a body. Although shown as being directly coupled to a distal end portion of the medicament container 12200, in other embodiments, the delivery member 12300 can be indirectly coupled to the medicament container 12200, (e.g., via the housing 12100).

Moreover, in some embodiments, the delivery member 12300 can be coupled to, but fluidically isolated from, the medicament container 12200 prior to actuation of the medicament container 12200 (e.g., by manually depressing a plunger, squeezing a trigger, or the like). In this manner, the medicament delivery device 12000 can be stored for extended periods of time while maintaining the sterility of the naloxone composition 12220 contained within the medicament container 12200, reducing (or eliminating) any leakage of the naloxone composition 12220 from the medicament container 12200 or the like. This arrangement also reduces and/or eliminates the assembly operations (e.g., the operation of coupling the delivery member 12300 to the medicament container 12200) before the medicament delivery device 12000 can be used to administer the naloxone composition 12220. In this manner, the medicament delivery device 12000 produces a quick and accurate mechanism for delivering the naloxone composition 12220. Similarly stated by reducing and/or eliminating the assembly operations prior to use, this arrangement reduces likelihood that performance of medicament delivery device 12000 and/or the delivery member 12300 will be compromised (e.g., by an improper coupling, a leak or the like).

In some embodiments, the delivery member 12300 can be coupled to the medicament container 12200 via a coupling member (not shown in FIG. 139) having similar functionality to the carrier 9370 shown and described above with respect to the medicament delivery device 9000. In such an embodiment, the medicament container 12200 and/or the delivery member 12300 can be configured to move relative to the coupling member when the medicament container 12200 is actuated. For example, in use, upon depressing a plunger to actuate the medicament container 12200, the coupling member can move relative to the medicament container 12200 before a substantial portion of the energy produced by movement of the plunger is exerted on the naloxone composition 12220. Such movement can fluidically couple the delivery member 12300 and the medicament container 12200, thereby defining a flow path through which the naloxone composition 12220 can be delivered to the patient.

In some embodiments, at least one of the medicament container 12200 and the case 12190 can include an electronic circuit system (not shown in FIG. 139) similar to the electronic circuit systems shown and described herein. In such embodiments, the electronic circuit system can be actuated when the medicament container is removed from the case 12190. Any suitable mechanism can be used to actuate the electronic circuit system when the medicament container 12200 is removed from the case 12190. Such mechanisms include those mechanisms disclosed in U.S. Pat. No. 8,172,082, entitled "Devices, Systems and Methods for Medicament Delivery," filed on Feb. 5, 2007, which is incorporated herein by reference in its entirety.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the first surface 3341 of the piston member 3330 is shown as being substantially parallel to the second surface 3342 of the piston member 3330, in other embodiments, the first surface of a movable member can be at any suitable angular orientation to a second surface of the movable member.

Although the carrier 3370 is shown as substantially surrounding the medicament container 3200, in other embodiments, a carrier and/or the contact shoulders (analogous to the first shoulder 3377 and the second shoulder 3381) need not substantially surround the medicament container 3200. For example, in some embodiments, a carrier can be a single piece member that only partially surrounds the flange 3214 of the medicament container 3200. Similarly stated, in some embodiments, a carrier need not be movable between an opened configuration and a closed configuration, but rather can receive and/or retain the medicament container in a single configuration.

Although the carrier 4370 is described above as being configured to accommodate an o-ring or other suitable damping member to reduce the forces exerted on the medicament container 4200 during insertion and/or injection, in other embodiments, any suitable mechanisms or structures for reducing the energy, impulse and/or forces applied to the carrier, the medicament container, the housing and/or the actuation member can be employed. For example, in some embodiments, a carrier can include a deformable portion (e.g., a "crush rib") configured to deform when contacting the housing during an insertion event. In this manner, the deformable portion can absorb at least a portion of the energy and/or force generated during the impact, thereby reducing the magnitude of the energy, impulse and/or force applied to the medicament container. Similarly, in some embodiments, a portion of a medicament delivery mechanism, such as medicament delivery mechanism 4300 can include a crush rib or an impact portion configured to plastically and/or elastically deform to absorb and/or dampen the forces from the needle insertion operation.

In some embodiments, the outer surface 3815 of the needle sheath 3810 can include a cap or cover that has different material properties than the remainder of the needle sheath 3810. For example, in some embodiments, the outer surface 3815 can be constructed of a material having greater hardness and/or rigidity than the remainder of the needle sheath 3810. This arrangement allows for sufficient structural rigidity to assembly the needle sheath 3810 within the engagement portion 3720 of the safety lock 3700. In other embodiments, however, any of the needle sheaths described herein need not include an outer cover or cap. The use of a cap-less design can reduce manufacturing and/or assembly costs.

Although the medical injector 3000 is shown above as including a gas container 3410 that is actuated by a puncturer that moves within the housing 3100 with the release member 3550, in other embodiments a system actuation assembly 3500 can include a puncturer that is substantially fixed within the housing and a gas container that moves within the housing into contact with the puncturer upon actuation of the device.

Although the medicament delivery mechanism 5300 is shown above as being a monolithically constructed member (i.e., a "first movable member"), in other embodiments, the medicament delivery mechanism 5300 can include multiple members that are separately constructed and/or that are coupled together. For example, in some embodiments, a medicament delivery mechanism can include a first member that corresponds to the latch portion 5310 and the piston portion 5330, and a second, separately constructed member that produces a retraction force (e.g., similar to the function of the bias portion 5350. In such embodiments, for example, second member can be a separately constructed coil spring or the like.

Although the medical injector 3000 includes the electronic circuit system cavity 3153, the gas cavity 3154 and/or the medicament cavity 3157 that are shown and described as being fluidically and/or physically isolated from each other, in other embodiments, any of the electronic circuit system cavity 3153, the gas cavity 3154 and/or the medicament cavity 3157 can be fluidically coupled to and/or share a common boundary with each other. In some embodiments, for example, a housing can define a single cavity within which a medicament container, an energy storage member and an electronic circuit system are disposed.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications. Any of the medicament containers described herein can contain any of the naloxone compositions and/or formulations described herein.

Any of the devices and/or medicament containers shown and described herein can include any suitable medicament or therapeutic agent. In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a rabies vaccine and/or a meningococcus vaccine. In other embodiments, the medicament contained within any of the medicament containers shown herein can be a catecholamine, such as epinephrine. In other embodiments, the medicament contained within any of the medicament containers shown herein can be an opioid receptor antagonist, such as naloxone, including any of the naloxone formulations described in U.S. patent application Ser. No. 13/036,720, entitled "Medicament Delivery Device for Administration of Opioid Antagonists Including Formulation for Naloxone," filed on Feb. 28, 2011. In yet other embodiments, the medicament contained within any of the medicament containers shown herein can include peptide hormones such as insulin and glucagon, human growth hormone (HGH), erythropoiesis-stimulating agents (ESA) such as darbepoetin alfa, monoclonal antibodies such as denosumab and adalimumab, interferons, etanercept, pegfilgrastim, and other chronic therapies, or the like. In yet other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament or the naloxone compositions disclosed herein. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include a "configuration switch" (similar to the configuration switch 3974 shown and described above) that, when actuated during the assembly of the delivery device, can select an electronic output corresponding to the dose contained within the medicament container.

Any of the medicament containers described herein can include any of the elastomeric members described herein. For example, the medicament container 5200 can include an elastomeric member 5217 that is formulated to be compatible with the medicament contained therein. Although the medical injector 5000 includes a single elastomeric member 5217, in other embodiments, any number of elastomeric members 5217 can be disposed within the medicament container 5200. For example, in some embodiments, a medicament container can include a dry portion of a medicament and a fluid portion of the medicament, configured to be mixed before injection. The piston portion 5330 of the medicament delivery mechanism 5300 can be configured to engage multiple elastomeric members 5217 associated with the portions of the medicament. In this manner, multiple elastomeric members 5217 can be engaged to mix the dry portion with the fluid portion of the medicament before the completion of an injection event. In some embodiments, for example, any of the devices shown and described herein can include a mixing actuator similar to the mixing actuators shown and described in U.S. Patent Publication No. 2013/0023822, entitled "Devices and Methods for Delivering Medicaments from a Multi-Chamber Container," filed on Jan. 25, 2012, which is incorporated herein by reference in its entirety.

Any of the medicament containers described herein can include any of the elastomeric members described herein. For example, the medicament container 9200 can include an elastomeric member that is formulated to be compatible with the naloxone composition contained therein, similar to the elastomeric member 7217 shown and described above.

Although the electronic circuit system 3900 is shown and described above as having two irreversible switches (e.g., switch 3972 and switch 3973), in other embodiments, an electronic circuit system can have any number of switches. Such switches can be either reversible or irreversible.

Although the electronic circuit system 3900 is shown and described above as producing an electronic output in response to the actuation of two switches (e.g., switch 3972 and switch 3973), in other embodiments, an electronic circuit system can produce an electronic output in response to any suitable input, command or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input.

Although medical devices having two LEDs and an audio output device have been shown, in other embodiments the medical device might have any number of LEDs and/or audio output devices. Additionally, other types of output devices, such as haptic output devices, can be used. In some embodiments, outputs from an electronic circuit system can include, for example, an audible or visual output related to the composition of the medicament (e.g., an indication of the expiration date, the symptoms requiring treatment with the medicament or the like), the use of the medicament delivery device, and/or post-administration procedures (e.g., a prompt to call 911, instructions for the disposal of the device or the like).

Any of the medicament delivery devices shown and described herein can include any of the electronic circuit systems shown and described herein. For example, although the medical injector 5000 is shown as being devoid of an electronic circuit system, in other embodiments, the medical injector 5000 can include an electronic circuit system similar to the electronic circuit system 3900 shown and described above with reference to FIGS. 29-39. Moreover, although the electronic circuit systems (e.g., the electronic circuit system 3900) are shown and described herein as being coupled the housing of the medicament delivery device, in other embodiments, all or a portion of an electronic circuit system can be coupled to a removable cover (e.g., cover 3190). For example, in some embodiments, the cover can include an electronic circuit system (the "master ECS") including an audible output device, and the electronic circuit system can be configured to receive one or more signals from an electronic circuit system (the "slave ECS") coupled to the medicament delivery device. In this manner, the master ECS can receive indications of when the safety tab has been removed, when the device has been actuated or the like, and can produce an audible output as described herein. In some such embodiments, the master ECS and the slave ECS can be similar to the electronic circuit systems shown and described in U.S. Pat. No. 8,172,082, entitled "Devices, Systems and Methods for Medicament Delivery," filed on Feb. 5, 2007, which is incorporated herein by reference in its entirety.

Although the electronic circuit system 3900 is shown and described above as producing an electronic output in response to the removal of the safety lock 3700 and/or movement of the base 3510, in other embodiments, any suitable component within a medicament delivery device can function to actuate the electronic circuit system. For example, in some embodiments, a carrier (similar to the carrier 3370) can include a protrusion configured to engage a portion of an electronic circuit system such that the electronic circuit system produces an output in response to movement of the carrier. In other embodiments, an electronic circuit system can produce an electronic output in response to the deformation of a portion of a movable member (e.g., the engagement portion 3379 of the carrier 3370). In such embodiments, the deformable portion may be configured to engage a portion of the electronic circuit system or may be configured such that a portion of the electronic circuit system is disposed therein (e.g., a copper trace) to activate the electronic circuit system.

In some embodiments, the electronic circuit system of the types shown and described herein can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Although various embodiments have been described as having particular features and/or combinations of components, other embodiments are possible having a combination of any features and/or components from any of embodiments where appropriate. For example, any of the devices shown and described herein can include an electronic circuit system as described herein. For example, although the medicament delivery device 4000 shown in FIGS. 56 and 57 is not shown as including an electronic circuit system, in other embodiments, a medicament delivery device similar to the device 4000 can include an electronic circuit system similar to the electronic circuit system 3900 shown and described above. Although the medicament delivery device 11000 shown in FIG. 138 is not shown as including an electronic circuit system, in other embodiments, a medicament delivery device similar to the device 11000 can include an electronic circuit system similar to the electronic circuit system 3900 shown and described above.

What is claimed is:

1. A method, comprising:
    removing a medicament delivery device from a case; the medicament delivery device including a housing, a prefilled medicament container assembly disposed within the housing, a medicament delivery structure disposed within the housing, and a movable member configured to cause a force to be exerted on the prefilled medicament container assembly, the prefilled medicament container assembly including a container, a naloxone composition contained within the container, the naloxone composition including a tonicity-adjusting agent and a pH adjusting agent, the pH of the naloxone composition ranging from about 3 to about 5, and an elastomeric member disposed within the container to seal the naloxone composition within the container, the elastomeric member formulated to be compatible with the naloxone composition when in contact with the naloxone composition for a time period of at least one year; an end portion of the medicament delivery structure being fluidically isolated from the naloxone composition when the prefilled medicament container assembly is in a first position within the housing;
    placing a distal end portion of the medicament delivery device into a position relative to a target location of a patient; and
    moving the movable member to transmit the force to be exerted on the prefilled medicament container assembly to move the prefilled medicament container assembly from the first position to a second position within the housing, bringing the end portion of the medicament delivery structure into fluid communication with the naloxone composition when the prefilled medicament container assembly is in the second position within the housing, and delivering the naloxone composition via the medicament delivery structure.

2. The method of claim 1, wherein the medicament delivery structure is a needle.

3. The method of claim 2, wherein the force is a single force exerted in one direction on the prefilled medicament container assembly to both (1) move the prefilled medicament container assembly from the first position to the second position, and (2) deliver the naloxone composition via the needle.

4. The method of claim 1, wherein the medicament delivery structure is associated with an atomizer defining an orifice through which the naloxone composition is delivered intranasally to the patient.

5. The method of claim 1, wherein the medicament delivery structure is an atomizer configured to produce a spray of the naloxone composition having a droplet size distribution in which approximately 85 percent of the droplets have a size of between approximately 10 microns and 150 microns.

6. The method of claim 1, wherein the medicament delivery structure defines a part of a flow path through which the naloxone composition is delivered, the flow path in fluid communication with an orifice through which the naloxone composition is delivered intranasally to the patient.

7. The method of claim 1, wherein at least a portion of the elastomeric member is coated with a silicone-based material.

8. A method, comprising:
placing a distal end of a medicament delivery device into a delivery position, the medicament delivery device including a housing, a prefilled medicament container assembly disposed within the housing, a medicament delivery structure disposed within the housing, and a movable member configured to cause a force to be exerted on the prefilled medicament container assembly, the prefilled medicament container assembly including a container, a naloxone composition contained within the container, the naloxone composition including a tonicity-adjusting agent and a pH adjusting agent, the pH of the naloxone composition ranging from about 3 to about 5, and an elastomeric member disposed within the container to seal the naloxone composition within the container, the elastomeric member including a polymer and a curing agent, the elastomeric member formulated to minimize at least one of leaching or outgassing of compositions therein such that the elastomeric member is compatible with the naloxone composition when in contact with the naloxone composition for a time period of at least one year, an end portion of the medicament delivery structure being fluidically isolated from the naloxone composition when the prefilled medicament container assembly is in a first position within the housing; and
actuating the medicament delivery device by moving the movable member to transmit the force to be exerted on the prefilled medicament container assembly to move the prefilled medicament container assembly from the first position to a second position within the housing, bringing the end portion of the medicament delivery structure into fluid communication with the naloxone composition when the prefilled medicament container assembly is in the second position within the housing, and delivering the naloxone composition via the medicament delivery, structure.

9. The method of claim 8, wherein the medicament delivery structure is a needle.

10. The method of claim 9, wherein the force is a single force exerted in one direction on the prefilled medicament container assembly to both (1) move the prefilled medicament container assembly from the first position to the second position, and (2) deliver the naloxone composition via the needle.

11. The method of claim 8, wherein the medicament delivery structure is associated with an atomizer defining an orifice through which the naloxone composition is delivered intranasally to a patient.

12. The method of claim 8, wherein the medicament delivery structure is an atomizer configured to produce a spray of the naloxone composition having a droplet size distribution in which approximately 85 percent of the droplets have a size of between approximately 10 microns and 150 microns.

13. The method of claim 8, wherein the medicament delivery structure defines a part of a flow path through which the naloxone composition is delivered, the flow path in fluid communication with an orifice through which the naloxone composition is delivered intranasally to a patient.

14. The method of claim 8, wherein at least a portion of the elastomeric member is coated with a silicone-based material.

15. An apparatus, comprising:
a housing;
a prefilled syringe assembly disposed within the housing, the prefilled syringe assembly including a container, an elastomeric member disposed within the container, and a needle staked to a distal end portion of the container, the container containing a dose of a naloxone composition that includes a tonicity-adjusting agent and a pH adjusting agent, the pH of the naloxone composition ranging from about 3 to about 5, the elastomeric member disposed within the container to seal the naloxone composition within the container, the elastomeric member formulated to be compatible with the naloxone composition when in contact with the naloxone composition for a time period of at least one year; and
a movable member coupled to the housing, the movable member configured to transmit a force to be exerted on the elastomeric member of the prefilled syringe assembly to deliver the naloxone composition via the needle.

16. The apparatus of claim 15, further comprising a cover to at least partially enclose the housing and the prefilled syringe assembly.

17. The apparatus of claim 16, wherein the housing defines an opening through which the naloxone composition within the container can be viewed, and the cover obstructs a view through the opening when the housing is within the cover.

18. The apparatus of claim 15, further comprising:
an energy storage member configured to move the movable member to transmit the force to be exerted on the elastomeric member.

19. The apparatus of claim 15, wherein the housing defines an internal volume within which a proximal end portion of the prefilled syringe assembly is disposed before and during delivery of the naloxone composition via the needle, a distal end of the needle extending beyond a distal surface of the housing before and during delivery of the naloxone composition via the needle, a proximal end of the housing including a first stop surface and a second stop surface, the first stop surface configured to limit distal movement of the movable member when the movable member moves from a first position to a second position within the housing, the second stop surface configured limit distal movement of the elastomeric member within the prefilled syringe assembly.

20. The apparatus of claim 15, wherein the elastomeric member includes a silicone-based material.

21. The apparatus of claim 15, wherein the elastomeric member is formulated to be compatible with the naloxone composition when in contact with the naloxone composition for a time period of at least two years.

22. The apparatus of claim 15, wherein the elastomeric member is formulated to include a polymer and a curing agent, the polymer including at least one of bromobutyl or chlorobutyl, the curing agent including at least one of sulfur or a metal oxide.

23. The apparatus of claim 15, wherein the naloxone composition includes 4,5-epoxy-3,14-dihydroxy-17-(2-propenyl)morphinan-6-one in a concentration of between about 0.01 mg/mL and about 60 mg/mL.

24. The apparatus of claim 23, wherein the concentration of the 4,5-epoxy-3,14-dihydroxy-17-(2-propenyl)morphinan-6-one is about 10 mg/mL.

25. The apparatus of claim 15, wherein the movable member is configured to transmit the force to be exerted on the elastomeric member to deliver a single dose of between 3 mg and 24 mg of the naloxone composition via the needle.

26. The apparatus of claim 15, wherein the movable member is configured to transmit the force to be exerted on the elastomeric member to deliver a single dose of between 4 mg and 18 mg of the naloxone composition via the needle.

* * * * *